United States Patent
Okuyama et al.

(10) Patent No.: US 10,793,582 B2
(45) Date of Patent: Oct. 6, 2020

(54) BICYCLIC HETEROCYCLIC COMPOUND

(71) Applicant: MITSUBISHI TANABE PHARMA CORPORATION, Osaka-shi, Osaka (JP)

(72) Inventors: Masahiro Okuyama, Osaka (JP); Kenji Fukunaga, Osaka (JP); Kenji Usui, Osaka (JP); Norimitsu Hayashi, Osaka (JP); Daisuke Iijima, Osaka (JP); Hideki Horiuchi, Osaka (JP); Nobuaki Fujimoto, Osaka (JP)

(73) Assignee: MITSUBISHI TANABE PHARMA CORPORATION, Osaka-Shi (JP)

( * ) Notice: Subject to any disclaimer, the term of this patent is extended or adjusted under 35 U.S.C. 154(b) by 104 days.

(21) Appl. No.: 15/769,835

(22) PCT Filed: Oct. 21, 2016

(86) PCT No.: PCT/JP2016/081368
§ 371 (c)(1),
(2) Date: Apr. 20, 2018

(87) PCT Pub. No.: WO2017/069275
PCT Pub. Date: Apr. 27, 2017

(65) Prior Publication Data
US 2019/0233438 A1 Aug. 1, 2019

(30) Foreign Application Priority Data

Oct. 22, 2015 (JP) .................................. 2015-208176

(51) Int. Cl.
| | | |
|---|---|---|
| *A61K 31/437* | (2006.01) | |
| *A61K 31/5377* | (2006.01) | |
| *A61K 31/519* | (2006.01) | |
| *A61K 31/553* | (2006.01) | |
| *A61K 31/4985* | (2006.01) | |
| *C07D 513/04* | (2006.01) | |
| *C07D 471/04* | (2006.01) | |
| *C07D 519/00* | (2006.01) | |
| *A61P 25/28* | (2006.01) | |
| *A61P 25/18* | (2006.01) | |
| *C07D 487/04* | (2006.01) | |
| *C07D 498/04* | (2006.01) | |
| *A61P 25/24* | (2006.01) | |

(52) U.S. Cl.
CPC .......... *C07D 513/04* (2013.01); *A61K 31/437* (2013.01); *A61K 31/4985* (2013.01); *A61K 31/519* (2013.01); *A61K 31/5377* (2013.01); *A61K 31/553* (2013.01); *A61P 25/18* (2018.01); *A61P 25/24* (2018.01); *A61P 25/28* (2018.01); *C07D 471/04* (2013.01); *C07D 487/04* (2013.01); *C07D 498/04* (2013.01); *C07D 519/00* (2013.01)

(58) Field of Classification Search
None
See application file for complete search history.

(56) References Cited

U.S. PATENT DOCUMENTS

| | | |
|---|---|---|
| 6,232,308 B1 | 5/2001 | Askew |
| 7,470,716 B2 | 12/2008 | Eckhardt et al. |
| 2008/0161317 A1 | 7/2008 | Kelly et al. |
| 2009/0253734 A1 | 10/2009 | Kelly, III et al. |
| 2011/0092511 A1 | 4/2011 | Furuyama et al. |
| 2011/0160183 A1 | 6/2011 | Kelly, III et al. |
| 2012/0142729 A1 | 6/2012 | Dounay et al. |

FOREIGN PATENT DOCUMENTS

| | | |
|---|---|---|
| WO | WO 95/04714 A1 | 2/1995 |
| WO | WO 2007/077186 A1 | 7/2007 |
| WO | WO 2010/146488 A1 | 12/2010 |
| WO | WO 2012/073143 A1 | 6/2012 |
| WO | WO 2013/186666 A1 | 12/2013 |

OTHER PUBLICATIONS

Advancing Drug Discovery for Schizophrenia, The New York Academy of Sciences Mar. 9-11, 2011 (Final program, pp. 17-18).
Albuquerque et al., "Mammalian Nicotinic Acetylcholine Receptors: From Structure to Function," Physiol. Rev. (2009), vol. 89, pp. 73-120.
Alkondon et al., "Targeted Deletion of the Kynurenine Aminotransferase II Gene Reveals a Critical Role of Endogenous Kynurenic Acid in the Regulation of Synaptic Transmission via α7 Nicotinic Receptors in the Hippocampus," The Journal of Neuroscience (May 12, 2004), vol. 24, No. 19, pp. 4635-4648.
Baran et al., "Kynurenic Acid Metabolism in Various Types of Brain Pathology in HIV-1 Infected Patients," International Journal of Tryptophan Research (2012), vol. 5, pp. 49-64.
Baran et al., "Kynurenin metabolism in Alzheimer's disease," J. Neural Transm. (1999), vol. 106, pp. 165-181.

(Continued)

*Primary Examiner* — Samantha L Shterengarts
(74) *Attorney, Agent, or Firm* — Birch, Stewart, Kolasch & Birch, LLP

(57) ABSTRACT

Provided are a novel compound having a superior inhibitory action on KAT-II, a production method thereof, use thereof, and a pharmaceutical composition containing the aforementioned compound and the like.
A compound represented by the formula (I) or a pharmacologically acceptable salt thereof.

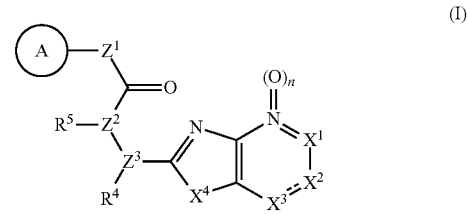

(I)

wherein each symbol is as defined in the DESCRIPTION.

15 Claims, No Drawings

(56) References Cited

OTHER PUBLICATIONS

Chess et al., "Elevations of Endogenous Kynurenic Acid Produce Spatial Working Memory Deficits," Schizophrenia Bulletin (2007), vol. 33, No. 3, pp. 797-804.

Chess et al., "Increased concentration of cerebral kynurenic acid alters stimulus processing and conditioned responding," Behavioural Brain Research (2006), vol. 170, pp. 326-332.

Chess et al., "L-kynurenine treatment alters contextual fear conditioning and context discrimination but not cue-specific fear conditioning," Behavioural Brain Research (2009), vol. 201, pp. 325-331.

English translation of International Search Report dated Jan. 17, 2017, in PCT International Application No. PCT/JP2016/081368.

Ghattas et al., "Synthesis and reactions of some new oxazolo[4,5-b]pyridines and related compounds," Synthetic Communications (2000), vol. 30, No. 18, pp. 3423-3438.

Gold et al., "The relationship between indoleamine 2,3-dioxygenase activity and post-stroke cognitive impairment," Journal of Neuroinflammation (2011), vol. 8, No. 17, pp. 1-8.

Henderson et al., "Competitive antagonists and partial antagonists at the glycine modulatory site of the mouse N-methyl-$_D$-asparate receptor," Journal of Physiology (1990), vol. 430, pp. 189-212.

Linderholm et al., "Increased Levels of kynurenine and kynurenic Acid in the CSF of Patients with Schizophrenia," Schizophrenia Bulletin (2012), vol. 38, No. 3, pp. 426-432.

McGehee, D. S., "Nicotinic receptors and hippocampal synaptic plasticity . . . it's all in the timing," TRENDS in Neurosciences (Apr. 2002), vol. 25, No. 4, pp. 171-172.

McTighe et al., "The BTBR Mouse Model of Autism Spectrum Disorders has Learning and Attentional Impairments and Alternations in Acetylcholine and Kynurenic Acid in Prefrontal Cortex," PLOS ONE (Apr. 2013), vol. 8, Issue 4, e62189, pp. 1-11.

Morris et al., "Hippocampal synaptic plasticity and NMDA receptors: a role in information storage?," Phil. Trans. R. Soc. Lond. (1990), vol. 329, pp. 187-204.

Olsson et al., "Cerebrospinal fluid kynurenic acid is associated with manic and psychotic features in patients with bipolar I disorder," Bipolar Disorders (2012), vol. 14, pp. 719-726.

Potter et al., "Reduction of Endogenous Kynurenic Acid Fomation Enhances Extracellular Glutamate, Hippocampal Plasticity, and Cognitive Behavior," Neurophyschopharmacology (2010), vol. 35, pp. 1734-1742.

Rassoulpour et al., "Nanomolar concentrations of kynurenic acid reduce extracellular dopamine levels in the striatum," Journal of Neurochemistry (2005), vol. 93, pp. 762-765.

Schwarcz et al., "Kynurenines in the mammalian brain: when physiology meets pathology," Nature Reviews (Jul. 2012), vol. 13, pp. 465-477.

Shrimali et al., "Efficient Heterocyclizations Leading to Substituted Isoxazoles and Pyrimidines and their Biological Activity," Indian Journal of Heterocyclic Chemistry (Jan.-Mar. 2010), vol. 19, pp. 257-260.

Wu et al., "The Atrocyte-Derived α7 Nicotinic Receptor Antagonist Kynurenic Acid Controls Extracellular Glutamate Levels in the Prefrontal Cortex," J. Mol. Neurosci. (2010), vol. 40, pp. 204-210.

Zmarowski et al., "Astrocyte-derived kynurenic acid modulates basal and evoked cortical acetylcholine release," European Journal of Neuroscience (2009), vol. 29, pp. 529-538.

BICYCLIC HETEROCYCLIC COMPOUND

TECHNICAL FIELD

The present invention relates to a bicyclic heterocyclic compound. More particularly, the present invention relates to a novel bicyclic heterocyclic compound having a Kynurenine Aminotransferase-II (hereinafter sometimes to be also indicated as KAT-II) inhibitory action, and useful as a medicament for cognitive impairment, neurodegenerative disease, or schizophrenia, and use thereof.

BACKGROUND ART

N-methyl-D-aspartic acid receptor (hereinafter sometimes to be also indicated as NMDAR) and nicotinic acetylcholine receptor (hereinafter sometimes to be also indicated as nAChR) are known to be involved in some cognitive function processes. It is shown from animal studies that activation of NMDAR or nAChR improves some psychiatric diseases including schizophrenia, dementia, depression, and stress vulnerability (see non-patent document 1 for NMDAR, non-patent documents 2 and 3 for nAChR).

Kynurenic acid (hereinafter sometimes to be also indicated as KYNA) is an endogenous tryptophan metabolite produced in the brain by kynurenine pathway. Tryptophan is metabolized by indoleamine 2,3-dioxygenase (IDO) and the like to produce kynurenine, and kynurenine is metabolized to produce KYNA. There are 4 kinds of known enzymes that catalyze the reaction to produce KYNA from kynurenine. That is, kynurenine-aminotransferases 1, 2, 3, and 4. Of these, KAT-II plays a key role in the production of KYNA in the brain, and it is known that KYNA concentration significantly decreases in hippocampus in KAT-II knockout mouse, as compared to that in wild-type mouse (see non-patent document 4).

KYNA is known to be an antagonist of NMDAR and nicotinic acetylcholine α7 receptor (hereinafter sometimes to be also indicated as α7nAChR). Therefore, KYNA is considered to be mainly involved in the control of presynaptic activity of GABA neuron, glutamic acid neuron via α7nAChR in the brain, and control of postsynaptic activity of glutamic acid neuron via NMDAR (see non-patent documents 5, 6 and 7).

Therefore, KAT-II inhibitor is expected to be useful for the treatment of central diseases such as schizophrenia, attention deficit/hyperactivity disorder, Alzheimer's disease, major depression and the like through activation of NMDAR and/or nAChR based on a decrease in the KYNA concentration in the brain. As documents describing the relationship between KAT-II and/or KYNA and dementia, depression, or stress vulnerability, the following are reported.

In the studies of mammals, it was confirmed that an increase in the KYNA concentration in the brain causes disorders of cognitive functions such as context learning, working memory and the like, and it is discussed that an increase in the KYNA concentration may be involved in the cognitive dysfunction such as schizophrenia and the like (see non-patent documents 8-10).

R. Schwarcz et al. show that topical injection of KYNA into the brain of rodents suppresses release of dopamine, acetylcholine or glutamic acid in the site, and a possibility is proposed that attenuation of KYNA production in the brain improves cognitive function of schizophrenia (see non-patent document 11 for dopamine, non-patent document 12 for acetylcholine, non-patent document 13 for glutamic acid).

It has been reported that KYNA concentration in the cerebrospinal fluid of schizophrenia patients and bipolar disorder patients is significantly higher than that of normal volunteers and patients free of psychiatric diseases, and the results support involvement of KYNA in the pathophysiology of schizophrenia and bipolar disorder (see non-patent document 14 for schizophrenia, and non-patent document 15 for bipolar disorder).

It has been reported that administration of a KAT-II inhibitor decreases the KYNA concentration in the brain dialysates in a dose-dependent manner, and KAT-II inhibitors show activity in anhedonia model [chronic mild stress], which is one kind of depression models, and it has been reported that KAT-II inhibitors may be suitable for cognitive function and negative symptoms of schizophrenia (see non-patent document 16).

BTBR mouse, which is one kind of autism spectrum disorder mice, is reported to show high KYNA concentration in the medial prefrontal cortex, as compared to C57 Bl/6J mouse (see non-patent document 17).

It is known that KYNA concentration is significantly high in the putamen and caudate nucleus of postmortem brain of Alzheimer's disease patients, as compared to the control group free of dementia. It has been reported that inhibition of NMDAR by KYNA possibly causes memory disorder, learning and cognition function of Alzheimer's disease patients (see non-patent document 18).

It has been reported that patients with ischemic cerebrovascular diseases (cerebral infarction) and showing a greater kynurenine/tryptophan ratio show degraded cognitive function, and correlation between inflammatory reactions characterized by an increased IDO activity and cerebrovascular dementia is suggested (see non-patent document 19).

It has been reported that the concentration of kynurenic acid in the frontal cortex of postmortem brain of a subgroup such as HIV encephalopathy (HIV in brain) and the like in the HIV-1 (human immunodeficiency virus 1) infected patients is significantly higher than that of the control group. In addition, it is suggested that a decrease in the kynurenic acid production can be useful for an antidementia drug (see non-patent document 20).

As a compound having a KAT-II inhibitory activity, for example, the following compound has been reported.

R. Schwarcz et al. disclosed that a novel kynurenine derivative having a KAT-II inhibitory activity is effective for the treatment of cognitive impairment related to the aging of the brain and perinatal brain damage (see patent document 1).

M. M. Claffey et al. and A. B. Dounay et al. disclose that the compounds represented by the following formulas are KAT-II inhibitory compounds, and useful for the treatment of schizophrenia and cognitive deficit relating to other neurodegeneration and/or neurological disorder (see patent documents 2-4).

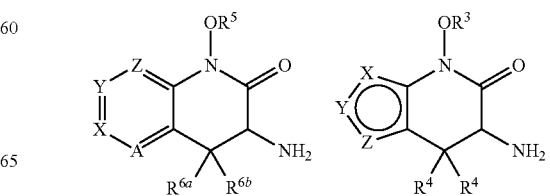

-continued

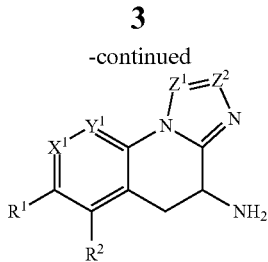

However, a KAT-II inhibitory action of a bicyclic heterocyclic compound like that of the compound of the present invention has not been reported.

While Pichota et al. discloses (S)-2-oxazolo[4,5-b]pyridin-2-yl-pyrrolidine-1-carboxylic acid benzyl ester, it merely discloses that the compound can be used as a synthetic intermediate, and does not disclose that the compound has a KAT-II inhibitory action or other pharmacological activities. The patent document relates to a novel compound as an inhibitor of peptidyl deformylase (PDF) useful as an antibacterial agent or antibiotic, and does not describe a compound having a KAT-II inhibitory action (patent document 5).

DOCUMENT LIST

Patent Documents patent document 1: WO 1995/004714
patent document 2: WO 2010/146488
patent document 3: WO 2012/073143
patent document 4: WO 2013/186666
patent document 5: WO 2007/077186

Non-Patent Documents non-patent document 1: R. G. M. Morris et al., "Philosophical transactions of the Royal Society of London" vol. 329, pages 187-204, 1990
non-patent document 2: E. X. Albuquerque et al., "Physiological Reviews" vol. 89, pages 73-120, 2009
non-patent document 3: D. S. McGehee, "Trends in Neurosciences" vol. 25, pages 171-172, 2002
non-patent document 4: M. C. Potter et al., "Neuropsychopharmacology" vol. 35, pages 1734-1742, 2010
non-patent document 5: R. Schwarcz et al., "Nature Reviews Neuroscience" vol. 13, pages 465-477, 2012
non-patent document 6: M. Alkondon et al., "The Journal of Neuroscience" vol. 24, pages 4635-4648, 2004
non-patent document 7: G. Henderson et al., "Journal of Physiology" vol. 430, pages 189-212, 1990
non-patent document 8: A. C. Chess et al., "Behavioural Brain Research" vol. 170, pages 326-332, 2006
non-patent document 9: A. C. Chess et al., "Schizophrenia Bulletin" vol. 33, pages 797-804, 2007
non-patent document 10: A. C. Chess et al., "Behavioural Brain Research" vol. 201, pages 325-331, 2009
non-patent document 11: A. Rassoulpour et al., "Journal of Neurochemistry" vol. 93, pages 762-765, 2005
non-patent document 12: A. Zmarowski et al., "European Journal of Neuroscience" vol. 29, pages 529-538, 2009
non-patent document 13: H.-Q. Wu et al., "Journal of Molecular Neuroscience" vol. 40, pages 204-210, 2010
non-patent document 14: K. R. Linderholm et al., "Schizophrenia Bulletin" vol. 38, pages 426-432, 2012
non-patent document 15: S. K. Olssona et al., "Bipolar Disorders" vol. 14, pages 719-726, 2012
non-patent document 16: B. Campbell et al., "Advancing Drug Discovery for Schizophrenia" The New York Academy of Sciences Mar. 9-11, 2011 (Final program, pages 17-18)
non-patent document 17: S. M. McTighe et al., "PLoS ONE" vol. 8, e62189, 2013
non-patent document 18: H. Baran et al., "Journal of Neural Transmission" vol. 106, pages 165-181, 1999
non-patent document 19: A. B. Gold et al., "Journal of Neuroinflammation" vol. 8, 17, 2011
non-patent document 20: H. Baran et al., "International Journal of Tryptophan Research" vol. 5, pages 49-64, 2012

SUMMARY OF THE INVENTION

Problems to be Solved by the Invention

An object to be solved by the present invention is provision of a novel compound having a superior inhibitory action on KAT-II, a production method thereof, use thereof, and a pharmaceutical composition containing the aforementioned compound and the like.

Means of Solving the Problems

The present inventors have conducted intensive studies in an attempt to solve the above-mentioned problems and found a novel bicyclic heterocyclic compound having a superior KAT-II inhibitory action and completed the present invention.

That is, the present invention relates to a compound represented by the formula (I):

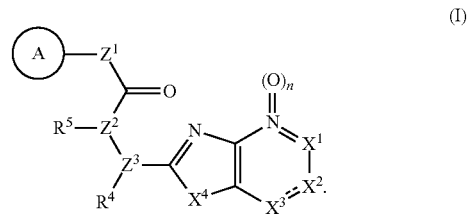

(I)

wherein
ring A is an optionally substituted aromatic group,
$X^1$ is $CR^1$ or a nitrogen atom,
a part represented by the following formula in the formula (I):

is the following A) or B), A) ----
is a double bond,
$X^2$ is a nitrogen atom or $CR^2$, and
$X^3$ is a nitrogen atom or $CR^3$; B) ==
is a single bond,
$X^2$ is $NR^2$, and
$X^3$ is carbonyl;
$X^4$ is sulfur atom, an oxygen atom or —CH=CH—,
$Z^1$ is an oxygen atom, —C($R^6$)($R^7$)—, —NH—, —C($R^6$)($R^7$)—NH—, —NH—C($R^6$)($R^7$)—, —C($R^6$)($R^7$)—O—, —O—C($R^6$)($R^7$)— or a single bond (where the left end shows a bond to ring A, and the right end shows a bond to the adjacent carbonyl), one of $Z^2$ and $Z^3$ is CH and the other is a nitrogen atom, or both are nitrogen atoms, $R^1$ is a group represented by the following formula (i-a), (i-b) or (i-c):

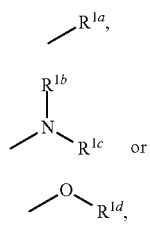

$R^2$ is a group represented by the following formula (ii-a), (ii-b) or (ii-c):

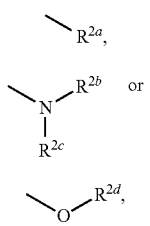

$R^3$ is a group represented by the following formula (iii-a), (iii-b) or (iii-c):

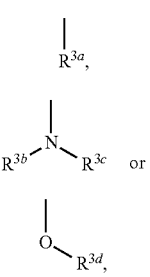

$R^4$ and $R^5$ are each independently optionally substituted alkyl or optionally substituted cycloalkyl, or $R^4$ and $R^5$ are bonded to each other to form, together with the adjacent $Z^2$ and $Z^3$, an optionally substituted nitrogen-containing non-aromatic heterocycle, $R^6$ and $R^7$ are each independently a hydrogen atom, optionally substituted alkyl, or optionally substituted cycloalkyl, or $R^6$ and $R^7$ are bonded to each other to form, together with the adjacent carbon atom, an optionally substituted cycloalkane, $R^{1a}$, $R^{1b}$, $R^{1c}$, $R^{1d}$, $R^{2a}$, $R^{2b}$, $R^{2c}$, $R^{2d}$, $R^{3a}$, $R^{3b}$ and $R^{3d}$ are each independently a hydrogen atom, optionally substituted alkyl, cyano, a halogen atom, optionally substituted cycloalkyl, optionally substituted aryl, optionally substituted non-aromatic heterocyclic group or optionally substituted heteroaryl, $R^{3c}$ is optionally substituted alkyl, cyano, optionally substituted alkoxy, a halogen atom, optionally substituted cycloalkyl, optionally substituted aryl, optionally substituted non-aromatic heterocyclic group or optionally substituted heteroaryl, and n is 0 or 1, or a pharmacologically acceptable salt thereof, excluding 2-oxazolo[4,5-b]pyridin-2-yl-pyrrolidine-1-carboxylic acid benzyl ester or a pharmacologically acceptable salt thereof.

The present invention also relates to a method for the prophylaxis or treatment of various diseases (e.g., schizophrenia) involving KAT-II, which comprises administering an effective amount of a compound represented by the aforementioned formula (I) (hereinafter to be also indicated as compound (I)), or a pharmacologically acceptable salt to a patient (an individual to be the subject of treatment or prophylaxis).

The present invention also relates to a pharmaceutical composition comprising the aforementioned compound (I) or a pharmacologically acceptable salt thereof as an active ingredient, and use of the aforementioned compound (I) or a pharmacologically acceptable salt thereof for the production of the pharmaceutical composition.

Effect of the Invention

Since a compound represented by the formula (I) or a pharmacologically acceptable salt thereof affords a superior KAT-II inhibitory action, a pharmaceutical composition containing same as an active ingredient is useful for the prophylaxis or treatment of various diseases (e.g., schizophrenia) involving KAT-II.

DESCRIPTION OF EMBODIMENTS

The definition of each term used in the present specification is as follows.

The term "alkyl" means a linear or branched chain saturated hydrocarbon group having 1 to 6 carbon atoms ($C_1$-$C_6$), and specific examples include methyl, ethyl, propyl, isopropyl, butyl, tert-butyl, isobutyl, pentyl, hexyl, and various branched chain isomers thereof.

The term "alkenyl" means a linear or branched chain unsaturated hydrocarbon group having 1 or 2 carbon-carbon double bonds and 2 to 6 carbon atoms ($C_2$-$C_6$), and specific examples include vinyl, propenyl, isopropenyl, butenyl, butadienyl, pentenyl, pentadienyl, hexenyl, hexadienyl, and various branched chain isomers thereof.

The term "alkylene" means a linear or branched chain divalent saturated hydrocarbon group having 1 to 6 carbon atoms ($C_1$-$C_6$), and specific examples include methylene, ethylene, propylene, trimethylene, butylene, tetramethylene, pentamethylene, 1,1,2,2-tetramethylethylene, and various branched chain isomers thereof.

The term "alkylidene" means a linear or branched chain hydrocarbon group having 1 to 6 carbon atoms ($C_1$-$C_6$) and bonded via a double bond to the residue of the molecule. Specific examples include methylidene, ethylidene, propylidene, butylidene, pentylidene, hexylidene, and various branched chain isomers thereof.

The term "cycloalkyl" means a 3-8-membered ($C_3$-$C_8$) monocyclic alicyclic saturated hydrocarbon group, and specific examples include cyclopropyl, cyclobutyl, cyclopentyl, cyclohexyl, cycloheptyl, and cyclooctyl.

The term "cycloalkane" means a 3-8-membered ($C_3$-$C_8$) monocyclic alicyclic saturated hydrocarbon, and specific examples include cyclopropane, cyclobutane, cyclopentane, cyclohexane, cycloheptane, and cyclooctane.

The term "aryl" means a monocyclic or bicyclic aromatic hydrocarbon group having 6-11 ring-constituting carbon atoms ($C_6$-$C_{11}$), and specific examples include monocyclic aryl such as phenyl and the like; and optionally partly saturated bicyclic aryl having 9-11 ring-constituting carbon atoms ($C_9$-$C_{11}$) such as naphthyl, tetrahydronaphthyl, indenyl, indanyl and the like.

The term "arene" means monocyclic or bicyclic aromatic hydrocarbon having 6-11 ring-constituting carbon atoms ($C_6$-$C_{11}$), and specific examples include monocyclic arene such as benzene and the like; and optionally partly saturated bicyclic arene having 9-11 ring-constituting carbon atoms ($C_9$-$C_{11}$) such as naphthalene, tetrahydronaphthalene, indene, indane and the like.

The term "non-aromatic heterocyclic group" means a 4- to 12-membered monocyclic or bicyclic non-aromatic heterocyclic group containing, besides carbon atom, 1-4 hetero atoms selected from the group consisting of oxygen atom, sulfur atom and nitrogen atom, and specific examples include a 4- to 7-membered monocyclic non-aromatic heterocyclic group containing, besides carbon atom, 1 or 2 hetero atoms selected from the group consisting of oxygen atom, sulfur atom and nitrogen atom such as azetidinyl, pyrrolidyl, pyrazolidinyl, piperidyl, homopiperidyl, oxetanyl, tetrahydrofuryl, dihydropyranyl, tetrahydropyranyl, tetrahydrothienyl, dihydroimidazolyl, imidazolidinyl, tetrahydropyrazinyl, piperazinyl, morpholinyl, homomorpholinyl, thiazolidyl and the like; and a 6- to 12-membered bicyclic non-aromatic heterocyclic group containing, besides carbon atom, 1-4 hetero atoms selected from the group consisting of oxygen atom, sulfur atom and nitrogen atom such as azabicyclo[3.1.0]hexyl, oxaazabicyclo[3.2.1]octyl and the like.

The term "nitrogen-containing non-aromatic heterocyclic group" means the aforementioned non-aromatic heterocyclic group containing at least one nitrogen atom, and specific examples include azetidinyl, pyrrolidyl, pyrazolidinyl, piperidyl, homopiperidyl, dihydroimidazolyl, imidazolidinyl, tetrahydropyrazinyl, piperazinyl, morpholinyl, homomorpholinyl, thiazolidyl, azabicyclo[3.1.0]hexyl and oxaazabicyclo[3.2.1]octyl.

The term "non-aromatic heterocycle" means a 4- to 12-membered monocyclic or bicyclic non-aromatic heterocycle containing, besides carbon atom, 1-4 hetero atoms selected from the group consisting of oxygen atom, sulfur atom and nitrogen atom, and specific examples include a 4- to 7-membered monocyclic non-aromatic heterocycle containing, besides carbon atom, 1 or 2 hetero atoms selected from the group consisting of oxygen atom, sulfur atom and nitrogen atom such as azetidine, pyrrolidine, pyrazolidine, piperidine, homopiperidine, oxetane, tetrahydrofuran, tetrahydropyran, tetrahydrothiophene, dihydroimidazole, imidazolidine, tetrahydropyrazine, piperazine, morpholine, homomorpholine, thiazolidine and the like; and a 6-12-membered bicyclic non-aromatic heterocycle containing, besides carbon atom, 1-4 hetero atoms selected from the group consisting of oxygen atom, sulfur atom and nitrogen atom such as azabicyclo[3.1.0]hexane, oxaazabicyclo[3.2.1]octane and the like.

The term "nitrogen-containing non-aromatic heterocycle" means the aforementioned non-aromatic heterocycle containing at least one nitrogen atom, and specific examples include azetidine, pyrrolidine, pyrazolidine, piperidine, homopiperidine, dihydroimidazole, imidazolidine, tetrahydropyrazine, piperazine, morpholine, homomorpholine, thiazolidine, azabicyclo[3.1.0]hexane and oxaazabicyclo[3.2.1]octane.

The term "heteroaryl" means a 5- to 11-membered monocyclic or bicyclic aromatic heterocyclic group containing, besides carbon atom, 1-4 hetero atoms selected from the group consisting of oxygen atom, sulfur atom and nitrogen atom, and specific examples include 5- to 6-membered monocyclic heteroaryl containing, besides carbon atom, 1-4 hetero atoms selected from the group consisting of oxygen atom, sulfur atom and nitrogen atom such as pyrrolyl, furyl, thienyl, pyrazolyl, imidazolyl, triazolyl, oxazolyl, isoxazolyl, oxadiazolyl, thiazolyl, isothiazolyl, thiadiazolyl, pyridyl, pyrazyl, pyrimidinyl, pyridazinyl and the like; and optionally partly saturated 8- to 11-membered bicyclic heteroaryl containing, besides carbon atom, 1-4 hetero atoms selected from the group consisting of oxygen atom, sulfur atom and nitrogen atom such as indolinyl, isoindolinyl, dihydrobenzofuranyl, dihydroisobenzofuranyl, benzodioxolanyl, thienopyridyl, thiazolopyridyl, thiazolopyrimidinyl, thiazolopyridazyl, thiadiazolopyridyl, thiadiazolopyrimidinyl, quinolyl, tetrahydroquinolyl, isoquinolyl, tetrahydroisoquinolyl, pyridopyrimidinyl, pyrimidopyridazyl, triazolopyridyl and the like.

The term "nitrogen-containing heteroaryl" means the aforementioned heteroaryl containing at least one nitrogen atom, and specific examples include 5- to 6-membered monocyclic nitrogen-containing heteroaryl such as pyrrolyl, pyrazolyl, imidazolyl, triazolyl, oxazolyl, isoxazolyl, oxadiazolyl, thiazolyl, isothiazolyl, thiadiazolyl, pyridyl, pyrazyl, pyrimidinyl, pyridazinyl and the like; and optionally partly saturated 8- to 11-membered bicyclic nitrogen-containing heteroaryl such as indolinyl, isoindolinyl, thienopyridyl, thiazolopyridyl, thiazolopyrimidinyl, thiazolopyridazyl, thiadiazolopyridyl, thiadiazolopyrimidinyl, quinolyl, tetrahydroquinolyl, isoquinolyl, tetrahydroisoquinolyl, pyridopyrimidinyl, pyrimidopyridazyl, triazolopyridyl and the like.

The term "heteroarene" means a 5- to 11-membered monocyclic or bicyclic aromatic heterocycle containing, besides carbon atom, 1-4 hetero atoms selected from the group consisting of oxygen atom, sulfur atom and nitrogen atom, and specific examples include a 5- to 6-membered monocyclic heteroarene containing, besides carbon atom, 1-4 hetero atoms selected from the group consisting of oxygen atom, sulfur atom and nitrogen atom such as pyrrole, furan, thiophene, pyrazole, imidazole, triazole, oxazole, isoxazole, oxadiazole, thiazole, isothiazole, thiadiazole, pyridine, pyrazine, pyrimidine, pyridazine and the like; and an optionally partly saturated 8- to 11-membered bicyclic heteroarene containing, besides carbon atom, 1-4 hetero atoms selected from the group consisting of oxygen atom, sulfur atom and nitrogen atom such as indoline, isoindoline, dihydrobenzofuran, dihydroisobenzofuran, benzodioxolane, thienopyridine, thiazolopyridine, thiazolopyrimidine, thiazolopyridazine, thiadiazolopyridine, thiadiazolopyrimidine, quinoline, tetrahydroquinoline, isoquinoline, tetrahydroisoquinoline, pyridopyrimidine, pyrimidopyridazine, triazolopyridine and the like.

The term "nitrogen-containing heteroarene" means the aforementioned heteroarene containing at least one nitrogen atom, and specific examples include 5- to 6-membered monocyclic nitrogen-containing heteroarene such as pyrrole, pyrazole, imidazole, triazole, oxazole, isoxazole, oxadiazole, thiazole, isothiazole, thiadiazole, pyridine, pyrazine, pyrimidine, pyridazine and the like; and 8- to 11-membered bicyclic nitrogen-containing heteroarene such as indoline, isoindoline, thienopyridine, thiazolopyridine, thiazolopyrimidine, thiazolopyridazine, thiadiazolopyridine, thiadiazolopyrimidine, quinoline, tetrahydroquinoline, isoquinoline, tetrahydroisoquinoline, pyridopyrimidine, pyrimidopyridazine, triazolopyridine and the like.

The term "aromatic group" means a 5- to 11-membered monocyclic or bicyclic aromatic group optionally containing, besides carbon atom, 1-4 hetero atoms selected from the group consisting of oxygen atom, sulfur atom and nitrogen atom, and specific examples include the aforementioned aryl, heteroaryl, more specifically, monocyclic aryl such as phenyl and the like; optionally partly saturated bicyclic aryl having 9-11 ring-constituting carbon atoms ($C_9$-$C_{11}$) such as naphthyl, tetrahydronaphthyl, indenyl, indanyl and the like; 5- to 6-membered monocyclic heteroaryl containing, besides carbon atom, 1-4 hetero atoms selected from the group consisting of oxygen atom, sulfur atom and nitrogen atom such as pyrrolyl, furyl, thienyl, pyrazolyl, imidazolyl, triazolyl, oxazolyl, isoxazolyl, oxadiazolyl, thiazolyl, isothiazolyl, thiadiazolyl, pyridyl, pyrazyl, pyrimidinyl, pyridazinyl and the like; and optionally partly saturated 8- to 11-membered bicyclic heteroaryl containing, besides carbon atom, 1-4 hetero atoms selected from the group consisting of oxygen atom, sulfur atom and nitrogen atom such as indolinyl, isoindolinyl, dihydrobenzofuranyl, dihydroisobenzofuranyl, benzodioxolanyl, thienopyridyl, thiazolopyridyl, thiazolopyrimidinyl, thiazolopyridazyl, thiadiazolopyridyl, thiadiazolopyrimidinyl, quinolyl, tetrahydroquinolyl, isoquinolyl, tetrahydroisoquinolyl, pyridopyrimidinyl, pyrimidopyridazyl, triazolopyridyl and the like.

The term "aromatic ring" means a 5- to 11-membered monocyclic or bicyclic aromatic ring optionally containing, besides carbon atom, 1-4 hetero atoms selected from the group consisting of oxygen atom, sulfur atom and nitrogen atom, and specific examples include the aforementioned arene, heteroarene, more specifically, monocyclic arene such as benzene and the like; optionally partly saturated bicyclic arene having 9-11 ring-constituting carbon atoms ($C_9$-$C_{11}$) such as naphthalene, tetrahydronaphthalene, indene, indane and the like; a 5- to 6-membered monocyclic heteroarene containing, besides carbon atom, 1-4 hetero atoms selected from the group consisting of oxygen atom, sulfur atom and nitrogen atom such as pyrrole, furan, thiophene, pyrazole, imidazole, triazole, oxazole, isoxazole, oxadiazole, thiazole, isothiazole, thiadiazole, pyridine, pyrazine, pyrimidine, pyridazine and the like; and optionally partly saturated 8- to 11-membered bicyclic heteroarene containing, besides carbon atom, 1-4 hetero atoms selected from the group consisting of oxygen atom, sulfur atom and nitrogen atom such as indoline, isoindoline, dihydrobenzofuran, dihydroisobenzofuran, benzodioxolane, thienopyridine, thiazolopyridine, thiazolopyrimidine, thiazolopyridazine, thiadiazolopyridine, thiadiazolopyrimidine, quinoline, tetrahydroquinoline, isoquinoline, tetrahydroisoquinoline, pyridopyrimidine, pyrimidopyridazine, triazolopyridine and the like.

The term "ring" means a 5- to 11-membered monocyclic or bicyclic ring optionally containing, besides carbon atom, 1-4 hetero atoms selected from the group consisting of oxygen atom, sulfur atom and nitrogen atom, and specific examples include the aforementioned cycloalkane, arene, non-aromatic heterocycle, and heteroarene.

The term "halogen atom" or "halogeno" means fluorine atom, chlorine atom, bromine atom or iodine atom.

The term "alkoxy" means a group wherein an oxygen atom is bonded to the aforementioned linear or branched chain alkyl having 1 to 6 carbon atoms ($C_1$-$C_6$), and specific examples include methoxy, ethoxy, propoxy, isopropoxy, butoxy, tert-butoxy, isobutoxy, pentyloxy, hexyloxy, and various branched chain isomers thereof.

The term "alkoxyphenyl" means phenyl substituted by 1, 2 or 3 alkoxys mentioned above, and specific examples include methoxyphenyl, and dimethoxyphenyl.

The term "halogenoalkyl" means the aforementioned alkyl substituted by 1 to 7 halogen atoms, and specific examples include trifluoromethyl.

The term "alkanoyl" means a group having 2 to 7 carbon atoms ($C_2$-$C_7$) wherein carbonyl is bonded to the aforementioned linear or branched chain alkyl having 1 to 6 carbon atoms ($C_1$-$C_6$), and specific examples include acetyl, propanoyl, butyryl, and various branched chain isomers thereof.

The term "aralkyl" means a group wherein the aforementioned linear or branched chain alkylene having 1 to 6 carbon atoms ($C_1$-$C_6$) is bonded to the aforementioned monocyclic or bicyclic aromatic hydrocarbon group having 6-11 ring-constituting carbon atoms ($C_6$-$C_{11}$), and specific examples include phenylmethyl.

The term "non-aromatic heterocyclic oxy" means a group in which an oxygen atom is bonded to a 4- to 12-membered monocyclic or bicyclic non-aromatic heterocyclic group containing, besides carbon atom, 1-4 hetero atoms selected from the group consisting of oxygen atom, sulfur atom and nitrogen atom, and specific examples include azetidinyloxy, pyrrolidyloxy, pyrazolidinyloxy, piperidyloxy, homopiperidyloxy, oxetanyloxy, tetrahydrofuryloxy, dihydropyranyloxy, tetrahydropyranyloxy, tetrahydrothienyloxy, dihydroimidazolyloxy, imidazolidinyloxy, tetrahydropyrazinyloxy, piperazinyloxy, morpholinyloxy, homomorpholinyloxy, thiazolidyloxy.

The term "treatment" means the act of administering the compound of the present invention or a pharmacologically acceptable salt thereof, or a pharmaceutical composition containing these as an active ingredient to an individual who has already developed an illness, a disease or a symptom. Therefore, the act of administering the compound of the present invention or a pharmacologically acceptable salt thereof, or a pharmaceutical composition containing these as an active ingredient to an individual who has already developed an illness, a disease or a symptom in an attempt to prevent deterioration of symptoms etc., prevention of seizure or prevention of recurrence is one embodiment of the "treatment".

In the present specification, a part represented by the following formula:

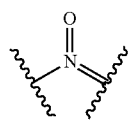 [SMILES: *[N+](=*)[O-]]

is amine oxide, and has the same meaning as a partial structure represented by the following formula:

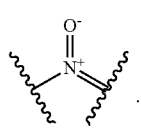

Each abbreviation used in the present specification means the following unless particularly defined.

Boc: tert-butoxycarbonyl
D: deuterium ($^2$H)
DBU: 1,8-diazabicyclo[5.4.0]undec-7-ene
DMF: N,N-dimethylformamide
EDC hydrochloride: 1-(3-dimethylaminopropyl)-3-ethylcarbodiimide hydrochloride
HATU: O-(7-azabenzotriazol-1-yl)-N,N,N',N'-tetramethyluronium hexafluorophosphate
HOBt monohydrate: 1-hydroxybenzotriazole monohydrate
HPLC: high performance liquid chromatography
mCPBA: methachloroperbenzoic acid
THF: tetrahydrofuran
Lawesson's reagent: 2,4-bis(4-methoxyphenyl)-1,3,2,4-dithiadiphosphetane-2,4-disulfide In the following, each symbol in the aforementioned compound represented by the formula (I) is explained by showing specific examples.

The aromatic group of the "optionally substituted aromatic group" for ring A is as defined above, and specific examples thereof include aryl and heteroaryl. Preferable aryl or heteroaryl includes phenyl, tetrahydronaphthyl, indanyl, furyl, thienyl, pyrazolyl, isoxazolyl, thiazolyl, pyridyl, pyrimidinyl, pyrazyl, indolinyl, tetrahydroquinolyl, thienopyridyl, dihydrobenzofuranyl, benzodioxolanyl, and triazolopyridyl. Of these, phenyl or indanyl is more preferable, and phenyl is particularly preferable.

$X^1$ is as defined above, of which $CR^1$ is preferable.

$X^4$ is as defined above, of which a sulfur atom or —CH=CH— is preferable.

$Z^1$ is as defined above, of which an oxygen atom, —C($R^6$)($R^7$)—, —NH—, —C($R^6$)($R^7$)—NH— or —C($R^6$)($R^7$)—O— is preferable, and oxygen atom or —O($R^6$)($R^7$)—NH— is more preferable.

$Z^2$ and $Z^3$ are as defined above. Preferably, one is CH and the other is a nitrogen atom.

When $R^4$ or $R^5$ is "optionally substituted alkyl", the alkyl moiety of the group is as defined above, and is preferably $C_1$-$C_6$ alkyl, more preferably $C_1$-$C_4$ alkyl.

When $R^4$ or $R^5$ is "optionally substituted cycloalkyl", the cycloalkyl moiety of the group is as defined above, and is preferably $C_3$-$C_8$ cycloalkyl, more preferably $C_3$-$C_6$ cycloalkyl.

When $R^4$ and $R^5$ are bonded to each other to form, together with the adjacent $Z^2$ and $Z^3$, "optionally substituted nitrogen-containing non-aromatic heterocycle", the nitrogen-containing non-aromatic heterocycle moiety of the group is as defined above, of which a 4- to 12-membered monocyclic or bicyclic non-aromatic heterocyclic group containing, besides carbon atom, at least one nitrogen atom, and containing 1 to 4 hetero atoms selected from the group consisting of oxygen atom, sulfur atom and nitrogen atom is preferable, azetidine, pyrrolidine, pyrazolidine, piperidine, morpholine, thiazolidine or azabicyclo[3.1.0]hexane is more preferable, pyrrolidine or thiazolidine is particularly preferable, and pyrrolidine is most preferable.

When $R^6$ or R is "optionally substituted alkyl", the alkyl moiety of the group is as defined above, and is preferably $C_1$-$C_6$ alkyl, more preferably $C_1$-$C_4$ alkyl.

When $R^6$ or $R^7$ is "optionally substituted cycloalkyl", the cycloalkyl moiety of the group is as defined above, and is preferably $C_3$-$C_8$ cycloalkyl, more preferably $C_3$-$C_8$ cycloalkyl.

Preferable examples of $R^6$ and $R^7$ include a hydrogen atom, optionally substituted $C_1$-$C_4$ alkyl, and optionally substituted $C_3$-$C_8$ cycloalkyl, more preferably, a hydrogen atom, and optionally substituted $C_1$-$C_4$ alkyl.

When $R^6$ and $R^7$ are bonded to each other to form, together with the adjacent carbon atom, "optionally substituted cycloalkane", the cycloalkane moiety of the group is as defined above, of which $C_3$-$C_8$ cycloalkane is preferable, $C_3$-$C_6$ cycloalkane is more preferable.

When $R^{1a}$, $R^{1b}$, $R^{1c}$, $R^{1d}$, $R^{2a}$, $R^{2b}$, $R^{2c}$, $R^{2d}$, $R^{3a}$, $R^{3c}$ or $R^{3d}$ is "optionally substituted alkyl", the alkyl moiety of the group is as defined above, and is preferably $C_1$-$C_5$ alkyl, more preferably $C_1$-$C_4$ alkyl.

When $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3c}$ or $R^{3d}$ is "optionally substituted cycloalkyl", the cycloalkyl moiety of the group is as defined above, and is preferably $C_3$-$C_8$ cycloalkyl, more preferably $C_3$-$C_6$ cycloalkyl.

When $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3c}$ or $R^{3d}$ is "optionally substituted aryl", the aryl moiety of the group is as defined above, preferably phenyl.

When $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3c}$ or $R^{3d}$ is "optionally substituted non-aromatic heterocyclic group", the non-aromatic heterocyclic group moiety of the group is as defined above, and is preferably a 4- to 12-membered monocyclic or bicyclic non-aromatic heterocyclic group containing, besides carbon atom, 1 to 4 hetero atoms selected from the group consisting of oxygen atom, sulfur atom and nitrogen atom. Of these, azetidinyl, pyrrolidyl, piperidyl, oxetanyl, tetrahydrofuryl, tetrahydropyranyl, piperazinyl, morpholinyl, homomorpholinyl or oxaazabicyclo[3.2.1]octyl is more preferable, and azetidinyl, pyrrolidyl, oxetanyl, tetrahydropyranyl, morpholinyl, homomorpholinyl or oxaazabicyclo[3.2.1]octyl is particularly preferable.

When $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3c}$ and $R^{3d}$ is "optionally substituted heteroaryl", the heteroaryl moiety of the group is as defined above, and is preferably a 5- to 6-membered monocyclic containing, besides carbon atom, 1 to 4 hetero atoms selected from the group consisting of oxygen atom, sulfur atom and nitrogen atom. Of these, thienyl, pyrazolyl, imidazolyl, triazolyl, oxadiazolyl, pyridyl or pyrimidinyl is more preferable, and pyrazolyl, imidazolyl, triazolyl, oxadiazolyl or pyridyl is particularly preferable.

When $R^{3c}$ is "optionally substituted alkoxy", the alkoxy moiety of the group is as defined above, and is preferably $C_1$-$C_5$ alkoxy, more preferably $C_1$-$C_4$ alkoxy.

Preferable examples of $R^{1a}$ include a hydrogen atom, optionally substituted alkyl, a halogen atom, optionally substituted cycloalkyl, optionally substituted aryl, optionally substituted non-aromatic heterocyclic group and optionally substituted heteroaryl. Of these, a hydrogen atom, optionally substituted alkyl, a halogen atom, optionally substituted cycloalkyl, optionally substituted phenyl, optionally substituted tetrahydropyranyl and optionally substituted heteroaryl, and heteroaryl selected from the group consisting of pyrazolyl, triazolyl and pyridyl is more preferable. Of these, a hydrogen atom; $C_1$-$C_6$ alkyl optionally substituted by 1, 2 or 3 groups selected from the group consisting of amino optionally substituted by 1 or 2 $C_1$-$C_6$ alkyl, hydroxy, $C_1$-$C_6$ alkoxy, tetrahydropyranyloxy, a halogen atom, tetrahydropyranyl, piperidinyl and morpholinyl; a halogen atom; $C_3$-$C_8$ cycloalkyl; phenyl optionally substituted by 1, 2 or 3 halogen atoms; tetrahydropyranyl; pyrazolyl optionally substituted by 1, 2 or 3 $C_1$-$C_6$ alkyls; triazolyl; or pyridyl is more preferable.

Preferable examples of $R^{1b}$ and $R^{1c}$ include alkyls that are each independently optionally substituted. Of these, $C_1$-$C_6$ alkyl is more preferable.

Preferable examples of $R^{1d}$ include optionally substituted alkyl and optionally substituted non-aromatic heterocyclic group. Of these, optionally substituted alkyl or optionally substituted tetrahydropyranyl is more preferable, and $C_1$-$C_6$ alkyl or tetrahydropyranyl is further preferable.

Preferable examples of $R^{2a}$ include a hydrogen atom, optionally substituted alkyl, cyano, a halogen atom, optionally substituted cycloalkyl, optionally substituted aryl, an optionally substituted non-aromatic heterocyclic group and optionally substituted heteroaryl. Of these, a hydrogen atom, optionally substituted alkyl, cyano, a halogen atom, optionally substituted cycloalkyl, optionally substituted phenyl, an optionally substituted non-aromatic heterocyclic group selected from the group consisting of oxetanyl and tetrahydropyranyl or optionally substituted heteroaryl selected from the group consisting of pyrazolyl, imidazolyl and oxadiazolyl is more preferable. Of these, a hydrogen atom; $C_1$-$C_6$ alkyl optionally substituted by 1, 2 or 3 groups selected from the group consisting of cyano, $C_1$-$C_6$ alkoxycarbonyl, amino optionally substituted by 1 or 2 $C_1$-$C_6$ alkyl, hydroxy, $C_1$-$C_6$ alkoxy, a halogen atom, piperidinyl, and oxadiazolyl optionally substituted by one $C_1$-$C_6$ alkyl; cyano; a halogen atom; $C_3$-$C_8$ cycloalkyl optionally substituted by 1, 2 or 3 groups selected from the group consisting of $C_1$-$C_6$ alkyl optionally substituted by 1, 2 or 3 $C_1$-$C_6$ alkoxys, cyano, hydroxy and $C_1$-$C_6$ alkoxy; phenyl; oxetanyl optionally substituted 1, 2 or 3 $C_1$-$C_6$ alkoxys; tetrahydropyranyl optionally substituted by 1, 2 or 3 cyanos; pyrazolyl optionally substituted by 1, 2 or 3 $C_1$-$C_6$ alkyls; imidazolyl optionally substituted 1, 2 or 3 $C_1$-$C_6$ alkyls; or oxadiazolyl optionally substituted by one $C_1$-$C_6$ alkyl is more preferable.

Preferable examples of $R^{2b}$ and $R^{2c}$ include alkyls that are each independently optionally substituted. Of these, $C_1$-$C_6$ alkyl is more preferable.

Preferable examples of $R^{2d}$ include optionally substituted alkyl and optionally substituted non-aromatic heterocyclic group. Of these, optionally substituted alkyl or optionally substituted oxetanyl is more preferable, and $C_1$-$C_6$ alkyl or oxetanyl is further preferable.

Preferable examples of $R^{1a}$ include a hydrogen atom, optionally substituted alkyl, cyano, a halogen atom, optionally substituted cycloalkyl, an optionally substituted non-aromatic heterocyclic group and optionally substituted heteroaryl. Of these, a hydrogen atom, optionally substituted alkyl, cyano, a halogen atom, optionally substituted cycloalkyl, an optionally substituted non-aromatic heterocyclic group selected from the group consisting of azetidinyl, pyrrolidyl, tetrahydropyranyl, morpholinyl, homomorpholinyl and oxaazabicyclo[3.2.1]octyl or optionally substituted heteroaryl selected from the group consisting of oxadiazolyl and pyridyl is more preferable. Of these, a hydrogen atom; $C_1$-$C_6$ alkyl optionally substituted by 1, 2 or 3 groups selected from the group consisting of cyano, $C_1$-$C_6$ alkoxy and a halogen atom; cyano; a halogen atom; $C_3$-$C_8$ cycloalkyl optionally substituted by 1, 2 or 3 $C_1$-$C_6$ alkyls; azetidinyl; pyrrolidyl; tetrahydropyranyl; morpholinyl optionally substituted by 1, 2 or 3 $C_1$-$C_6$ alkyls; homomorpholinyl; oxaazabicyclo[3.2.1]octyl; oxadiazolyl optionally substituted by one $C_1$-$C_6$ alkyl; or pyridyl is more preferable.

Preferable examples of $R^{3b}$ include a hydrogen atom and optionally substituted alkyl. Of these, a hydrogen atom; or $C_1$-$C_6$ alkyl optionally substituted by 1, 2 or 3 $C_1$-$C_6$ alkoxys is more preferable.

Preferable examples of $R^{3c}$ include optionally substituted alkyl and optionally substituted alkoxy. Of these, $C_1$-$C_6$ alkyl optionally substituted by 1, 2 or 3 $C_1$-$C_6$ alkoxys; or $C_1$-$C_6$ alkoxy is more preferable.

Preferable examples of $R^{3d}$ include optionally substituted alkyl, optionally substituted cycloalkyl, optionally substituted aryl and optionally substituted non-aromatic heterocyclic group. Of these, optionally substituted alkyl, optionally substituted cycloalkyl, optionally substituted phenyl or optionally substituted non-aromatic heterocyclic group selected from the group consisting of azetidinyl and tetrahydropyranyl is more preferable. Of these, $C_1$-$C_6$ alkyl optionally substituted by 1, 2 or 3 groups selected from the group consisting of $C_1$-$C_6$ alkoxy, a halogen atom and $C_3$-$C_8$ cycloalkyl; $C_3$-$C_8$ cycloalkyl; phenyl; azetidinyl optionally substituted by 1, 2 or 3 groups selected from the group consisting of $C_1$-$C_6$ alkyl and $C_1$-$C_6$ alkoxycarbonyl; or tetrahydropyranyl is more preferable.

When the "ring" or "group" defined by each symbol in the aforementioned formula (I) or a combination of each symbol is "optionally substituted alkyl", "optionally substituted cycloalkyl", "optionally substituted aryl", "optionally substituted non-aromatic heterocyclic group", "optionally substituted heteroaryl", "optionally substituted aromatic group", "optionally substituted alkoxy", "optionally substituted nitrogen-containing non-aromatic heterocycle" or "optionally substituted cycloalkane", these "ring" and "group" may be unsubstituted, or have one or more, the same or different substituent(s) at substitutable position(s) of each "ring" or "group". The aforementioned "ring" or "group" has substituent(s), the number thereof is preferably 1-7, more preferably 1, 2, or 3.

Examples of the aforementioned substituent of the "ring" or "group" include, unless particularly indicated, (1) alkyl optionally substituted by the same or different 1 to 7 groups selected from the group consisting of amino optionally substituted by 1 or 2 alkyls, hydroxy, alkoxy, a halogen atom and phenyl optionally substituted by 1, 2 or 3 alkoxys (preferably, alkyl optionally substituted by the same or different 1, 2 or 3 groups selected from the group consisting of amino optionally substituted by 1 or 2 alkyls, hydroxy, alkoxy, a halogen atom and phenyl optionally substituted by 1, 2 or 3 alkoxys);

(2) cyano;
(3) alkoxycarbonyl;
(4) alkylidene;
(5) amino optionally substituted by 1 or 2 groups selected from the group consisting of alkyl, alkoxyalkyl, halogenoalkyl, alkoxycarbonyl and phenylalkoxycarbonyl;
(6) hydroxy;
(7) alkoxy optionally substituted by 1-7 halogen atoms (preferably, alkoxy optionally substituted by 1, 2 or 3 halogen atoms);
(8) alkanoyloxy;
(9) non-aromatic heterocyclyloxy (preferably, tetrahydropyranyloxy);
(10) oxo;
(11) alkylsulfonyl;
(12) phenylsulfonyl;
(13) a halogen atom;
(14) cycloalkyl;
(15) aryl optionally substituted by 1, 2 or 3 alkoxys (preferably, phenyl optionally substituted by 1, 2 or 3 alkoxys);
(16) a non-aromatic heterocyclic group optionally substituted by the same or different 1, 2 or 3 groups selected from the group consisting of alkyl, alkoxycarbonyl and alkoxy (preferably, non-aromatic heterocyclic group which is selected from the group consisting of azetidinyl, pyrrolidyl, piperidyl, oxetanyl, tetrahydrofuryl, tetrahydropyranyl, and morpholinyl and optionally substituted by the same or different 1, 2 or 3 groups selected from the group consisting of alkyl, alkoxycarbonyl and alkoxy); or

(17) heteroaryl optionally substituted by the same or different 1 or 2 groups selected from the group consisting of alkyl and oxo (preferably, oxadiazolyl optionally substituted by one alkyl, pyridyl or isoindolinyl optionally substituted by 1 or 2 oxos). Of these, more preferred is (1) alkyl optionally substituted by the same or different 1 to 7 groups selected from the group consisting of alkoxy and a halogen atom (preferably, alkyl optionally substituted by the same or different 1, 2 or 3 groups selected from the group consisting of alkoxy and a halogen atom);
(2) cyano;
(3) alkoxycarbonyl;
(4) amino optionally substituted by 1 or 2 alkyls;
(5) hydroxy;
(6) alkoxy;
(7) non-aromatic heterocyclyloxy (preferably, tetrahydropyranyloxy);
(8) oxo;
(9) a halogen atom;
(10) cycloalkyl;
(11) a non-aromatic heterocyclic group (preferably, non-aromatic heterocyclic group selected from the group consisting of piperidyl, tetrahydropyranyl and morpholinyl); or
(12) heteroaryl optionally substituted by 1 or 2 alkyls (preferably, oxadiazolyl optionally substituted by one alkyl or pyridyl).

The substituent of the aforementioned "ring" or "group" defined by each symbol or a combination of each symbol is more specifically explained below.

Examples of preferable substituent of ring A (optionally substituted aromatic group) include (1) alkyl optionally substituted by the same or different 1-7 groups selected from the group consisting of a halogen atom, amino optionally substituted by 1 or 2 alkyls, and alkoxy (preferably alkyl optionally substituted by the same or different 1, 2 or 3 groups selected from the group consisting of a halogen atom, amino optionally substituted by 1 or 2 alkyls, and alkoxy);
(2) cyano;
(3) a halogen atom;
(4) amino optionally substituted by 1 or 2 alkyls; and
(5) alkoxy optionally substituted by 1 to 7 halogen atoms (preferably alkoxy optionally substituted by 1, 2 or 3 halogen atoms).

Of those mentioned above, more preferable substituent is
(1) alkyl optionally substituted by 1, 2 or 3 halogen atoms,
(2) cyano or (3) a halogen atom.

When $R^4$ and $R^5$ are each "optionally substituted alkyl" or "optionally substituted cycloalkyl", and when $R^4$ and $R^5$ are bonded to each other to form, together with the adjacent $Z^2$ and $Z^3$, "optionally substituted nitrogen-containing non-aromatic heterocycle", preferable substituent of the group or on the ring includes, respectively,
(1) heteroaryl (preferably, pyridyl);
(2) a halogen atom;
(3) amino optionally substituted by the same or different 1 or 2 groups selected from the group consisting of alkoxycarbonyl and phenylalkoxycarbonyl; and
(4) alkoxy.

Of these, (1) pyridyl, (2) alkoxy or (3) a halogen atom is more preferable.

When $R^6$ and $R^7$ are each "optionally substituted alkyl" or "optionally substituted cycloalkyl", and when $R^6$ and $R^7$ are bonded to each other to form, together with the adjacent carbon atom, "optionally substituted cycloalkane", preferable substituent of the group or on the ring includes, respectively, a halogen atom, and alkoxy.

When $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3c}$ and $R^{3d}$ are each "optionally substituted alkyl", and when $R^{3c}$ is "optionally substituted alkoxy", a preferable substituent of the group is, unless particularly indicated,
(1) cyano;
(2) alkoxycarbonyl;
(3)) amino optionally substituted by the same or different 1 or 2 groups selected from the group consisting of alkyl, halogenoalkyl, alkoxyalkyl and alkoxycarbonyl;
(4) hydroxy;
(5) alkoxy optionally substituted by 1 to 7 halogen atoms (preferably alkoxy optionally substituted by 1, 2 or 3 halogen atoms);
(6) alkanoyloxy;
(7) non-aromatic heterocyclyloxy (preferably, tetrahydropyranyloxy);
(8) oxo;
(9) alkylsulfonyl;
(10) phenylsulfonyl;
(11) a halogen atom;
(12) cycloalkyl;
(13) aryl optionally substituted by 1, 2 or 3 alkoxys (preferably, phenyl optionally substituted by 1, 2 or 3 alkoxys);
(14) non-aromatic heterocyclic group optionally substituted by 1, 2 or 3 alkoxys (preferably, non-aromatic heterocyclic group which is selected from the group consisting of azetidinyl, pyrrolidyl, piperidyl, tetrahydropyranyl and morpholinyl and optionally substituted by 1, 2 or 3 alkoxys); or
(15) heteroaryl optionally substituted by the same or different 1 or 2 groups selected from the group consisting of alkyl and oxo (preferably, oxadiazolyl optionally substituted by one alkyl, pyridyl or isoindolinyl optionally substituted by 1 or 2 oxos). Of these, more preferred is
(1) cyano;
(2) alkoxycarbonyl;
(3) amino optionally substituted by 1 or 2 alkyls;
(4) hydroxy;
(5) alkoxy;
(6) non-aromatic heterocyclyloxy (preferably, tetrahydropyranyloxy);
(7) oxo;
(8) a halogen atom;
(9) cycloalkyl;
(10) a non-aromatic heterocyclic group (preferably, non-aromatic heterocyclic group selected from the group consisting of piperidyl, tetrahydropyranyl and morpholinyl); or
(11) heteroaryl optionally substituted by 1 or 2 alkyls (preferably, oxadiazolyl optionally substituted by one alkyl or pyridyl).

When $R^{1a}$, $R^{1b}$, $R^{1c}$, $R^{1d}$, $R^{2a}$, $R^{2b}$, $R^{2c}$, $R^{2d}$, $R^{3a}$, $R^{3b}$, $R^{3c}$ and $R^{3d}$ are each "optionally substituted cycloalkyl", "optionally substituted aryl", "optionally substituted non-aromatic heterocyclic group" or "optionally substituted heteroaryl", a preferable substituent of the group is, unless particularly indicated,
(1) alkyl optionally substituted by the same or different 1 to 7 groups selected from the group consisting of amino optionally substituted by 1 or 2 alkyls, hydroxy, alkoxy, a halogen atom and phenyl optionally substituted by 1, 2 or 3 alkoxys (preferably, alkyl optionally substituted by the same or different 1, 2 or 3 groups selected from the group consisting of amino optionally substituted by 1 or 2 alkyls, hydroxy, alkoxy, a halogen atom and phenyl optionally substituted by 1, 2 or 3 alkoxys);
(2) cyano;
(3) alkoxycarbonyl;
(4) amino optionally substituted by the same or different 1 or 2 groups selected from the group consisting of alkyl, alkoxyalkyl, halogenoalkyl and alkoxycarbonyl;
(5) hydroxy;
(6) alkoxy optionally substituted by 1 to 7 halogen atoms (preferably, alkoxy optionally substituted by 1, 2 or 3 halogen atoms);
(7) alkanoyloxy;
(8) non-aromatic heterocyclyloxy (preferably, tetrahydropyranyloxy);
(9) oxo;
(10) alkylsulfonyl;
(11) phenylsulfonyl;
(12) a halogen atom;
(13) cycloalkyl;
(14) aryl optionally substituted by 1, 2 or 3 alkoxys (preferably, phenyl optionally substituted by 1, 2 or 3 alkoxys);
(15) a non-aromatic heterocyclic group optionally substituted by 1, 2 or 3 alkoxys (preferably, non-aromatic heterocyclic group which is selected from the group consisting of azetidinyl, pyrrolidyl, piperidyl, tetrahydropyranyl and morpholinyl and optionally substituted by 1, 2 or 3 alkoxys); or
(16) heteroaryl optionally substituted by the same or different 1 or 2 groups selected from the group consisting of alkyl and oxo (preferably, oxadiazolyl optionally substituted by one alkyl, pyridyl or isoindolinyl optionally substituted by 1 or 2 oxos). Of these, more preferred is
(1) alkyl optionally substituted by 1, 2 or 3 alkoxys;
(2) cyano;
(3) alkoxycarbonyl;
(4) amino optionally substituted by 1 or 2 alkyls;
(5) hydroxy;
(6) alkoxy;
(7) non-aromatic heterocyclyloxy (preferably, tetrahydropyranyloxy);
(8) oxo;
(9) a halogen atom;
(10) cycloalkyl;
(11) a non-aromatic heterocyclic group (preferably, non-aromatic heterocyclic group selected from the group consisting of piperidyl, tetrahydropyranyl and morpholinyl); or
(12) heteroaryl optionally substituted by 1 or 2 alkyls (preferably, oxadiazolyl optionally substituted by one alkyl or pyridyl).

One embodiment of the present invention (hereinafter sometimes to be abbreviated as embodiment A) is a compound of the aforementioned formula (I) wherein $X^4$ is a sulfur atom, or a pharmacologically acceptable salt thereof.

Other embodiment of the present invention (hereinafter sometimes to be abbreviated as embodiment B) is a compound of the aforementioned formula (I) wherein $X^4$ is —CH═CH—, or a pharmacologically acceptable salt thereof.

A preferable embodiment of the present invention including the above-mentioned embodiments A, B (hereinafter sometimes to be abbreviated as embodiment C) is specifically a compound represented by the above-mentioned formula (I) wherein the part represented by the following formula:

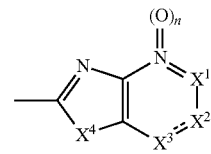

(hereinafter sometimes to be abbreviated as partial structure A) is a group represented by the following formula (iv-a), (iv-b), (iv-c), (iv-d) or (iv-e):

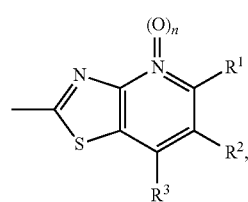
(iv-a)

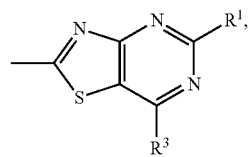
(iv-b)

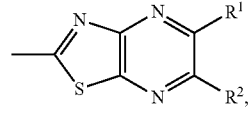
(iv-c)

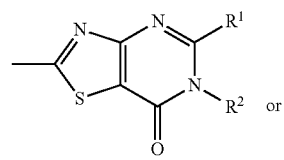
(iv-d)

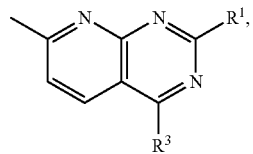
(iv-e)

wherein the symbols are as defined above, or a pharmacologically acceptable salt thereof.

Of the compounds of the aforementioned embodiment C, a compound wherein the partial structure A is a group represented by the following formula (iv-a1), (iv-b) or (iv-c):

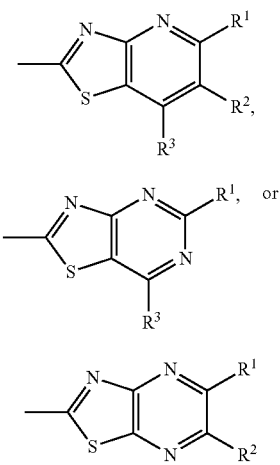

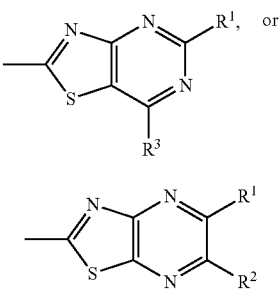

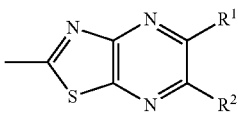

wherein the symbols are as defined above, or a pharmacologically acceptable salt thereof is more preferable.

Other embodiment of the present invention including the above-mentioned embodiments A, B (hereinafter sometimes to be abbreviated as embodiment D) is specifically a compound wherein partial structure A is represented by the above-mentioned formula (iv-a), or a pharmacologically acceptable salt thereof.

Of the compounds of the aforementioned embodiment D, a compound wherein the partial structure A is a group represented by the following formula (iv-a1):

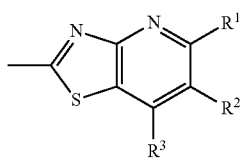

wherein the symbols are as defined above, or a pharmacologically acceptable salt thereof is more preferable.

Other embodiment of the present invention including the above-mentioned embodiments A, B (hereinafter sometimes to be abbreviated as embodiment E) is specifically a compound wherein partial structure A is represented by the following formula (iv-b):

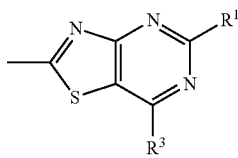

wherein the symbols are as defined above, or a pharmacologically acceptable salt thereof.

Other further embodiment of the present invention including the above-mentioned embodiments A, B (hereinafter sometimes to be abbreviated as embodiment F) is specifically a compound wherein partial structure A is represented by the above-mentioned formula (iv-c):

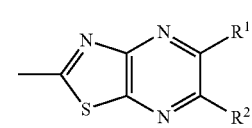

wherein the symbols are as defined above, or a pharmacologically acceptable salt thereof.

Other embodiment of the present invention including the above-mentioned embodiments A, B (hereinafter sometimes to be abbreviated as embodiment G) is specifically a compound wherein partial structure A is represented by the above-mentioned formula (iv-d):

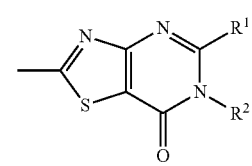

wherein the symbols are as defined above, or a pharmacologically acceptable salt thereof.

Other further preferable embodiment of the present invention including the above-mentioned embodiments A, B (hereinafter sometimes to be abbreviated as embodiment H) is specifically a compound wherein partial structure A is represented by the above-mentioned formula (iv-e):

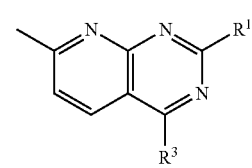

wherein the symbols are as defined above, or a pharmacologically acceptable salt thereof.

A preferable embodiment of the present invention including the above-mentioned embodiments A, B, C, D, E, F, G, H (hereinafter sometimes to be abbreviated as embodiment J) is specifically a compound represented by the above-mentioned formula (I), wherein a part represented by the following formula:

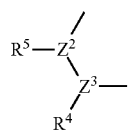

(hereinafter sometimes to be referred to as partial structure B) is shown by the following formula (v-a):

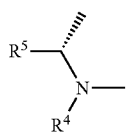

wherein the symbols are as defined above, or a pharmacologically acceptable salt thereof.

In the compounds of embodiment J, a compound wherein $R^4$ and $R^5$ are bonded to each other to form, together with the adjacent carbon atom and nitrogen atom, optionally substituted nitrogen-containing non-aromatic heterocycle is more preferable.

Of these, the optionally substituted nitrogen-containing non-aromatic heterocycle is particularly preferably a nitrogen-containing non-aromatic heterocycle optionally substituted by 1, 2 or 3 halogen atoms and selected from the group consisting of pyrrolidine, and thiazolidine.

As other compound of embodiment J, a compound wherein $R^4$ and $R^5$ are each independently (a) alkyl optionally substituted by 1, 2 or 3 groups selected from the group consisting of $C_1$-$C_6$ alkoxy and monocyclic heteroaryl (e.g., pyridyl); or (b) $C_3$-$C_8$ cycloalkyl can be mentioned.

Other preferable embodiment of the present invention including the above-mentioned embodiments A, B, C, D, E, F, G, H (hereinafter sometimes to be abbreviated as embodiment K) is specifically a compound represented by the above-mentioned formula (I), wherein partial structure B is shown by the following formula (v-a1):

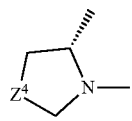

wherein $Z^4$ is $CH_2$, $CF_2$ or a sulfur atom], or a pharmacologically acceptable salt thereof.

In the compounds of embodiment K, a compound wherein $Z^4$ is $CH_2$ is more preferable.

A preferable embodiment of the present invention including the above-mentioned embodiments A, B, C, D, E, F, G, H (hereinafter sometimes to be abbreviated as embodiment L) is specifically a compound represented by the above-mentioned formula (I) wherein partial structure B is shown by the following formula (v-a2):

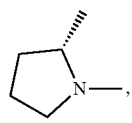

or a pharmacologically acceptable salt thereof.

Other preferable embodiment of the present invention including the above-mentioned embodiments A, B, C, D, E, F, G, H (hereinafter sometimes to be abbreviated as embodiment M) is specifically a compound represented by the above-mentioned formula (I), wherein partial structure B is shown by the following formula (v-a3):

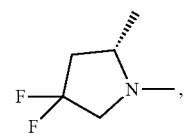

or a pharmacologically acceptable salt thereof.

Other preferable embodiment of the present invention including the above-mentioned embodiments A, B, C, D, E, F, G, H (hereinafter sometimes to be abbreviated as embodiment N) is specifically a compound represented by the above-mentioned formula (I), wherein partial structure B is shown by the following formula (v-a4):

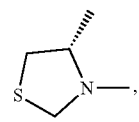

or a pharmacologically acceptable salt thereof.

A preferable embodiment of the present invention including the above-mentioned embodiments J, K, L, M, N (hereinafter sometimes to be abbreviated as embodiment O) is a compound wherein $Z^1$ is —C($R^6$)($R^7$)—NH—, or a pharmacologically acceptable salt thereof.

Of the compounds of embodiment O, a compound wherein $R^6$ and $R^7$ are each independently a hydrogen atom or alkyl, or $R^6$ and $R^7$ are bonded to each other to form cycloalkane together with the adjacent carbon atom is more preferable.

Other further preferable embodiment of the present invention including the above-mentioned embodiments A, B, C, D, E, F, G, H (hereinafter sometimes to be abbreviated as embodiment P) is specifically a compound represented by the above-mentioned formula (I), wherein partial structure B is shown by the following formula (v-b):

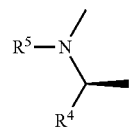

wherein the symbols are as defined above, or a pharmacologically acceptable salt thereof.

In the compounds of embodiment P, a compound wherein $R^4$ and $R^5$ are bonded to each other to form, together with the adjacent nitrogen atom and carbon atom, optionally substituted nitrogen-containing non-aromatic heterocycle is more preferable, and a compound wherein $R^4$ and $R^5$ are bonded to each other to form, together with the adjacent nitrogen atom and carbon atom, optionally substituted pyrrolidine is particularly preferable.

In the compounds of embodiment P, a compound wherein $Z^1$ is an oxygen atom, —C($R^6$) ($R^7$)—, —NH— or —C($R^6$)($R^7$)—NH— is more preferable.

A preferable embodiment of the present invention including the above-mentioned embodiments A, B, C, D, E, F, G, H, J, K, L, M, N, O, P is specifically a compound wherein ring A is a group represented by the formula (vi):

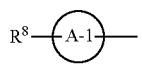

wherein ring A-1 is $C_6$-$C_{11}$ monocyclic or bicyclic aryl, $R^6$ is a hydrogen atom, $C_1$-$C_6$ alkyl, $C_1$-$C_6$ halogenoalkyl, cyano or a halogen atom, $R^1$ is a group represented by the following formula (i-a), (i-b) or (i-c):

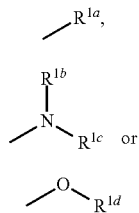

$R^{1a}$ is (a) a hydrogen atom; (b) $C_1$-$C_6$ alkyl optionally substituted by 1, 2 or 3 groups selected from the group consisting of amino (optionally substituted by 1 or 2 $C_1$-$C_6$ alkyls), hydroxy, $C_1$-$C_6$ alkoxy, monocyclic non-aromatic heterocyclyloxy, a halogen atom, and a monocyclic nonaromatic heterocyclic group; (c) a halogen atom; (d) $C_3$-$C_8$ cycloalkyl; (e) phenyl optionally substituted by 1, 2 or 3 halogen atoms; (f) a monocyclic nonaromatic heterocyclic group; or (g) monocyclic heteroaryl optionally substituted by 1, 2 or 3 $C_1$-$C_6$ alkyls, $R^{1b}$ is $C_1$-$C_6$ alkyl,
$R^{1c}$ is $C_1$-$C_6$ alkyl,
$R^{1d}$ is (a) $C_1$-$C_6$ alkyl or (b) a monocyclic nonaromatic heterocyclic group, $R^2$ is a group represented by the following formula (ii-a), (ii-b) or (ii-c):

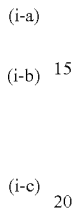

$R^{2a}$ is (a) a hydrogen atom; (b) $C_1$-$C_6$ alkyl optionally substituted by 1, 2 or 3 groups selected from the group consisting of cyano, $C_1$-$C_6$ alkoxycarbonyl, amino (optionally substituted by 1 or 2 $C_1$-$C_6$ alkyls), hydroxy, $C_1$-$C_6$ alkoxy, a halogen atom, a monocyclic nonaromatic heterocyclic group and monocyclic heteroaryl (optionally substituted by one $C_1$-$C_6$ alkyl); (c) cyano; (d) a halogen atom; (e) $C_3$-$C_8$ cycloalkyl optionally substituted by 1, 2 or 3 groups selected from the group consisting of $C_1$-$C_6$ alkyl (optionally substituted by 1, 2 or 3 $C_1$-$C_6$ alkoxys), cyano, hydroxy and $C_1$-$C_6$ alkoxy; (f) phenyl; (g) a monocyclic nonaromatic heterocyclic group optionally substituted by 1, 2 or 3 groups selected from the group consisting of cyano and $C_1$-$C_6$ alkoxy; or (h) monocyclic heteroaryl optionally substituted by 1, 2 or 3 $C_1$-$C_6$ alkyls, $R^{2b}$ is $C_1$-$C_6$ alkyl,
$R^{2c}$ is $C_1$-$C_6$ alkyl,
$R^{2d}$ is (a) $C_1$-$C_6$ alkyl or (b) a monocyclic nonaromatic heterocyclic group, $R^3$ is a group represented by the following formula (iii-a), (iii-b) or (iii-c):

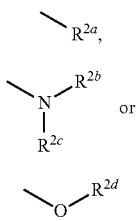

$R^{3a}$ is (a) a hydrogen atom; (b) $C_1$-$C_6$ alkyl optionally substituted by 1, 2 or 3 groups selected from the group consisting of cyano, $C_1$-$C_6$ alkoxy and a halogen atom; (c) cyano; (d) a halogen atom; (e) $C_3$-$C_8$ cycloalkyl optionally substituted by 1, 2 or 3 $C_1$-$C_6$ alkyls; (f) a monocyclic or bicyclic nonaromatic heterocyclic group optionally substituted by 1, 2 or 3 $C_1$-$C_6$ alkyls; or (g) monocyclic heteroaryl optionally substituted by 1, 2 or 3 $C_1$-$C_6$ alkyls, $R^{3b}$ is (a) a hydrogen atom; or (b) $C_1$-$C_6$ alkyl optionally substituted by 1, 2 or 3 $C_1$-$C_6$ alkoxys, $R^{3c}$ is (a) $C_1$-$C_6$ alkyl optionally substituted by 1, 2 or 3 $C_1$-$C_6$ alkoxys; or (b) $C_1$-$C_6$ alkoxy, $R^{3d}$ is (a) $C_1$-$C_6$ alkyl optionally substituted by 1, 2 or 3 groups selected from the group consisting of $C_1$-$C_6$ alkoxy, a halogen atom and $C_3$-$C_8$ cycloalkyl; (b) $C_3$-$C_8$ cycloalkyl; (c) phenyl; or (d) a monocyclic nonaromatic heterocyclic group optionally substituted by 1, 2 or 3 groups selected from the group consisting of $C_1$-$C_6$ alkyl and $C_1$-$C_6$ alkoxycarbonyl, or a pharmacologically acceptable salt thereof.

Specific examples of the compound (I) or a pharmacologically acceptable salt thereof of the present invention non-limitatively include the compounds described in the following Examples, and pharmacologically acceptable salts thereof. Of these, examples of preferable compound or a pharmacologically acceptable salt thereof include compounds selected from the group consisting of (R)—N-benzyl-1-[7-(N-methoxy-N-methylamino)[1,3]thiazolo[4,5-d]pyrimidin-2-yl]pyrrolidine-2-carboxamide (Example 10);

(R)—N-benzyl-1-[7-(N,N-dimethylamino)-5-methyl[1,3]thiazolo[4,5-d]pyrimidin-2-yl]pyrrolidine-2-carboxamide (Example 18);

(R)—N-benzyl-1-(7-ethoxy[1,3]thiazolo[4,5-d]pyrimidin-2-yl)pyrrolidine-2-carboxamide (Example 19);

(R)—N-benzyl-1-(7-cyclopropyl[1,3]thiazolo[4,5-d]pyrimidin-2-yl)pyrrolidine-2-carboxamide (Example 23);

(R)—N-benzyl-1-[7-(1-methylcyclopropyl)[1,3]thiazolo[4,5-d]pyrimidin-2-yl]pyrrolidine-2-carboxamide (Example 31);

(R)—N-benzyl-2-[N'-(7-cyclopropyl[1,3]thiazolo[4,5-d]pyrimidin-2-yl)-N'-methylamino]propionamide (Example 36);

(R)—N-benzyl-1-[6-(2-cyanopropan-2-yl)[1,3]thiazolo[4,5-b]pyridin-2-yl]pyrrolidine-2-carboxamide (Example 113);

(R)-1-[6-(5-methyl-1,2,4-oxadiazol-3-yl)[1,3]thiazolo[4,5-b]pyridin-2-yl]-N-[(1R)-1-phenylethyl]pyrrolidine-2-carboxamide (Example 148); and (R)—N-benzyl-1-(6-cyclopropyl[1,3]thiazolo[4,5-b]
pyrazin-2-yl)pyrrolidine-2-carboxamide (Example 192),
or a pharmacologically acceptable salt thereof can be
mentioned.

The compound (I) of the present invention can be present in the form of tautomer or a mixture thereof. The compound (I) of the present invention can be present in the form of a stereoisomer such as enantiomer, diastereomer and the like or a mixture thereof. The compound (I) of the present invention encompasses a mixture of tautomer or stereoisomer and a pure or substantially pure isomer thereof.

When compound (I) is obtained in the form of a diastereomer or enantiomer, it can be resolved by a method conventionally used in the pertinent field, for example, chromatography, and a fractional crystallization method.

The present invention encompasses compound (I) wherein one or more atoms are substituted by one or more isotopes. Examples of the isotope include $^2$H(D), $^3$H, $^{13}$C, and $^{14}$C.

Examples of the pharmacologically acceptable salt of compound (I) include alkali metal salts such as lithium, sodium, potassium and the like; group 2 metal salts such as magnesium, calcium and the like; salts with aluminum and zinc; salts with amine such as ammonia, choline, diethanolamine, lysine, ethylenediamine, tert-butylamine, tert-octylamine, tris(hydroxymethyl)aminomethane, N-methylglucosamine, triethanolamine, dehydroabiethylamine and the like; salts with inorganic acids such as hydrogen chloride, hydrogen bromide, hydrogen iodide, sulfuric acid, nitric acid, phosphoric acid and the like; salts with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid and the like; and salts with acidic amino acid such as aspartic acid, glutamic acid and the like.

Moreover, the pharmacologically acceptable salt of compound (I) encompasses intramolecular salt, hydrate, solvate of compound (I).

The compound (I) or a pharmacologically acceptable salt thereof of the present invention can be administered orally or parenterally. In addition, it can be used as a conventionally-used drug preparation such as tablet, granule, capsule, powder, injection, inhalant and the like.

While the dose of the compound (I) or a pharmacologically acceptable salt thereof of the present invention varies depending on the administration method, age, body weight and condition of the patient, generally, it is preferably set to 0.001-500 mg/kg, particularly 0.01-10 mg/kg.

The compound (I) or a pharmacologically acceptable salt thereof of the present invention has a superior KAT-II inhibitory activity. A pharmaceutical composition containing compound (I) or a pharmacologically acceptable salt thereof of the present invention is useful for the prophylaxis or treatment of a disease or symptom (e.g., dementia, depression, stress vulnerability) in which inhibition of KAT-II activity is expected to improve the pathology. More specific examples of such disease and symptom include, for example, schizophrenia, bipolar disorder, attention deficit/ hyperactivity disorder, Alzheimer's disease, major depression, autism, cerebrovascular dementia, HIV encephalopathy, and age-related cognitive dysfunction. Preferably, a pharmaceutical composition containing the compound (I) or a pharmacologically acceptable salt thereof of the present invention is useful for the prophylaxis or treatment of schizophrenia, attention deficit/hyperactivity disorder, Alzheimer's disease, or major depression, particularly for the prophylaxis or treatment of schizophrenia.

A therapeutic or prophylactic method including administering an effective amount of compound (I) or a pharmacologically acceptable salt thereof of the present invention to a patient (individual to be the subject of prophylaxis or treatment) is also applied to the aforementioned object and encompassed in the present invention.

Also, use of compound (I) or a pharmacologically acceptable salt thereof of the present invention for the production of a medicament having a KAT-II inhibitory action is also applied to the aforementioned object and encompassed in the present invention.

According to the present invention, compound (I) or a pharmacologically acceptable salt thereof can be produced by the following method, but the method is not limited thereto.

In each production step of compound (I) to be described below, when protection of functional group contained in the compound is necessary, the functional group can be appropriately protected by a conventional method. The protecting group and general description of the use thereof are contained in T. W. Greene et al., "Protective Groups in Organic Synthesis", John Wiley & Sons, New York, 2006. The protecting group is removed by a conventional method in a subsequent step.

[Production of Compound (I)]

Of compound (I), a compound represented by the formula (I-a):

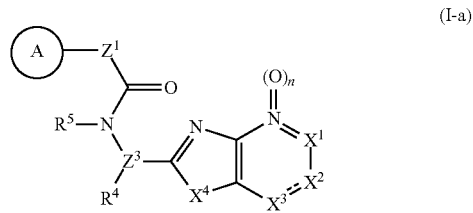

wherein the symbols are as defined above, can be produced by reacting a compound represented by the formula (II):

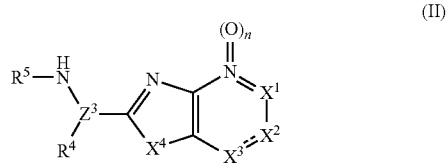

wherein the symbols are as defined above, with a compound represented by the formula (III-a):

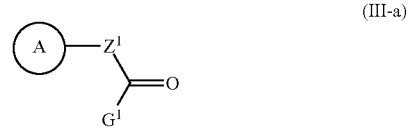

wherein $G^1$ is a leaving group, and other symbols are as defined above, in a solvent in the presence of a base.

Examples of the leaving group for $G^1$ include a halogen atom (chlorine atom etc.) and optionally substituted aryloxy (methoxyphenyloxy etc.).

Examples of the base include amine such as triethylamine, N,N-diisopropylethylamine, pyridine, 1,8-diazabicyclo[5.4.0]-undec-7-ene (DBU) and the like.

The solvent may be any as long as it does not influence the reaction, and examples thereof include halogenohydrocarbon such as methylene chloride, chloroform, 1,2-dichloroethane and the like; ether such as tetrahydrofuran, 1,4-dioxane, 1,2-dimethoxyethane and the like; alkylnitrile such as acetonitrile, propionitrile and the like; or a mixed solvent thereof.

This reaction can be performed at 0-150° C., preferably 20-90° C.

Of compounds (I), a compound represented by the formula (I-b):

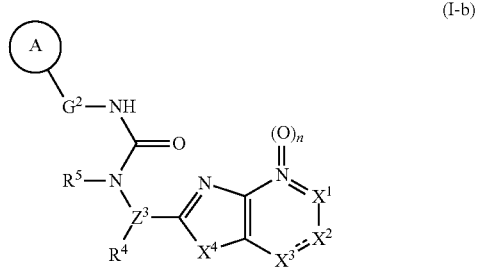

(I-b)

wherein $G^2$ is —C($R^6$) ($R^7$)— or a single bond, and other symbols are as defined above, can be produced by reacting the aforementioned compound (II) with a compound represented by the formula (III-b):

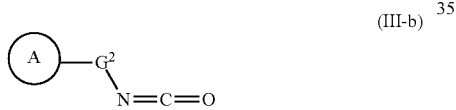

(III-b)

wherein the symbols are as defined above, in a solvent in the presence of a base.

Examples of the base include amine such as triethylamine, N,N-diisopropylethylamine, pyridine, 1,8-diazabicyclo[5.4.0]-undec-7-ene (DBU) and the like.

The solvent may be any as long as it does not influence the reaction, and examples thereof include halogenohydrocarbon such as methylene chloride, chloroform, 1,2-dichloroethane and the like.

This reaction can be performed at 0-50° C., preferably 10-30° C.

Alternatively, compound (I-b) can be produced from the aforementioned compound (II) according to a method describe below. Compound (II) is reacted with a carbonylating agent to give a reactive intermediate. Furthermore, the reactive intermediate is reacted with a compound represented by the formula (III-c):

(III-c)

wherein the symbols are as defined above, whereby compound (I-b) can be produced.

The reaction of compound (II) and a carbonylating agent can be performed in a solvent in the presence of a base.

Examples of the carbonylating agent include triphosgene, phosgene, and carbonyldiimidazole. Examples of the base include amine such as triethylamine, N,N-diisopropylethylamine, pyridine and the like. The solvent may be any as long as it does not influence the reaction, and examples thereof include halogenohydrocarbon such as methylene chloride, chloroform, 1,2-dichloroethane and the like; aromatic hydrocarbon such as benzene, toluene, xylene and the like. This reaction can be performed at −20 to 50° C., preferably 0-30° C.

The reaction of the obtained reactive intermediate and compound (III-c) can be performed in a solvent in the presence of a base.

Examples of the base include amine such as triethylamine, N,N-diisopropylethylamine, N,N-dimethyl-4-aminopyridine and the like. The solvent may be any as long as it does not influence the reaction, and examples thereof include halogenohydrocarbon such as methylene chloride, chloroform, 1,2-dichloroethane and the like. This reaction can be performed at 0-50° C., preferably 10-30° C.

Of compounds (I), a compound represented by the formula (I-c)

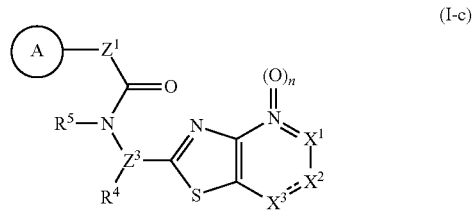

(I-c)

wherein the symbols are as defined above, can be produced by reacting a compound represented by the formula (IV):

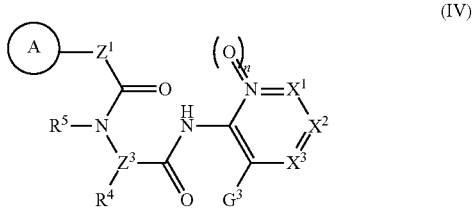

(IV)

wherein $G^3$ is a leaving group, and other symbols are as defined above, in a solvent in the presence of a sulfating agent.

Examples of the leaving group for $G^3$ include halogen atom such as bromine atom and the like. Examples of the sulfating agent include Lawesson's reagent (2,4-bis(4-methoxyphenyl)-1,3,2,4-dithiadiphosphetane-2,4-disulfide). The solvent may be any as long as it does not influence the reaction, and examples thereof include aromatic hydrocarbon such as toluene, xylene and the like; ether such as tetrahydrofuran, 1,4-dioxane, 1,2-dimethoxyethane and the like and hexamethylphosphoric acid triamide.

This reaction can be performed at 50-180° C., preferably 100-180° C.

Of compounds (I), a compound represented by the formula (I-g)

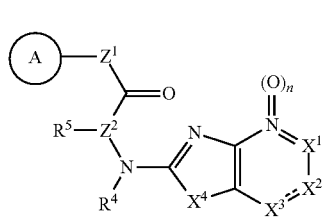
(I-g)

wherein the symbols are as defined above, can be produced by reacting a compound represented by the formula (XI):

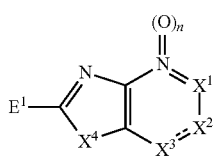
(XI)

wherein $E^1$ is a leaving group, and other symbols are as defined above, with a compound represented by the formula (XII):

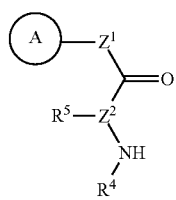
(XII)

wherein the symbols are as defined above, in a solvent or without solvent in the presence of a base.

Examples of the leaving group for $E^1$ include halogen atom (bromine atom etc.), optionally substituted alkylsulfinyl (methylsulfinyl, benzylsulfinyl etc.), and optionally substituted alkylsulfonyl (methylsulfonyl, benzylsulfonyl etc.).

Examples of the base include amine such as triethylamine, N,N-diisopropylethylamine, pyridine and the like; and alkali metal carbonate such as sodium carbonate, potassium carbonate, cesium carbonate and the like. The solvent may be any as long as it does not influence the reaction, and examples thereof include ether such as tetrahydrofuran, 1,4-dioxane, 1,2-dimethoxyethane and the like; amide such as N,N-dimethylformamide, N,N-dimethylacetamide, 1,3-dimethyl-2-imidazolidinone and N-methylpyrrolidone and the like; amine such as pyridine and the like; or a mixed solvent thereof.

This reaction can be performed at 60° C.-180° C., preferably 100° C.-150° C.

Of compound (I), a compound represented by the formula (I-h):

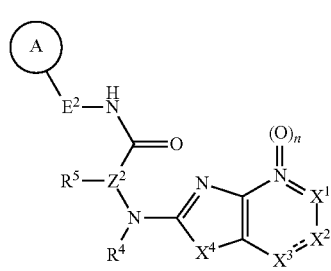
(I-h)

wherein $E^2$ is —C($R^6$)($R^7$)—, or a single bond, and other symbols are as defined above, can be produced from the aforementioned compound (XI) according to a method describe below.

Compound (XI) and a compound represented by the formula (XIII-a):

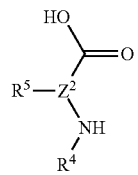
(XIII-a)

wherein the symbols are as defined above, are reacted to give a compound represented by the formula (XIV-a):

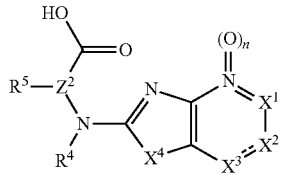
(XIV-a)

wherein the symbols are as defined above. The compound (XIV-a) is reacted with a compound represented by the formula (XV):

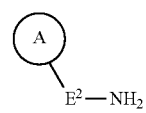
(XV)

wherein the symbols are as defined above, whereby compound (I-h) can be produced.

Compound (XIV-a) can be produced by reacting compound (XI) and compound (XIII-a), which is similar to the method of producing the aforementioned compound (I-g) from compound (XI) and compound (XII).

Compound (I-h) can be produced by reacting compound (XIV-a) and compound (XV) in a solvent with or without an activator in the presence of a condensing agent in the presence of a base.

Examples of the condensing agent include 1-(3-dimethylaminopropyl)-3-ethylcarbodiimide hydrochloride (EDC hydrochloride), and O-(7-azabenzotriazol-1-yl)-N,N,N',N'- tetramethyluronium hexafluorophosphate (HATU). Examples of the activator include 1-hydroxybenzotriazole monohydrate (HOBt monohydrate), 1-hydroxy-7-azabenzotriazole (HOAt). Examples of the base include amine such as triethylamine, N,N-diisopropylethylamine, pyridine and the like. The solvent may be any as long as it does not influence the reaction, and examples thereof include ether such as tetrahydrofuran, 1,4-dioxane, 1,2-dimethoxyethane and the like; amide such as N,N-dimethylformamide, N,N-dimethylacetamide, 1,3-dimethyl-2-imidazolidinone and N-methylpyrrolidone and the like; or a mixed solvent thereof.

This reaction can be performed at 0° C.-80° C., preferably 10-40° C.

Alternatively, compound (I-h) can be produced from the aforementioned compound (XI) according to a method described below.

Compound (XI) and a compound represented by the formula (XIII-b):

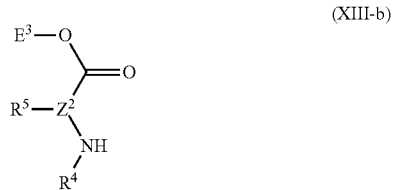

wherein $E^3$ is a carboxylic acid-protecting group, and other symbols are as defined above, are reacted to give a compound represented by the formula (XIV-b):

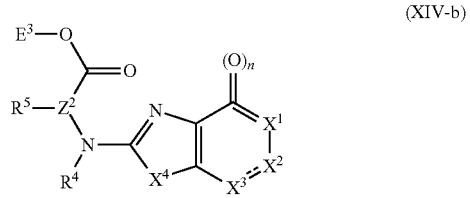

wherein the symbols are as defined above. $E^3$ of the compound (XIV-b) is removed to give compound (XIV-a). This is reacted with the aforementioned compound (XV) to give compound (I-h).

Examples of the protecting group for $E^3$ include optionally substituted alkyl (tert-butyl etc.).

Compound (XIV-b) can be produced by reacting compound (XI) and compound (XIII-b), which is similar to the method of producing the aforementioned compound (I-g) from compound (XI) and compound (XII).

Compound (XIV-a) can be produced by a conventional method such as acid treatment, base treatment and the like according to the kind of $E^3$ of compound (XIV-b).

For example, compound (XIV-b) wherein $E^3$ is tert-butyl can be deprotected in a solvent in the presence of an acid.

Examples of the acid include trifluoroacetic acid, formic acid and hydrogen chloride. The solvent may be any as long as it does not influence the reaction, and examples thereof include halogenohydrocarbon such as methylene chloride, chloroform and 1,2-dichloroethane and the like. This reaction can be performed at 0° C.-100° C.

Compound (I-h) can be produced by reacting compound (XIV-a) and compound (XV) in a solvent with or without an activator in the presence of a condensing agent in the presence of a base, as mentioned above.

Compound (I) produced by the above-mentioned production method may be subjected to interconversion of substituents by a conventional method. As a method of interconversion of substituents, the following methods 1-38 can be specifically mentioned.

These methods can also be applied to an intermediate compound obtained during production of compound (I).

Method 1:

Compound (I) having optionally substituted amino, an optionally substituted nitrogen-containing non-aromatic heterocyclic group wherein a bond of the group is a nitrogen atom, or optionally substituted nitrogen-containing heteroaryl wherein a bond of the group is a nitrogen atom as a substituent can be produced by, for example, reacting corresponding compound (I) having a halogen atom (chlorine atom etc.) as a substituent, in a solvent (e.g., alkylnitrile such as acetonitrile and the like) in the presence of a base (e.g., alkali metal carbonate such as potassium carbonate and the like), with corresponding optionally substituted amine, optionally substituted nitrogen-containing non-aromatic heterocyclic group, or optionally substituted nitrogen-containing heteroarene to perform amination.

Method 2:

Compound (I) having a carbon-carbon double bond is subjected to catalytic reduction under a hydrogen atmosphere in a solvent (e.g., alkyl alcohol such as ethanol and the like) in the presence of palladium carbon, whereby compound (I) having a carbon-carbon single bond instead can be produced.

Method 3:

Compound (I) having NH as a substituent can be produced by reacting compound (I) having a nitrogen atom substituted by an alkoxyphenylmethyl group and in a solvent in the presence of an acid in the presence or absence of a hydrogenating agent.

Examples of the acid include trifluoroacetic acid. Examples of the hydrogenating agent include trialkylsilane such as triethylsilane and the like. The solvent may be any as long as it does not influence the reaction, and examples thereof include a solvent amount of the above-mentioned acid, a solvent amount of the above-mentioned trialkylsilane, water, or a mixed solvent thereof.

Method 4:

Compound (I) wherein $R^{1a}$, $R^{2a}$ or $R^{3a}$ is a halogen atom can be produced by reacting compound (I) wherein $R^{1a}$, $R^{2a}$ or $R^{3a}$ is a hydrogen atom in a solvent in the presence of a halogenating agent.

Examples of the halogenating agent include corresponding N-halogenosuccinimide. The solvent may be any as long as it does not influence the reaction, and examples thereof include ether such as tetrahydrofuran, 1,2-dimethoxyethane and the like, amide such as N,N-dimethylformamide, N-methylpyrrolidone and the like.

Method 5:

Compound (I) wherein $R^{1a}$ is optionally substituted pyrazolyl can be produced by reacting compound (I) wherein $R^{1a}$ is hydrazino in a solvent (e.g., alkyl alcohol such as ethanol and the like, water or a mixed solvent of these) in the presence of a corresponding 1,3-dioxypropane compound or a tetraalkoxyacetal derivative thereof in the presence or absence of an acid (e.g., inorganic acid such as hydrogen chloride and the like).

Method 6:

Compound (I) having optionally substituted cyclopropane as a substituent can be produced by reacting compound (I)

having corresponding optionally substituted alkenyl as a substituent in a solvent (e.g., aromatic hydrocarbon such as toluene and the like) in the presence of methylene iodide in the presence of diethyl zinc.

Method 7:

Compound (I) having hydroxy as a substituent can be produced by hydrolysis of compound (I) having alkanoyloxy as a substituent by a conventional method.

The hydrolysis can be performed by reacting compound (I) having alkanoyloxy as a substituent in a solvent (e.g., tetrahydrofuran, 1,4-dioxane, methanol, ethanol, water, or these used in combination) in the presence of a base (e.g., alkali metal hydroxide such as sodium hydroxide, potassium hydroxide, lithium hydroxide and the like; alkali metal alkoxide such as sodium methoxide, sodium ethoxide and the like).

Method 8:

Compound (I) having hydroxymethyl as a substituent can be produced by reacting compound (I) having alkoxycarbonyl as a substituent in a solvent (e.g., ether such as tetrahydrofuran and the like) in the presence of a reducing agent (e.g., lithium aluminum hydride).

Method 9:

Compound (I) having hydroxy as a substituent can be produced by reacting compound (I) having methoxy as a substituent in a solvent (e.g., halogenohydrocarbon such as methylene chloride and the like) in the presence of boron tribromide.

Method 10:

Compound (I) having hydroxy as a substituent can be produced by reacting compound (I) having halogen (e.g., fluorine atom) as a substituent in a solvent (e.g., alkylnitrile such as acetonitrile and the like, water, or a mixed solvent thereof) in the presence of a base (e.g., alkali metal carbonate such as sodium hydrogen carbonate and the like).

Method 11:

Compound (I) having oxo as a substituent can be produced by reacting compound (I) having hydroxy as a substituent in a solvent (e.g., halogenohydrocarbon such as chloroform and the like) in the presence of an oxidant (e.g., manganese dioxide).

Method 12:

Compound (I) having optionally substituted alkoxy as a substituent can be produced by reacting compound (I) having hydroxy as a substituent in a solvent (e.g., amide such as N,N-dimethylformamide and the like) in the presence of the corresponding optionally substituted alkyl halide (e.g., alkyl iodide) in the presence of a base (e.g., alkali metal hydride such as sodium hydride and the like).

Method 13:

Compound (I) having optionally substituted alkoxy as a substituent can be produced by reacting compound (I) having a halogen atom (e.g., chlorine atom, bromine atom) as a substituent in the presence of a solvent amount of the corresponding optionally substituted alkyl alcohol in the presence of a base (e.g., alkali metal carbonate such as potassium carbonate and the like, alkali metal alkoxide such as corresponding sodium alkoxide and the like).

Method 14:

Compound (I) having optionally substituted aryloxy as a substituent can be produced by reacting compound (I) having a halogen atom (e.g., chlorine atom) as a substituent in a solvent (e.g., amide such as N,N-dimethylformamide and the like) in the presence of a corresponding optionally substituted hydroxyarene in the presence of a base (e.g., sodium hydride).

Method 15:

Compound (I) having optionally substituted amino as a substituent can be produced by reacting compound (I) having a halogen atom (e.g., chlorine atom) as a substituent in a solvent (e.g., alkylnitrile such as acetonitrile and the like) in the presence of the corresponding optionally substituted amine in the presence of a base (e.g., alkali metal carbonate such as potassium carbonate and the like) in the presence of an additive (e.g., alkali metal iodide such as potassium iodide and the like).

Method 16:

Compound (I) having, as a substituent, optionally substituted amino, an optionally substituted nitrogen-containing non-aromatic heterocyclic group having a nitrogen atom as a bond of a group or optionally substituted nitrogen-containing heteroaryl having a nitrogen atom as a bond of a group can be produced from compound (I) having hydroxy as a substituent according to the method described below. Compound (I) having hydroxy as a substituent is reacted in a solvent (e.g., halogenohydrocarbon such as methylene chloride and the like), in the presence of methanesulfonyl chloride, in the presence of a base (e.g., trialkylamine such as triethylamine and the like) to give a compound having methanesulfonyloxy as the corresponding substituent. This is reacted in a solvent (e.g., alkylnitrile such as acetonitrile and the like), in the presence of the corresponding optionally substituted amine, optionally substituted nitrogen-containing non-aromatic heterocyclic group or optionally substituted nitrogen-containing heteroarene in the presence or absence of an additive (e.g., alkali metal iodide such as sodium iodide and the like), whereby compound (I) having optionally substituted amino as a substituent can be produced.

Method 17:

Compound (I) having carbobenzoxyamino as a substituent can be produced from compound (I) having hydroxy as a substituent, according to a method describe below. Compound (I) having hydroxy as a substituent is reacted in a solvent (e.g., ether such as tetrahydrofuran and the like, aromatic hydrocarbon such as toluene and the like, or a mixed solvent thereof) in the presence of diphenylphosphoryl azide in the presence of triarylphosphine such as triphenylphosphine and the like in the presence of dialkyl azodicarboxylate such as diethyl azodicarboxylate and the like to give a compound having an azide group as the corresponding substituent. This is reacted in a solvent (e.g., alkyl alcohol such as methanol and the like) in the presence of tin(II) chloride to give a compound having amino as a substituent. This is reacted in a solvent (e.g., dialkylketone such as acetone and the like, water, or a mixed solvent thereof) in the presence of N-(carbobenzoxy)succinimide in the presence of a base (e.g., alkali metal carbonate such as sodium hydrogen carbonate and the like), whereby compound (I) having carbobenzoxyamino as a substituent can be produced.

Method 18:

Compound (I) having optionally substituted alkylamino can be produced by reacting compound (I) having NH in a solvent (e.g., halogenohydrocarbon such as methylene chloride and the like) in the presence of the corresponding compound having carbonyl in the presence of a reducing agent (e.g., boron hydride compound such as sodium triacetoxyborohydride and the like).

Method 19:

Compound (I) having NH can be produced by reacting compound (I) having tert-butoxycarbonylamino in a solvent (e.g., halogenohydrocarbon such as methylene chloride and the like, acid described blow in a solvent amount, or a mixed solvent thereof) in the presence of an acid (e.g., trifluoroacetic acid).

Method 20:

Compound (I) having NH can be produced by reacting compound (I) having carbobenzoxyamino in a solvent (e.g., halogenohydrocarbon such as methylene chloride and the like) in the presence of iodotrialkylsilane such as trimethylsilyl iodide and the like.

Method 21:

Compound (I) having an optionally substituted nitrogen-containing non-aromatic heterocyclic group as a substituent can be produced by reacting compound (I) having a halogen atom (e.g., chlorine atom) as a substituent in a solvent (e.g., alkylnitrile such as acetonitrile and the like) in the presence of the corresponding optionally substituted nitrogen-containing non-aromatic heterocyclic compound in the presence of a base (e.g., alkali metal carbonate such as potassium carbonate and the like) in the presence or absence of an additive (e.g., alkali metal iodide such as potassium iodide and the like).

Method 22:

Compound (I) having, as a substituent, optionally substituted alkoxy, optionally substituted cycloalkyl or optionally substituted non-aromatic heterocyclic group can be produced by reacting compound (I) having hydroxy as a substituent in a solvent in the presence of alcohol corresponding to the substituent in the presence of a phosphine compound in the presence of an azodicarboxylic acid compound in the presence or absence of a base.

Method 23:

Compound (I) having, as a substituent, optionally substituted alkyl, optionally substituted cycloalkyl or an optionally substituted non-aromatic heterocyclic group can be produced, for example, by reacting compound (I) having a halogen atom (bromine atom etc.) as a substituent in a solvent in the presence of $M^1B$ $(OG^{4a})$ $(OG^{4b})$ or $M^1BF_3K$ [wherein $M^1$ is corresponding optionally substituted alkyl, optionally substituted cycloalkyl or an optionally substituted non-aromatic heterocyclic group and $G^{4a}$ and $G^{4b}$ are each a hydrogen atom or alkyl, or bonded to each other to form alkylene] in the presence or presence of a base in the presence of a palladium compound in the presence or absence of a phosphine compound.

Method 24:

Compound (I) wherein $R^2$ is represented by the following formula (ii-m-1):

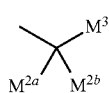
(ii-m-1)

wherein $M^{2a}$ and $M^{2b}$ are each optionally substituted alkyl, or $M^{2a}$ and $M^{2b}$ are bonded to each other to form, together with the adjacent carbon atom, optionally substituted cycloalkane or optionally substituted non-aromatic heterocycle, and $M^3$ is cyano or alkoxycarbonyl] can be produced by reacting a compound wherein $R^2$ is the following formula (ii-m-2):

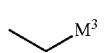
(ii-m-2)

wherein the symbols are as defined above in a solvent (e.g., N,N-dimethylformamide) in the presence of a halide corresponding to $M^{2a}$ and $M^{2b}$ in the presence of a base (e.g., sodium hydride).

Method 25:

Compound (I) having hydroxymethyl as a substituent can be produced by converting compound (I) having carboxy as a substituent by the method shown below.

Compound (I) having carboxy as a substituent is reacted in a solvent (e.g., tetrahydrofuran) in the presence of carbonyldiimidazole to give a corresponding compound having imidazolylcarbonyl.

Then, the compound having imidazolylcarbonyl is reacted in a solvent (e.g., mixed solvent of tetrahydrofuran and water) in the presence of a reducing agent (e.g., sodium borohydride), whereby compound (I) having hydroxymethyl as a substituent can be produced.

Method 26:

Compound (I) having a halogen atom (e.g., bromine atom) as a substituent is treated with alkyllithium (e.g., n-butyllithium) in a solvent (e.g., tetrahydrofuran) and then treated with water, whereby compound (I) wherein the halogen atom is substituted by a hydrogen atom can be produced.

Method 27:

Compound (I) having a halogen atom (e.g., bromine atom) as a substituent is treated with alkyllithium (e.g., n-butyllithium) in a solvent (e.g., tetrahydrofuran) and then reacted with a ketone compound, whereby compound (I) as a corresponding tertiary alcohol can be produced.

Method 28:

Compound (I) having carboxy as a substituent can be produced by hydrolyzing compound (I) having alkoxycarbonyl as a substituent with an acid or base according to the kind of alkoxycarbonyl. When alkoxycarbonyl is primary alkylcarboxyl such as methoxycarbonyl, ethoxycarbonyl or the like or secondary alkylcarboxy, the hydrolysis can be performed in a solvent (e.g., mixed solvent of ether such as tetrahydrofuran and the like, corresponding alkyl alcohol and water) in the presence of a base (e.g., alkali metal hydroxide such as sodium hydroxide and the like). When alkoxycarbonyl is tertiary alkylcarboxy such as t-butoxycarbonyl and the like, the hydrolysis can be performed in a solvent (e.g., ether such as 1,4-dioxane and the like, halogenohydrocarbon such as chloroform and the like) in the presence of an acid (e.g., hydrogen chloride, trifluoroacetic acid).

Method 29:

Compound (I) having carboxy as a substituent can be produced by treating compound (I) having cyano as a substituent with an acid in a solvent.

Method 30:

Compound (I) having optionally substituted aminocarbonyl as a substituent can be produced by reacting compound (I) having carboxy as a substituent in a solvent in the presence of corresponding optionally substituted amine in the presence or absence of an activator in the presence of a condensing agent in the presence of a base.

Method 31:

Compound (I) having optionally substituted carbonylamino can be produced by reacting compound (I) having amino in a solvent in the presence of corresponding optionally substituted carboxylic acid in the presence or absence of an activator in the presence of a condensing agent in the presence of a base.

Alternatively, compound (I) having optionally substituted carbonylamino can be produced by reacting compound (I)

having amino in a solvent in the presence of a reactive derivative of the corresponding optionally substituted carboxylic acid in the presence of a base.

Method 32:

Compound (I) having cyano as a substituent can be produced by reacting compound (I) having halogen atom (e.g., bromine atom) as a substituent in a solvent in the presence of a cyanide compound (e.g., zinc cyanide, cuprous cyanide) in the presence or absence of a palladium compound in the presence or absence of a phosphine compound.

Method 33:

Compound (I) having cyano as a substituent can be produced by reacting compound (I) having aminocarbonyl as a substituent in a solvent in the presence of trifluoromethanesulfonic anhydride in the presence of a base.

Method 34:

Compound (I) having alkoxycarbonyl as a substituent can be produced by reacting compound (I) having carboxy as a substituent in a solvent amount of corresponding alkyl alcohol in the presence of an acid.

Method 35:

Compound (I) having hydroxy as a substituent is converted by the method shown below, whereby compound (I) having a hydrogen atom as the moiety can be produced.

Compound (I) having hydroxy as a substituent is reacted in a solvent in the presence of methanesulfonyl chloride in the presence of a base to give a compound having methanesulfonyloxy as the corresponding substituent. Then, the compound having methanesulfonyloxy is reacted in a solvent in the presence of formic acid in the presence of a palladium compound (e.g., tetrakis(triphenylphosphine)palladium), whereby compound (I) having a hydrogen atom as the moiety can be produced.

Method 36:

Compound (I) having tert-butoxycarbonylamino can be produced by reacting compound (I) having carboxy in tert-butanol in the presence of diphenylphosphoryl azide in the presence of a base.

Method 37:

Compound (I) having hydroxy as a substituent can be produced by converting compound (I) having a halogen atom as a substituent by the method shown below.

Compound (I) having a halogen atom (e.g., bromine atom) as a substituent is reacted in a solvent in the presence of bis(pinacolato)diboron in the presence of a palladium compound in the presence or absence of a phosphine compound, whereby a corresponding boric acid pinacol ester compound is obtained. The boric acid pinacol ester compound is reacted in a solvent in the presence of an oxidant, whereby compound (I) having hydroxy as a substituent can be produced.

Method 38:

Compound (I) having a bromine atom as a substituent can be produced by reacting compound (I) having hydroxy as a substituent in a solvent in the presence of phosphorus tribromide.

[Production of Intermediate Compound]

The aforementioned compound (IV) of the present invention can be produced, for example, by the method shown in the following Scheme 1.

Scheme 1:

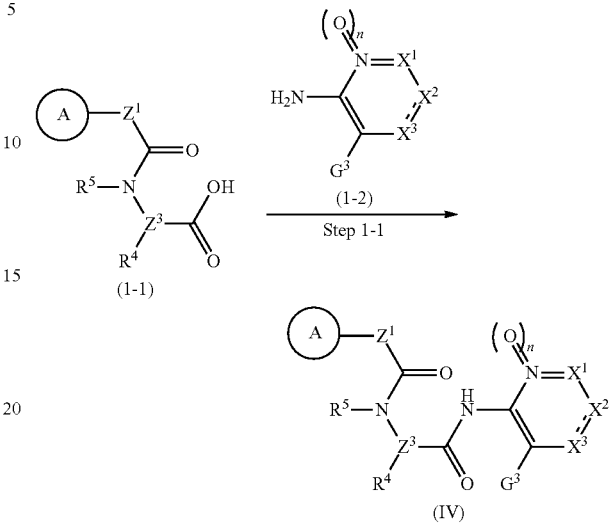

[in the Scheme, the symbols are as defined above.]

Step 1-1:

Compound (IV) can be produced by reacting compound (1-1) and compound (1-2) in a solvent in the presence of a condensing agent in the presence of a base.

Examples of the condensing agent include chloroformic acid alkyl ester such as methyl chloroformate, ethyl chloroformate, propyl chloroformate, isopropyl chloroformate, butyl chloroformate, isobutyl chloroformate and the like. Examples of the base include amine such as triethylamine, N,N-diisopropylethylamine, pyridine and the like. The solvent may be any as long as it does not influence the reaction, and examples thereof include ether such as tetrahydrofuran, 1,4-dioxane, 1,2-dimethoxyethane and the like.

This reaction can be performed at −20-60° C., preferably 0-30° C.

The aforementioned compound (II) of the present invention can be produced from compound (I-z) having carbobenzoxy by, for example, a method shown in the following Scheme 2.

Scheme 2:

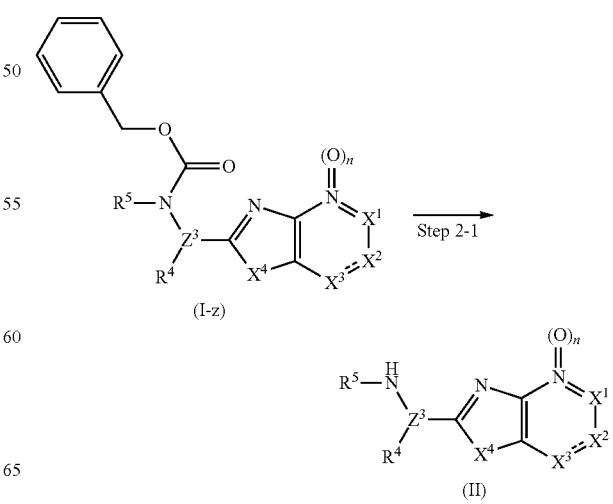

[in the Scheme, the symbols are as defined above.]
Step 2-1:

Compound (II) can be produced by de-carbobenzoxylation of compound (I-z) by a conventional method.

Compound (II) can be produced by, for example, treating compound (I-z) with iodosilane in a solvent in the presence or absence of a silane compound.

Examples of iodosilane include iodotrialkylsilane such as trimethylsilyl iodide and the like. Examples of the silane compound include trialkylsilane such as triethylsilane and the like. The solvent may be any as long as it does not influence the reaction, and examples thereof include alkylnitrile such as acetonitrile, propionitrile and the like.

This reaction can be performed at 0-50° C., preferably 10-30° C.

Compound (II) can be produced by treating compound (I-z) with palladium hydroxide carbon under a hydrogen atmosphere, in a solvent (e.g., methanol).

Alternatively, compound (II) can be produced by treating compound (I-z) with an acid (e.g., hydrogen bromide-acetic acid solution, sulfuric acid-acetic acid solution) in a solvent (e.g., methylene chloride, acetic acid, or a mixed solvent thereof).

Of the aforementioned compound (XI) of the present invention, a compound represented by the formula (XI-a):

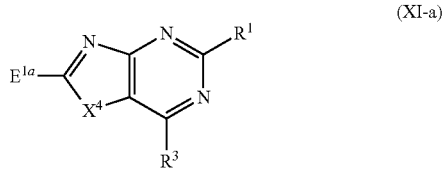

wherein $E^{1a}$ is a halogen atom, optionally substituted alkylsulfinyl or optionally substituted alkylsulfonyl, and other symbols are as defined above can be produced, for example, by a method shown in the following Scheme 3.

Scheme 3:

wherein $L^{1a}$ is optionally substituted alkyl and other symbols are as defined above.

Compound (3-1) and compound (3-2) or a reactive derivative thereof are reacted to give compound (3-3). This is cyclized to give compound (3-4). This is oxidized to give compound (XI-a).

Alternatively, compound (3-5) and compound (3-2) or a reactive derivative thereof are reacted to give compound (3-6). This is cyclized to give compound (XI-a).

Step 3-1:

Compound (3-3) can be produced by reacting compound (3-1) and compound (3-2) in a solvent in the presence of a condensing agent, in the presence or absence of an activator, in the presence or absence of a base.

Examples of the condensing agent include carbodiimide such as 1-(3-dimethylaminopropyl)-3-ethylcarbodiimide hydrochloride (EDC hydrochloride) and the like, uronium salt such as O-(7-azabenzotriazol-1-yl)-N,N,N',N'-tetramethyluronium hexafluorophosphate (HATU) and the like. Examples of the activator include 1-hydroxybenzotriazole monohydrate (HOBt monohydrate). The solvent may be any as long as it does not influence the reaction, and examples thereof include amide such as N,N-dimethylformamide, N,N-dimethylacetamide, 1,3-dimethyl-2-imidazolidinone, N-methylpyrrolidone and the like.

This reaction can be performed at 0-50° C., preferably 10-30° C.

Alternatively, compound (3-3) can be produced by reacting compound (3-1) and a reactive derivative of the abovementioned compound (3-2) in a solvent in the presence of a base.

Examples of the base include amine such as triethylamine, N,N-diisopropylethylamine, pyridine and the like. The solvent may be any as long as it does not influence the reaction, and examples thereof include halogenohydrocarbon such as methylene chloride, chloroform, 1,2-dichloroethane and the like; alkylnitrile such as acetonitrile, propionitrile and the like; or a mixed solvent thereof.

This reaction can be performed at 0-50° C., preferably 10-30° C.

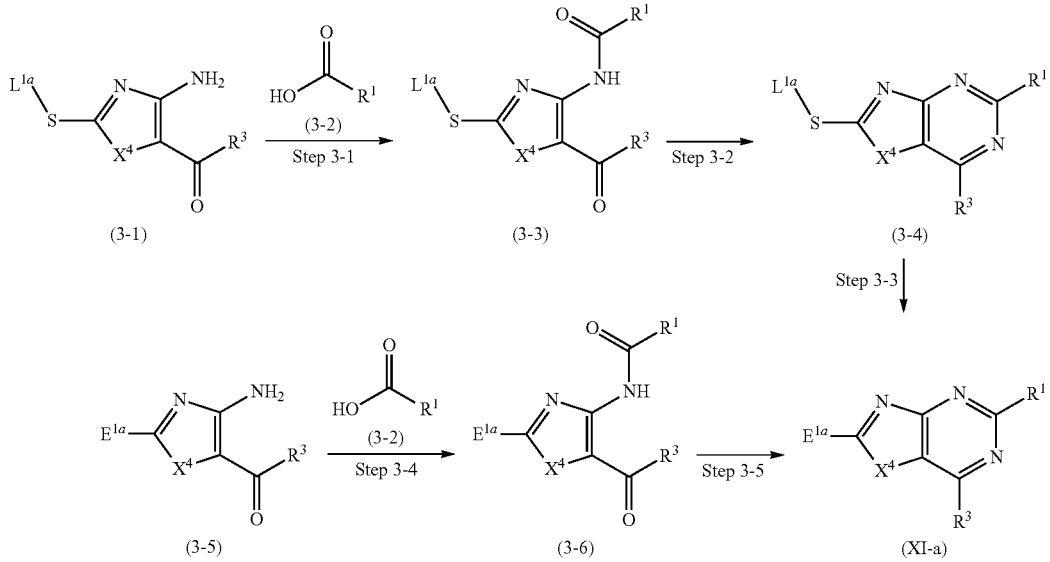

The reactive derivative of compound (3-2) to be used can be a commercially available reactive derivative.

Alternatively, the reactive derivative of compound (3-2) can be produced by reacting compound (3-2) or a salt thereof, in a solvent or without solvent in the presence of a halogenating agent, in the presence or absence of an activator.

Examples of the halogenating agent include oxalyl chloride, thionyl chloride. Examples of the activator include N,N-dimethylformamide. The solvent may be any as long as it does not influence the reaction, and examples thereof include halogenohydrocarbon such as methylene chloride, chloroform, 1,2-dichloroethane and the like; alkylnitrile such as acetonitrile, propionitrile and the like.

This reaction can be performed at 0-100° C., preferably 10-30° C.

Step 3-2:

Compound (3-4) can be produced by reacting compound (3-3) in the presence of an ammonium salt and an acid.

Examples of the ammonium salt include carboxylic acid ammonium salt such as ammonium formate and the like. Examples of the acid include a carboxylic acid compound such as acetic acid and the like.

This reaction can be performed at 80-180° C., preferably 100-150° C.

Step 3-3:

Compound (XI-a) wherein $E^{1a}$ is optionally substituted alkylsulfinyl or optionally substituted alkylsulfonyl can be produced by treating compound (3-4) with an oxidant in a solvent.

Examples of the oxidant include methachloroperbenzoic acid (mCPBA). The solvent may be any as long as it does not influence the reaction, and examples thereof include halogenohydrocarbon such as methylene chloride, chloroform, 1,2-dichloroethane and the like.

When compound (XI-a) wherein $E^{1a}$ is optionally substituted alkylsulfinyl is produced in this reaction, the amount of the oxidant to be used is 0.9-1.5 mol, preferably 1.0-1.2 mol, per 1 mol of compound (3-4). When compound (XI-a) wherein $E^{1a}$ is optionally substituted alkylsulfonyl is produced, the amount of the oxidant to be used is 2.0-5.0 mol, preferably 2.4-3.5 mol, per 1 mol of compound (3-4). This reaction can be performed at −20 to 30° C., preferably −10 to 30° C.

Step 3-4:

Compound (3-6) can be produced in the same manner as in the Step 3-1 by reacting compound (3-5) and compound (3-2) or a reactive derivative thereof.

Step 3-5:

Compound (XI-a) can be produced in the same manner as in the Step 3-2 by reacting compound (3-6) in the presence of ammonium salt and acid.

Of the aforementioned compound (XI) of the present invention, a compound represented by the formula (XI-b):

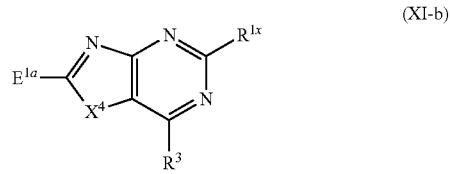

wherein $R^{1x}$ is a halogen atom or a group represented by the following formula (i-cx):

$R^{1dx}$ is optionally substituted alkyl, optionally substituted cycloalkyl or an optionally substituted non-aromatic heterocyclic group, and other symbols are as defined above can be produced by, for example, a method shown in the following Scheme 4.

Scheme 4:

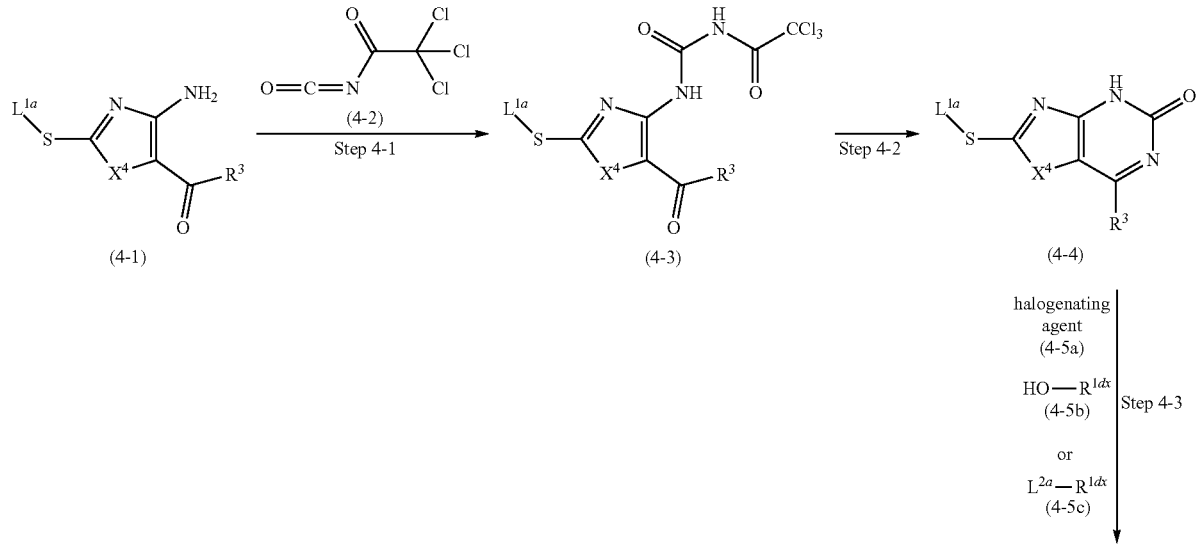

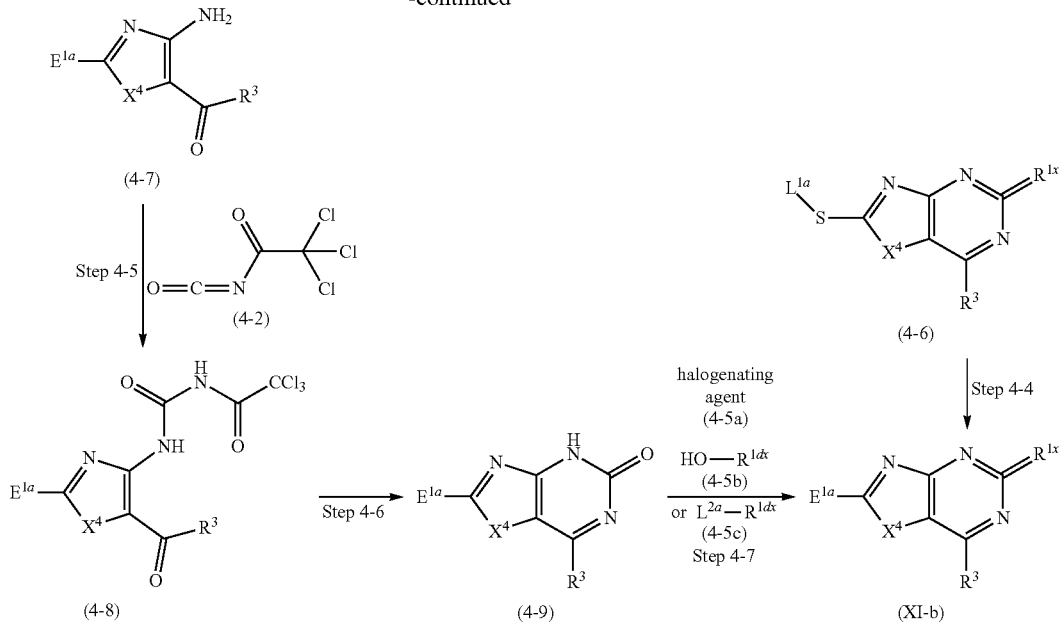

wherein $L^{2a}$ is a leaving group, and other symbols are as defined above.

Compound (4-1) and compound (4-2) are reacted to give compound (4-3). This is cyclized to give compound (4-4). This is reacted with compound (4-5a), compound (4-5b) or compound (4-5c) to give compound (4-6). This is oxidized to give compound (XI-b).

Alternatively, compound (4-7) and compound (4-2) are reacted to give compound (4-8). This is cyclized to give compound (4-9). This is reacted with compound (4-5a), compound (4-5b) or compound (4-5c) to give compound (XI-b).

Step 4-1:

Compound (4-3) can be produced by reacting compound (4-1) and compound (4-2) in a solvent.

The solvent may be any as long as it does not influence the reaction, and ether such as tetrahydrofuran, 1,4-dioxane, 1,2-dimethoxyethane and the like can be mentioned.

This reaction can be performed at 0-50° C., preferably 10-30° C.

Step 4-2:

Compound (4-4) can be produced by treating compound (4-3) with a base in a solvent.

Examples of the base include alkali metal carbonate such as sodium carbonate, potassium carbonate, cesium carbonate and the like. The solvent may be any as long as it does not influence the reaction, and alkyl alcohol such as methanol, ethanol, isopropyl alcohol and the like; ether such as tetrahydrofuran, 1,4-dioxane, 1,2-dimethoxyethane and the like; water; and a mixed solvent thereof can be mentioned.

This reaction can be performed at 0-50° C., preferably 10-30° C.

Step 4-3:

Compound (4-6) wherein $R^{1x}$ is a halogen atom can be produced by reacting compound (4-4) and compound (4-5a) corresponding to $R^{1x}$.

Examples of the compound (4-5a) corresponding to $R^{1x}$ include phosphorus oxychloride and phosphorus oxybromide. When phosphorus oxychloride or phosphorus oxybromide is used as compound (4-5a), this reaction can be performed without solvent in the presence or absence of a base. Examples of the base include N,N-dialkylaniline such as N,N-diethylaniline and the like.

This reaction can be performed at 80-200° C., preferably 100-120° C.

Compound (4-6) wherein $R^{1x}$ is represented by the formula (i-cx) can be produced by reacting compound (4-4) and compound (4-5b) corresponding to $R^{1x}$ in a solvent in the presence of a phosphine compound in the presence of an azodicarboxylic acid compound in the presence or absence of a base.

Examples of the phosphine compound include trialkylphosphine such as tributylphosphine and the like and triarylphosphine such as triphenylphosphine and the like. Examples of the azodicarboxylic acid compound include azodicarboxylic acid diamide such as N,N,N',N'-tetramethylazodicarboxamide and the like and dialkyl azodicarboxylate such as diethyl azodicarboxylate and the like. Examples of the base include N-methylmorpholine. The solvent may be any as long as it does not influence the reaction and ether such as tetrahydrofuran, 1,4-dioxane, 1,2-dimethoxyethane and the like can be mentioned.

This reaction can be performed at 0-120° C., preferably 15-80° C.

Alternatively, compound (4-6) wherein $R^{1x}$ is represented by the formula (i-cx) a can be produced by reacting compound (4-4) and compound (4-5c) corresponding to $R^{1x}$ in a solvent in the presence of a base.

Examples of the $L^{2a}$ include a halogen atom such as iodine atom and the like. Examples of the base include alkali metal carbonate such as potassium carbonate and the like. The solvent may be any as long as it does not influence the reaction, and, for example, amide such as N,N-dimethylformamide and the like can be mentioned.

This reaction can be performed at 0-80° C., preferably 10-50° C.

Step 4-4:

Compound (XI-b) wherein $E^{1a}$ is optionally substituted alkylsulfinyl or optionally substituted alkylsulfonyl can be produced by treating compound (4-6) with an oxidant in a solvent in the same manner as in Scheme 3, Step 3-3.

Step 4-5:

Compound (4-8) can be produced by reacting compound (4-7) and compound (4-2) in a solvent in the same manner as in Step 4-1.

Step 4-6:

Compound (4-9) can be produced by reacting compound (4-8) with a base in a solvent in the same manner as in Step 4-2.

Step 4-7:

Compound (XI-b) can be produced by reacting compound (4-9) and compound (4-5a), compound (4-5b) or compound (4-5c) in the same manner as in Step 4-3.

Of the aforementioned compound (XI) of the present invention, a compound represented by the formula (XI-c):

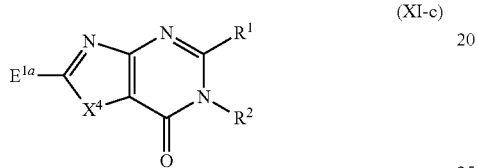

wherein the symbols are as defined above, can be produced by, for example, a method shown in the following Scheme 5.

Scheme 5:

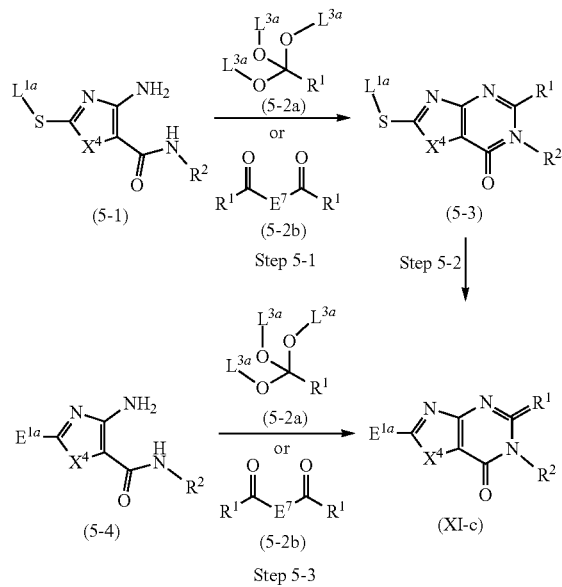

wherein $E^7$ is methylene or an oxygen atom, $L^{3a}$ is alkyl, and other symbols are as defined above.

Compound (5-1) and compound (5-2a) or compound (5-2b) are reacted to give compound (5-3). This is oxidized to give compound (XI-c).

Alternatively, compound (5-4) and compound (5-2a) or compound (5-2b) are reacted to give compound (XI-c).

Step 5-1:

Compound (5-3) can be produced by reacting compound (5-1) and compound (5-2a) in a solvent (e.g., xylene) or without solvent in the presence or absence of an acid anhydride (e.g., acetic anhydride) in the presence or absence of an acid (e.g., paratoluenesulfonic acid). This reaction can be performed at 60-180° C., preferably 100-150° C.

Alternatively, compound (5-3) can be produced by reacting compound (5-1) and compound (5-2b) in a solvent (e.g., alkyl alcohol such as ethanol and the like) in the presence of an acid (e.g., hydrochloric acid). This reaction can be performed at 0-60° C., preferably 10-40° C.

Step 5-2:

Compound (XI-c) wherein $E^{1a}$ is optionally alkylsulfinyl or optionally substituted alkylsulfonyl can be produced in the same manner as in Scheme 3, Step 3-3, by treating compound (5-3) with an oxidant in a solvent.

Step 5-3:

Compound (XI-c) can be produced by reacting compound (5-4) and compound (5-2a) or compound (5-2b) in the same manner as in Step 5-1.

Of the aforementioned compounds (XI) of the present invention, a compound represented by the formula (XI-d):

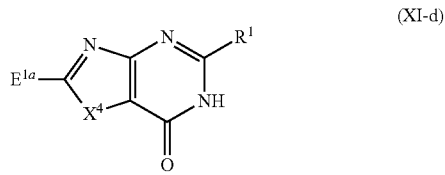

wherein the symbols are as defined above, can be produced, for example, by a method shown in the following Scheme 6.

Scheme 6:

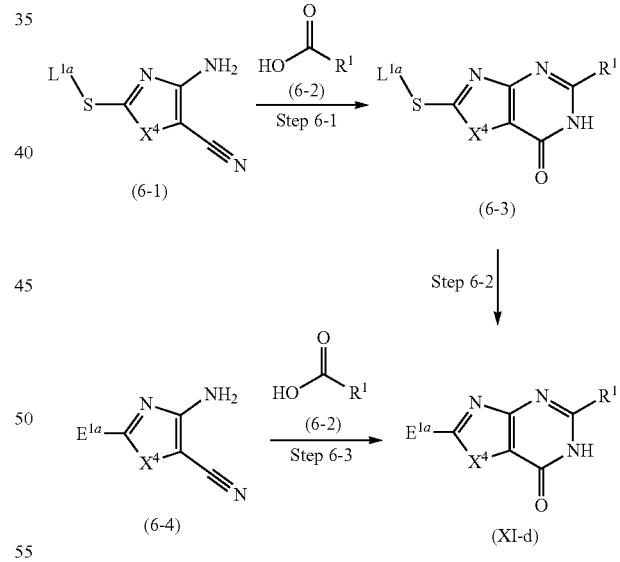

wherein the symbols are as defined above.

Compound (6-1) and compound (6-2) are reacted to give compound (6-3). This is oxidized to give compound (XI-d).

Alternatively, compound (6-4) and compound (6-2) are reacted to give compound (XI-d).

Step 6-1:

Compound (6-3) can be produced by reacting compound (6-1) and compound (6-2) in a solvent.

The solvent may be any as long as it does not influence the reaction and a solvent amount of compound (6-2), water, and a mixed solvent thereof can be mentioned.

This reaction can be performed at 50-150° C., preferably 80-120° C.

Step 6-2:

Compound (XI-d) can be produced by treating compound (6-3) with an oxidant in a solvent in the same manner as in Scheme 3, Step 3-3.

Step 6-3:

Compound (XI-d) can be produced by reacting compound (6-4) and compound (6-2) in a solvent in the same manner as in Step 3-1.

Alternatively, compound (XI-d) can be produced, for example, by a method shown in the following Scheme 7.

Scheme 7:

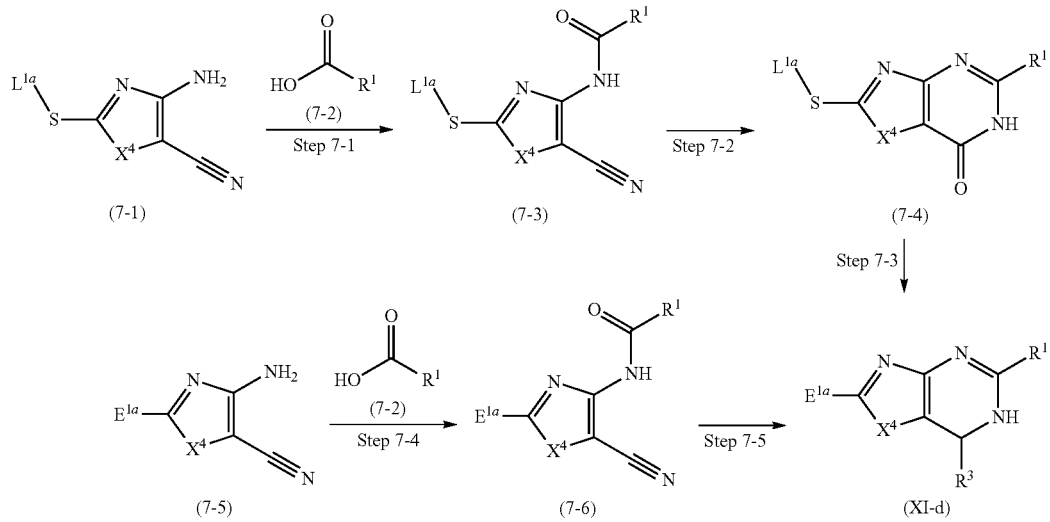

wherein the symbols are as defined above.

Compound (7-1) and compound (7-2) or a reactive derivative thereof are reacted to give compound (7-3). This is cyclized to give compound (7-4). This is oxidized to give compound (XI-d).

Alternatively, compound (7-5) and compound (7-2) or a reactive derivative thereof are reacted to give compound (7-6). This is cyclized to give compound (XI-d).

Step 7-1:

Compound (7-3) can be produced by reacting compound (7-1) and compound (7-2) or a reactive derivative thereof in the same manner as in Scheme 3, Step 3-1.

Step 7-2:

Compound (7-4) can be produced by reacting compound (7-3) in the presence of an acid (e.g., acetic acid) and a base (e.g., sodium acetate).

This reaction can be performed at 80-180° C., preferably 100-150° C.

Alternatively, compound (7-4) can be produced by reacting compound (7-3) in a solvent (e.g., alkyl alcohol such as methanol and the like, dimethyl sulfoxide or a mixture of these) in the presence of a base (e.g., alkali metal carbonate such as potassium carbonate and the like) in the presence of peroxide (e.g., hydrogen peroxide).

This reaction can be performed at 0-50° C., preferably 10-40° C.

Step 7-3:

Compound (XI-d) wherein $E^{1a}$ is optionally substituted alkylsulfinyl or optionally substituted alkylsulfonyl can be produced by treating compound (7-4) with an oxidant in a solvent in the same manner as in Scheme 3, Step 3-3.

Step 7-4:

Compound (7-6) can be produced by reacting compound (7-5) and compound (7-2) or a reactive derivative thereof in the same manner as in Scheme 3, Step 3-1.

Step 7-5:

Compound (XI-d) can be produced by reacting compound (7-6) in the same manner as in Step 7-2.

Of the aforementioned compounds (XI) of the present invention, a compound represented by the formula (XI-e):

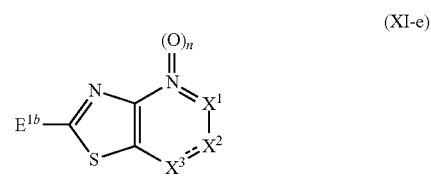

wherein $E^{1b}$ is optionally substituted alkylsulfinyl or optionally substituted alkylsulfonyl, and other symbols are as defined above can be produced, for example, by a method shown in the following Scheme 8.

Scheme 8:

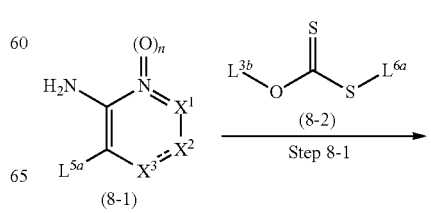

-continued

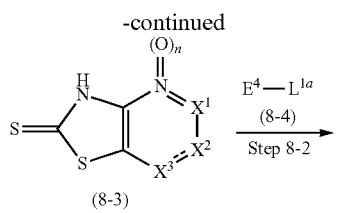
(8-3)

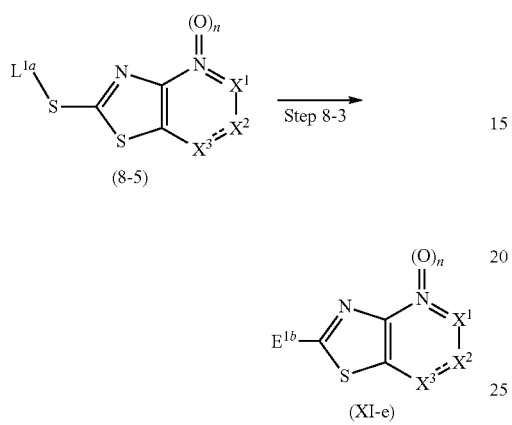
(8-5)

(XI-e)

wherein $L^{5a}$ is a leaving group, $L^{3b}$ is alkyl, $L^{6a}$ is alkali metal, $E^4$ is a leaving group, and other symbols are as defined above.

Compound (8-1) and compound (8-2) are reacted to give compound (8-3). This is reacted with compound (8-4) to give compound (8-5). This is oxidized to give compound (XI-e).

Step 8-1:
Compound (8-3) can be produced by reacting compound (8-1) and compound (8-2) in a solvent (e.g., amide such as N-methylpyrrolidone, N,N-dimethylformamide and the like).

Examples of the leaving group for $L^{5a}$ include a halogen atom such as bromine atom and the like. This reaction can be performed at 80-200° C., preferably 100-150° C.

Step 8-2:
Compound (8-5) can be produced by reacting compound (8-3) and compound (8-4) in a solvent in the presence of a base.

Examples of the leaving group for $E^4$ include alkoxysulfonyloxy shown by $L^{1a}O$—$SO_3$— and a halogen atom. Examples of the base include alkali metal hydroxide such as sodium hydroxide and the like; and alkali metal carbonate such as sodium hydrogen carbonate, sodium carbonate and the like. The solvent may be any as long as it does not influence the reaction, and examples thereof include water and amide such as N,N-dimethylformamide and the like.

This reaction can be performed at −20-60° C., preferably 0-30° C.

Step 8-3:
Compound (XI-e) can be produced by treating compound (8-5) with an oxidant in a solvent in the same manner as in Scheme 3, Step 3-3.

Of the aforementioned compounds (XI) of the present invention, a compound represented by the formula (XI-f):

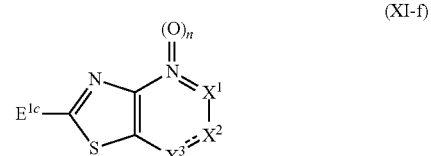

wherein $E^{1a}$ is a halogen atom, and other symbols are as defined above, can be produced, for example, by a method shown in the following Schemes 9, 10.

Scheme 9:

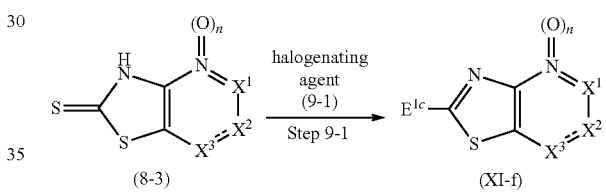

wherein the symbols are as defined above.

Step 9-1:
Compound (XI-f) can be produced by reacting compound (8-3) and compound (9-1) in a solvent.

Examples of the halogenating agent shown by compound (9-1) include chlorinating agent such as sulfuryl chloride and the like. The solvent may be any as long as it does not influence the reaction and halogenohydrocarbon such as methylene chloride, chloroform, 1,2-dichloroethane and the like can be mentioned.

This reaction can be performed at 0-80° C., preferably 20-60° C.

Scheme 10:

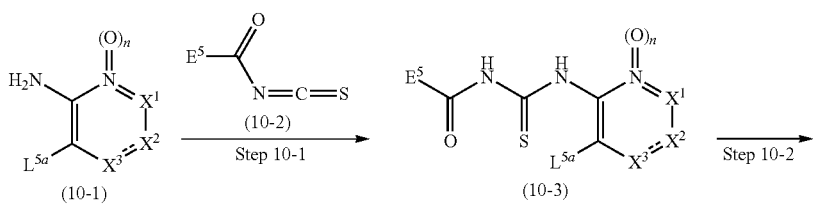

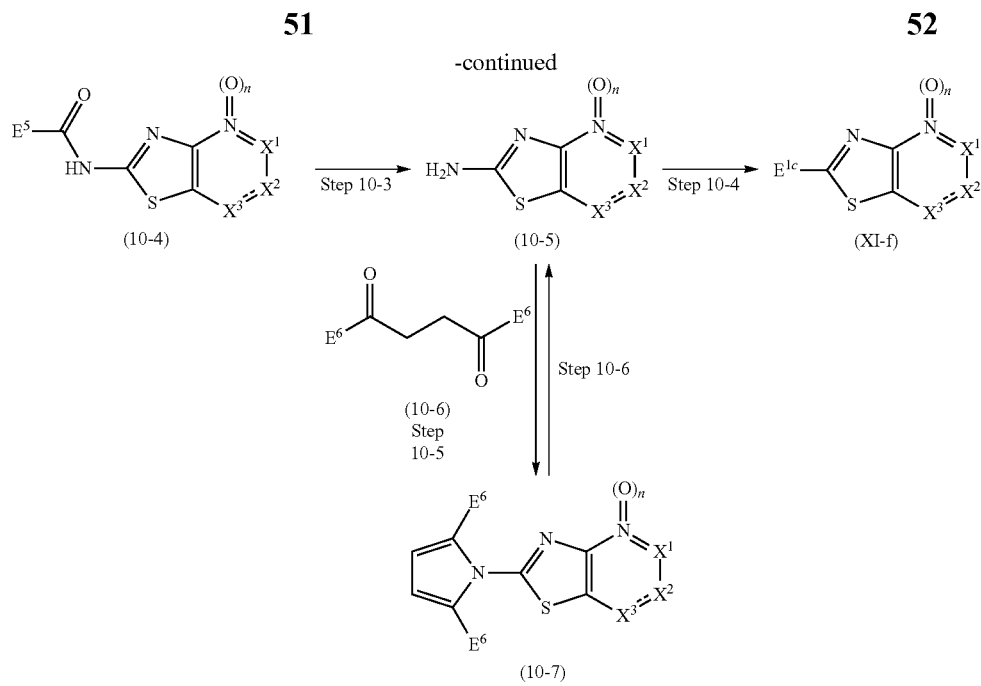

wherein $E^5$ is optionally substituted aryl, $E^6$ is optionally substituted alkyl, and other symbols are as defined above.

Compound (10-1) and compound (10-2) are reacted to give compound (10-3). This is cyclized to give compound (10-4). This is converted to give compound (10-5). This is halogenated to give compound (XI-f).

Alternatively, compound (10-5) and compound (10-6) are reacted to give compound (10-7). $X^1$, $X^2$ or $X^3$ therein is converted to give converted compound (10-7). This is deprotected to give compound (10-5) wherein $X^1$, $X^2$ or $X^3$ is converted.

Step 10-1:

Compound (10-3) can be produced by reacting compound (10-1) and compound (10-2) in a solvent.

Examples of the optionally substituted aryl for $E^5$ include phenyl. As compound (10-2), a commercially available product can be used. Alternatively, it can be prepared from corresponding carboxylic acid chloride and ammonium thiocyanate. The solvent may be any as long as it does not influence the reaction and dialkylketone such as acetone and the like can be mentioned.

This reaction can be performed at 20-100° C., preferably 40-80° C.

Step 10-2:

Compound (10-4) can be produced by reacting compound (10-3) in a solvent in the presence of a base.

Examples of the base include alkali metal alkoxide such as sodium alkoxide and the like. The solvent may be any as long as it does not influence the reaction and amide such as N,N-dimethylformamide, N,N-dimethylacetamide, 1,3-dimethyl-2-imidazolidinone and N-methylpyrrolidone and the like can be mentioned.

This reaction can be performed at 80-180° C., preferably 100-150° C.

Step 10-3:

Compound (10-5) can be produced by treating compound (10-4) by a conventional method such as acid treatment, base treatment and the like according to the kind of $E^5$.

When $E^5$ is phenyl, compound (10-5) can be produced by treating compound (10-4) with an acid (e.g., sulfuric acid) in a solvent (e.g., water).

This reaction can be performed at 60-150° C., preferably 80-120° C.

Step 10-4:

Compound (XI-f) can be produced by reacting compound (10-5) in a solvent in the presence of a nitrous acid compound in the presence of a halogenating agent.

Examples of the nitrous acid compound include alkyl nitrite such as t-butyl nitrite and the like. Examples of the halogenating agent include corresponding cupric halide. The solvent may be any as long as it does not influence the reaction, and examples thereof include alkylnitrile such as acetonitrile, propionitrile and the like.

This reaction can be performed at 40-100° C., preferably 50-80° C.

Step 10-5:

Compound (10-7) can be produced by reacting compound (10-5) and compound (10-6) in a solvent in the presence of an acid.

Examples of the acid include arylsulfonic acid such as p-toluenesulfonic acid and the like. The solvent may be any as long as it does not influence the reaction, and aromatic hydrocarbon such as toluene, xylene and the like can be mentioned.

This reaction can be performed at 60-150° C., preferably 80-120° C.

In the obtained compound (10-7), $X^1$, $X^2$ and $X^3$ can be interconverted by a conventional method. As a method for interconversion, the aforementioned methods 1-38 can be specifically mentioned.

Step 10-6:

Compound (10-5) can be produced by treating compound (10-7) with an acid (e.g., trifluoroacetic acid) in a solvent (e.g., water).

Of the aforementioned compounds (XI) of the present invention, a compound represented by the formula (XI-g):

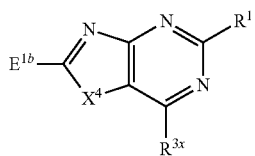

(XI-g)

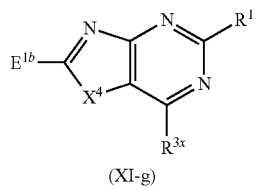

(XI-g)

wherein $R^{3x}$ is a halogen atom or a group represented by the following formula (iii-cx):

(iii-cx)

$R^{3dx}$ is optionally substituted alkyl, optionally substituted cycloalkyl or an optionally substituted non-aromatic heterocyclic group, and other symbols are as defined above, can be produced, for example, by a method shown in the following Scheme 11.

Scheme 11:

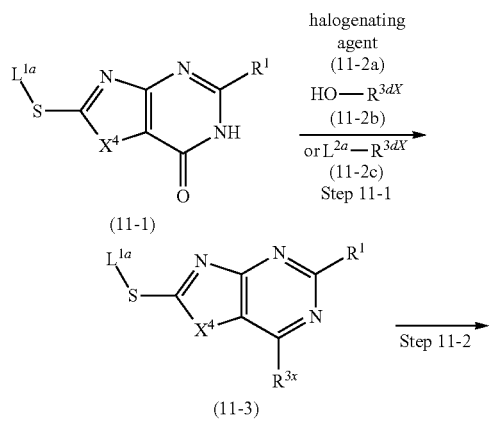

wherein the symbols are as defined above.

Compound (11-1) and compound (11-2a), compound (11-2b) or compound (11-2c) are reacted to give compound (11-3). This is oxidized to give compound (XI-g).

Step 11-1:

Compound (11-3) can be produced by reacting compound (11-1) and compound (11-2a), compound (11-2b) or compound (11-2c) in the same manner as in Scheme 4, Step 4-3.

Step 11-2:

Compound (XI-g) can be produced by treating compound (11-3) with an oxidant in a solvent in the same manner as in Scheme 3, Step 3-3.

Of the aforementioned compounds (XI) of the present invention, a compound represented by the formula (XI-h):

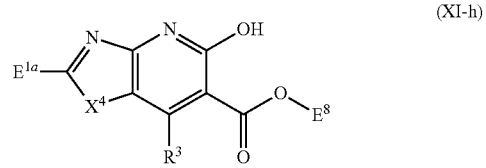

(XI-h)

wherein $E^8$ is alkyl, and other symbols are as defined above can be produced, for example, by a method shown in the following Scheme 12.

Scheme 12:

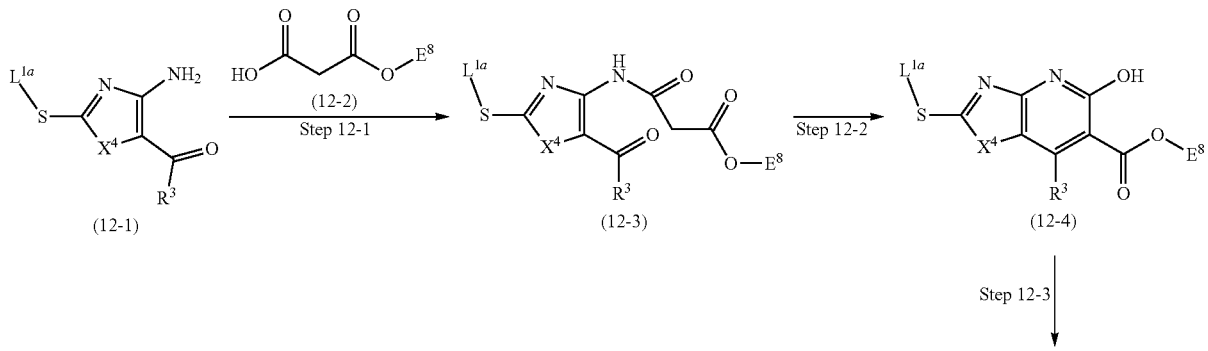

Step 12-3

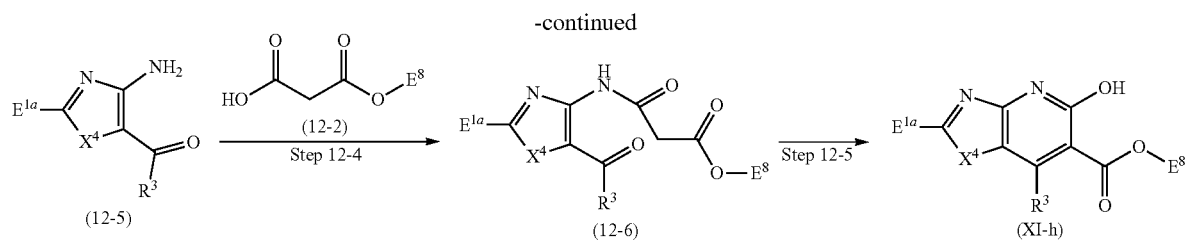

wherein the symbols are as defined above.

Compound (12-1) and compound (12-2) or a reactive derivative thereof are reacted to give compound (12-3). This is cyclized to give compound (12-4). This is oxidized to give compound (XI-h).

Alternatively, compound (12-5) and compound (12-2) or a reactive derivative thereof are reacted to give compound (12-6).

This is cyclized to give compound (XI-h).

Step 12-1:
Compound (12-3) can be produced by reacting compound (12-1) and compound (12-2) or a reactive derivative thereof in the same manner as in Scheme 3, Step 3-1.

Step 12-2:
Compound (12-4) can be produced by reacting compound (12-3) in a solvent in the presence of a base.

Examples of the base include alkali metal alkoxide such as potassium tert-butoxide and the like. The solvent may be any as long as it does not influence the reaction and ether such as tetrahydrofuran, 1,4-dioxane, 1,2-dimethoxyethane and the like can be mentioned.

This reaction can be performed at 30-110° C., preferably 50-90° C.

Step 12-3:
Compound (XI-h) wherein $E^{1a}$ is optionally substituted alkylsulfinyl or optionally substituted alkylsulfonyl can be produced by treating compound (12-4) with an oxidant in a solvent in the same manner as in Scheme 3, Step 3-3.

Step 12-4:
Compound (12-6) can be produced by reacting compound (12-5) and compound (12-2) or a reactive derivative thereof in the same manner as in Scheme 3, Step 3-1.

Step 12-5:
Compound (XI-h) can be produced by reacting compound (12-6) in a solvent in the presence of a base in the same manner as in Step 12-2.

Of the aforementioned compounds (XII) of the present invention, a compound represented by the formula (XII-a):

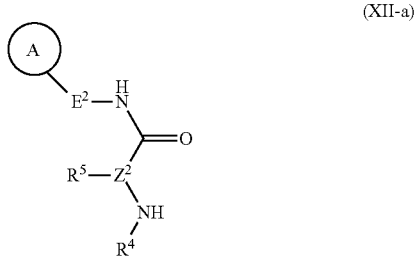

(XII-a)

wherein the symbols are as defined above can be produced, for example, by a method shown in the following Scheme 13.

Scheme 13:

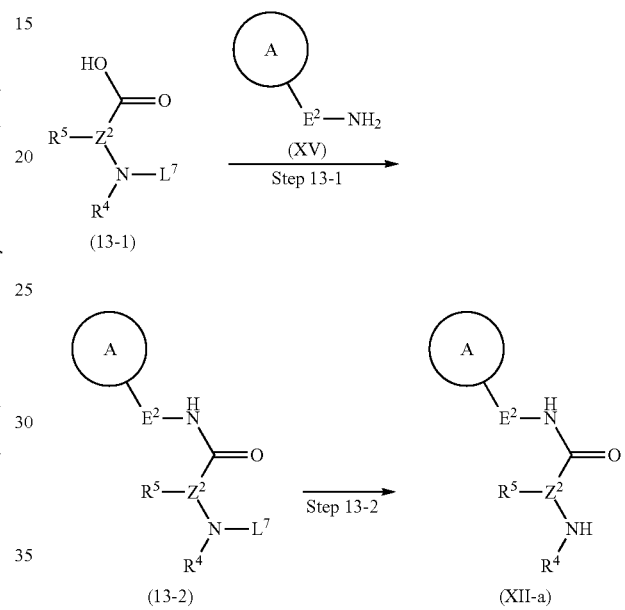

wherein $L^7$ is alkyloxycarbonyl or aralkyloxycarbonyl, and other symbols are as defined above.

Compound (13-1) and compound (XV) are reacted to give compound (13-2). $L^7$ is removed from compound (13-2) to give compound (XII-a).

Step 13-1:
Compound (13-2) can be produced by reacting compound (13-1) and compound (XV) in the same manner as in the method for producing compound (I-h) from compound (XIV-a) and compound (XV).

Step 13-2:
Compound (XII-a) can be produced by removing $L^7$ of compound (13-2) by a conventional method such as acid treatment, hydrogenation and the like according to the kind of $L^7$.

Other starting compounds of the aforementioned production methods ([Production of compound (I)], and [Production of intermediate compound]) are commercially available, or can be easily produced by a method well known to those of ordinary skill in the art.

The present invention is explained in more detail in the following by referring to Examples and the like, which are not to be construed as limitative. Note that % described in the following Examples and the like means wt % unless specifically indicated, and the solvent ratio in column chromatography means volume ratio.

Example 1

(R)—N-benzyl-1-[7-(pyrrolidin-1-yl)[1,3]thiazolo[4,5-d]pyrimidin-2-yl]pyrrolidine-2-carboxamide

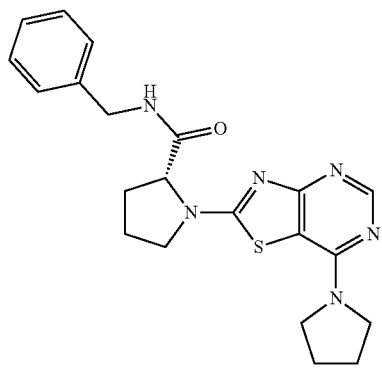 [SMILES: O=C(NCc1ccccc1)[C@H]1CCCN1c1nc2ncnc(N3CCCC3)c2s1]

A mixture of the compound (200 mg) obtained in Reference Example 166, the compound (360 mg) obtained in Reference Example 471, N,N-diisopropylethylamine (2.00 g) and N-methylmorpholine (1.00 mL) was stirred with heating at 120° C. for 30 min. After confirmation of the completion of the reaction, under ice-cooling, water was added to the reaction mixture and the mixture was extracted twice with ethyl acetate. The combined organic layer was washed with saturated brine, dried over anhydrous sodium sulfate, filtered and concentrated. The obtained residue was purified by silica gel column chromatography (solvent; ethyl acetate/methanol=100/0-90/10). To the obtained resultant product was added diisopropy ether, and the solid was collected by filtration to give the title compound (100 mg).

MS(ESI)m/z; 409[M+H]$^+$

Examples 2 to 18 are shown below. These compounds were obtained by a method similar to that in Example 1 except that the starting materials in the following Tables were used instead of Reference Example 166 and an appropriate compound was used instead of Reference Example 471 as necessary.

TABLE 1

| Example | structure | starting material | yield | MS(ESI) m/z [M + H]$^+$ |
|---|---|---|---|---|
| 2 | 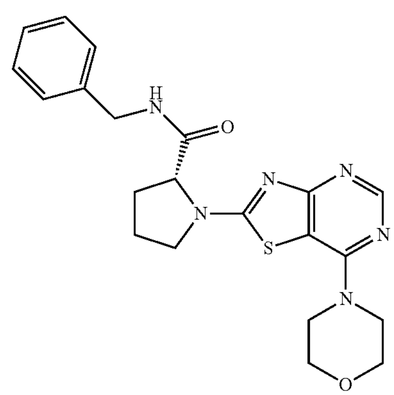 [SMILES: O=C(NCc1ccccc1)[C@H]1CCCN1c1nc2ncnc(N3CCOCC3)c2s1] | Reference Example 167 (110 mg) | 102 mg | 425 |
| 3 | 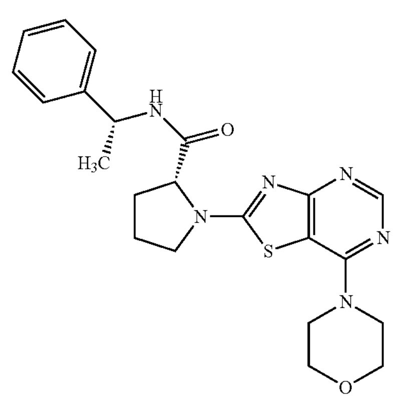 [SMILES: C[C@@H](NC(=O)[C@H]1CCCN1c1nc2ncnc(N3CCOCC3)c2s1)c1ccccc1] | Reference Example 167 (116 mg) | 70.0 mg | 439 |

TABLE 1-continued

| Example | structure | starting material | yield | MS(ESI) m/z [M + H]+ |
|---|---|---|---|---|
| 4 | 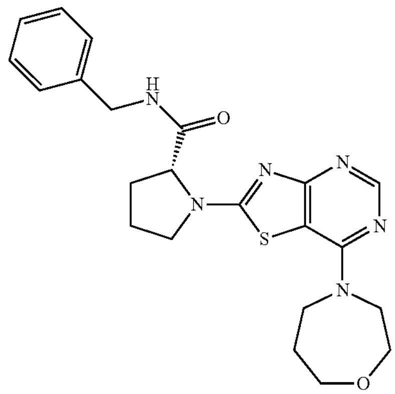 [SMILES: O=C(NCc1ccccc1)[C@H]1CCCN1c1nc2ncnc(N3CCCOCC3)c2s1] | Reference Example 168 (280 mg) | 140 mg | 439 |
| 5 | 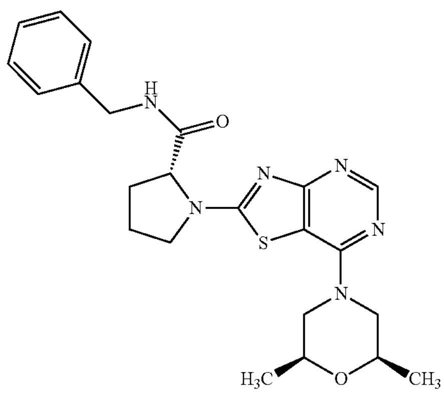 [SMILES: C[C@@H]1CN(c2ncnc3nc(N4CCC[C@@H]4C(=O)NCc4ccccc4)sc23)C[C@H](C)O1] | Reference Example 169 (293 mg) | 210 mg | 453 |
| 6 | 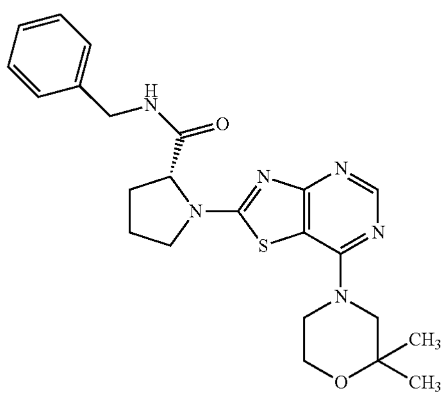 [SMILES: CC1(C)CN(c2ncnc3nc(N4CCC[C@@H]4C(=O)NCc4ccccc4)sc23)CCO1] | Reference Example 170 (280 mg) | 140 mg | 453 |
| 7 | 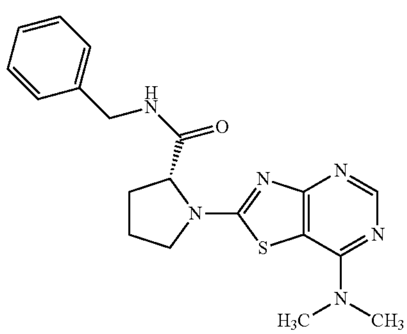 [SMILES: CN(C)c1ncnc2nc(N3CCC[C@@H]3C(=O)NCc3ccccc3)sc12] | Reference Example 171 (220 mg) | 197 mg | 383 |

TABLE 1-continued

| Example | structure | starting material | yield | MS(ESI) m/z [M + H]+ |
|---|---|---|---|---|
| 8 | 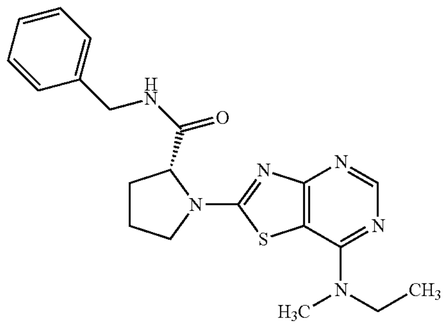 | Reference Example 172 (186 mg) | 187 mg | 397 |
| 9 | 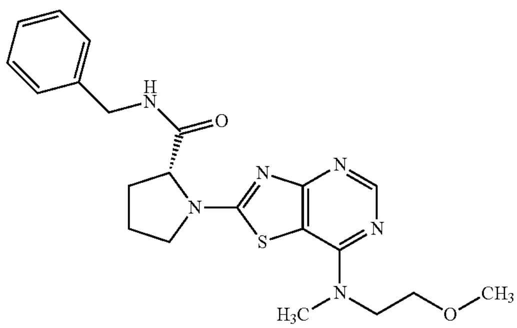 [SMILES: COCCN(C)c1ncnc2nc(N3CCC[C@@H]3C(=O)NCc3ccccc3)sc12] | Reference Example 173 (140 mg) | 176 mg | 427 |
| 10 | 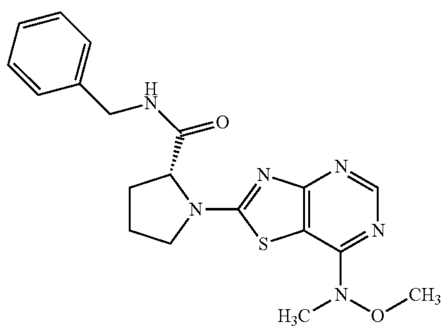 [SMILES: CON(C)c1ncnc2nc(N3CCC[C@@H]3C(=O)NCc3ccccc3)sc12] | Reference Example 174 (260 mg) | 260 mg | 399 |
| 11 | 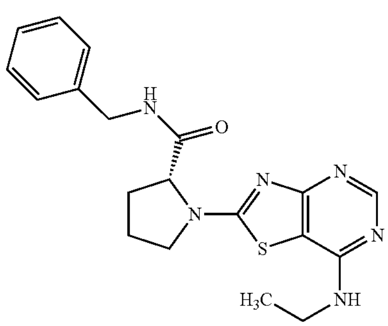 [SMILES: CCNc1ncnc2nc(N3CCC[C@@H]3C(=O)NCc3ccccc3)sc12] | Reference Example 175 (100 mg) | 81.0 mg | 383 |

TABLE 1-continued

| Example | structure | starting material | yield | MS(ESI) m/z [M + H]+ |
|---|---|---|---|---|
| 12 | 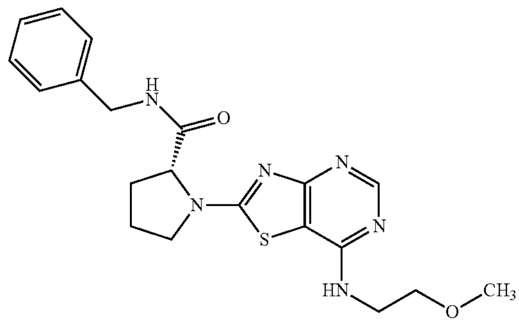 [SMILES: COCCNc1ncnc2nc(N3CCC[C@@H]3C(=O)NCc3ccccc3)sc12] | Reference Example 176 (117 mg) | 106 mg | 413 |
| 13 | 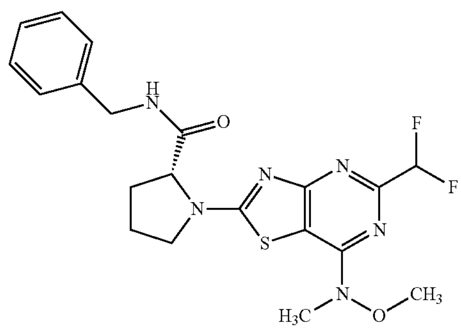 [SMILES: CON(C)c1nc(C(F)F)nc2nc(N3CCC[C@@H]3C(=O)NCc3ccccc3)sc12] | Reference Example 177 (240 mg) | 180 mg | 449 |
| 14 | 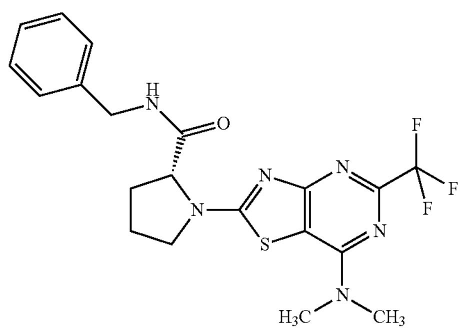 [SMILES: CN(C)c1nc(C(F)(F)F)nc2nc(N3CCC[C@@H]3C(=O)NCc3ccccc3)sc12] | Reference Example 178 (160 mg) | 130 mg | 451 |
| 15 | 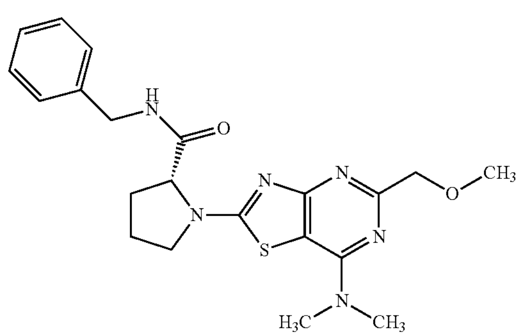 [SMILES: COCc1nc(N(C)C)c2sc(N3CCC[C@@H]3C(=O)NCc3ccccc3)nc2n1] | Reference Example 179 (300 mg) | 180 mg | 427 |

TABLE 1-continued

| Example | structure | starting material | yield | MS(ESI) m/z [M + H]+ |
|---|---|---|---|---|
| 16 | 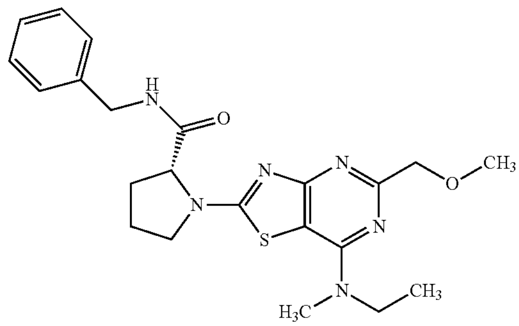 [SMILES: CCN(C)c1nc(COC)nc2nc(N3CCC[C@@H]3C(=O)NCc3ccccc3)sc12] | Reference Example 180 (280 mg) | 260 mg | 441 |
| 17 | 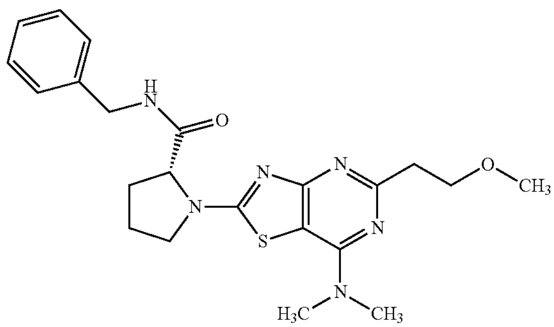 [SMILES: COCCc1nc(N(C)C)c2sc(N3CCC[C@@H]3C(=O)NCc3ccccc3)nc2n1] | Reference Example 181 (260 mg) | 100 mg | 441 |
| 18 | 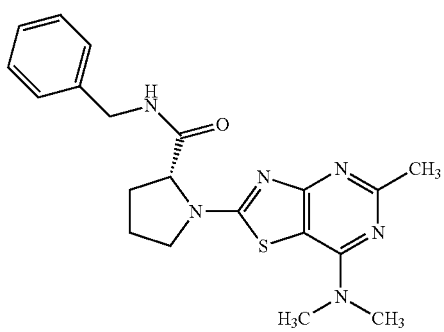 [SMILES: Cc1nc(N(C)C)c2sc(N3CCC[C@@H]3C(=O)NCc3ccccc3)nc2n1] | Reference Example 182 (190 mg) | 210 mg | 397 |

Example 19

(R)—N-benzyl-1-(7-ethoxy[1,3]thiazolo[4,5-d]pyrimidin-2-yl)pyrrolidine-2-carboxamide

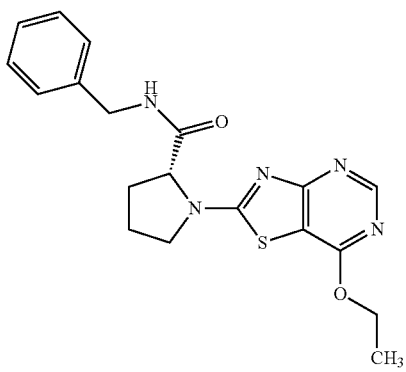 [SMILES: CCOc1ncnc2nc(N3CCC[C@@H]3C(=O)NCc3ccccc3)sc12]

A mixture of the compound (650 mg) obtained in Reference Example 165, the compound (700 mg) obtained in Reference Example 471, N,N-diisopropylethylamine (1.88 g) and 1,4-dioxane (5.00 mL) was stirred with heating at 65° C. for 1 hr. After confirmation of the completion of the reaction, under ice-cooling, water was added to the reaction mixture, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=70/30-30/70). To the obtained resultant product was added diisopropy ether, m and the solid was collected by filtration to give the title compound (760 mg).

MS(ESI)m/z; 384[M+H]+

Examples 20 to 22 are shown below. These compounds were obtained by a method similar to that in Example 19 except that the starting materials in the following Table were used instead of Reference Example 165.

TABLE 2
| Example | structure | starting material | yield | MS(ESI) m/z [M + H]+ |
|---|---|---|---|---|
| 20 | 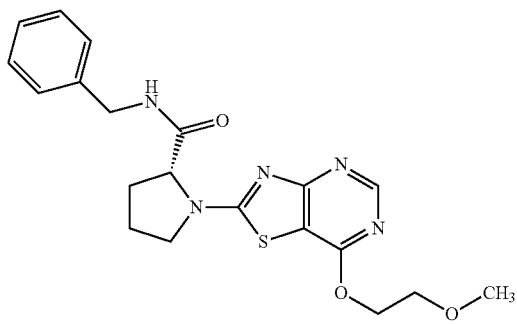 [SMILES: COCCOc1ncnc2nc(N3CCC[C@@H]3C(=O)NCc3ccccc3)sc12] | Reference Example 185 (187 mg) | 234 mg | 414 |
| 21 | 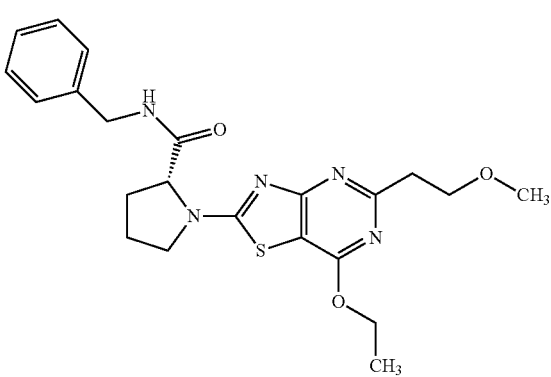 [SMILES: CCOc1nc(CCOC)nc2nc(N3CCC[C@@H]3C(=O)NCc3ccccc3)sc12] | Reference Example 187 (250 mg) | 180 mg | 442 |
| 22 | 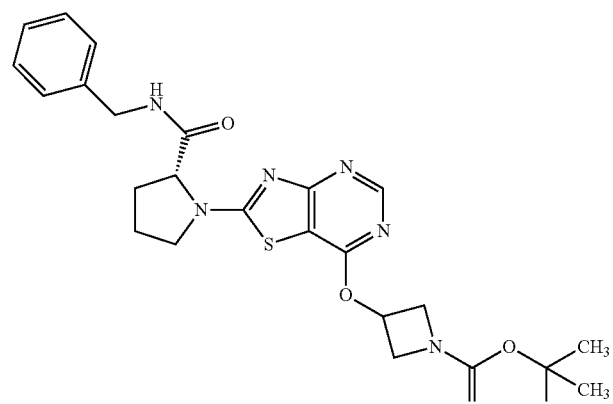 | Reference Example 188 (350 mg) | 377 mg | 511 |

Example 23

(R)—N-benzyl-1-(7-cyclopropyl[1,3]thiazolo[4,5-d]pyrimidin-2-yl)pyrrolidine-2-carboxamide

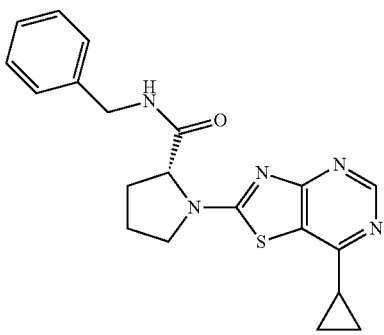

A mixture of the compound (167 mg) obtained in Reference Example 189, the compound (168 mg) obtained in Reference Example 471, N,N-diisopropylethylamine (271 mg) and THF (1.00 mL) was stirred with heating at 100° C. for 40 min. After confirmation of the completion of the reaction, under ice-cooling, water was added to the reaction mixture, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=60/40-0/100). To the obtained resultant product was added diisopropy ether, and the solid was collected by filtration to give the title compound (171 mg).

MS(ESI)m/z; 380[M+H]$^+$

Examples 24 to 62 are shown below. These compounds were obtained by a method similar to that in Example 23 except that the starting materials in the following Tables were used instead of Reference Example 189 and an appropriate compound was used instead of Reference Example 471 as necessary.

TABLE 3

| Example | structure | starting material | yield | MS (ESI) m/z [M + H]$^+$ |
|---|---|---|---|---|
| 24 | 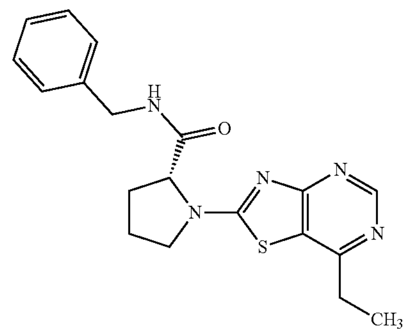 [SMILES: CCc1ncnc2nc(N3CCC[C@@H]3C(=O)NCc3ccccc3)sc12] | Reference Example 190 (130 mg) | 134 mg | 368 |
| 25 | 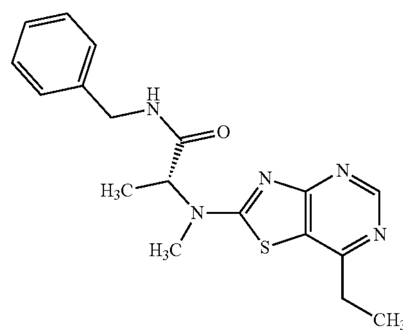 [SMILES: CCc1ncnc2nc(N(C)[C@H](C)C(=O)NCc3ccccc3)sc12] | Reference Example 190 (120 mg) | 80.0 mg | 356 |
| 26 | 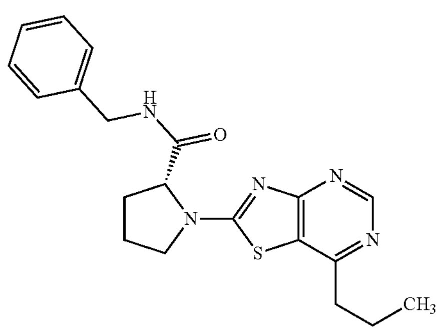 [SMILES: CCCc1ncnc2nc(N3CCC[C@@H]3C(=O)NCc3ccccc3)sc12] | Reference Example 191 (168 mg) | 152 mg | 382 |

TABLE 3-continued

| Example | structure | starting material | yield | MS (ESI) m/z [M + H]+ |
|---|---|---|---|---|
| 27 | 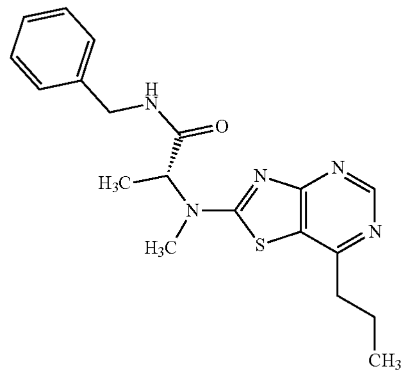 [SMILES: CCCc1ncnc2nc(N(C)[C@H](C)C(=O)NCc3ccccc3)sc12] | Reference Example 191 (150 mg) | 90.0 mg | 370 |
| 28 | 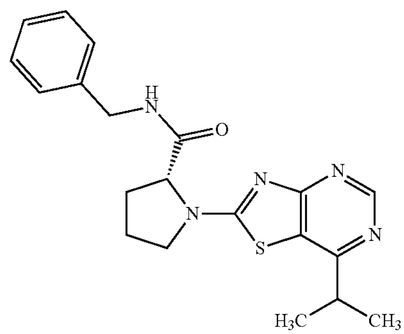 [SMILES: CC(C)c1ncnc2nc(N3CCC[C@@H]3C(=O)NCc3ccccc3)sc12] | Reference Example 192 (159 mg) | 152 mg | 382 |
| 29 | 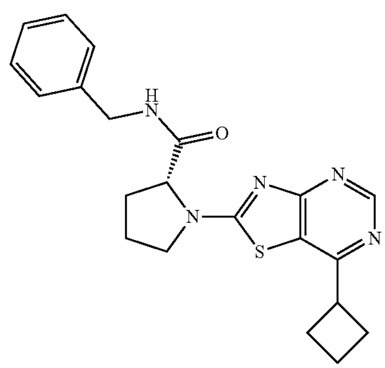 [SMILES: O=C(NCc1ccccc1)[C@H]1CCCN1c1nc2ncnc(C3CCC3)c2s1] | Reference Example 193 (160 mg) | 151 mg | 394 |
| 30 | 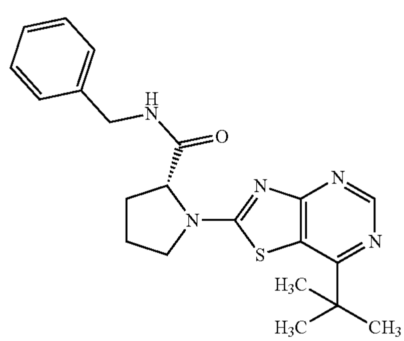 [SMILES: CC(C)(C)c1ncnc2nc(N3CCC[C@@H]3C(=O)NCc3ccccc3)sc12] | Reference Example 194 (300 mg) | 190 mg | 396 |

TABLE 3-continued

| Example | structure | starting material | yield | MS (ESI) m/z [M + H]+ |
|---|---|---|---|---|
| 31 | 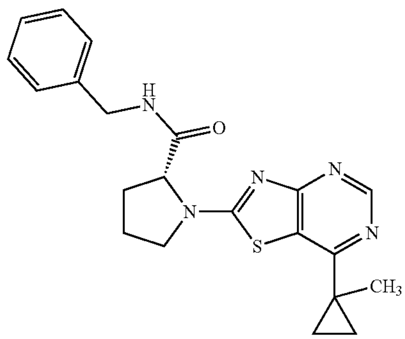 [SMILES: CC1(c2ncnc3nc(N4CCC[C@@H]4C(=O)NCc4ccccc4)sc23)CC1] | Reference Example 195 (300 mg) | 300 mg | 394 |
| 32 | 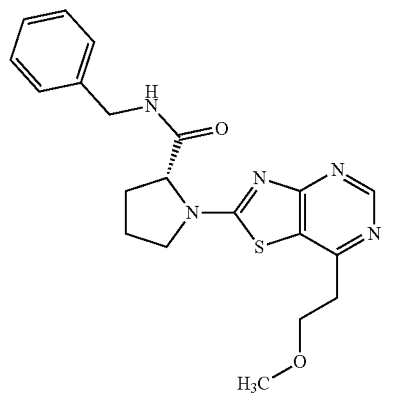 [SMILES: COCCc1ncnc2nc(N3CCC[C@@H]3C(=O)NCc3ccccc3)sc12] | Reference Example 196 (100 mg) | 80.0 mg | 398 |
| 33 | 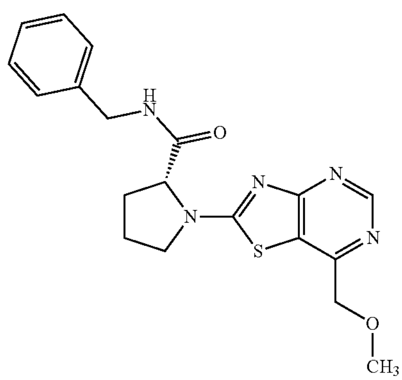 [SMILES: COCc1ncnc2nc(N3CCC[C@@H]3C(=O)NCc3ccccc3)sc12] | Reference Example 197 (140 mg) | 166 mg | 384 |
| 34 | 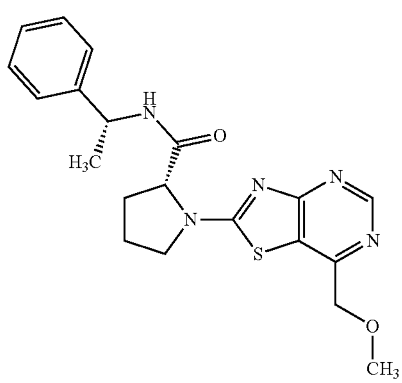 [SMILES: COCc1ncnc2nc(N3CCC[C@@H]3C(=O)N[C@H](C)c3ccccc3)sc12] | Reference Example 197 (137 mg) | 175 mg | 398 |

TABLE 3-continued

| Example | structure | starting material | yield | MS (ESI) m/z [M + H]+ |
|---|---|---|---|---|
| 35 | 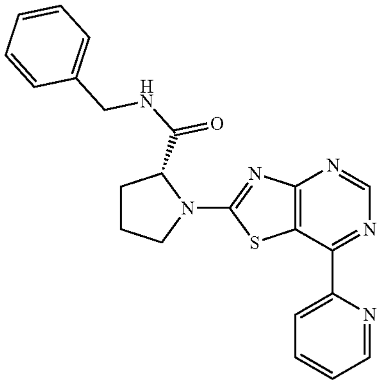 [SMILES: O=C(NCc1ccccc1)[C@H]1CCCN1c1nc2ncnc(-c3ccccn3)c2s1] | Reference Example 198 (150 mg) | 115 mg | 417 |
| 36 | 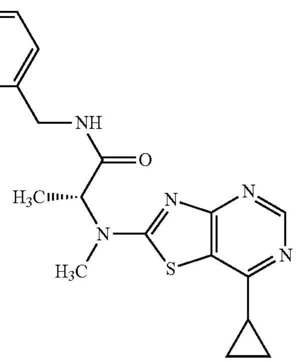 | Reference Example 189 (100 mg) | 60.0 mg | 368 |
| 37 | 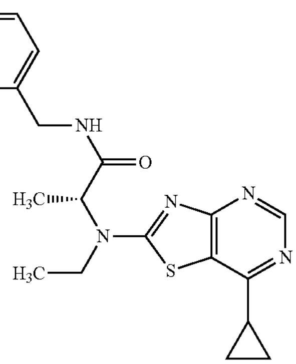 | Reference Example 189 (153 mg) | 35.0 mg | 382 |
| 38 | 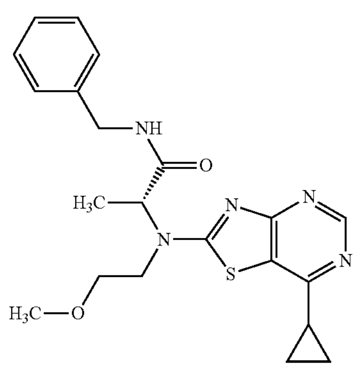 [SMILES: COCCN(c1nc2ncnc(C3CC3)c2s1)[C@H](C)C(=O)NCc1ccccc1] | Reference Example 189 (100 mg) | 7.50 mg | 412 |

TABLE 3-continued

| Example | structure | starting material | yield | MS (ESI) m/z [M + H]+ |
|---|---|---|---|---|
| 39 | 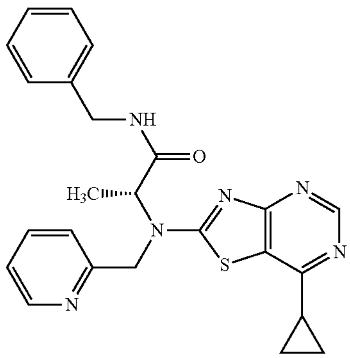 [SMILES: C[C@H](C(=O)NCc1ccccc1)N(Cc1ccccn1)c1nc2ncnc(C3CC3)c2s1] | Reference Example 189 (209 mg) | 15.0 mg | 445 |
| 40 | 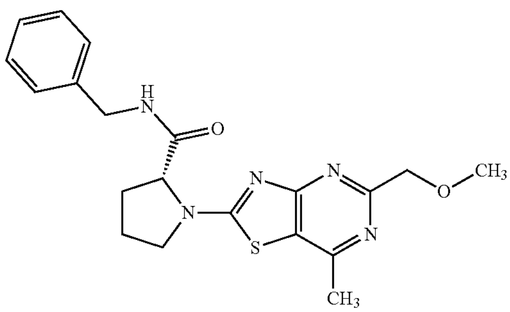 [SMILES: COCc1nc(C)c2sc(N3CCC[C@@H]3C(=O)NCc3ccccc3)nc2n1] | Reference Example 199 (55.0 mg) | 62.0 mg | 398 |
| 41 | 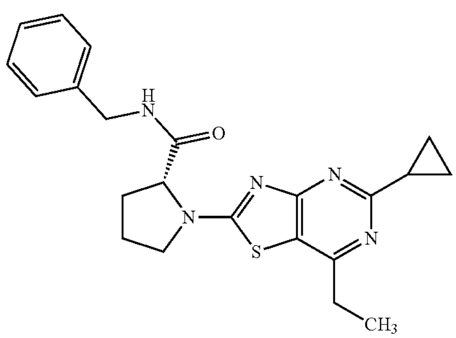 [SMILES: CCc1nc(C2CC2)nc2nc(N3CCC[C@@H]3C(=O)NCc3ccccc3)sc12] | Reference Example 201 (202 mg) | 229 mg | 408 |
| 42 | 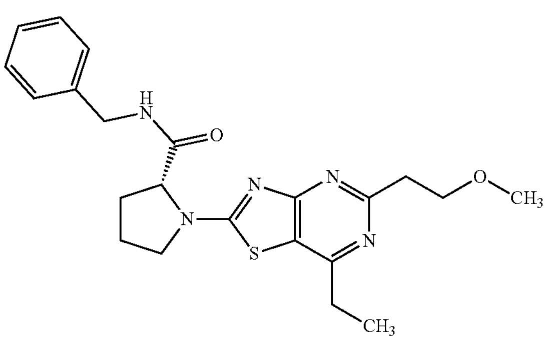 [SMILES: CCc1nc(CCOC)nc2nc(N3CCC[C@@H]3C(=O)NCc3ccccc3)sc12] | Reference Example 202 (250 mg) | 170 mg | 426 |

TABLE 3-continued

| Example | structure | starting material | yield | MS (ESI) m/z [M + H]+ |
|---|---|---|---|---|
| 43 | 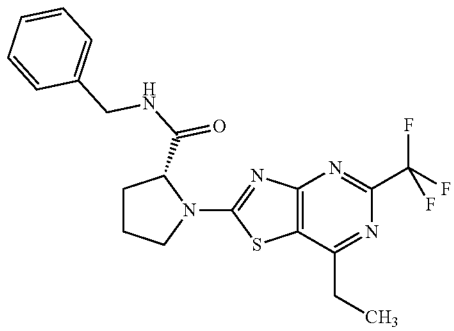 [SMILES: CCc1nc(C(F)(F)F)nc2nc(N3CCC[C@@H]3C(=O)NCc3ccccc3)sc12] | Reference Example 203 (230 mg) | 110 mg | 436 |
| 44 | 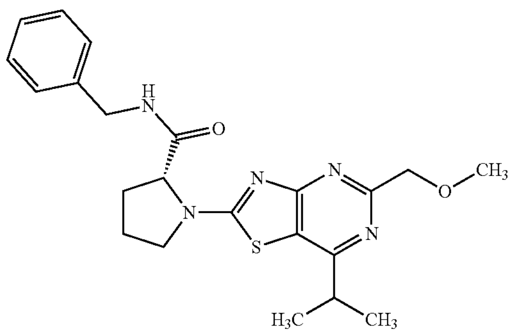 [SMILES: COCc1nc(C(C)C)c2sc(N3CCC[C@@H]3C(=O)NCc3ccccc3)nc2n1] | Reference Example 204 (75.0 mg) | 66.0 mg | 426 |
| 45 | 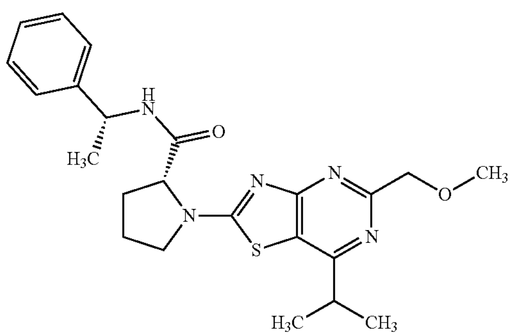 [SMILES: COCc1nc(C(C)C)c2sc(N3CCC[C@@H]3C(=O)N[C@H](C)c3ccccc3)nc2n1] | Reference Example 204 (75.0 mg) | 67.0 mg | 440 |
| 46 | 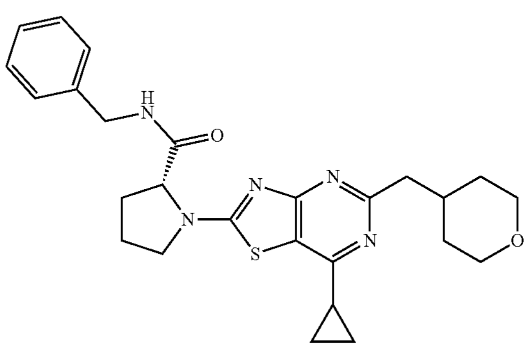 [SMILES: O=C(NCc1ccccc1)[C@H]1CCCN1c1nc2nc(CC3CCOCC3)nc(C3CC3)c2s1] | Reference Example 206 (197 mg) | 169 mg | 478 |

TABLE 3-continued

| Example | structure | starting material | yield | MS (ESI) m/z [M + H]+ |
|---|---|---|---|---|
| 47 | 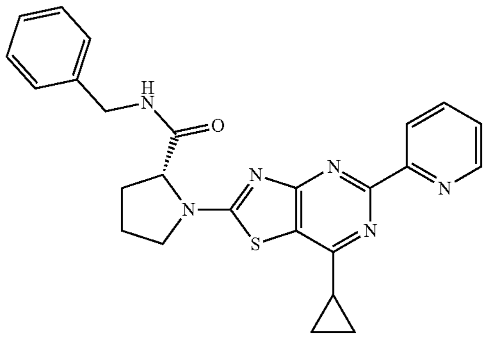 [SMILES: O=C(NCc1ccccc1)[C@H]1CCCN1c1nc2nc(-c3ccccn3)nc(C3CC3)c2s1] | Reference Example 207 (260 mg) | 170 mg | 457 |
| 48 | 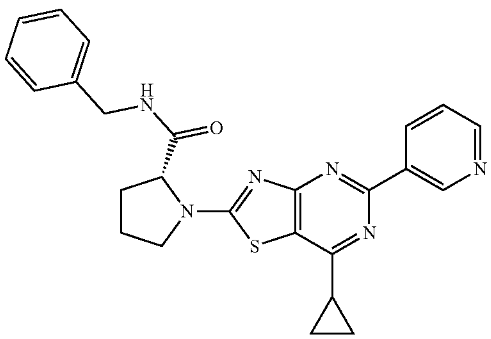 [SMILES: O=C(NCc1ccccc1)[C@H]1CCCN1c1nc2nc(-c3cccnc3)nc(C3CC3)c2s1] | Reference Example 208 (198 mg) | 194 mg | 457 |
| 49 | 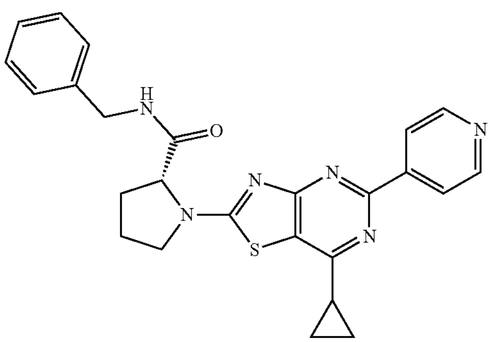 [SMILES: O=C(NCc1ccccc1)[C@H]1CCCN1c1nc2nc(-c3ccncc3)nc(C3CC3)c2s1] | Reference Example 209 (86.5 mg) | 96.8 mg | 457 |
| 50 | 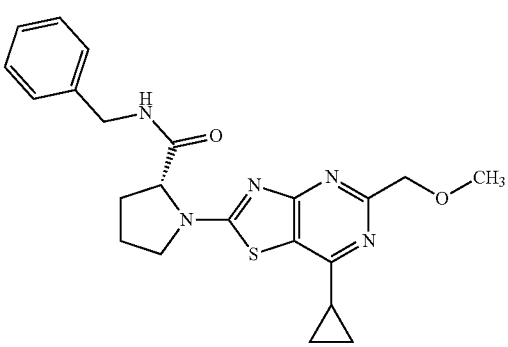 [SMILES: COCc1nc(C2CC2)c2sc(N3CCC[C@@H]3C(=O)NCc3ccccc3)nc2n1] | Reference Example 210 (135 mg) | 143 mg | 424 |

TABLE 3-continued
| Example | structure | starting material | yield | MS (ESI) m/z [M + H]+ |
|---|---|---|---|---|
| 51 | 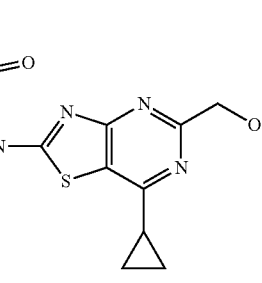 | Reference Example 210 (135 mg) | 161 mg | 438 |
| 52 | 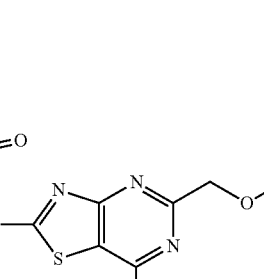 | Reference Example 211 (126 mg) | 131 mg | 452 |
| 53 | 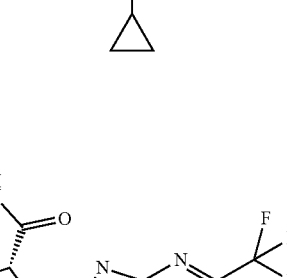 | Reference Example 212 (147 mg) | 81.0 mg | 452 |
| 54 | 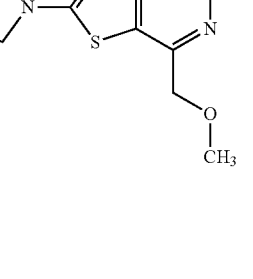 | Reference Example 213 (180 mg) | 175 mg | 424 |

TABLE 3-continued

| Example | structure | starting material | yield | MS (ESI) m/z [M + H]+ |
|---|---|---|---|---|
| 55 | 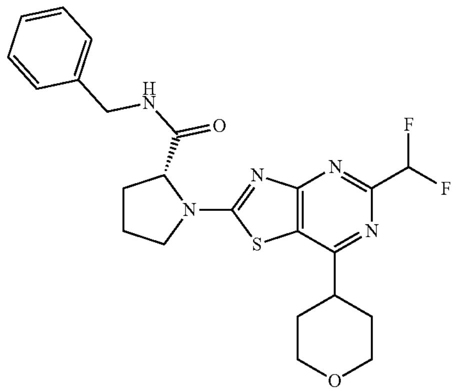 [SMILES: O=C(NCc1ccccc1)[C@H]1CCCN1c1nc2nc(C(F)F)nc(C3CCOCC3)c2s1] | Reference Example 214 (170 mg) | 70.0 mg | 474 |
| 56 | 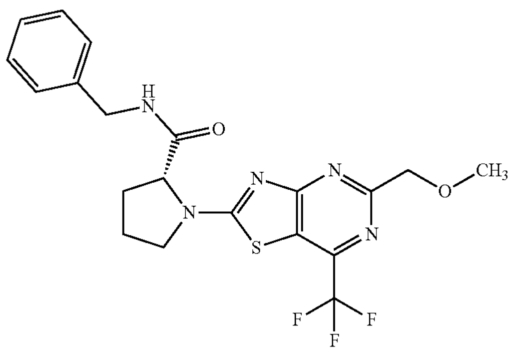 [SMILES: COCc1nc(C(F)(F)F)c2sc(N3CCC[C@@H]3C(=O)NCc3ccccc3)nc2n1] | Reference Example 215 (90.0 mg) | 48.0 mg | 452 |
| 57 | 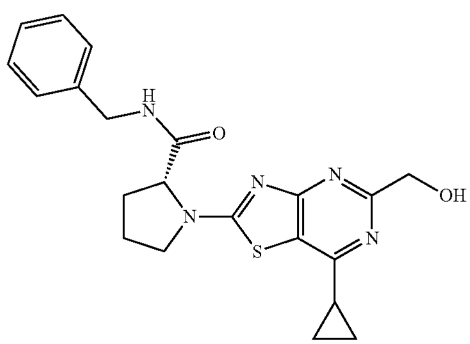 [SMILES: O=C(NCc1ccccc1)[C@H]1CCCN1c1nc2nc(CO)nc(C3CC3)c2s1] | Reference Example 216 (283 mg) | 336 mg | 410 |
| 58 | 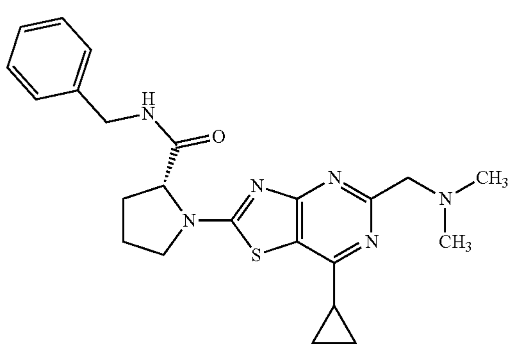 [SMILES: CN(C)Cc1nc(C2CC2)c2sc(N3CCC[C@@H]3C(=O)NCc3ccccc3)nc2n1] | Reference Example 221 (95.0 mg) | 82.0 mg | 437 |

TABLE 3-continued
| Example | structure | starting material | yield | MS (ESI) m/z [M + H]+ |
|---|---|---|---|---|
| 59 | 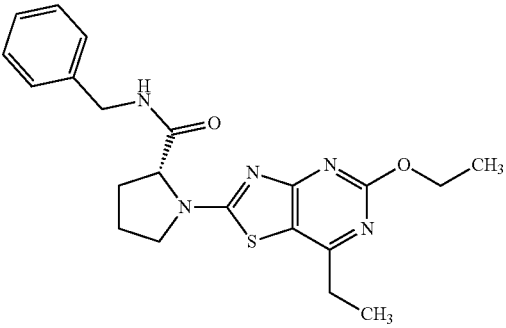 [SMILES: CCOc1nc(CC)c2sc(N3CCC[C@@H]3C(=O)NCc3ccccc3)nc2n1] | Reference Example 217 (197 mg) | 204 mg | 412 |
| 60 | 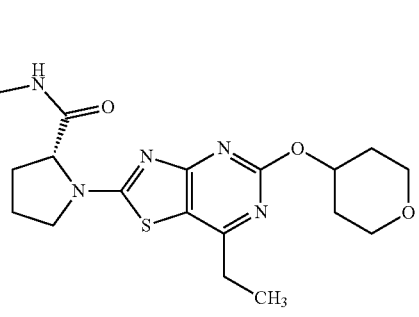 | Reference Example 218 (136 mg) | 72.4 mg | 468 |
| 61 | 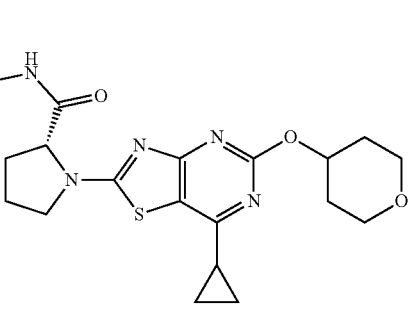 | Reference Example 219 (124 mg) | 144 mg | 480 |
| 62 | 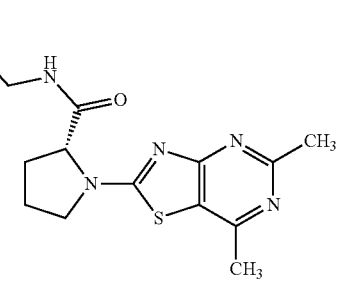 | Reference Example 220 (170 mg) | 175 mg | 368 |

Example 63

(R)-1-[7-(azetidin-1-yl)[1,3]thiazolo[4,5-d]pyrimidin-2-yl]-N-benzylpyrrolidine-2-carboxamide

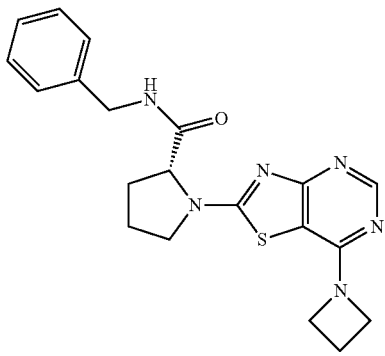 [SMILES: O=C(NCc1ccccc1)[C@H]1CCCN1c1nc2ncnc(N3CCC3)c2s1]

To a methylene chloride solution (10.0 mL) of the compound (57.0 mg) obtained in Reference Example 93 was added, under ice-cooling, mCPBA (69-75% w/w, 60.0 mg), and the reaction mixture was stirred at room temperature for 2 hr. To the reaction mixture were added aqueous sodium thiosulfate solution and saturated aqueous sodium hydrogen carbonate solution, and the mixture was extracted twice with chloroform. The organic layer was dried over anhydrous sodium sulfate, filtered and concentrated. To the obtained residue were added the compound (70.0 mg) obtained in Reference Example 471, N,N-diisopropylethylamine (0.21 mL) and 1,4-dioxane (1.00 mL), and the reaction mixture was stirred with heating at 120° C. for 6 hr. After confirmation of the completion of the reaction, under ice-cooling, water was added to the reaction mixture, and the mixture was extracted twice with chloroform. The combined organic layer was washed with saturated brine, dried over anhydrous sodium sulfate, filtered and concentrated. The obtained residue was purified by silica gel column chromatography (solvent; ethyl acetate/methanol=100/0-90/10). To the obtained resultant product was added diisopropy ether, and the solid was collected by filtration to give the title compound (100 mg).

MS(ESI)m/z; 395[M+H]$^+$

Examples 64 to 67 are shown below. These compounds were obtained by a method similar to that in Example 63 except that the starting materials in the following Table were used instead of Reference Example 93.

TABLE 4

| Example | structure | starting material | yield | MS (ESI) m/z [M + H]$^+$ |
|---|---|---|---|---|
| 64 | 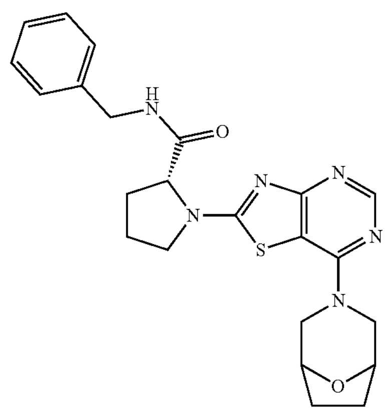 [SMILES: O=C(NCc1ccccc1)[C@H]1CCCN1c1nc2ncnc(N3CC4CCC(C3)O4)c2s1] | Reference Example 94 (224 mg) | 253 mg | 451 |
| 65 | 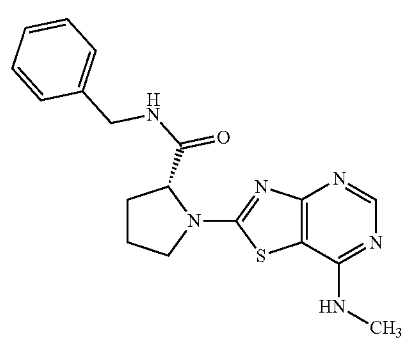 [SMILES: CNc1ncnc2nc(N3CCC[C@@H]3C(=O)NCc3ccccc3)sc12] | Reference Example 95 (188 mg) | 14.0 mg | 369 |

TABLE 4-continued

| Example | structure | starting material | yield | MS (ESI) m/z [M + H]+ |
|---|---|---|---|---|
| 66 | 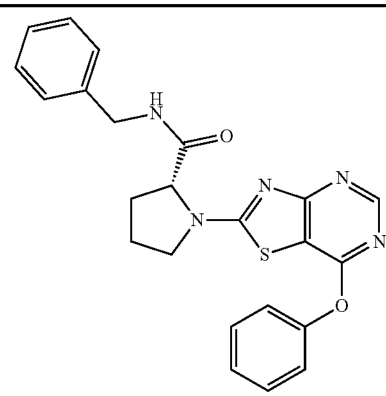 | Reference Example 103 (210 mg) | 180 mg | 432 |
| 67 | 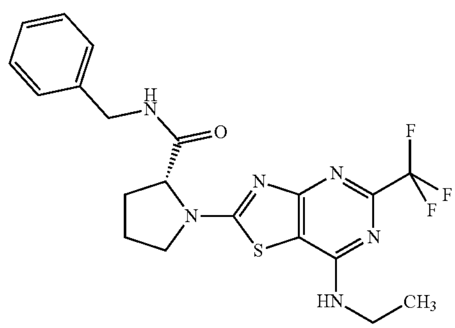 [SMILES: CCNc1nc(C(F)(F)F)nc2nc(N3CCC[C@@H]3C(=O)NCc3ccccc3)sc12] | Reference Example 95 (220 mg) | 60.0 mg | 451 |

Example 68

(R)—N-benzyl-1-{7-[(propan-2-yl)oxy][1,3]thiazolo[4,5-d]pyrimidin-2-yl}pyrrolidine-2-carboxamide

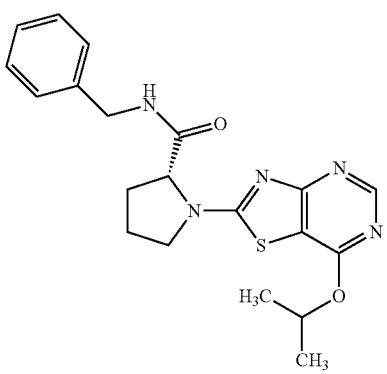 [SMILES: CC(C)Oc1ncnc2nc(N3CCC[C@@H]3C(=O)NCc3ccccc3)sc12]

To a methylene chloride solution (5.00 mL) of the compound (965 mg) obtained in Reference Example 113 was added, under ice-cooling, mCPBA (69-75% w/w, 101 mg), and the reaction mixture was stirred at room temperature for 1 hr. To the reaction mixture were added aqueous sodium thiosulfate solution and saturated aqueous sodium hydrogen carbonate solution, and the mixture was extracted twice with chloroform. The organic layer was dried over anhydrous sodium sulfate, filtered and concentrated. To the obtained residue were added the compound (96.3 mg) obtained in Reference Example 471, N,N-diisopropylethylamine (0.21 mL) and THF (1.00 mL), and the reaction mixture was stirred with heating at 100° C. for 2 hr. After confirmation of the completion of the reaction, under ice-cooling, water was added to the reaction mixture, and the mixture was extracted twice with chloroform. The combined organic layer was washed with saturated brine, dried over anhydrous sodium sulfate, filtered and concentrated. The obtained residue was purified by silica gel column chromatography (solvent; hexane/ethyl acetate=50/50-0/100). To the obtained resultant product was added diisopropy ether, and the solid was collected by filtration to give the title compound (65.0 mg).

MS(ESI)m/z; 398[M+H]+

Examples 69 to 75 are shown below. These compounds were obtained by a method similar to that in Example 68 except that the starting materials in the following Tables were used instead of Reference Example 113.

TABLE 5

| Example | structure | starting material | yield | MS (ESI) m/z [M + H]+ |
|---|---|---|---|---|
| 69 | 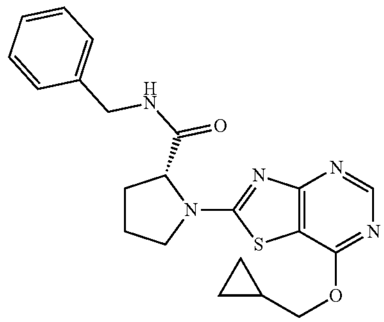 [SMILES: O=C(NCc1ccccc1)[C@H]1CCCN1c1nc2ncnc(OCC3CC3)c2s1] | Reference Example 114 (89.9 mg) | 66.7 mg | 410 |
| 70 | 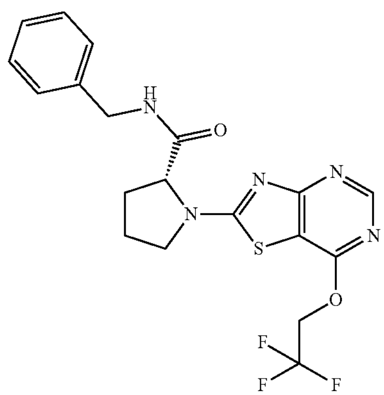 [SMILES: O=C(NCc1ccccc1)[C@H]1CCCN1c1nc2ncnc(OCC(F)(F)F)c2s1] | Reference Example 110 (160 mg) | 90.0 mg | 438 |
| 71 | 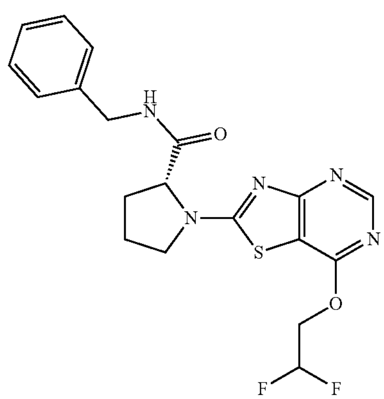 [SMILES: O=C(NCc1ccccc1)[C@H]1CCCN1c1nc2ncnc(OCC(F)F)c2s1] | Reference Example 111 (500 mg) | 275 mg | 420 |
| 72 | 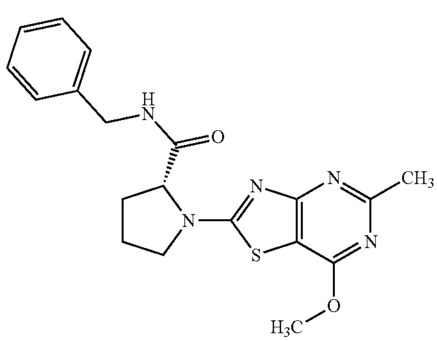 [SMILES: COc1nc(C)nc2nc(N3CCC[C@@H]3C(=O)NCc3ccccc3)sc12] | Reference Example 115 (54.1 mg) | 57.7 mg | 384 |

TABLE 5-continued

| Example | structure | starting material | yield | MS (ESI) m/z [M + H]+ |
|---|---|---|---|---|
| 73 | 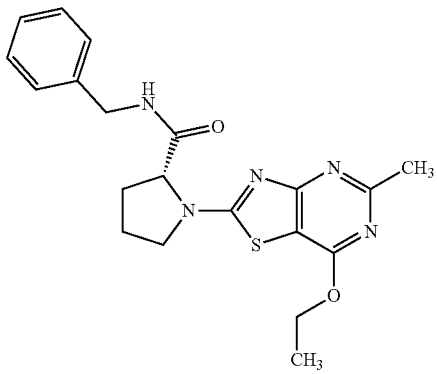 [SMILES: CCOc1nc(C)nc2nc(N3CCC[C@@H]3C(=O)NCc3ccccc3)sc12] | Reference Example 116 (157 mg) | 181 mg | 398 |
| 74 | 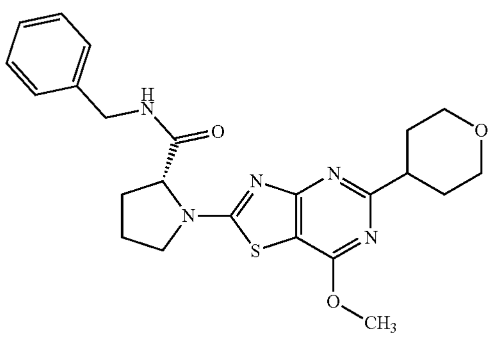 [SMILES: COc1nc(C2CCOCC2)nc2nc(N3CCC[C@@H]3C(=O)NCc3ccccc3)sc12] | Reference Example 117 (115 mg) | 103 mg | 454 |
| 75 | 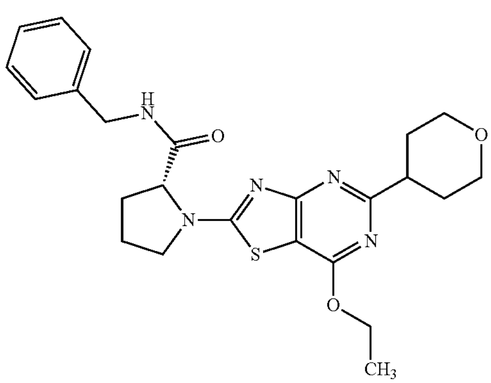 [SMILES: CCOc1nc(C2CCOCC2)nc2nc(N3CCC[C@@H]3C(=O)NCc3ccccc3)sc12] | Reference Example 118 (142 mg) | 140 mg | 468 |

Example 76

(R)—N-benzyl-1-[7-(2-cyanopropan-2-yl)[1,3]thiazolo[4,5-d]pyrimidin-2-yl]pyrrolidine-2-carboxamide

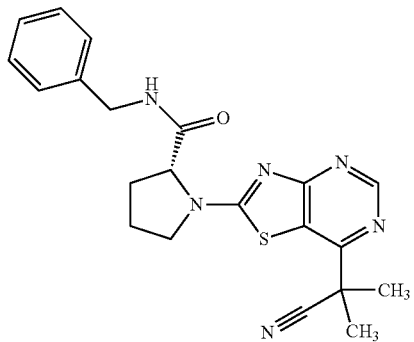 [SMILES: CC(C)(C#N)c1ncnc2nc(N3CCC[C@@H]3C(=O)NCc3ccccc3)sc12]

To a methylene chloride solution (5.00 mL) of the compound (53.0 mg) obtained in Reference Example 129 was added, under ice-cooling, mCPBA (69-75% w/w, 50.0 mg), and the reaction mixture was stirred at room temperature for 1 hr. To the reaction mixture were added aqueous sodium thiosulfate solution and saturated aqueous sodium hydrogen carbonate solution, and the mixture was extracted twice with chloroform. The organic layer was dried over anhydrous sodium sulfate, filtered and concentrated. To the obtained residue were added the compound (60.0 mg) obtained in Reference Example 471, N,N-diisopropylethylamine (0.190 mL) and 1,4-dioxane (1.00 mL), and the reaction mixture was stirred with heating at 120° C. for 1 hr. After confirmation of the completion of the reaction, under ice-cooling, water was added to the reaction mixture, and the mixture was extracted twice with chloroform. The combined organic layer was washed with saturated brine, dried over anhydrous sodium sulfate, filtered and concentrated. The obtained residue was purified by silica gel column chromatography (solvent; hexane/ethyl acetate=70/30-0/100). To the obtained resultant product was added diisopropy ether, and the solid was collected by filtration to give the title compound (34.0 mg).

MS(ESI)m/z; 407[M+H]$^+$

Examples 77 to 88 are shown below. These compounds were obtained by a method similar to that in Example 76 except that the starting materials in the following Tables were used instead of Reference Example 129.

TABLE 6

| Example | structure | starting material | yield | MS (ESI) m/z [M + H]$^+$ |
|---|---|---|---|---|
| 77 | 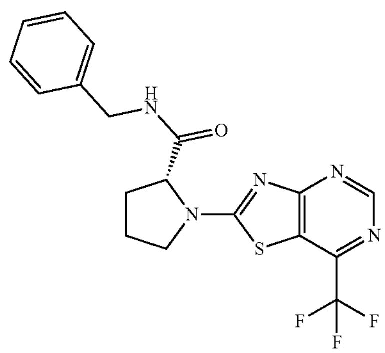 [SMILES: O=C(NCc1ccccc1)[C@H]1CCCN1c1nc2ncnc(C(F)(F)F)c2s1] | Reference Example 130 (113 mg) | 9.70 mg | 408 |
| 78 | 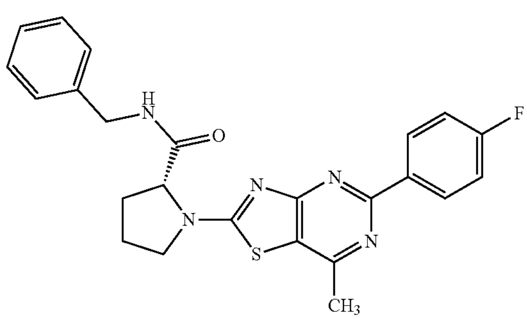 [SMILES: Cc1nc(-c2ccc(F)cc2)nc2nc(N3CCC[C@@H]3C(=O)NCc3ccccc3)sc12] | Reference Example 148 (130 mg) | 108 mg | 448 |

TABLE 6-continued

| Example | structure | starting material | yield | MS (ESI) m/z [M + H]+ |
|---|---|---|---|---|
| 79 | 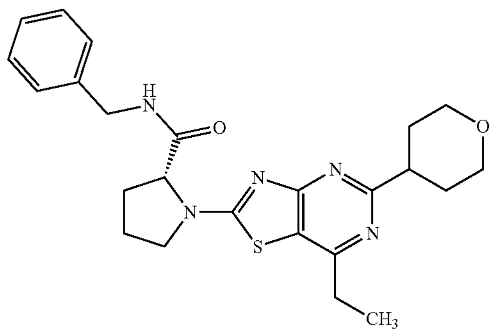 [SMILES: CCc1nc(C2CCOCC2)nc2nc(N3CCC[C@@H]3C(=O)NCc3ccccc3)sc12] | Reference Example 149 (416 mg) | 419 mg | 452 |
| 80 | 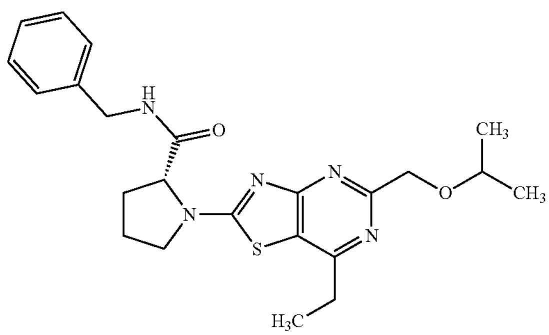 [SMILES: CCc1nc(COC(C)C)nc2nc(N3CCC[C@@H]3C(=O)NCc3ccccc3)sc12] | Reference Example 150 (230 mg) | 134 mg | 440 |
| 81 | 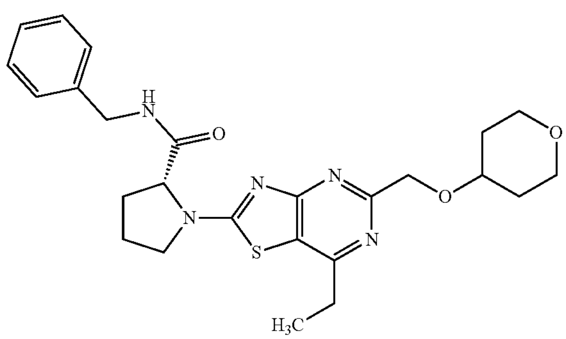 [SMILES: CCc1nc(COC2CCOCC2)nc2nc(N3CCC[C@@H]3C(=O)NCc3ccccc3)sc12] | Reference Example 151 (130 mg) | 165 mg | 482 |
| 82 | 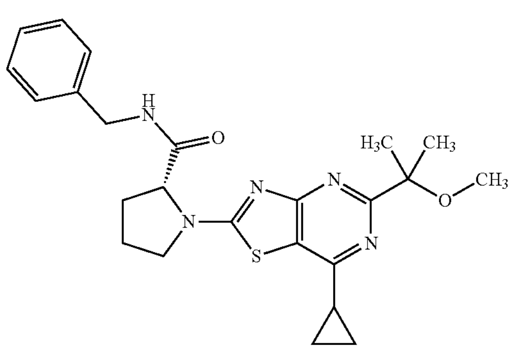 [SMILES: COC(C)(C)c1nc(C2CC2)c2sc(N3CCC[C@@H]3C(=O)NCc3ccccc3)nc2n1] | Reference Example 152 (142 mg) | 84.6 mg | 452 |

TABLE 6-continued

| Example | structure | starting material | yield | MS (ESI) m/z [M + H]+ |
|---|---|---|---|---|
| 83 | 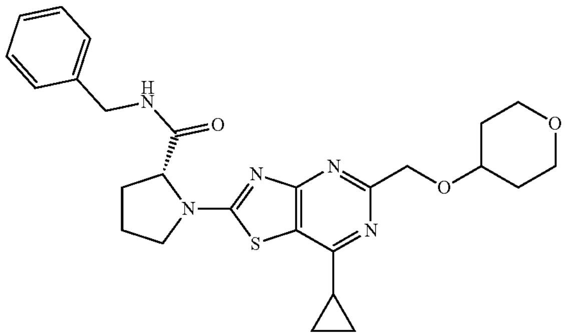 [SMILES: O=C(NCc1ccccc1)[C@H]1CCCN1c1nc2nc(COC3CCOCC3)nc(C3CC3)c2s1] | Reference Example 153 (51.0 mg) | 62.0 mg | 494 |
| 84 | 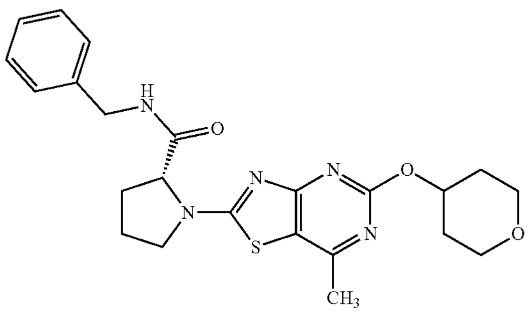 [SMILES: Cc1nc(OC2CCOCC2)nc2nc(N3CCC[C@@H]3C(=O)NCc3ccccc3)sc12] | Reference Example 156 (163 mg) | 109 mg | 454 |
| 85 | 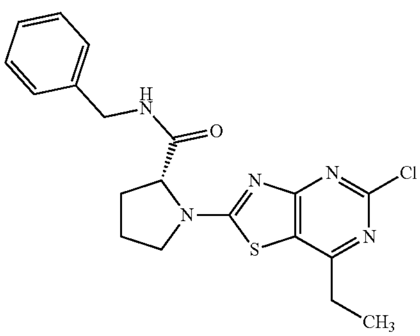 [SMILES: CCc1nc(Cl)nc2nc(N3CCC[C@@H]3C(=O)NCc3ccccc3)sc12] | Reference Example 161 (1.44 g) | 1.28 g | 402, 404 |
| 86 | 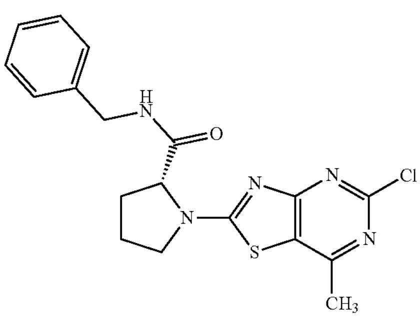 [SMILES: Cc1nc(Cl)nc2nc(N3CCC[C@@H]3C(=O)NCc3ccccc3)sc12] | Reference Example 160 (432 mg) | 470 mg | 388, 390 |

TABLE 6-continued

| Example | structure | starting material | yield | MS (ESI) m/z [M + H]+ |
|---|---|---|---|---|
| 87 | 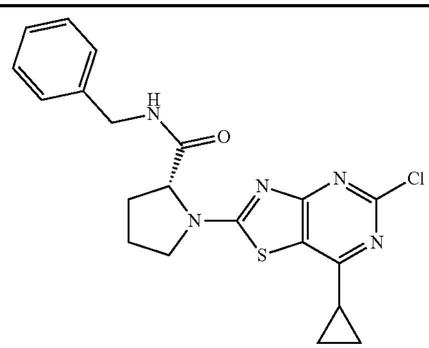 | Reference Example 162 (150 mg) | 77.0 mg | 414, 416 |
| 88 | 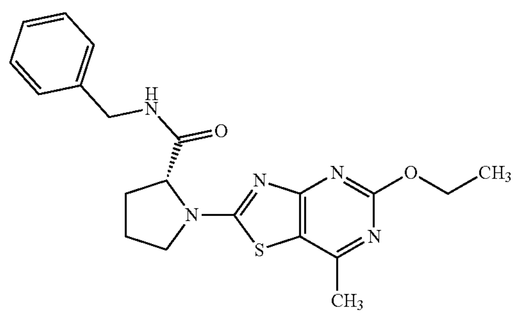 | Reference Example 164 (345 mg) | 427 mg | 398 |

Example 89

(R)—N-benzyl-1-[7-(cyclobutyloxy)[1,3]thiazolo[4,5-d]pyrimidin-2-yl]pyrrolidine-2-carboxamide

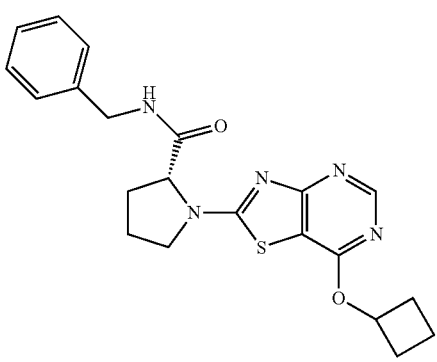 [SMILES: O=C(NCc1ccccc1)[C@H]1CCCN1c1nc2ncnc(OC3CCC3)c2s1]

To a DMF solution (13.0 mL) of the compound (260 mg) obtained in Reference Example 183 were added (D)-proline (230 mg) and potassium carbonate (420 mg), and the reaction mixture was stirred with heating at 70° C. for 1.5 hr. After cooling to room temperature, the reaction mixture was acidified with 1.0 mol/L hydrochloric acid, sodium chloride was added, and the mixture was extracted twice with chloroform. The organic layer was dried over anhydrous sodium sulfate, filtered and concentrated. To a DMF solution of the obtained residue were added N,N-diisopropylethylamine (210 mg), benzylamine (170 mg), EDC hydrochloride (300 mg) and HOBt monohydrate (240 mg), and the reaction mixture was stirred at room temperature overnight. Water was added, the mixture was extracted with ethyl acetate, and the organic layer was dried over anhydrous sodium sulfate, filtered and concentrated. The obtained residue was purified by silica gel column chromatography (solvent; ethyl acetate/methanol=100/0-95/5) to give the title compound (105 mg).

MS(ESI)m/z; 410[M+H]+

Examples 90 to 96 are shown below. These compounds were obtained by a method similar to that in Example 89 except that the starting materials in the following Tables were used instead of Reference Example 183 and an appropriate compound was used instead of (D)-proline and/or benzylamine as necessary.

TABLE 7

| Example | structure | starting material | yield | MS (ESI) m/z [M + H]⁺ |
|---|---|---|---|---|
| 90 | 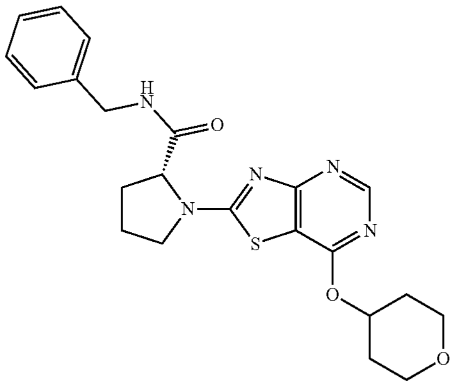 [SMILES: O=C(NCc1ccccc1)[C@H]1CCCN1c1nc2ncnc(OC3CCOCC3)c2s1] | Reference Example 184 (300 mg) | 270 mg | 440 |
| 91 | 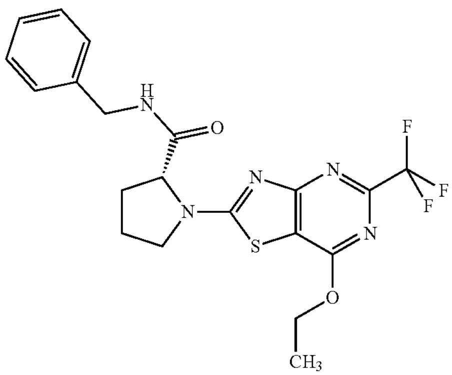 [SMILES: CCOc1nc(C(F)(F)F)nc2nc(N3CCC[C@@H]3C(=O)NCc3ccccc3)sc12] | Reference Example 186 (300 mg) | 170 mg | 452 |
| 92 | 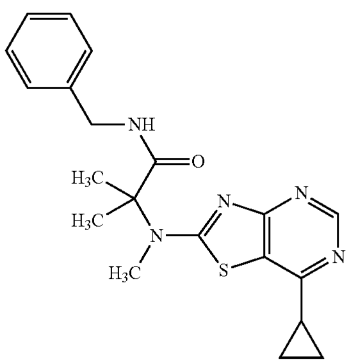 [SMILES: CN(c1nc2ncnc(C3CC3)c2s1)C(C)(C)C(=O)NCc1ccccc1] | Reference Example 189 (134 mg) | 35.0 mg | 382 |
| 93 | 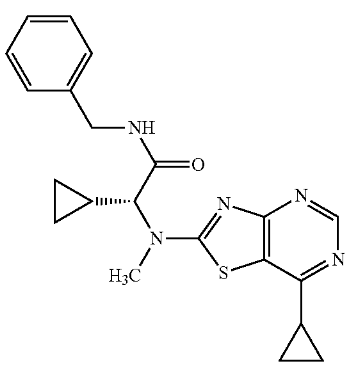 [SMILES: CN(c1nc2ncnc(C3CC3)c2s1)[C@@H](C(=O)NCc1ccccc1)C1CC1] | Reference Example 189 (100 mg) | 73.0 mg | 394 |

TABLE 7-continued

| Example | structure | starting material | yield | MS (ESI) m/z [M + H]+ |
|---|---|---|---|---|
| 94 | 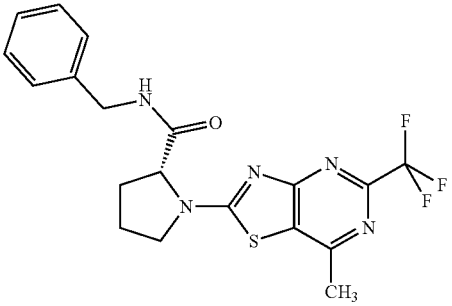 [SMILES: Cc1nc(C(F)(F)F)nc2nc(N3CCC[C@@H]3C(=O)NCc3ccccc3)sc12] | Reference Example 200 (280 mg) | 160 mg | 422 |
| 95 | 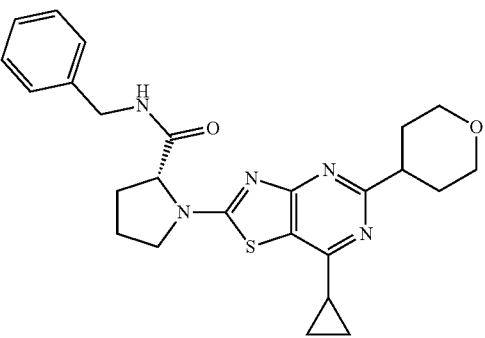 [SMILES: O=C(NCc1ccccc1)[C@H]1CCCN1c1nc2nc(C3CCOCC3)nc(C3CC3)c2s1] | Reference Example 205 (250 mg) | 257 mg | 464 |
| 96 | 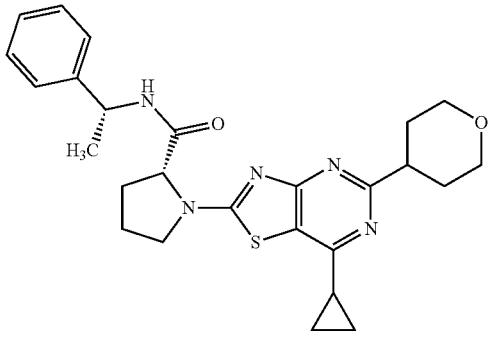 [SMILES: C[C@@H](NC(=O)[C@H]1CCCN1c1nc2nc(C3CCOCC3)nc(C3CC3)c2s1)c1ccccc1] | Reference Example 205 (250 mg) | 267 mg | 478 |

Example 97

(R)—N-benzyl-1-{7-cyclopropyl-5-[(piperidin-1-yl)methyl][1,3]thiazolo[4,5-d]pyrimidin-2-yl}pyrrolidine-2-carboxamide

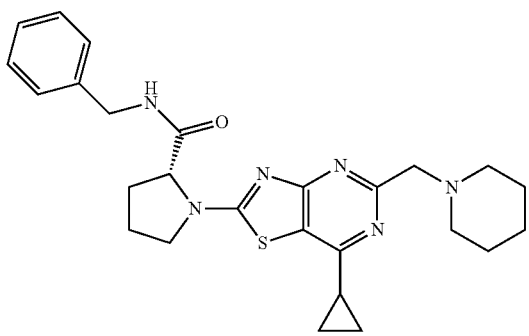 [SMILES: O=C(NCc1ccccc1)[C@H]1CCCN1c1nc2nc(CN3CCCCC3)nc(C3CC3)c2s1]

To a dichloromethane solution (1.00 mL) of the compound (100 mg) obtained in Example 57 were added, under ice-cooling, triethylamine (0.0410 mL) and methanesulfonyl chloride (0.0210 mL), and the reaction mixture was stirred at the same temperature for 1 hr. The reaction mixture was diluted with DMF (1.00 mL), added to a DMF solution (1.00 mL) of piperidine (0.0720 mL) at 0° C., and the mixture was stirred at room temperature for 1 hr. After confirmation of the completion of the reaction, saturated aqueous sodium hydrogen carbonate solution was added, and the mixture was extracted twice with chloroform. The combined organic layer was washed with saturated brine, dried over anhydrous sodium sulfate, filtered and concentrated. The obtained residue was purified by NH silica gel column chromatography (solvent; hexane/ethyl acetate=50/50-0/100) to give the title compound (64.0 mg).

MS(ESI)m/z; 477[M+H]+

Examples 98 and 99 are shown below. These compounds were obtained by a method similar to that in Example 97 except that an appropriate compound was used instead of piperidine.

TABLE 8

| Example | structure | starting material | yield | MS (ESI) m/z [M + H]+ |
|---|---|---|---|---|
| 98 | 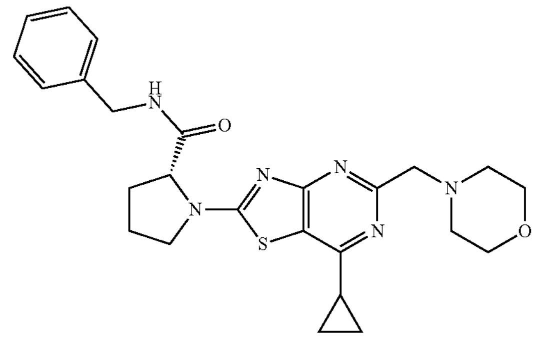 | Example 57 (100 mg) | 94.0 mg | 479 |
| 99 | 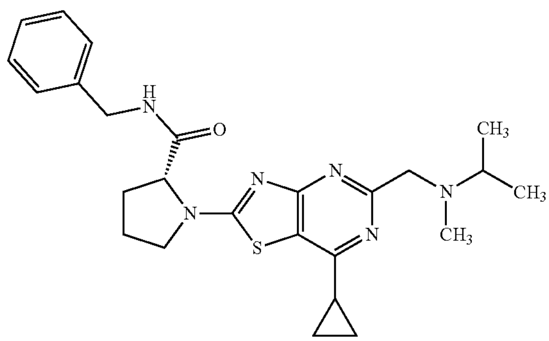 [SMILES: CC(C)N(C)Cc1nc(C2CC2)c2sc(N3CCC[C@@H]3C(=O)NCc3ccccc3)nc2n1] | Example 57 (100 mg) | 61.0 mg | 465 |

Example 100

(S)—N-benzyl-3-(7-cyclopropyl[1,3]thiazolo[4,5-d]pyrimidin-2-yl)-1,3-thiazolidine-4-carboxamide

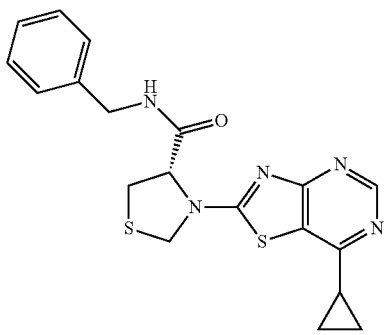 [SMILES: O=C(NCc1ccccc1)[C@H]1CSCN1c1nc2ncnc(C3CC3)c2s1]

To a DMF solution (3.00 mL) of the compound (150 mg) obtained in Reference Example 189 were added (S)—thiazolidine-4-carboxylic acid (125 mg) and N,N-diisopropylethylamine (0.328 mL), and the reaction mixture was stirred at 80° C. for 1.5 hr. After cooling to room temperature, benzylamine (0.137 mL), EDC hydrochloride (240 mg) and HOBt monohydrate (191 mg) were added, and the reaction mixture was stirred at room temperature overnight. Water was added, the mixture was extracted with ethyl acetate, and the organic layer was dried over anhydrous sodium sulfate, filtered and concentrated. The obtained residue was purified by silica gel column chromatography (solvent; hexane/ethyl acetate=70/30-20/80) to give the title compound (180 mg).

MS(ESI)m/z; 398[M+H]+

Example 101

(R)—N-benzyl-1-[7-ethyl-5-(2H-1,2,3-triazol-2-yl)[1,3]thiazolo[4,5-d]pyrimidin-2-yl]pyrrolidine-2-carboxamide

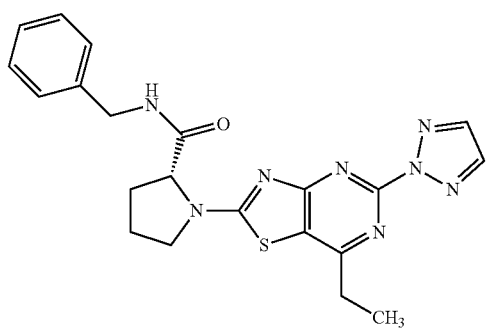 [SMILES: CCc1nc(-n2nccn2)nc2nc(N3CCC[C@@H]3C(=O)NCc3ccccc3)sc12]

Example 102

(R)—N-benzyl-1-[7-ethyl-5-(1H-1,2,3-triazol-1-yl)[1,3]thiazolo[4,5-d]pyrimidin-2-yl]pyrrolidine-2-carboxamide

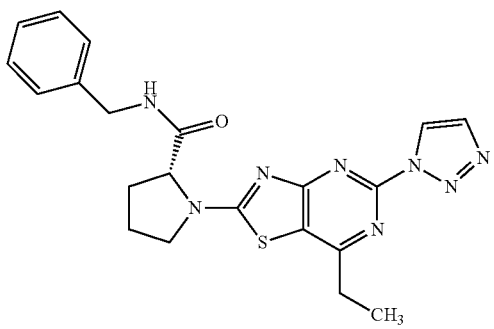 [SMILES: CCc1nc(-n2ccnn2)nc2nc(N3CCC[C@@H]3C(=O)NCc3ccccc3)sc12]

To an N-methylpyrrolidone solution (3.00 mL) of the compound (300 mg) obtained in Example 85 were added potassium carbonate (516 mg) and [1,2,3]triazole (0.130 mL), and the reaction mixture was stirred with heating at 80° C. for 6 hr. Potassium carbonate (208 mg) and [1,2,3]triazole (0.0860 mL) were further added, and the reaction mixture was stirred with heating at 80° C. for 6 hr. After cooling to room temperature, water was added, the mixture was extracted with ethyl acetate, and the organic layer was dried over anhydrous sodium sulfate, filtered and concentrated. The obtained crude product was purified by reversed-phase HPLC (Capcelpak C18; 0.05% trifluoroacetic acid-water/acetonitrile=55/45-45/55) to give a highly-polar compound (Example 101; 31.7 mg) and a low polar compound (Example 102; 58.4 mg).

Example 101; MS(ESI)m/z; 435[M+H]$^+$
Example 102; MS(ESI)m/z; 435[M+H]$^+$

Example 103

(R)—N-benzyl-1-[5-(3,5-dimethyl-1H-pyrazol-1-yl)-7-ethyl[1,3]thiazolo[4,5-d]pyrimidin-2-yl]pyrrolidine-2-carboxamide

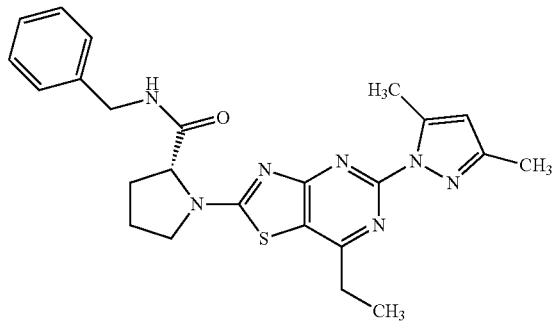 [SMILES: CCc1nc(-n2nc(C)cc2C)nc2nc(N3CCC[C@@H]3C(=O)NCc3ccccc3)sc12]

To an ethanol solution (10.0 mL) of the compound (500 mg) obtained in Example 85 was added hydrazine monohydrate (0.617 mL) at room temperature, and the reaction mixture was stirred with heating at 80° C. for 5 hr. After cooling to room temperature, saturated aqueous sodium hydrogen carbonate solution was added, and the mixture was extracted twice with chloroform. The combined organic layer was washed with saturated brine, dried over anhydrous sodium sulfate, filtered and concentrated under reduced pressure. The obtained residue was purified by silica gel column chromatography (solvent; chloroform/methanol=100/0-98/2) to give a viscous product (438 mg). To an ethanol solution (5.00 mL) of the obtained viscous product (200 mg) was added acetylacetone (0.104 mL) at room temperature, and the reaction mixture was stirred with heating at 80° C. for 1 hr. After cooling to room temperature, the solvent was concentrated under reduced pressure. The obtained residue was purified by silica gel column chromatography (solvent; chloroform/methanol=100/0-98/2) to give the title compound (173 mg).

MS(ESI)m/z; 462[M+H]$^+$

Example 104

(R)—N-benzyl-1-[5-(3,5-dimethyl-1H-pyrazol-1-yl)-7-methyl[1,3]thiazolo[4,5-d]pyrimidin-2-yl]pyrrolidine-2-carboxamide

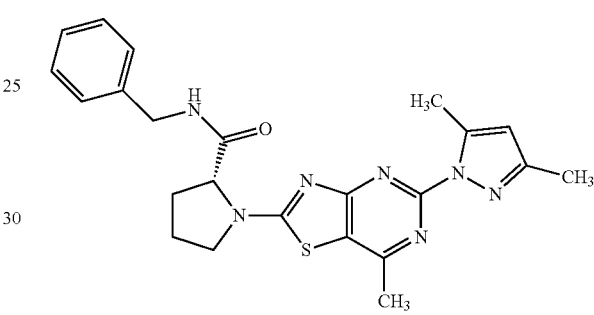

The compound (100 mg) obtained in Example 86 was treated by a method similar to that in Example 103 to give the title compound (57.6 mg).

MS (ESI)m/z; 448[M+H]$^+$

Example 105

(R)—N-benzyl-1-[7-ethyl-5-(1H-pyrazol-1-yl)[1,3]thiazolo[4,5-d]pyrimidin-2-yl]pyrrolidine-2-carboxamide

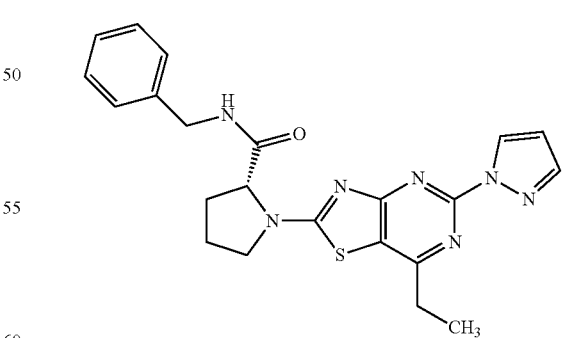

To an ethanol solution (10.0 mL) of the compound (500 mg) obtained in Example 85 was added hydrazine monohydrate (0.617 mL) at room temperature, and the reaction mixture was stirred with heating at 80° C. for 5 hr. After cooling to room temperature, saturated aqueous sodium hydrogen carbonate solution was added, and the mixture was extracted twice with chloroform. The combined organic layer was washed with saturated brine, dried over anhydrous sodium sulfate, filtered and concentrated under reduced pressure. The obtained residue was purified by silica gel column chromatography (solvent; chloroform/methanol=100/0-98/2) to give a viscous product (438 mg). To an ethanol solution (10.0 mL) of the obtained viscous product (210 mg) was added 1,1,3,3-tetramethoxypropane (0.0880 mL) at room temperature, and the reaction mixture was stirred with heating at 80° C. for 1 hr. Furthermore, concentrated hydrochloric acid (0.0280 mL) was added, and the reaction mixture was stirred with heating at 80° C. for 4 hr. After cooling to room temperature, the reaction mixture was concentrated under reduced pressure. The obtained residue was dissolved in chloroform, washed with saturated aqueous sodium hydrogen carbonate solution, dried over anhydrous sodium sulfate, filtered and concentrated under reduced pressure. The obtained residue was purified by silica gel column chromatography (solvent; chloroform/methanol=100/0-98/2) to give the title compound (185 mg).

MS(ESI)m/z; 434[M+H]$^+$

Example 106

(R)—N-benzyl-1-[7-cyclopropyl-5-(N,N-dimethylamino)[1,3]thiazolo[4,5-d]pyrimidin-2-yl]pyrrolidine-2-carboxamide

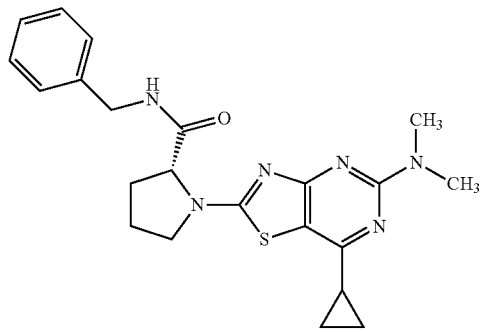 [SMILES: CN(C)c1nc(C2CC2)c2sc(N3CCC[C@@H]3C(=O)NCc3ccccc3)nc2n1]

To a DMF solution (1.00 mL) of the compound (77.0 mg) obtained in Example 87 was added dimethylamine (2.0 mol/L THF solution, 0.500 mL) at room temperature, and the reaction mixture was stirred with heating at 50° C. for 14 hr. After cooling to room temperature, water was added, and the mixture was extracted twice with ethyl acetate. The combined organic layer was washed with saturated brine, dried over anhydrous sodium sulfate, filtered and concentrated under reduced pressure. The obtained residue was purified by silica gel column chromatography (solvent; hexane/ethyl acetate=50/50-100/0) to give the title compound (39.0 mg).

MS(ESI)m/z; 423[M+H]$^+$

Example 107

(R)—1-{7-[(azetidin-3-yl)oxy][1,3]thiazolo[4,5-d]pyrimidin-2-yl}-N-benzylpyrrolidine-2-carboxamide

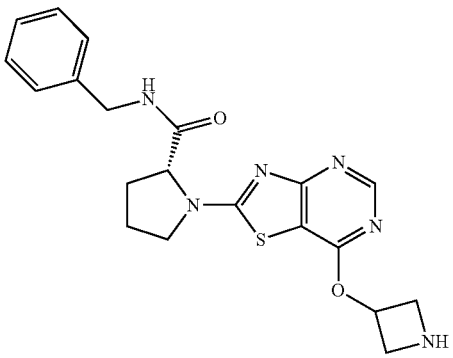 [SMILES: O=C(NCc1ccccc1)[C@H]1CCCN1c1nc2ncnc(OC3CNC3)c2s1]

To a methylene chloride solution (10.0 mL) of the compound (370 mg) obtained in Example 22 was added, under ice-cooling, trifluoroacetic acid (1.00 mL), and the reaction mixture was stirred at room temperature for 3 hr. To the reaction mixture was added saturated aqueous sodium hydrogen carbonate solution, and the mixture was extracted with chloroform. The organic layer was dried over anhydrous sodium sulfate, filtered and concentrated. The obtained residue was purified by silica gel column chromatography (solvent; chloroform/methanol=100/0-95/5) to give the title compound (137 mg).

MS(ESI)m/z; 411[M+H]$^+$

Example 108

(R)—N-benzyl-1-{7-[(1-methylazetidin-3-yl)oxy][1,3]thiazolo[4,5-d]pyrimidin-2-yl}pyrrolidine-2-carboxamide

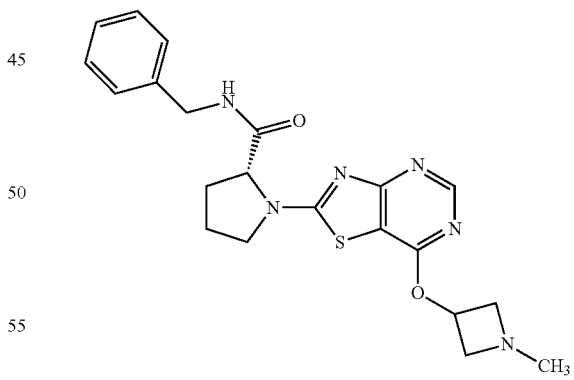

To a methylene chloride solution (2.00 mL) of the compound (130 mg) obtained in Example 107 was added, under ice-cooling, formalin (35-38% w/w, 0.11 mL). Sodium triacetoxyborohydride (164 mg) was further added, and the reaction mixture was stirred at room temperature for 3 hr. After confirmation of the completion of the reaction, to the reaction mixture was added saturated aqueous sodium hydrogen carbonate solution, and the mixture was extracted twice with chloroform. The organic layer was dried over anhydrous sodium sulfate, filtered and concentrated. The obtained residue was purified by silica gel column chromatography (solvent; chloroform/methanol=100/0-95/5). To the obtained resultant product was added diisopropy ether, and the solid was collected by filtration to give the title compound (70.0 mg).

MS(ESI)m/z; 425[M+H]⁺

Example 109

(R)—N-benzyl-1-(5,6-dimethyl-7-oxo-6,7-dihydro[1,3]thiazolo[4,5-d]pyrimidin-2-yl)pyrrolidine-2-carboxamide

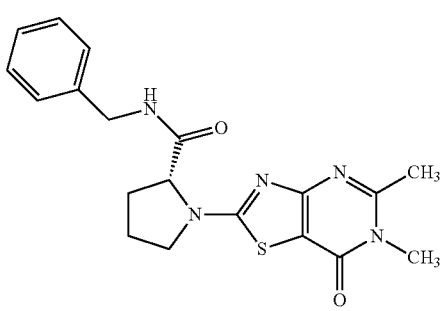 [SMILES: Cc1nc2nc(N3CCC[C@@H]3C(=O)NCc3ccccc3)sc2c(=O)n1C]

To a methylene chloride solution (3.00 mL) of the compound (70.0 mg) obtained in Reference Example 470 was added, under ice-cooling, mCPBA (69-75% w/w, 85.0 mg), and the reaction mixture was stirred at room temperature for 1 hr. To the reaction mixture were added aqueous sodium thiosulfate solution and saturated aqueous sodium hydrogen carbonate solution, and the mixture was extracted 3 times with chloroform. The organic layer was dried over anhydrous sodium sulfate, filtered and concentrated. To a DMF solution (3.00 mL) of the residue were added (D)-proline (47.0 mg) and cesium carbonate (206 mg), and the reaction mixture was stirred with heating at 70° C. for 2 hr. After cooling to room temperature, the reaction mixture was neutralized with concentrated hydrochloric acid, N,N-diisopropylethylamine (0.0960 mL), benzylamine (0.0600 mL), EDC hydrochloride (105 mg) and HOBt monohydrate (84.0 mg) were added, and the reaction mixture was stirred at room temperature overnight. Water was added, the mixture was extracted with ethyl acetate, and the organic layer was dried over anhydrous sodium sulfate, filtered and concentrated. The obtained residue was purified by silica gel column chromatography (solvent; ethyl acetate/methanol=100/0-90/10) and concentrated under reduced pressure. To the obtained resultant product was added ethyl acetate-hexane (50:50), and the solid was collected by filtration and dried to give the title compound (72.0 mg). MS(ESI)m/z; 384[M+H]⁺

Example 110

(R)—N-benzyl-1-(6-cyclopropyl[1,3]thiazolo[4,5-b]pyridin-2-yl)pyrrolidine-2-carboxamide

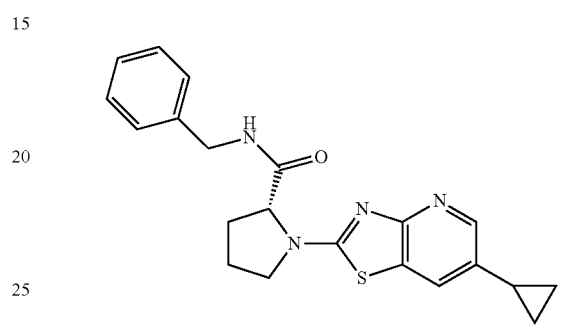

A mixture of the compound (22.0 mg) obtained in Reference Example 289, the compound (24.0 mg) obtained in Reference Example 471, N,N-diisopropylethylamine (52.0 µL) and THF (0.100 mL) was stirred with heating at 120° C. for 4 hr. After confirmation of the completion of the reaction, under ice-cooling, water was added to the reaction mixture, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=50/50-9/100). To the obtained resultant product was added diisopropy ether, and the solid was collected by filtration to give the title compound (53.0 mg).

MS(ESI)m/z; 379[M+H]⁺

Examples 111 to 130 are shown below. These compounds were obtained by a method similar to that in Example 110 except that the starting materials in the following Tables were used instead of Reference Example 289 and an appropriate compound was used instead of Reference Example 471 as necessary.

TABLE 9

| Example | structure | starting material | yield | MS (ESI) m/z [M + H]⁺ |
|---|---|---|---|---|
| 111 | 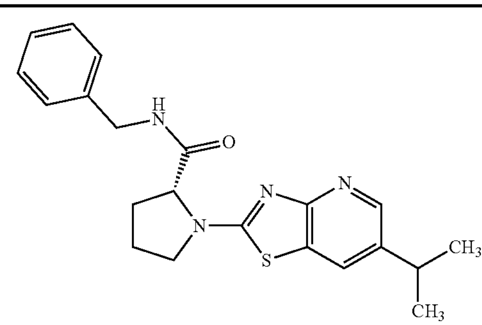 | Reference Example 290 (152 mg) | 214 mg | 381 |

TABLE 9-continued

| Example | structure | starting material | yield | MS (ESI) m/z [M + H]+ |
|---|---|---|---|---|
| 112 | 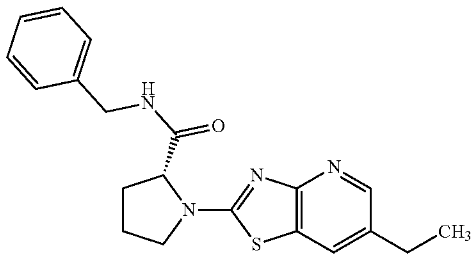 [SMILES: CCc1cnc2nc(N3CCC[C@@H]3C(=O)NCc3ccccc3)sc2c1] | Reference Example 291 (150 mg) | 187 mg | 367 |
| 113 | 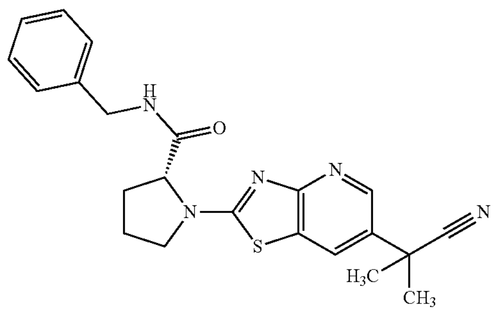 [SMILES: CC(C)(C#N)c1cnc2nc(N3CCC[C@@H]3C(=O)NCc3ccccc3)sc2c1] | Reference Example 294 (1.52 g) | 2.31 g | 406 |
| 114 | 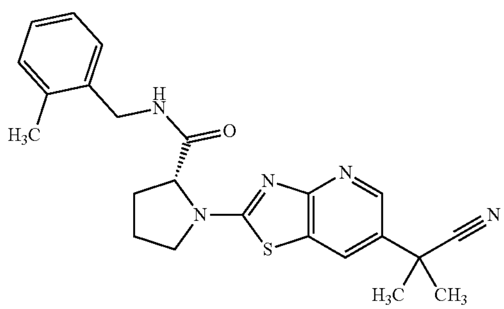 [SMILES: Cc1ccccc1CNC(=O)[C@H]1CCCN1c1nc2ncc(C(C)(C)C#N)cc2s1] | Reference Example 294 (93.0 mg) | 125 mg | 420 |
| 115 | 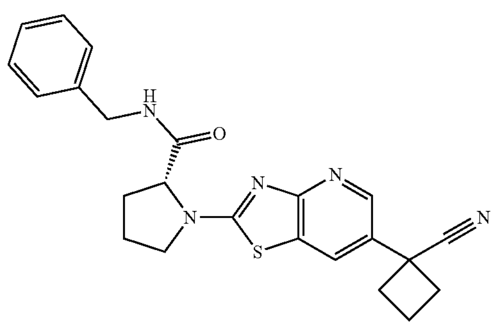 [SMILES: N#CC1(c2cnc3nc(N4CCC[C@@H]4C(=O)NCc4ccccc4)sc3c2)CCC1] | Reference Example 295 (144 mg) | 217 mg | 418 |
| 116 | 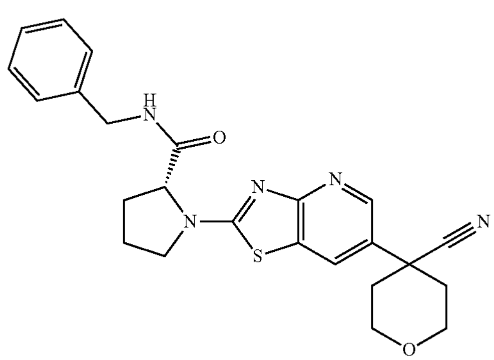 [SMILES: N#CC1(c2cnc3nc(N4CCC[C@@H]4C(=O)NCc4ccccc4)sc3c2)CCOCC1] | Reference Example 296 (200 mg) | 264 mg | 448 |

TABLE 9-continued

| Example | structure | starting material | yield | MS (ESI) m/z [M + H]+ |
|---|---|---|---|---|
| 117 | 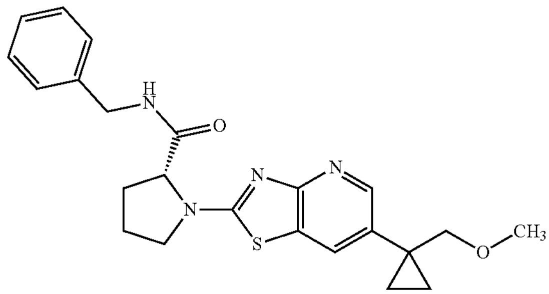 [SMILES: COCC1(c2cnc3nc(N4CCC[C@@H]4C(=O)NCc4ccccc4)sc3c2)CC1] | Reference Example 297 (122 mg) | 153 mg | 423 |
| 118 | 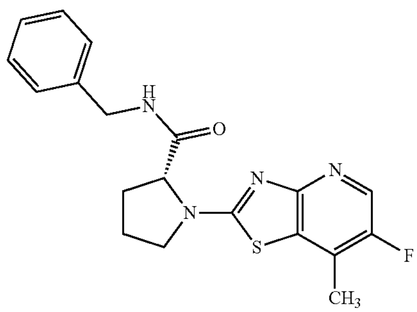 [SMILES: Cc1c(F)cnc2nc(N3CCC[C@@H]3C(=O)NCc3ccccc3)sc12] | Reference Example 298 (146 mg) | 202 mg | 371 |
| 119 | 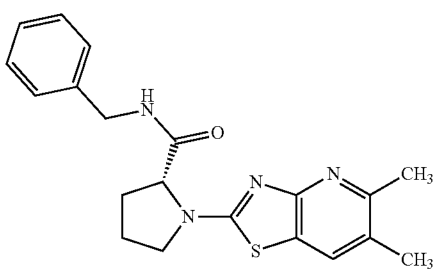 [SMILES: Cc1cc2sc(N3CCC[C@@H]3C(=O)NCc3ccccc3)nc2nc1C] | Reference Example 299 (35.0 mg) | 41.0 mg | 379 |
| 120 | 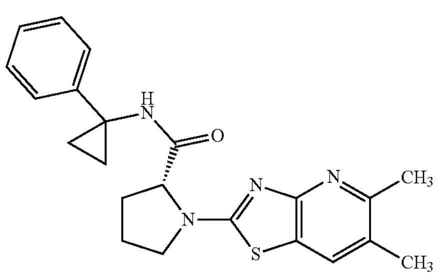 [SMILES: Cc1cc2sc(N3CCC[C@@H]3C(=O)NC3(c4ccccc4)CC3)nc2nc1C] | Reference Example 299 (200 mg) | 312 mg | 393 |
| 121 | 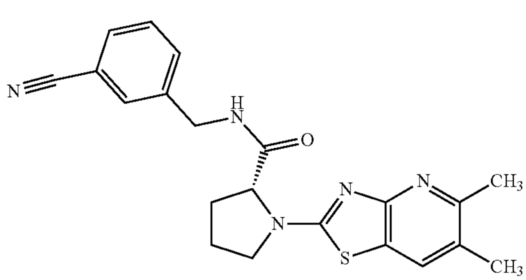 [SMILES: Cc1cc2sc(N3CCC[C@@H]3C(=O)NCc3cccc(C#N)c3)nc2nc1C] | Reference Example 299 (150 mg) | 94.0 mg | 392 |

TABLE 9-continued

| Example | structure | starting material | yield | MS (ESI) m/z [M + H]+ |
|---|---|---|---|---|
| 122 | 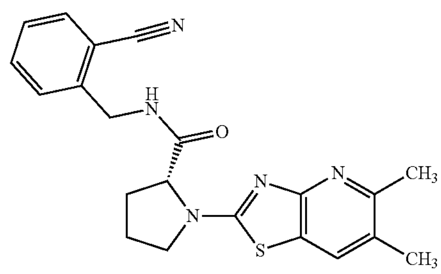 [SMILES: Cc1cc2sc(N3CCC[C@@H]3C(=O)NCc3ccccc3C#N)nc2nc1C] | Reference Example 299 (96.0 mg) | 92.0 mg | 392 |
| 123 | 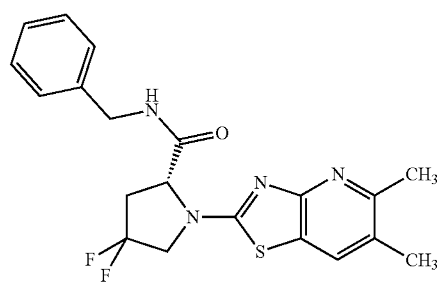 [SMILES: Cc1cc2sc(N3CC(F)(F)C[C@@H]3C(=O)NCc3ccccc3)nc2nc1C] | Reference Example 299 (131 mg) | 161 mg | 403 |
| 124 | 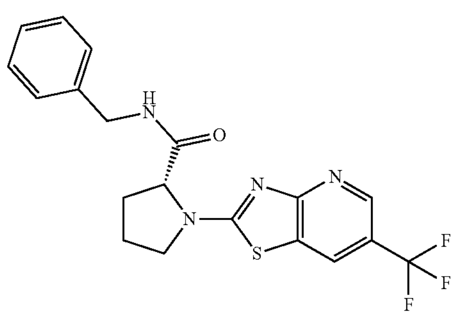 [SMILES: O=C(NCc1ccccc1)[C@H]1CCCN1c1nc2ncc(C(F)(F)F)cc2s1] | Reference Example 300 (170 mg) | 237 mg | 407 |
| 125 | 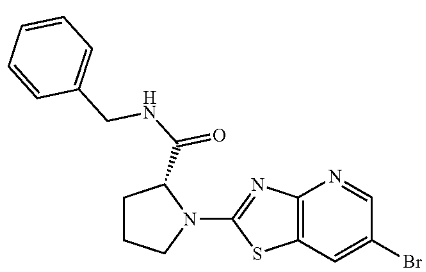 [SMILES: O=C(NCc1ccccc1)[C@H]1CCCN1c1nc2ncc(Br)cc2s1] | Reference Example 302 (650 mg) | 996 mg | 417, 419 |
| 126 | 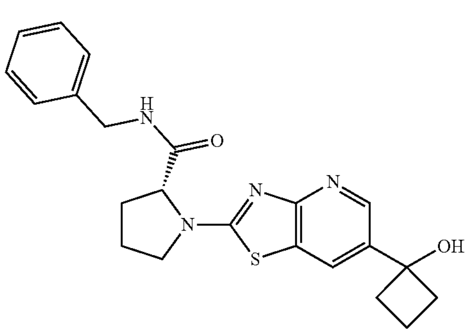 [SMILES: O=C(NCc1ccccc1)[C@H]1CCCN1c1nc2ncc(C3(O)CCC3)cc2s1] | Reference Example 303 (48.0 mg) | 67.0 mg | 409 |

TABLE 9-continued

| Example | structure | starting material | yield | MS (ESI) m/z [M + H]+ |
|---|---|---|---|---|
| 127 | 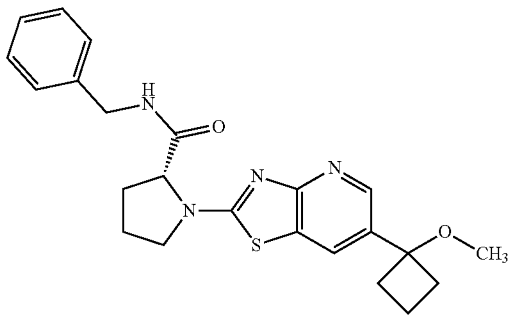 [SMILES: COC1(c2cnc3nc(N4CCC[C@@H]4C(=O)NCc4ccccc4)sc3c2)CCC1] | Reference Example 304 (55.0 mg) | 50.0 mg | 423 |
| 128 | 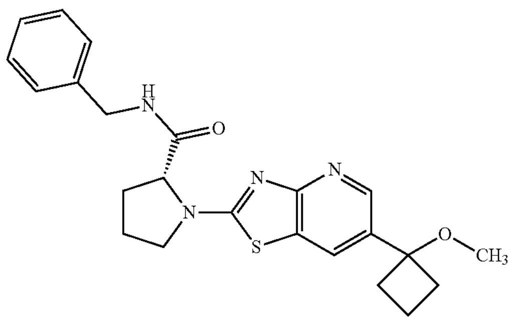 [SMILES: COC1(c2cnc3nc(N4CCC[C@@H]4C(=O)NCc4ccccc4)sc3c2)CCC1] | Reference Example 305 (18.0 mg) | 18.0 mg | 425 |
| 129 | 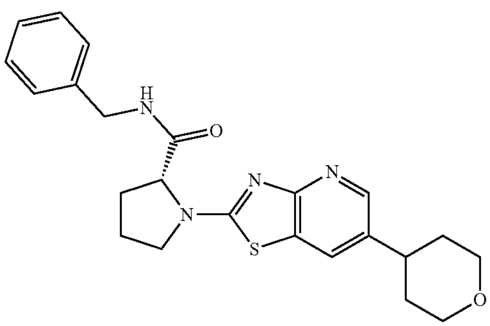 [SMILES: O=C(NCc1ccccc1)[C@H]1CCCN1c1nc2ncc(C3CCOCC3)cc2s1] | Reference Example 306 (10.2 mg) | 13.0 mg | 423 |
| 130 | 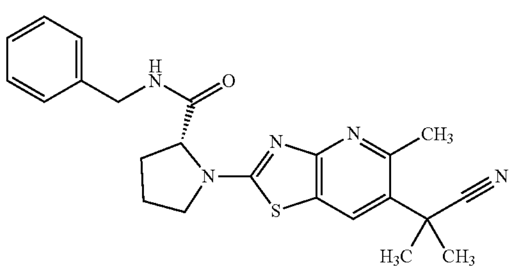 [SMILES: Cc1nc2nc(N3CCC[C@@H]3C(=O)NCc3ccccc3)sc2cc1C(C)(C)C#N] | Reference Example 307 (109 mg) | 143 mg | 420 |

Example 131

(R)-1-(6-ethyl[1,3]thiazolo[4,5-b]pyridin-2-yl)-N-(4-fluorobenzyl)pyrrolidine-2-carboxamide hydrochloride

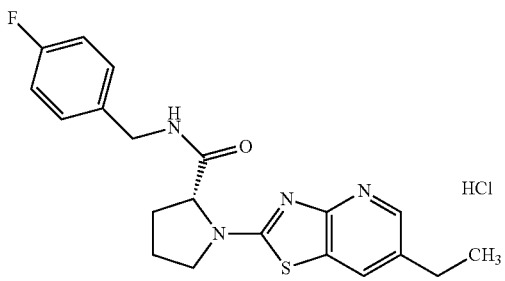 [SMILES: CCc1cnc2nc(N3CCC[C@@H]3C(=O)NCc3ccc(F)cc3)sc2c1 ; Cl]

A mixture of the compound (165 mg) obtained in Reference Example 291, the compound (215 mg) obtained in Reference Example 472, N,N-diisopropylethylamine (434 µL) and THF (500 µL) was stirred with heating at 120° C. for 4 hr. After confirmation of the completion of the reaction, under ice-cooling, water was added to the reaction mixture, and the mixture was extracted twice with ethyl acetate. The combined organic layer was washed with saturated brine, dried over anhydrous sodium sulfate, filtered and concentrated. The obtained residue was purified by NH silica gel column chromatography (solvent; hexane/ethyl acetate=70/30-0/100). The solvent was evaporated under reduced pressure. To an ethyl acetate solution (5.00 mL) of the obtained residue was added hydrogen chloride (4.0 mol/L ethyl acetate solution, 200 µL) at room temperature and the mixture was stirred in situ for 10 min. The resulting solid was collected by filtration and dried to give the title compound (224 mg).

MS(ESI)m/z; 385[M+H]$^+$

Examples 132 to 134 are shown below. These compounds were obtained by a method similar to that in Example 131 except that the starting materials in the following Table were used instead of Reference Example 291 and an appropriate compound was used instead of Reference Example 472 as necessary.

TABLE 10

| Example | structure | starting material | yield | MS (ESI) m/z [M + H]$^+$ |
|---|---|---|---|---|
| 132 | 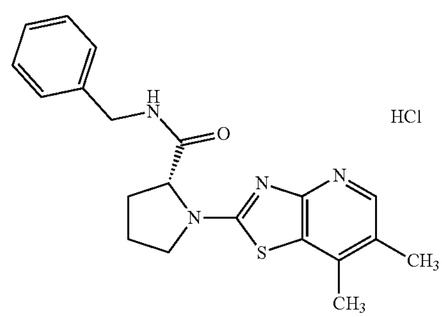 [SMILES: Cc1cnc2nc(N3CCC[C@@H]3C(=O)NCc3ccccc3)sc2c1C ; Cl] | Reference Example 292 (81.0 mg) | 117 mg | 367 |
| 133 | 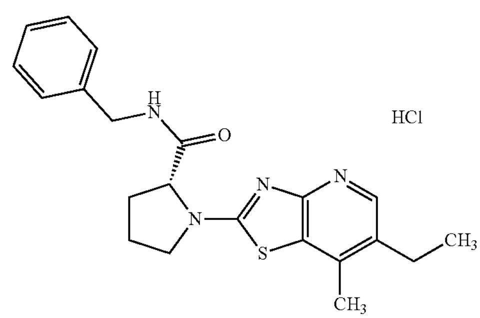 [SMILES: CCc1cnc2nc(N3CCC[C@@H]3C(=O)NCc3ccccc3)sc2c1C ; Cl] | Reference Example 293 (114 mg) | 195 mg | 381 |
| 135 | 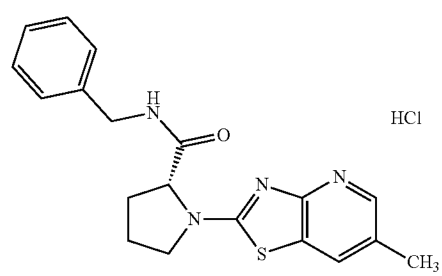 [SMILES: Cc1cnc2nc(N3CCC[C@@H]3C(=O)NCc3ccccc3)sc2c1 ; Cl] | Reference Example 301 (200 mg) | 362 mg | 353 |

Example 135

(R)—N-benzyl-1-(6-cyano-7-methyl[1,3]thiazolo[4,5-b]pyridin-2-yl)pyrrolidine-2-carboxamide

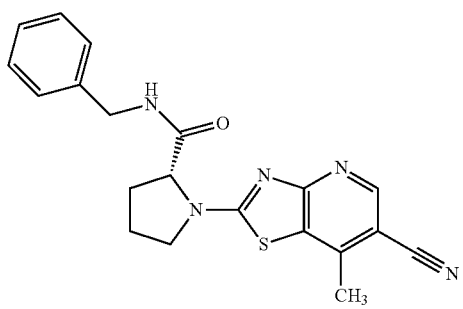 [SMILES: Cc1c(C#N)cnc2nc(N3CCC[C@@H]3C(=O)NCc3ccccc3)sc12]

A mixture of the compound (200 mg) obtained in Reference Example 409, the compound (190 mg) obtained in Reference Example 471, N,N-diisopropylethylamine (306 mg) and THF (1.00 mL) was stirred with heating at 120° C. for 4 hr. After confirmation of the completion of the reaction, under ice-cooling, water was added to the reaction mixture, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=70/30-0/100). To the obtained resultant product was added diisopropy ether, and the solid was collected by filtration to give the title compound (193 mg).

MS(ESI)m/z; 378[M+H]$^+$

Example 136

(R)—N-benzyl-1-(7-cyano-6-methyl[1,3]thiazolo[4,5-b]pyridin-2-yl)pyrrolidine-2-carboxamide

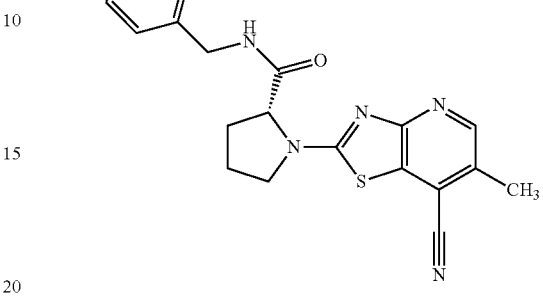

A mixture of the compound (115 mg) obtained in Reference Example 410, the compound (122 mg) obtained in Reference Example 471, N,N-diisopropylethylamine (250 µL) and THF (500 µL) was stirred with heating at 120° C. for 1.5 hr. After confirmation of the completion of the reaction, under ice-cooling, water was added to the reaction mixture, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=50/50-0/100). To the obtained resultant product was added diisopropy ether, and the solid was collected by filtration to give the title compound (163 mg).

MS(ESI)m/z; 378[M+H]$^+$

Examples 137 to 161 are shown below. These compounds were obtained by a method similar to that in Example 136 except that the starting materials in the following Tables were used instead of Reference Example 410 and an appropriate compound was used instead of Reference Example 471 as necessary.

TABLE 11

| Example | structure | starting material | yield | MS (ESI) m/z [M + H]$^+$ |
|---------|-----------|-------------------|-------|--------------------------|
| 137 | 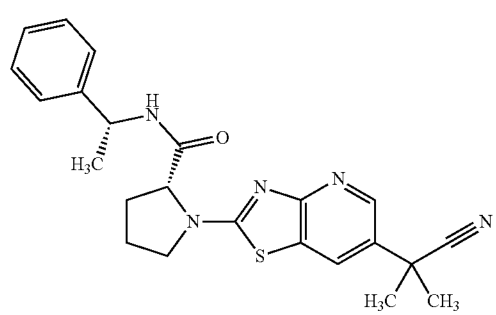 [SMILES: C[C@@H](NC(=O)[C@H]1CCCN1c1nc2ncc(C(C)(C)C#N)cc2s1)c1ccccc1] | Reference Example 411 (158 mg) | 161 mg | 420 |

TABLE 11-continued

| Example | structure | starting material | yield | MS (ESI) m/z [M + H]+ |
|---|---|---|---|---|
| 138 | 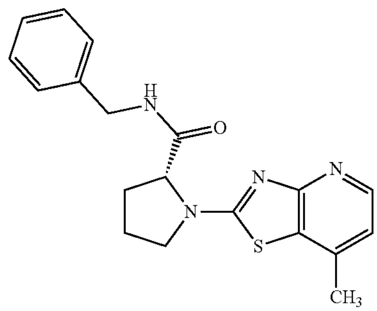 [SMILES: Cc1ccnc2nc(N3CCC[C@@H]3C(=O)NCc3ccccc3)sc12] | Reference Example 412 (140 mg) | 57.6 mg | 353 |
| 139 | 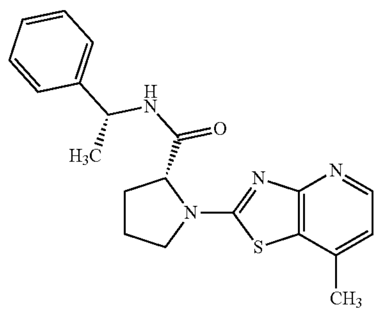 [SMILES: Cc1ccnc2nc(N3CCC[C@@H]3C(=O)N[C@H](C)c3ccccc3)sc12] | Reference Example 412 (130 mg) | 100 mg | 367 |
| 140 | 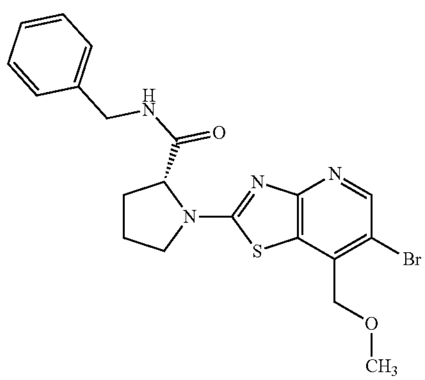 [SMILES: COCc1c(Br)cnc2nc(N3CCC[C@@H]3C(=O)NCc3ccccc3)sc12] | Reference Example 413 (230 mg) | 220 mg | 461, 463 |
| 141 | 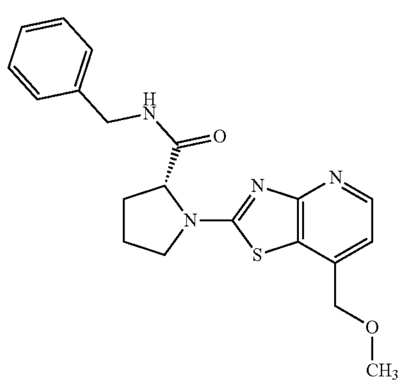 [SMILES: COCc1ccnc2nc(N3CCC[C@@H]3C(=O)NCc3ccccc3)sc12] | Reference Example 414 (180 mg) | 130 mg | 383 |

TABLE 11-continued

| Example | structure | starting material | yield | MS (ESI) m/z [M + H]+ |
|---|---|---|---|---|
| 142 | 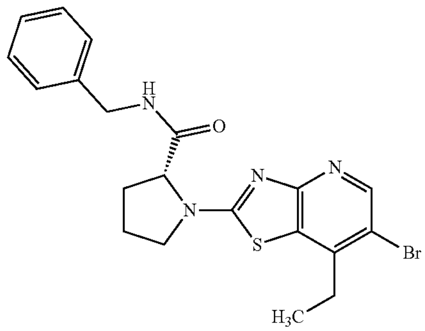 [SMILES: CCc1c(Br)cnc2nc(N3CCC[C@@H]3C(=O)NCc3ccccc3)sc12] | Reference Example 415 (1.70 g) | 1.30 g | 445, 447 |
| 143 | 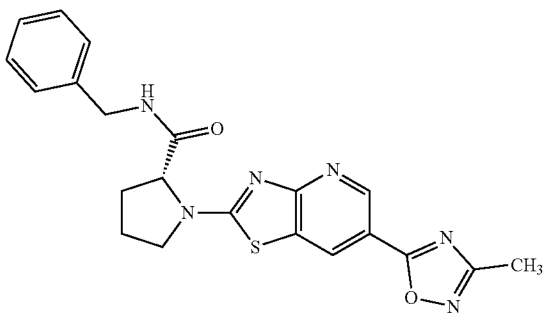 [SMILES: Cc1noc(-c2cnc3nc(N4CCC[C@@H]4C(=O)NCc4ccccc4)sc3c2)n1] | Reference Example 416 (150 mg) | 130 mg | 421 |
| 144 | 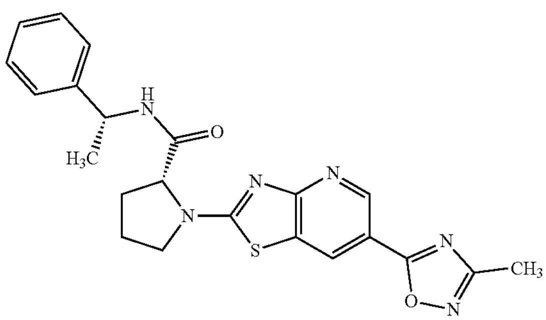 [SMILES: Cc1noc(-c2cnc3nc(N4CCC[C@@H]4C(=O)N[C@H](C)c4ccccc4)sc3c2)n1] | Reference Example 416 (150 mg) | 139 mg | 435 |
| 145 | 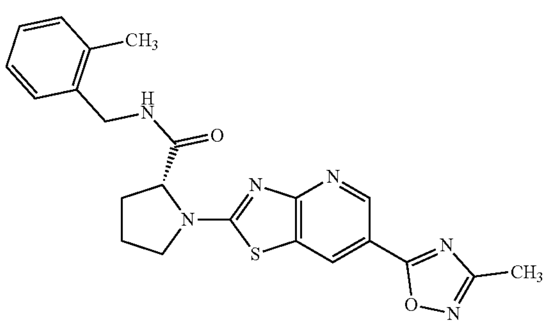 [SMILES: Cc1noc(-c2cnc3nc(N4CCC[C@@H]4C(=O)NCc4ccccc4C)sc3c2)n1] | Reference Example 416 (150 mg) | 125 mg | 435 |

TABLE 11-continued

| Example | structure | starting material | yield | MS (ESI) m/z [M + H]+ |
|---|---|---|---|---|
| 146 | 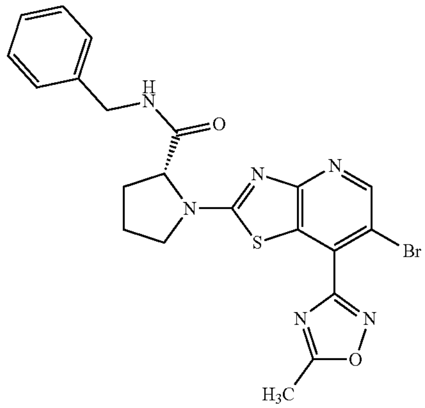 [SMILES: Cc1nc(-c2c(Br)cnc3nc(N4CCC[C@@H]4C(=O)NCc4ccccc4)sc23)no1] | Reference Example 417 (410 mg) | 390 mg | 499, 501 |
| 147 | 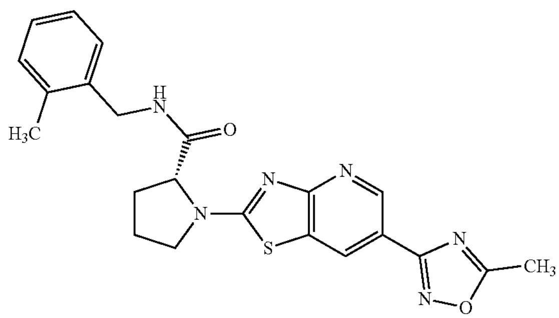 [SMILES: Cc1nc(-c2cnc3nc(N4CCC[C@@H]4C(=O)NCc4ccccc4C)sc3c2)no1] | Reference Example 418 (280 mg) | 165 mg | 435 |
| 148 | 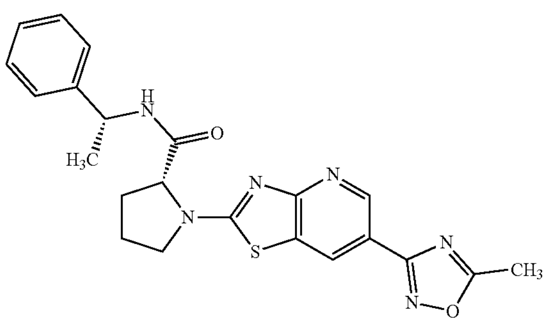 [SMILES: Cc1nc(-c2cnc3nc(N4CCC[C@@H]4C(=O)N[C@H](C)c4ccccc4)sc3c2)no1] | Reference Example 418 (280 mg) | 320 mg | 435 |
| 149 | 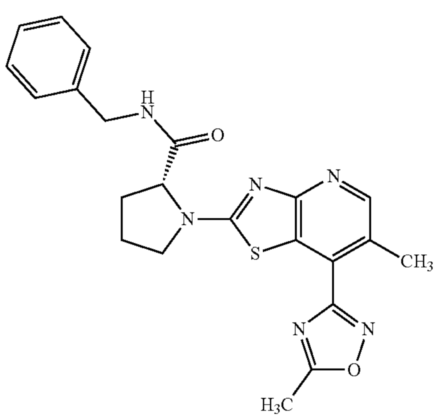 [SMILES: Cc1nc(-c2c(C)cnc3nc(N4CCC[C@@H]4C(=O)NCc4ccccc4)sc23)no1] | Reference Example 419 (120 mg) | 120 mg | 435 |

TABLE 11-continued

| Example | structure | starting material | yield | MS (ESI) m/z [M + H]+ |
|---|---|---|---|---|
| 150 | 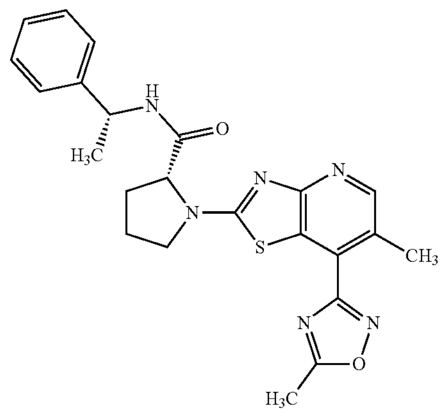 [SMILES: Cc1nc(-c2c(C)cnc3nc(N4CCC[C@@H]4C(=O)N[C@H](C)c4ccccc4)sc23)no1] | Reference Example 419 (110 mg) | 130 mg | 449 |
| 151 | 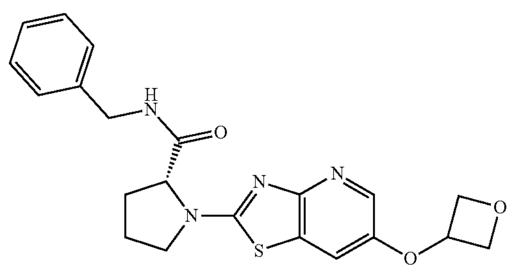 [SMILES: O=C(NCc1ccccc1)[C@H]1CCCN1c1nc2ncc(OC3COC3)cc2s1] | Reference Example 420 (83.0 mg) | 64.0 mg | 411 |
| 152 | 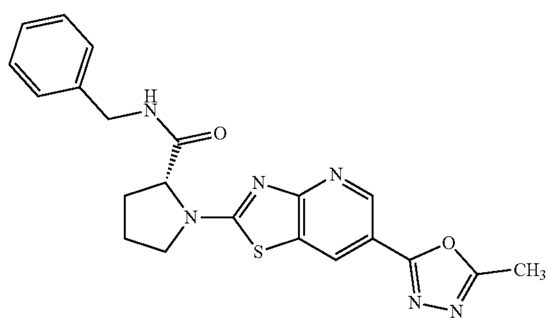 [SMILES: Cc1nnc(-c2cnc3nc(N4CCC[C@@H]4C(=O)NCc4ccccc4)sc3c2)o1] | Reference Example 421 (280 mg) | 184 mg | 421 |
| 153 | 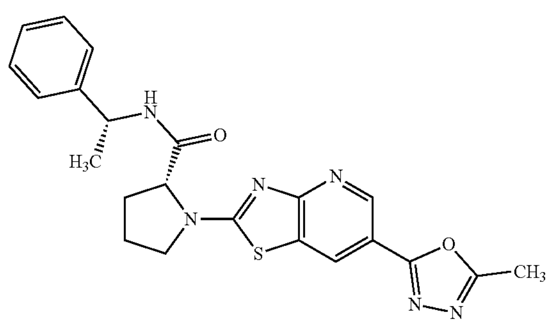 [SMILES: Cc1nnc(-c2cnc3nc(N4CCC[C@@H]4C(=O)N[C@H](C)c4ccccc4)sc3c2)o1] | Reference Example 421 (70.0 mg) | 39.8 mg | 435 |

TABLE 11-continued

| Example | structure | starting material | yield | MS (ESI) m/z [M + H]+ |
|---|---|---|---|---|
| 154 | 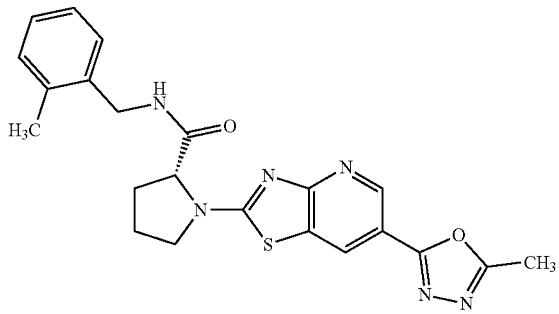 [SMILES: Cc1nnc(-c2cnc3nc(N4CCC[C@@H]4C(=O)NCc4ccccc4C)sc3c2)o1] | Reference Example 421 (70.0 mg) | 3.50 mg | 435 |
| 155 | 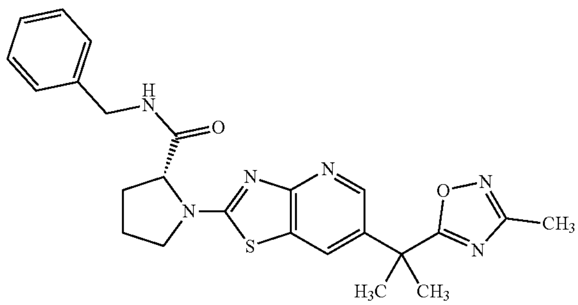 [SMILES: Cc1noc(C(C)(C)c2cnc3nc(N4CCC[C@@H]4C(=O)NCc4ccccc4)sc3c2)n1] | Reference Example 423 (82.0 mg) | 36.0 mg | 463 |
| 156 | 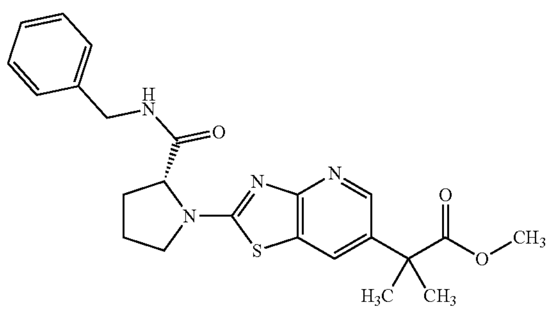 [SMILES: COC(=O)C(C)(C)c1cnc2nc(N3CCC[C@@H]3C(=O)NCc3ccccc3)sc2c1] | Reference Example 424 (162 mg) | 192 mg | 439 |
| 157 | 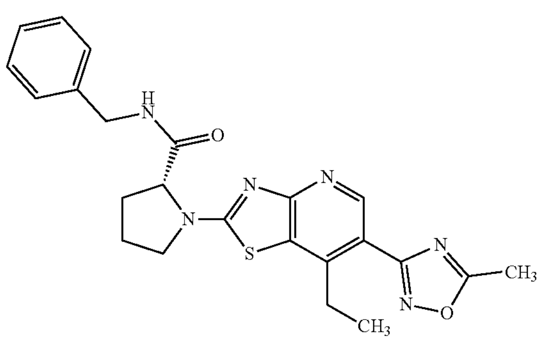 [SMILES: CCc1c(-c2noc(C)n2)cnc2nc(N3CCC[C@@H]3C(=O)NCc3ccccc3)sc12] | Reference Example 425 (116 mg) | 138 mg | 449 |

TABLE 11-continued

| Example | structure | starting material | yield | MS (ESI) m/z [M + H]+ |
|---|---|---|---|---|
| 158 | 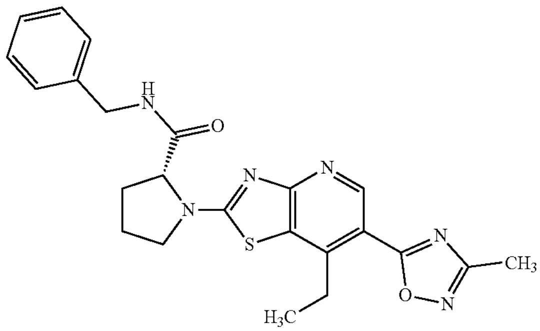 [SMILES: CCc1c(-c2nc(C)no2)cnc2nc(N3CCC[C@@H]3C(=O)NCc3ccccc3)sc12] | Reference Example 426 (57.0 mg) | 63.0 mg | 449 |
| 159 | 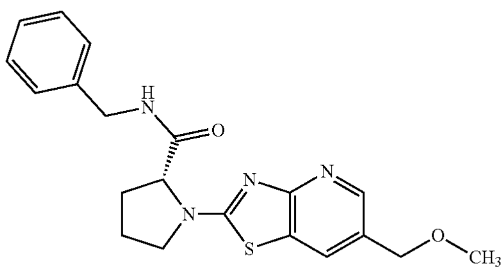 [SMILES: COCc1cnc2nc(N3CCC[C@@H]3C(=O)NCc3ccccc3)sc2c1] | Reference Example 427 (45.0 mg) | 38.0 mg | 383 |
| 160 | 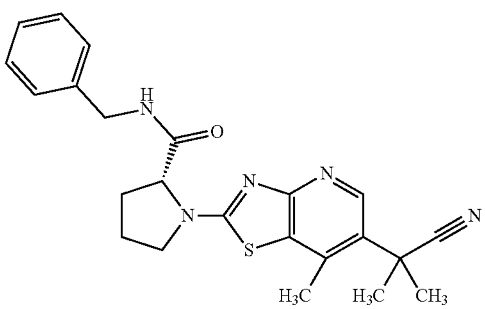 [SMILES: Cc1c(C(C)(C)C#N)cnc2nc(N3CCC[C@@H]3C(=O)NCc3ccccc3)sc12] | Reference Example 428 (45.0 mg) | 46.0 mg | 420 |
| 161 | 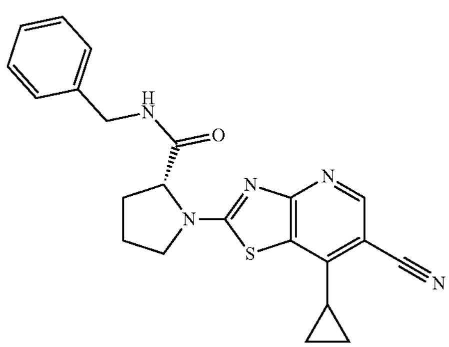 [SMILES: N#Cc1cnc2nc(N3CCC[C@@H]3C(=O)NCc3ccccc3)sc2c1C1CC1] | Reference Example 429 (51.0 mg) | 36.0 mg | 404 |

Example 162

(R)-1-(6-cyclopropyl[1,3]thiazolo[4,5-b]pyridin-2-yl)-N-(4-fluorobenzyl)pyrrolidine-2-carboxamide

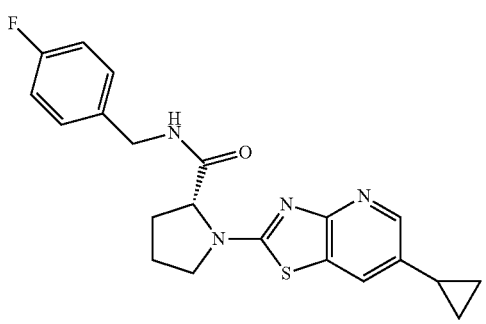 [SMILES: O=C(NCc1ccc(F)cc1)[C@H]1CCCN1c1nc2ncc(C3CC3)cc2s1]

A mixture of the compound (100 mg) obtained in Reference Example 277, the compound (248 mg) obtained in Reference Example 472, N,N-diisopropylethylamine (418 µL) and N-methylpyrrolidone (600 µL) was stirred with heating at 150° C. for 3 hr. After confirmation of the completion of the reaction, under ice-cooling, water was added to the reaction mixture, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=50/50-0/100). To the obtained resultant product was added diisopropy ether, and the solid was collected by filtration to give the title compound (18.0 mg).

MS(ESI)m/z; 397[M+H]⁺

Example 163

(R)—N-benzyl-1-[6-fluoro-7-(methoxymethyl)[1,3]thiazolo[4,5-b]pyridin-2-yl]pyrrolidine-2-carboxamide

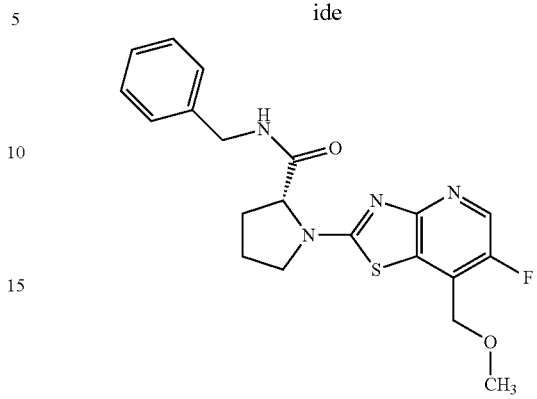

To a methylene chloride solution (10.0 mL) of the compound (170 mg) obtained in Reference Example 362 was added, under ice-cooling, mCPBA (69-75% w/w, 170 mg), and the reaction mixture was stirred at room temperature for 1 hr. To the reaction mixture were added 0.1 mol/L aqueous sodium thiosulfate solution and saturated aqueous sodium hydrogen carbonate solution, and the mixture was extracted twice with chloroform. The organic layer was dried over anhydrous sodium sulfate, filtered and concentrated. A mixture of the obtained residue, the compound (210 mg) obtained in Reference Example 471, N,N-diisopropylethylamine (610 µL) and 1,4-dioxane (1.00 mL) was stirred with heating at 120° C. for 5 hr. After confirmation of the completion of the reaction, under ice-cooling, water was added to the reaction mixture, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=50/50-0/100). To the obtained resultant product was added diisopropy ether, and the solid was collected by filtration to give the title compound (170 mg).

MS(ESI)m/z; 401[M+H]⁺

Examples 164 to 169 are shown below. These compounds were obtained by a method similar to that in Example 163 except that the starting materials in the following Table were used instead of Reference Example 362.

TABLE 12

| Example | structure | starting material | yield | MS (ESI) m/z [M + H]⁺ |
|---|---|---|---|---|
| 164 | 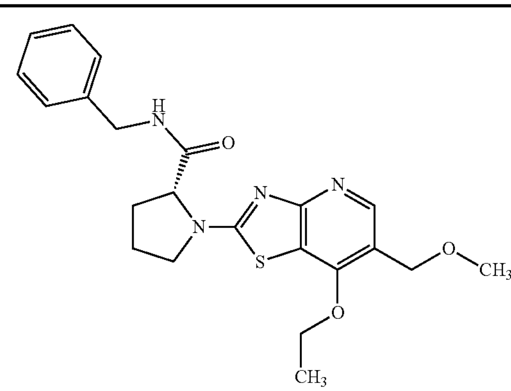 | Reference Example 355 (300 mg) | 410 mg | 427 |

TABLE 12-continued
| Example | structure | starting material | yield | MS (ESI) m/z [M + H]+ |
|---|---|---|---|---|
| 165 | 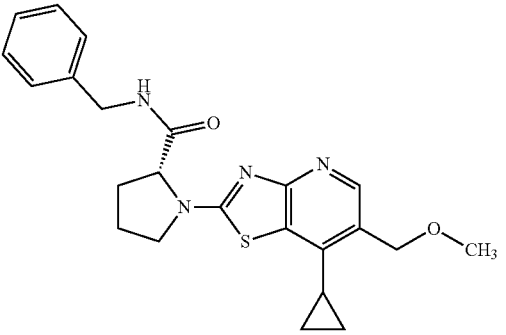 [SMILES: COCc1cnc2nc(N3CCC[C@@H]3C(=O)NCc3ccccc3)sc2c1C1CC1] | Reference Example 402 (110 mg) | 105 mg | 423 |
| 166 | 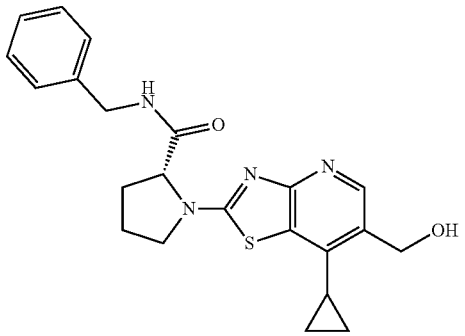 [SMILES: O=C(NCc1ccccc1)[C@H]1CCCN1c1nc2ncc(CO)c(C3CC3)c2s1] | Reference Example 401 (100 mg) | 130 mg | 409 |
| 167 | 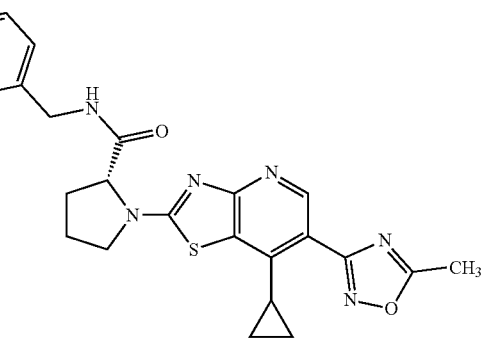 | Reference Example 405 (50.0 mg) | 41.0 mg | 461 |
| 168 | 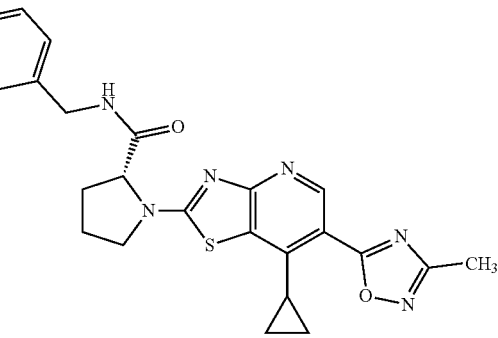 | Reference Example 406 (62.0 mg) | 31.0 mg | 461 |

TABLE 12-continued

| Example | structure | starting material | yield | MS (ESI) m/z [M + H]+ |
|---|---|---|---|---|
| 169 | 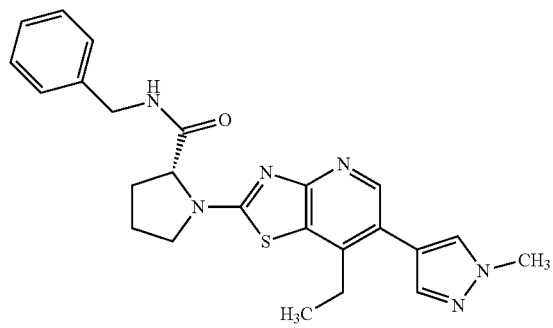 [SMILES: CCc1c(-c2cnn(C)c2)cnc2nc(N3CCC[C@@H]3C(=O)NCc3ccccc3)sc12] | Reference Example 408 (150 mg) | 167 mg | 461 |

Example 170

(R)—N-benzyl-1-[7-ethyl-6-(1-methyl-1H-pyrazol-4-yl)[1,3]thiazolo[4,5-b]pyridin-2-yl]pyrrolidine-2-carboxamide

Example 171

(R)—N-benzyl-1-{6-[2-(5-methyl-1,2,4-oxadiazol-3-yl)propan-2-yl][1,3]thiazolo[4,5-b]pyridin-2-yl}pyrrolidine-2-carboxamide

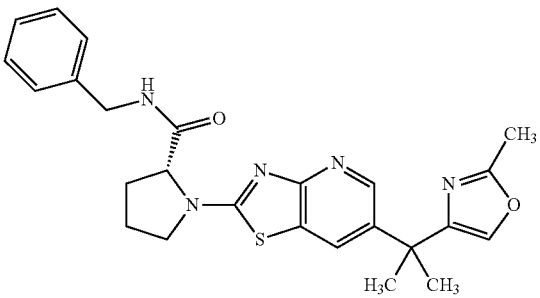 [SMILES: Cc1nc(C(C)(C)c2cnc3nc(N4CCC[C@@H]4C(=O)NCc4ccccc4)sc3c2)co1]

A DMF solution (4.00 mL) of the compound (180 mg) obtained in Example 142, tetrakis(triphenylphosphine)palladium (47.0 mg), sodium carbonate (128 mg) and 2-(1-methylpyrazol-4-yl)-4,4,5,5-tetramethyl-1,3,2-dioxaborolane was stirred with heating at 80° C. for 10 hr. After cooling to room temperature, water was added, and the mixture was extracted twice with ethyl acetate. The organic layer was dried over anhydrous sodium sulfate, filtered and concentrated. The obtained residue was purified by silica gel column chromatography (solvent; hexane/ethyl acetate=30/70-0/100). To the obtained resultant product was added diisopropy ether, and the solid was collected by filtration to give the title compound (40.0 mg).

MS(ESI)m/z; 447[M+H]+

To a DMF solution (12.0 mL) of the compound (230 mg) obtained in Reference Example 422 were added (D)-proline (165 mg) and potassium carbonate (300 mg), and the reaction mixture was stirred with heating at 70° C. for 1.5 hr. After cooling to room temperature, the reaction mixture was acidified with 1.0 mol/L aqueous hydrochloric acid solution, sodium chloride was added, and the mixture was extracted twice with chloroform. The organic layer was dried over anhydrous magnesium sulfate, filtered and concentrated. To a DMF solution of the obtained residue were added N,N-diisopropylethylamine (150 mg), benzylamine (120 mg), EDC hydrochloride (215 mg) and HOBt monohydrate (170 mg), and the reaction mixture was stirred at room temperature overnight. Water was added, and the mixture was extracted with ethyl acetate, and the organic layer was dried over anhydrous sodium sulfate, filtered and concentrated, and the residue was purified by silica gel column chromatography (solvent; ethyl acetate). To the obtained resultant product was added ethyl acetate, and the solid was collected by filtration and dried to give the title compound (90.0 mg).

MS(ESI)m/z; 463[M+H]+

Example 172

(R)—N-benzyl-1-{6-[2-(5-methyl-1,3,4-oxadiazol-2-yl)propan-2-yl][1,3]thiazolo[4,5-b]pyridin-2-yl}pyrrolidine-2-carboxamide

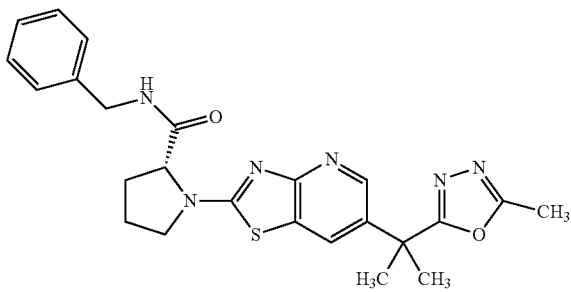 [SMILES: Cc1nnc(C(C)(C)c2cnc3nc(N4CCC[C@@H]4C(=O)NCc4ccccc4)sc3c2)o1]

To an ethanol solution (1.00 mL) of the compound (192 mg) obtained in Example 156 was added hydrazine monohydrate (110 mg), and the reaction mixture was stirred with heating at 70° C. for 13 hr. After cooling to room temperature, water was added, and the mixture was extracted with chloroform. The organic layer was dried over anhydrous magnesium sulfate, filtered and concentrated. To a DMF solution (0.400 mL) of the obtained residue were added dimethylacetamide dimethyl acetal (73.0 µL) and paratoluenesulfonic acid monohydrate (6.00 mg), and the reaction mixture was stirred with heating at 110° C. for 9 hr. After cooling to room temperature, water was added, the mixture was extracted with ethyl acetate, and the organic layer was dried over anhydrous sodium sulfate, filtered and concentrated. The residue was purified by NH silica gel column chromatography (solvent; hexane/ethyl acetate=50/50-0/100) to give the title compound (71.0 mg).
MS(ESI)m/z; 463[M+H]$^+$

Example 173

(R)—N-benzyl-1-[7-ethyl-6-(1-methyl-1H-imidazol-2-yl)[1,3]thiazolo[4,5-b]pyridin-2-yl]pyrrolidine-2-carboxamide

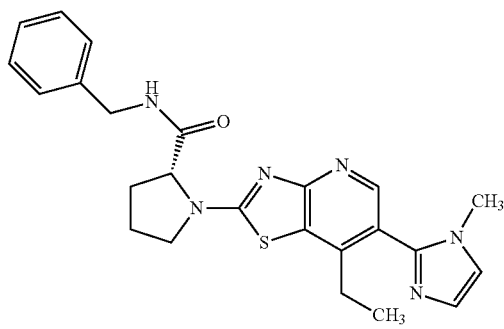 [SMILES: CCc1c(-c2nccn2C)cnc2nc(N3CCC[C@@H]3C(=O)NCc3ccccc3)sc12]

To a methylene chloride solution (2.00 mL) of the compound (30.0 mg) obtained in Reference Example 388 were added, under ice-cooling, trifluoroacetic acid (17.0 µL) and mCPBA (69-75% w/w, 28.0 mg), and the reaction mixture was stirred at 0° C. for 3 hr. To the reaction mixture were added aqueous sodium thiosulfate solution and saturated aqueous sodium hydrogen carbonate solution, and the mixture was extracted twice with chloroform. The organic layer was dried over anhydrous sodium sulfate, filtered and concentrated. To the obtained residue were added the compound (21.0 mg) obtained in Reference Example 471, N,N-diisopropylethylamine (38.0 µL) and THF (500 µL), and the reaction mixture was stirred with heating at 120° C. for 2.5 hr. After confirmation of the completion of the reaction, water was added to the reaction mixture under ice-cooling and the mixture was extracted twice with ethyl acetate. The combined organic layer was washed with saturated brine, dried over anhydrous sodium sulfate, filtered and concentrated. The obtained residue was purified by silica gel column chromatography (solvent; chloroform/methanol=100/0-95/5) to give the title compound (17.0 mg).
MS(ESI)m/z; 447[M+H]$^+$

Example 174

(R)—N-benzyl-1-[7-ethyl-6-(4-methyl-1H-imidazol-1-yl)[1,3]thiazolo[4,5-b]pyridin-2-yl]pyrrolidine-2-carboxamide

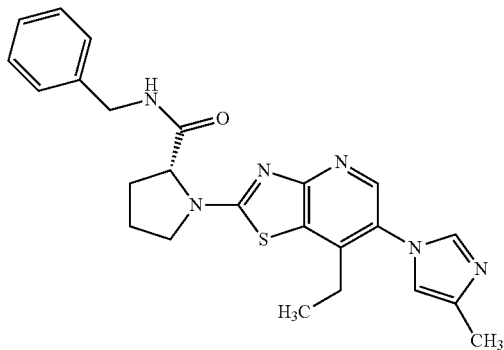 [SMILES: CCc1c(-n2cnc(C)c2)cnc2nc(N3CCC[C@@H]3C(=O)NCc3ccccc3)sc12]

The compound (200 mg) obtained in Reference Example 392 was treated by a method similar to that in Example 173 to give the title compound (229 mg).
MS(ESI)m/z; 447[M+H]$^+$

Example 175

(R)—N-benzyl-1-[7-cyclopropyl-6-(piperidin-1-ylmethyl)[1,3]thiazolo[4,5-b]pyridin-2-yl]pyrrolidine-2-carboxamide hydrochloride

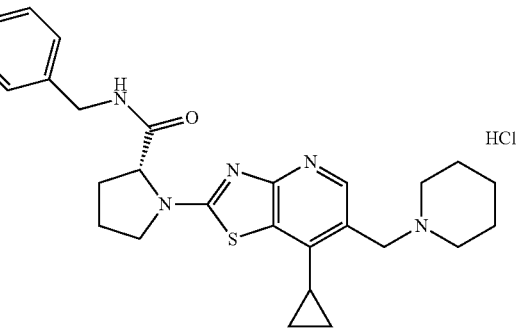

To a dichloromethane solution (3.00 mL) of the compound (130 mg) obtained in Example 166 were added triethylamine (70.0 μL) and methanesulfonyl chloride (30.0 μL) at 0° C., and the reaction mixture was stirred at room temperature for 1 hr. At the same temperature, piperidine (90.0 mg) was added and the reaction mixture was stirred overnight. Water was added, and the mixture was extracted twice with chloroform. The combined organic layer was washed with saturated brine, dried over anhydrous sodium sulfate, filtered and concentrated. The obtained residue was purified by NH silica gel column chromatography (solvent; chloroform/methanol=100/0-95/5). The solvent was evaporated under reduced pressure. To an ethyl acetate solution (5.00 mL) of the obtained residue was added hydrogen chloride (4.0 mol/L ethyl acetate solution, 40.0 μL) at room temperature, and the mixture was stirred at the same temperature for 10 min. The resulting solid was collected by filtration and dried to give the title compound (38.0 mg).
MS(ESI)m/z; 476[M+H]$^+$ Example 176

(R)—N-benzyl-1-{7-cyclopropyl-6-[(dimethylamino)methyl][1,3]thiazolo[4,5-b]pyridin-2-yl}pyrrolidine-2-carboxamide hydrochloride

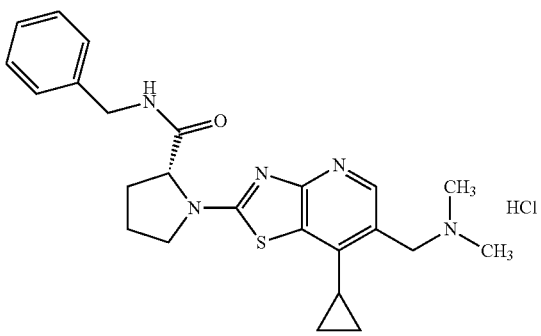 [SMILES: CN(C)Cc1cnc2nc(N3CCC[C@@H]3C(=O)NCc3ccccc3)sc2c1C1CC1 ; Cl]

The compound (176 mg) obtained in Example 166 was treated by a method similar to that in Example 175 to give the title compound (38.0 mg).
MS(ESI)m/z; 436[M+H]$^+$ Example 177

(R)—N-benzyl-1-(6-cyano[1,3]thiazolo[4,5-b]pyridin-2-yl)pyrrolidine-2-carboxamide

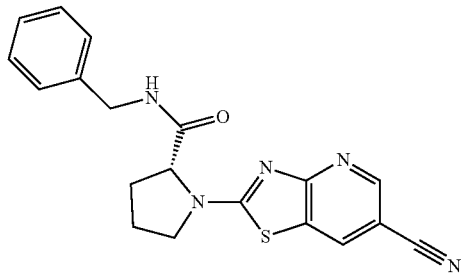 [SMILES: N#Cc1cnc2nc(N3CCC[C@@H]3C(=O)NCc3ccccc3)sc2c1]

To a DMF solution (75.0 mL) of the compound (2.26 g) obtained in Reference Example 432 were added benzylamine (1.40 mL), EDC hydrochloride (2.37 g), HOBt monohydrate (1.89 g) and N,N-diisopropylethylamine (2.20 mL), and the reaction mixture was stirred at room temperature overnight. After confirmation of the completion of the reaction, water was added to the reaction mixture, and the mixture was extracted twice with ethyl acetate. The organic layer was washed once with water, dried over anhydrous magnesium sulfate, filtered and concentrated. The residue was purified by silica gel column chromatography (solvent; hexane/ethyl acetate=40/60-0/100) to give the title compound (1.57 g).
MS(ESI)m/z; 364[M+H]$^+$ Examples 178 to 182 are shown below. These compounds were obtained by a method similar to that in Example 177 except that an appropriate compound was used instead of benzylamine.

TABLE 13

| Example | structure | starting material | yield | MS (ESI) m/z [M + H]$^+$ |
|---|---|---|---|---|
| 178 | 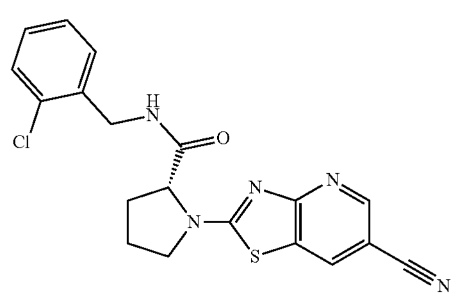 [SMILES: N#Cc1cnc2nc(N3CCC[C@@H]3C(=O)NCc3ccccc3Cl)sc2c1] | Reference Example 432 (150 mg) | 120 mg | 398, 400 |

TABLE 13-continued

| Example | structure | starting material | yield | MS (ESI) m/z [M + H]+ |
|---|---|---|---|---|
| 179 | 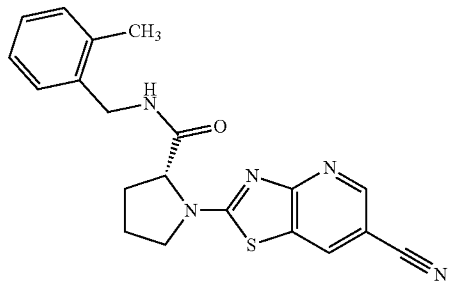 [SMILES: Cc1ccccc1CNC(=O)[C@H]1CCCN1c1nc2ncc(C#N)cc2s1] | Reference Example 432 (120 mg) | 97.0 mg | 378 |
| 180 | 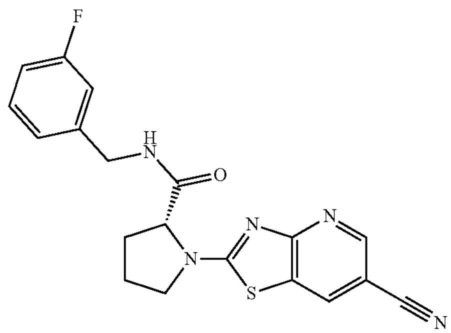 [SMILES: N#Cc1cnc2nc(N3CCC[C@@H]3C(=O)NCc3cccc(F)c3)sc2c1] | Reference Example 432 (120 mg) | 84.0 mg | 382 |
| 181 | 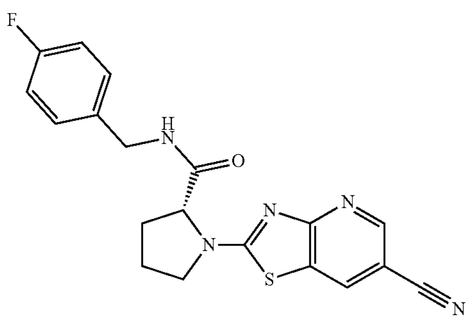 [SMILES: N#Cc1cnc2nc(N3CCC[C@@H]3C(=O)NCc3ccc(F)cc3)sc2c1] | Reference Example 432 (120 mg) | 78.0 mg | 382 |
| 182 | 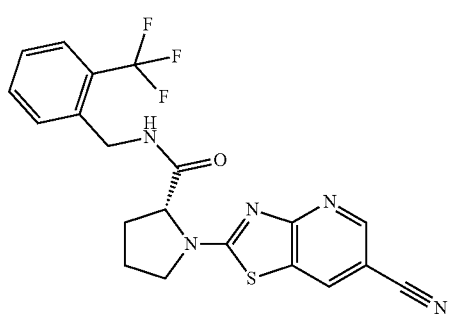 [SMILES: N#Cc1cnc2nc(N3CCC[C@@H]3C(=O)NCc3ccccc3C(F)(F)F)sc2c1] | Reference Example 432 (120 mg) | 101 mg | 432 |

Example 183

(R)—N-benzyl-1-[6-(5-methyl-1,2,4-oxadiazol-3-yl)[1,3]thiazolo[4,5-b]pyridin-2-yl]pyrrolidine-2-carboxamide

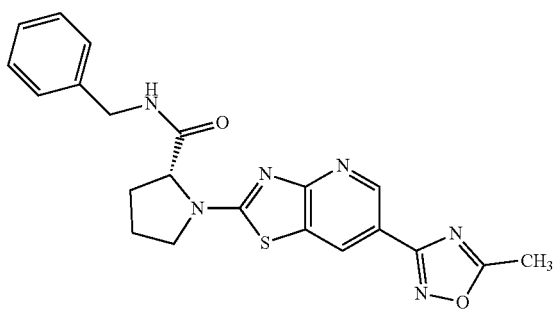 [SMILES: Cc1nc(-c2cnc3nc(N4CCC[C@@H]4C(=O)NCc4ccccc4)sc3c2)no1]

To an ethanol solution (30.0 mL) of the compound (1.56 g) obtained in Example 177 were added hydroxylamine hydrochloride (716 mg) and triethylamine (1.50 mL) at room temperature, and the reaction mixture was stirred with heating at 50° C. for 1.5 hr. After cooling to room temperature, water was added and the resulting solid was collected by filtration and dried. To an acetic acid solution (5.00 mL) of the obtained solid were added acetic anhydride (430 μL) and paratoluenesulfonic acid monohydrate (10.0 mg), and the reaction mixture was stirred with heating at 90° C. for 2.5 hr. After cooling to room temperature, the solvent was evaporated under reduced pressure, and the obtained residue was purified by NH silica gel column chromatography (solvent; hexane/ethyl acetate=50/50-0/100) to give the title compound (1.15 g).

MS(ESI)m/z; 421[M+H]$^+$

Example 184

(R)—N-benzyl-1-(5,6-dimethyl-4-oxido[1,3]thiazolo[4,5-b]pyridin-2-yl)pyrrolidine-2-carboxamide

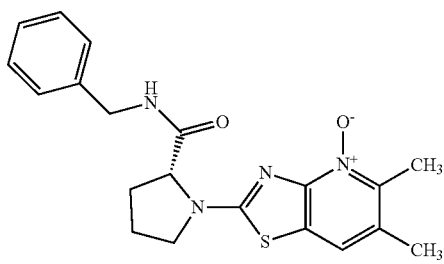 [SMILES: Cc1cc2sc(N3CCC[C@@H]3C(=O)NCc3ccccc3)nc2[n+]([O-])c1C]

To a dichloroethane solution (2.70 mL) of the compound (200 mg) obtained in Reference Example 299 was added, under ice-cooling, mCPBA (69-75% w/w, 277 mg), and the reaction mixture was stirred at room temperature for 1.5 hr. To the reaction mixture were added 0.1 mol/L aqueous sodium thiosulfate solution and saturated aqueous sodium hydrogen carbonate solution, and the mixture was extracted twice with chloroform. The organic layer was dried over anhydrous sodium sulfate, filtered and concentrated, and the residue was purified by silica gel column chromatography (solvent; chloroform/methanol=100/0-95/5). To a THF solution (1.00 mL) of the obtained compound were added the compound (203 mg) obtained in Reference Example 471 and N,N-diisopropylethylamine (440 μL), and the reaction mixture was stirred with heating at 120° C. for 2 hr. After confirmation of the completion of the reaction, under ice-cooling, water was added to the reaction mixture, and the mixture was extracted twice with ethyl acetate. The combined organic layer was washed with saturated brine, dried over anhydrous sodium sulfate, filtered and concentrated. The obtained residue was purified by silica gel column chromatography (solvent; chloroform/methanol=100/0-95/5) to give the title compound (249 mg).

MS(ESI)m/z; 383[M+H]$^+$

Example 185

(R)—N-benzyl-1-(6-methyl[1,3]thiazolo[4,5-b]pyrazin-2-yl)pyrrolidine-2-carboxamide

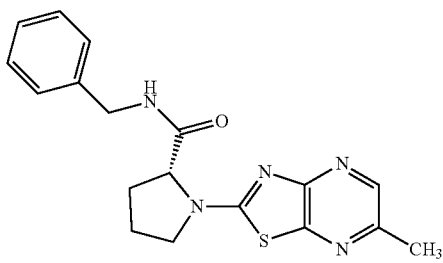 [SMILES: Cc1cnc2nc(N3CCC[C@@H]3C(=O)NCc3ccccc3)sc2n1]

A mixture of the compound (150 mg) obtained in Reference Example 451, the compound (390 mg) obtained in Reference Example 471, N,N-diisopropylethylamine (1.40 mL) and pyridine (2.40 mL) was stirred with heating at 130° C. for 4 hr. After confirmation of the completion of the reaction, under ice-cooling, water was added to the reaction mixture, and the mixture was extracted twice with ethyl acetate. The combined organic layer was washed with saturated brine, dried over anhydrous sodium sulfate, filtered and concentrated. The obtained residue was purified by silica gel column chromatography (solvent; chloroform/methanol-100/0-95/5). To the obtained resultant product was added diisopropy ether, and the solid was collected by filtration to give the title compound (225 mg).

MS(ESI)m/z; 354[M+H]$^+$

Examples 186 to 191 are shown below. These compounds were obtained by a method similar to that in Example 185 except that the starting materials in the following Table were used instead of Reference Example 451 and an appropriate compound was used instead of Reference Example 471 as necessary.

TABLE 14

| Example | structure | starting material | yield | MS (ESI) m/z [M + H]+ |
|---|---|---|---|---|
| 186 | 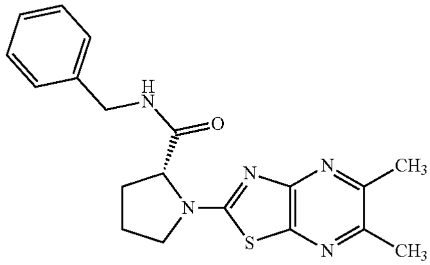 [SMILES: Cc1nc2nc(N3CCC[C@@H]3C(=O)NCc3ccccc3)sc2nc1C] | Reference Example 452 (238 mg) | 360 mg | 368 |
| 187 | 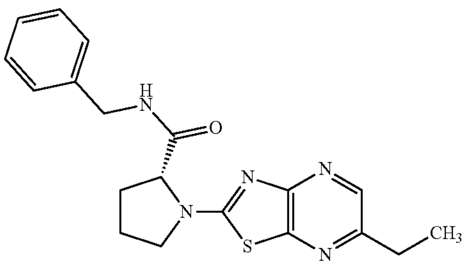 [SMILES: CCc1cnc2nc(N3CCC[C@@H]3C(=O)NCc3ccccc3)sc2n1] | Reference Example 453 (195 mg) | 360 mg | 368 |
| 188 | 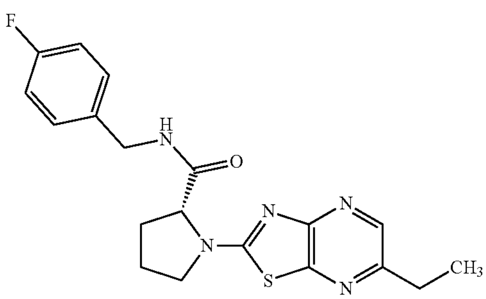 [SMILES: CCc1cnc2nc(N3CCC[C@@H]3C(=O)NCc3ccc(F)cc3)sc2n1] | Reference Example 453 (130 mg) | 250 mg | 386 |
| 189 | 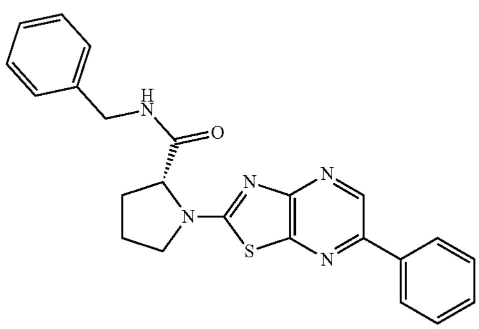 [SMILES: O=C(NCc1ccccc1)[C@H]1CCCN1c1nc2ncc(-c3ccccc3)nc2s1] | Reference Example 454 (48.0 mg) | 72.0 mg | 416 |
| 190 | 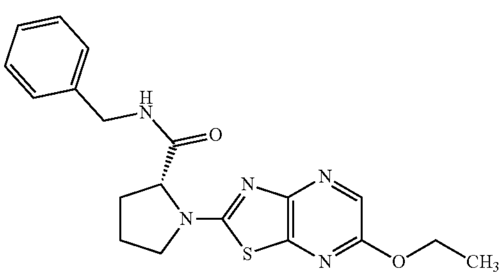 [SMILES: CCOc1cnc2nc(N3CCC[C@@H]3C(=O)NCc3ccccc3)sc2n1] | Reference Example 455 (109 mg) | 156 mg | 384 |

| Example | structure | starting material | yield | MS (ESI) m/z [M + H]+ |
|---|---|---|---|---|
| 191 | 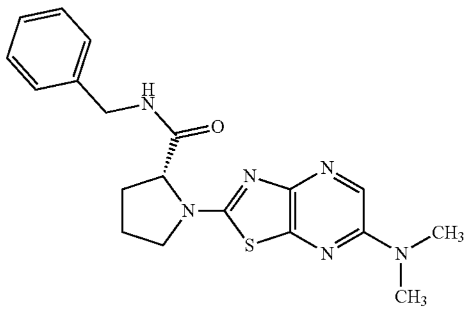 [SMILES: CN(C)c1cnc2nc(N3CCC[C@@H]3C(=O)NCc3ccccc3)sc2n1] | Reference Example 456 (48.0 mg) | 76.0 mg | 383 |

Example 192

(R)—N-benzyl-1-(6-cyclopropyl[1,3]thiazolo[4,5-b]pyrazin-2-yl)pyrrolidine-2-carboxamide

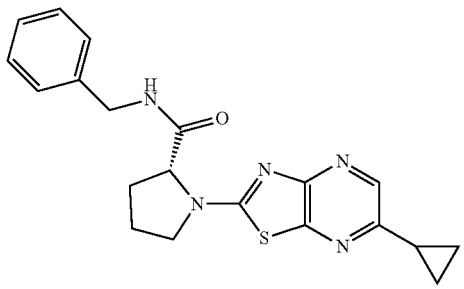 [SMILES: O=C(NCc1ccccc1)[C@H]1CCCN1c1nc2ncc(C3CC3)nc2s1]

A mixture of the compound (149 mg) obtained in Reference Example 458, the compound (150 mg) obtained in Reference Example 471, N,N-diisopropylethylamine (742 µL) and THF (700 µL) was stirred with heating at 120° C. for 3 hr. After confirmation of the completion of the reaction, under ice-cooling, water was added to the reaction mixture, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=70/30-0/100). To the obtained resultant product was added diisopropy ether and the solid was collected by filtration to give the title compound (193 mg).

MS(ESI)m/z; 380[M+H]+

Example 193 benzyl (R)-2-(6-methyl[1,3]thiazolo[4,5-b]pyridin-2-yl) pyrrolidine-1-carboxylate

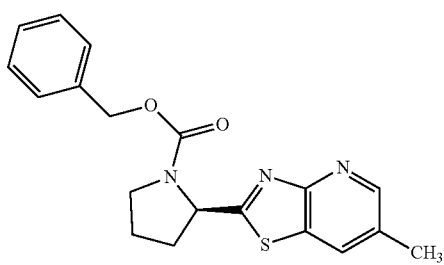 [SMILES: Cc1cnc2nc([C@H]3CCCN3C(=O)OCc3ccccc3)sc2c1]

A hexamethylphosphoric acid triamide solution (5.00 mL) of the compound (1.05 g) obtained in Reference Example 459 and Lawesson reagent (710 mg) was stirred with heating at 180° C. for 30 min. The reaction mixture was allowed to cool, water was added, and the mixture was extracted twice with ethyl acetate.

The combined organic layer was washed with saturated brine, dried over anhydrous sodium sulfate, filtered and concentrated. The residue was purified by silica gel column chromatography (solvent; ethyl acetate/methanol=100/0-95/5) to give the title compound (789 mg).

MS(ESI)m/z; 354[M+H]+

Example 194 benzyl (R)-2-(6-ethyl[1,3]thiazolo[4,5-b]pyridin-2-yl)pyrrolidine-1-carboxylate

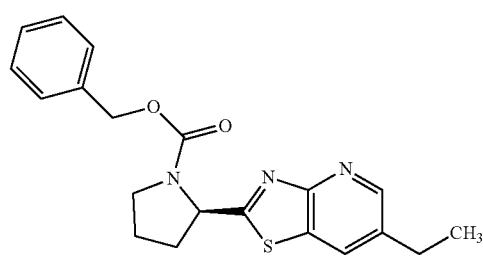 [SMILES: CCc1cnc2nc([C@H]3CCCN3C(=O)OCc3ccccc3)sc2c1]

The compound (2.79 g) obtained in Reference Example 460 was treated by a method similar to that in Example 193 to give the title compound (2.30 g).

MS(ESI)m/z; 368[M+H]+

Example 195 benzyl (R)-2-(5,6-dimethyl[1,3]thiazolo[4,5-b]pyridin-2-yl)pyrrolidine-1-carboxylate

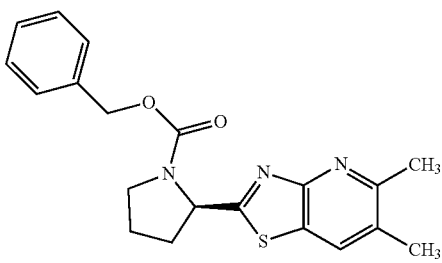 [SMILES: Cc1cc2sc([C@H]3CCCN3C(=O)OCc3ccccc3)nc2nc1C]

The compound (10.7 g) obtained in Reference Example 461 was treated by a method similar to that in Example 193 to give the title compound (6.00 g).
MS(ESI)m/z; 368[M+H]$^+$

Example 196

1-[(R)-2-(6-methyl[1,3]thiazolo[4,5-b]pyridin-2-yl)pyrrolidin-1-yl]-2-phenylethanone

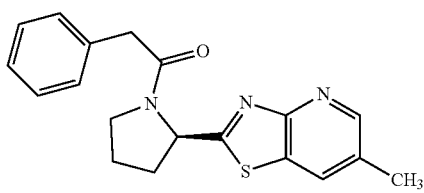

To a dichloromethane solution (3.00 mL) of the compound (72.0 mg) obtained in Reference Example 462 were added N,N-diisopropylethylamine (52.0 mg) and phenylacetyl chloride (52.0 mg) at room temperature, and the reaction mixture was stirred at the same temperature for 1 hr. To the reaction mixture was added water, and the mixture was extracted twice with chloroform. The organic layer was dried over anhydrous magnesium sulfate, filtered and concentrated, and the residue was purified by silica gel column chromatography (solvent; ethyl acetate/methanol=100/0-95/5) to give the title compound (65.0 mg).
MS(ESI)m/z; 338[M+H]$^+$

Example 197 phenyl (R)-2-(6-methyl[1,3]thiazolo[4,5-b]pyridin-2-yl) pyrrolidine-1-carboxylate

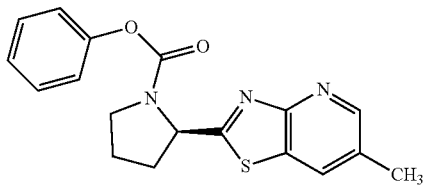 [SMILES: Cc1cnc2nc([C@H]3CCCN3C(=O)Oc3ccccc3)sc2c1]

The compound (200 mg) obtained in Reference Example 462 was treated by a method similar to that in Example 196 to give the title compound (115 mg).
MS(ESI)m/z; 340[M+H]$^+$

Example 198

1-[(R)-2-(6-ethyl[1,3]thiazolo[4,5-b]pyridin-2-yl)pyrrolidin-1-yl]-2-phenylethanone

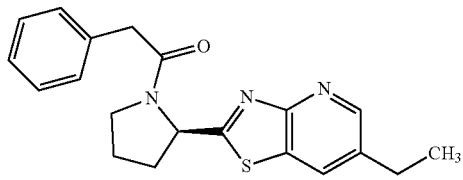 [SMILES: CCc1cnc2nc([C@H]3CCCN3C(=O)Cc3ccccc3)sc2c1]

The compound (90.0 mg) obtained in Reference Example 463 was treated by a method similar to that in Example 196 to give the title compound (130 mg).
MS(ESI)m/z; 352[M+H]$^+$

Example 199 phenyl (R)-2-(5,6-dimethyl[1,3]thiazolo[4,5-b]pyridin-2-yl)pyrrolidine-1-carboxylate

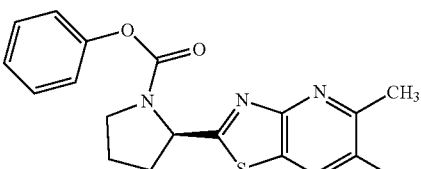

The compound (200 mg) obtained in Reference Example 464 was treated by a method similar to that in Example 196 to give the title compound (300 mg).
MS(ESI)m/z; 354[M+H]$^+$

Example 200

(R)—N-benzyl-2-(6-methyl[1,3]thiazolo[4,5-b]pyridin-2-yl)pyrrolidine-1-carboxamide

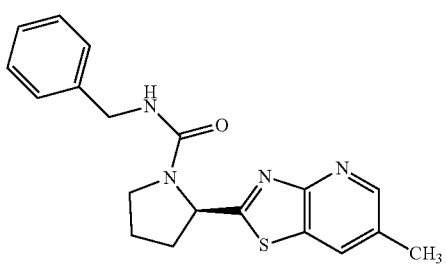

To a methylene chloride solution (10.0 mL) of the compound (200 mg) obtained in Reference Example 462 and N,N-diisopropylethylamine (150 mg) was added dropwise benzyl isocyanate (130 mg) under ice-cooling, and the reaction mixture was stirred at room temperature for 30 min. To the reaction mixture was added water, and the mixture was extracted twice with chloroform. The organic layer was dried over anhydrous magnesium sulfate, filtered and concentrated, and the residue was purified by silica gel column chromatography (solvent; ethyl acetate/methanol=100/0-95/5) to give the title compound (248 mg).

Example 201

(R)—N-benzyl-2-(5,6-dimethyl[1,3]thiazolo[4,5-b]pyridin-2-yl)pyrrolidine-1-carboxamide

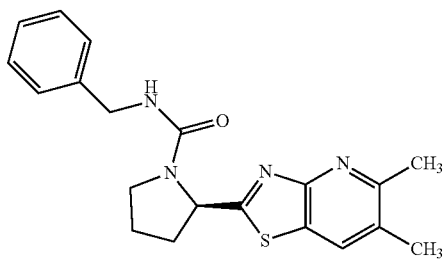 [SMILES: Cc1cc2sc([C@H]3CCCN3C(=O)NCc3ccccc3)nc2nc1C]

The compound (200 mg) obtained in Reference Example 464 was treated by a method similar to that in Example 200 to give the title compound (300 mg).
MS(ESI)m/z; 367[M+H]+

Example 202

(R)—N—[(R)-2,3-dihydro-1H-inden-1-yl]-2-(6-methyl[1,3]thiazolo[4,5-b]pyridin-2-yl)pyrrolidine-1-carboxamide

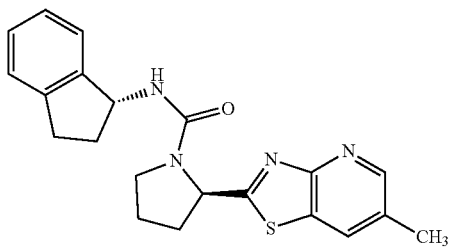 [SMILES: Cc1cnc2nc([C@H]3CCCN3C(=O)N[C@@H]3CCc4ccccc43)sc2c1]

To a dichloromethane solution (10.0 mL) of triphosgene (73.0 mg) was added pyridine (67.0 µL) at 0° C., and the reaction mixture was stirred at 0° C. for 30 min. The compound (90.0 mg) obtained in Reference Example 462 was added, and the reaction mixture was stirred at room temperature for 30 min. The solvent was evaporated under reduced pressure, dichloromethane (10 mL), N,N-dimethylaminopyridine (250 mg) and (R)-1-aminoindane (2800 mg) were added at room temperature, and the reaction mixture was stirred at the same temperature for 3 hr. To the reaction mixture was added water, and the mixture was extracted twice with chloroform. The organic layer was dried over anhydrous magnesium sulfate, filtered and concentrated, and the residue was purified by silica gel column chromatography (solvent; ethyl acetate/methanol=100/0-95/5) to give the title compound (130 mg).

Example 203

(R)-2-(6-methyl[1,3]thiazolo[4,5-b]pyridin-2-yl)-N-(1-phenylcyclopropyl)-pyrrolidine-1-carboxamide

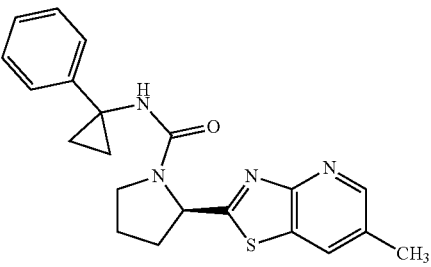 [SMILES: Cc1cnc2nc([C@H]3CCCN3C(=O)NC3(c4ccccc4)CC3)sc2c1]

The compound (90.0 mg) obtained in Reference Example 462 was treated by a method similar to that in Example 202 to give the title compound (20.0 mg).
MS(ESI)m/z; 379[M+H]+

Example 204

(R)—N-benzyl-1-(4-chloropyrido[2,3-d]pyrimidin-7-yl)pyrrolidine-2-carboxamide

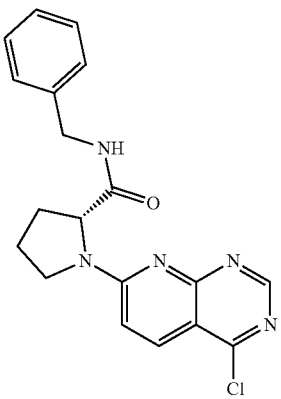 [SMILES: O=C(NCc1ccccc1)[C@H]1CCCN1c1ccc2c(Cl)ncnc2n1]

A mixture of (R)—N-benzylpyrrolidine-2-carboxamide hydrochloride (135 mg), the compound (98.0 mg) obtained in Reference Example 468, N,N-diisopropylethylamine (232 and THF (3.00 mL) was stirred at 0° C. for 30 min. After confirmation of the completion of the reaction, water was added to the reaction mixture, and the mixture was extracted twice with chloroform. The combined organic layer was washed with saturated brine, dried over anhydrous sodium sulfate, filtered and concentrated. The obtained residue was purified by silica gel column chromatography (solvent; ethyl acetate/methanol=100/0-90/10) to give the title compound (45.4 mg).
MS(ESI)m/z; 368, 370[M+H]+

Example 205

(R)—N-benzyl-1-[4-(N',N'-dimethylamino)pyrido[2,3-d]pyrimidin-7-yl]pyrrolidine-2-carboxamide

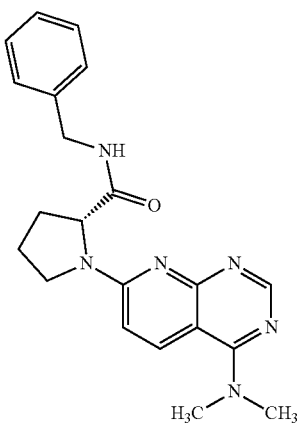 [SMILES: CN(C)c1ncnc2nc(N3CCC[C@@H]3C(=O)NCc3ccccc3)ccc12]

To a mixture of the compound (45.0 mg) obtained in Example 204, N,N-diisopropylethylamine (852 μL) and N-methylpyrrolidine (1.50 mL) was added dimethylamine hydrochloride (20.0 mg), and the reaction mixture was stirred at 50° C. for 1 hr. After confirmation of the completion of the reaction, saturated ammonium chloride water was added to the reaction mixture, and the mixture was extracted 3 times with ethyl acetate. The combined organic layer was washed with saturated brine, dried over anhydrous sodium sulfate, filtered and concentrated. The obtained residue was purified by NH silica gel column chromatography (solvent; ethyl acetate/methanol=100/0-90/10). To the obtained resultant product was added ethyl acetate, and the solid was collected by filtration to give the title compound (20.0 mg).

MS(ESI)m/z; 377, 379[M+11]$^+$

Reference Example 1

4-amino-5-cyano-2-(methylsulfanyl)-1,3-thiazole

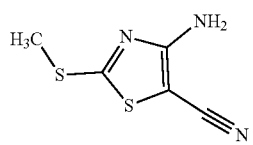

To an acetone suspension (100 mL) of cyanimidodithiocarbonic acid monomethyl ester monopotassium salt (10.0 g) was added, under ice-cooling, chloroacetonitrile (4.90 g), and the reaction mixture was stirred at room temperature for 1 hr. Triethylamine (1.80 g) was added at room temperature, and the reaction mixture was stirred at the same temperature for 3 days. Water was added, and the precipitated resultant product was collected by filtration. The obtained resultant product was washed with ethanol and diisopropy ether, and dried to give the title compound (9.50 g).

MS(ESI)m/z; 172[M+H]$^+$

Reference Example 2

2-(methylsulfanyl)[1,3]thiazolo[4,5-d]pyrimidin-7(6H)-one

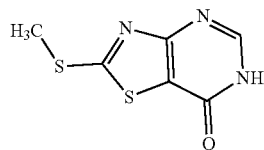

A mixture of the compound (4.10 g) obtained in Reference Example 1, formic acid (23.0 mL) and water (1.20 mL) was stirred at 110° C. for 5 hr. After cooling to room temperature, the precipitated resultant product was collected by filtration. The obtained resultant product was washed with ethanol and diisopropy ether, and dried to give the title compound (3.90 g).

MS(ESI)m/z; 200[M+H]$^+$

Reference Example 3

N-[5-cyano-2-(methylsulfanyl)-1,3-thiazol-4-yl]-2,2-difluoroacetamide

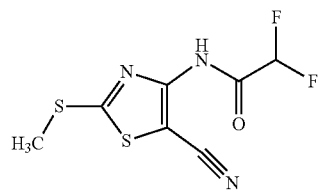

To a THF solution (20.0 mL) of the compound (2.00 g) obtained in Reference Example 1 were added, under ice-cooling, pyridine (1.05 g) and difluoroacetic anhydride (2.30 g), and the reaction mixture was stirred at the same temperature for 3 hr. After confirmation of the completion of the reaction, aqueous citric acid solution was added, and the mixture was extracted twice with chloroform. The organic layer was dried over anhydrous magnesium sulfate, filtered and concentrated. To the obtained resultant product was added diisopropy ether, and the solid was collected by filtration to give the title compound (2.60 g).

MS(ESI)m/z; 250[M+H]$^+$

Reference Example 4

N-[5-cyano-2-(methylsulfanyl)-1,3-thiazol-4-yl]-2,2,2-trifluoroacetamide

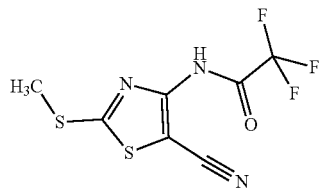 [SMILES: CSc1nc(NC(=O)C(F)(F)F)c(C#N)s1]

The compound (5.50 g) obtained in Reference Example 1 was treated by a method similar to that in Reference Example 3 to give the title compound (6.20 g).

MS(ESI)m/z; 268[M+H]+

Reference Example 5

N-[5-cyano-2-(methylsulfanyl)-1,3-thiazol-4-yl]-2-methoxyacetamide

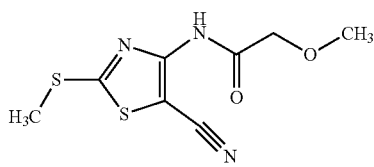

To a pyridine solution (12.0 mL) of the compound (2.50 g) obtained in Reference Example 1 was added, under ice-cooling, methoxyacetyl chloride (1.60 g), and the reaction mixture was stirred at the same temperature for 1 hr. After confirmation of the completion of the reaction, aqueous citric acid solution was added, and the mixture was extracted twice with chloroform. The organic layer was dried over anhydrous magnesium sulfate, filtered and concentrated. To the obtained resultant product was added diisopropy ether, and the solid was collected by filtration to give the title compound (3.60 g).

MS(ESI)m/z; 244[M+H]+

Reference Example 6

N-[5-cyano-2-(methylsulfanyl)-1,3-thiazol-4-yl] tetrahydro-2H-pyran-4-carboxamide

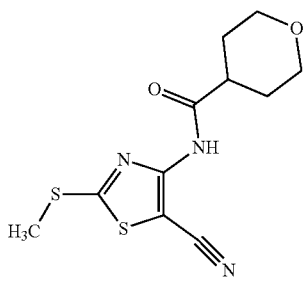 [SMILES: CSc1nc(NC(=O)C2CCOCC2)c(C#N)s1]

The compound (428 mg) obtained in Reference Example 1 was treated by a method similar to that in Reference Example 5 to give the title compound (516 mg).

MS(ESI)m/z; 284[M+H]+

Reference Example 7

N-[5-cyano-2-(methylsulfanyl)-1,3-thiazol-4-yl]-3-methoxypropanamide

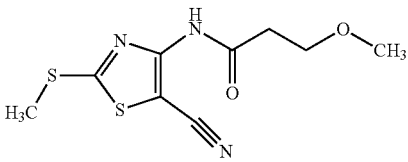

To a dichloroethane solution (23.0 mL) of 3-methoxypropionic acid (1.72 g) were added, under ice-cooling, oxalyl chloride (1.50 mL) and DMF (2 drops), and the reaction mixture was stirred at room temperature for 2 hr. This reaction mixture was added under ice-cooling to a pyridine solution (10.0 mL) of the compound (2.00 g) obtained in Reference Example 1, and the mixture was stirred at room temperature for 2 hr. After confirmation of the completion of the reaction, 1.0 mol/L hydrochloric acid was added, and the mixture was extracted twice with chloroform. The organic layer was dried over anhydrous magnesium sulfate, filtered and concentrated. The obtained residue was purified by silica gel column chromatography (solvent; hexane/ethyl acetate=50/50-0/100) to give the title compound (2.00 g).

MS(ESI)m/z; 258[M+H]+

Reference Example 8

5-(difluoromethyl)-2-(methylsulfanyl)[1,3]thiazolo[4,5-d]pyrimidin-7(6H)-one

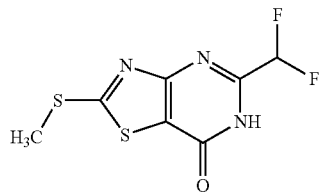

An acetic acid solution (25.0 mL) of the compound (2.40 g) obtained in Reference Example 3 and sodium acetate (5.53 g) was stirred with heating at 130° C. for 2.5 hr. After ice-cooling, the precipitated resultant product was collected by filtration and dried to give the title compound (1.53 g).

MS(ESI)m/z; 250[M+H]+

Reference Example 9

2-(methylsulfanyl)-5-(trifluoromethyl)[1,3]thiazolo[4,5-d]pyrimidin-7(6H)-one

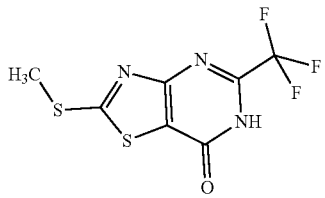 [SMILES: CSc1nc2nc(C(F)(F)F)[nH]c(=O)c2s1]

The compound (7.50 g) obtained in Reference Example 4 was treated by a method similar to that in Reference Example 8 to give the title compound (3.52 g).
MS(ESI)m/z; 268[M+H]+

Reference Example 10

5-(methoxymethyl)-2-(methylsulfanyl)[1,3]thiazolo[4,5-d]pyrimidin-7(6H)-one

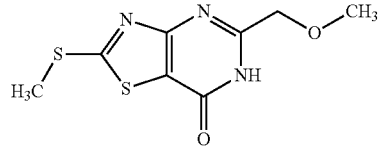

To a methanol solution (60.0 mL) of the compound (3.42 g) obtained in Reference Example 5 were added at room temperature dimethyl sulfoxide (4.50 mL), potassium carbonate (12.0 g) and hydrogen peroxide (30-35% w/w, 9.10 mL), and the reaction mixture was stirred at the same temperature for 2 hr. After ice-cooling, aqueous sodium thiosulfate solution was added, and the mixture was stirred at room temperature for 30 min. The mixture was acidified with 3.0 mol/L hydrochloric acid, and precipitated resultant product was collected by filtration and dried to give the title compound (2.65 g).
MS(ESI)m/z; 244[M+H]+

Reference Example 11

5-(2-methoxyethyl)-2-(methylsulfanyl)[1,3]thiazolo[4,5-d]pyrimidin-7(6H)-one

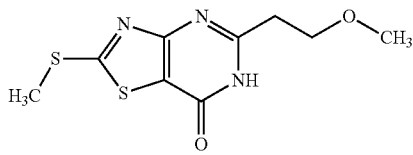

The compound (2.00 g) obtained in Reference Example 7 was treated by a method similar to that in Reference Example 10 to give the title compound (1.30 g).
MS(ESI)m/z; 258[M+H]+

Reference Example 12

2-(methylsulfanyl)-5-(tetrahydro-2H-pyran-4-yl)[1,3]thiazolo[4,5-d]pyrimidin-7(6H)-one

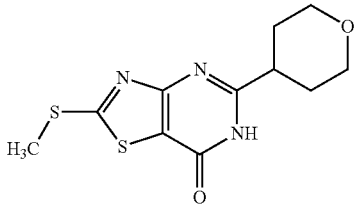 [SMILES: CSc1nc2nc(C3CCOCC3)[nH]c(=O)c2s1]

The compound (493 mg) obtained in Reference Example 6 was treated by a method similar to that in Reference Example 10 to give the title compound (410 mg).
MS(ESI)m/z; 284[M+H]+

Reference Example 13

7-chloro-2-(methylsulfanyl)[1,3]thiazolo[4,5-d]pyrimidine

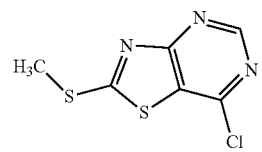

To the compound (3.90 g) obtained in Reference Example 2 was added at room temperature phosphorus oxychloride (13.0 mL), and the reaction mixture was stirred at 110° C. for 2 hr. After ice-cooling, the reaction mixture was poured into ice water by small portions, and the precipitated resultant product was collected by filtration. The obtained resultant product was washed with ethanol and diisopropy ether and dried to give the title compound (3.20 g).
MS(ESI)m/z; 218, 220[M+H]+

The following Table shows the compounds obtained by treating the corresponding compounds by a method similar to that in Reference Example 13.

TABLE 15

| Reference Example | structure | starting material | yield | MS (ESI) m/z [M + H]+ |
|---|---|---|---|---|
| 14 | ![structure] | Reference Example 8 (1.50 g) | 1.20 g | 268, 270 |

TABLE 15-continued

| Reference Example | structure | starting material | yield | MS (ESI) m/z [M + H]+ |
|---|---|---|---|---|
| 15 | ![structure 15] | Reference Example 9 (1.00 g) | 770 mg | 286, 288 |
| 16 | ![structure 16] | Reference Example 10 (1.80 g) | 950 mg | 262, 264 |
| 17 | ![structure 17] | Reference Example 11 (1.30 g) | 900 mg | 276, 278 |
| 18 | ![structure 18] | Reference Example 20 (1.25 g) | 900 mg | 232, 234 |

Reference Example 19

4-amino-2-(methylsulfanyl)-1,3-thiazole-5-carboxamide

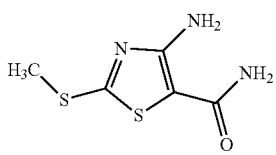

To an ethanol solution (15.0 mL) of cyanimidodithiocarbonic acid monomethyl ester monopotassium salt (5.00 g) was added, at room temperature, chloroacetamide (2.80 g), and the reaction mixture was heated under reflux for 1.5 hr. After cooling to room temperature, sodium methoxide (1.60 g) was added, and the reaction mixture was further heated under reflux for 3 hr. Ethanol was evaporated under reduced pressure, water was added, and the precipitated resultant product was collected by filtration and dried to give the title compound (2.70 g).

MS(ESI)m/z; 190[M+H]+

Reference Example 20

5-methyl-2-(methylsulfanyl) [1,3]thiazolo[4,5-d]pyrimidin-7(6H)-one

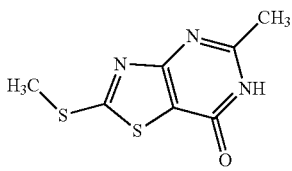

To an ethanol solution (15.0 mL) of the compound (2.70 g) obtained in Reference Example 19 were added at room temperature acetylacetone (2.50 g) and 2.0 mol/L hydrochloric acid (5.00 mL), and the reaction mixture was heated under reflux for 12 hr. Under ice-cooling, water was added, and the precipitated resultant product was collected by filtration and dried to give the title compound (1.85 g).

MS(ESI)m/z; 214[M+H]+

Reference Example 21

4-amino-5-(cyclopropanecarbonyl)-2-(methylsulfanyl)-1,3-thiazole

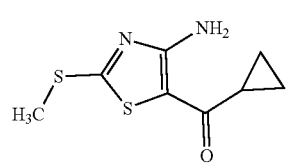

To a methanol solution (12.0 mL) of cyclopropyl methyl ketone (1.80 g) was added under ice-cooling bromine (1.10 mL), and the reaction mixture was stirred at the same temperature for 10 min. Water (6.00 mL) was added, and the reaction mixture was stirred at room temperature for 3 hr. The reaction mixture was added to saturated aqueous sodium hydrogen carbonate solution and the mixture was extracted 3 times with diethyl ether. The organic layer was dried over anhydrous magnesium sulfate, filtered and concentrated to give bromomethyl cyclopropyl ketone (3.48 g). To an acetone solution (30.0 mL) of cyanimidodithiocarbonic acid monomethyl ester monopotassium salt (3.02 g) was added at room temperature bromomethyl cyclopropyl ketone (3.48 g), and the reaction mixture was stirred at the same temperature for 1 hr. Triethylamine (0.740 mL) was added, and the reaction mixture was stirred for 2 hr. The resultant product was collected by filtration, washed with water and dried to give the title compound (3.29 g).

MS(ESI)m/z; 215[M+H]$^+$

The following Tables show the compounds obtained by treating the corresponding compounds by a method similar to that in Reference Example 21.

TABLE 16

| Reference Example | structure | starting material (cyanimido-dithiocarbonic acid monomethyl ester monopotassium salt) | yield | MS (ESI) m/z [M + H]$^+$ |
|---|---|---|---|---|
| 22 | 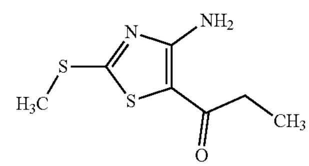 | 1.50 g | 1.68 g | 203 |
| 23 | 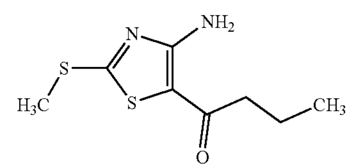 | 1.75 g | 1.80 g | 217 |
| 24 | 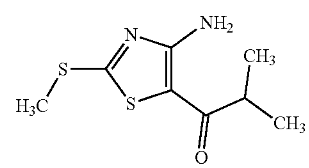 | 2.30 g | 1.19 g | 217 |
| 25 | 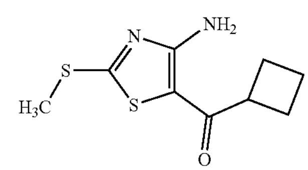 | 3.45 g | 4.45 g | 229 |
| 26 | 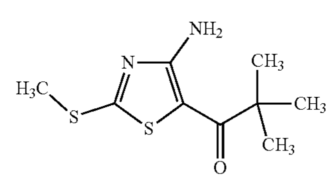 | 2.85 g | 2.89 g | 231 |
| 27 | 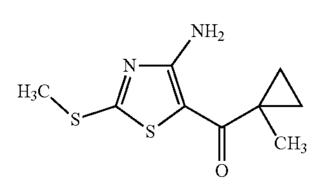 | 3.95 g | 4.35 g | 229 |

TABLE 16-continued

| Reference Example | structure | starting material (cyanimidodithiocarbonic acid monomethyl ester monopotassium salt) | yield | MS (ESI) m/z [M + H]+ |
|---|---|---|---|---|
| 28 | 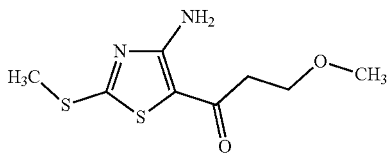 | 2.70 g | 1.23 g | 233 |
| 29 | 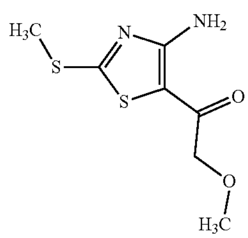 | 2.89 g | 1.42 g | 219 |
| 30 | 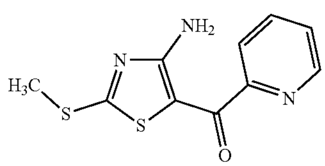 [SMILES: CSc1nc(N)c(C(=O)c2ccccn2)s1] | 1.00 g | 1.29 g | 252 |
| 31 | 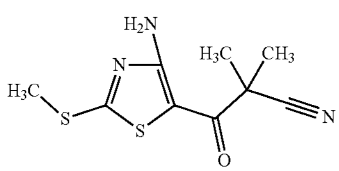 | 0.70 g | 0.92 g | 242 |
| 32 | 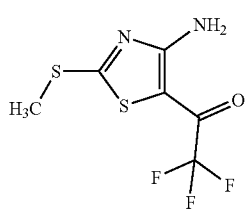 | 3.00 g | 3.30 g | 243 |
| 33 | 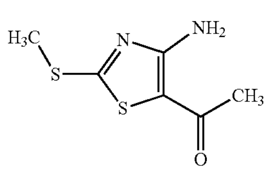 | 3.00 g | 2.74 g | 189 |
| 34 | 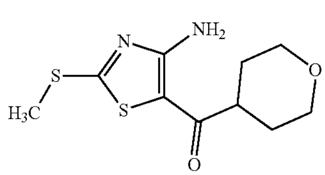 [SMILES: CSc1nc(N)c(C(=O)C2CCOCC2)s1] | 3.95 g | 4.60 g | 259 |

Reference Example 35

N-[5-(cyclopropylcarbonyl)-2-(methylsulfanyl)-1,3-thiazol-4-yl]formamide

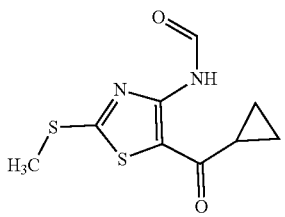

A mixed solution of formic acid (0.352 mL) and acetic anhydride (0.771 mL) was stirred with heating at 50° C. for 2 hr. After cooling to room temperature, the compound (500 mg) obtained in Reference Example 21 was added, and the reaction mixture was stirred with heating at 110° C. for 2 hr. After cooling to room temperature, the solvent was evaporated under reduced pressure and the obtained residue was purified by silica gel column chromatography (solvent; hexane/ethyl acetate=95/5-60/40) to give the title compound (538 mg).

MS(ESI)m/z; 243[M+H]$^+$

The following Tables show the compounds obtained by treating the corresponding compounds by a method similar to that in Reference Example 35.

TABLE 17

| Reference Example | structure | starting material | yield | MS (ESI) m/z [M + H]$^+$ |
|---|---|---|---|---|
| 36 | 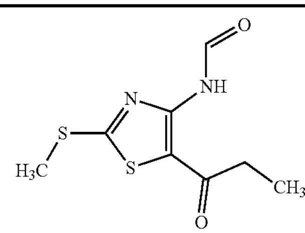 | Reference Example 22 (500 mg) | 433 mg | 231 |
| 37 | 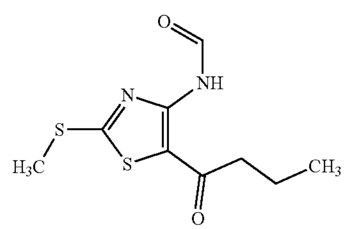 | Reference Example 23 (500 mg) | 523 mg | 245 |
| 38 | 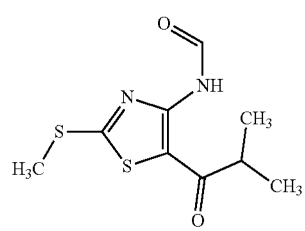 | Reference Example 24 (500 mg) | 537 mg | 245 |
| 39 | 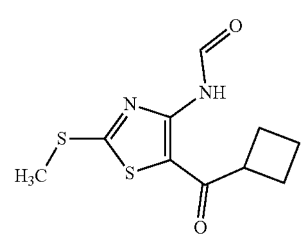 [SMILES: CSc1nc(NC=O)c(C(=O)C2CCC2)s1] | Reference Example 25 (500 mg) | 526 mg | 257 |
| 40 | 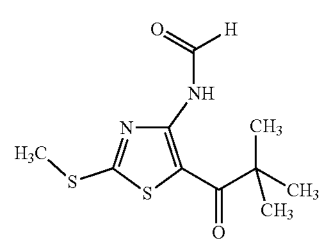 [SMILES: CSc1nc(NC=O)c(C(=O)C(C)(C)C)s1] | Reference Example 26 (1.20 g) | 1.17 g | 259 |

TABLE 17-continued

| Reference Example | structure | starting material | yield | MS (ESI) m/z [M + H]+ |
|---|---|---|---|---|
| 41 | 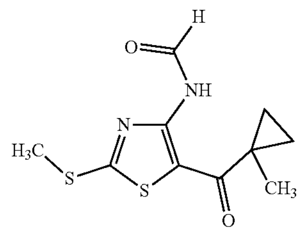 [SMILES: CSc1nc(NC=O)c(C(=O)C2(C)CC2)s1] | Reference Example 27 (1.20 g) | 1.18 g | 257 |
| 42 | 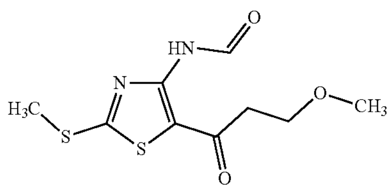 | Reference Example 28 (1.23 g) | 850 mg | 261 |
| 43 | 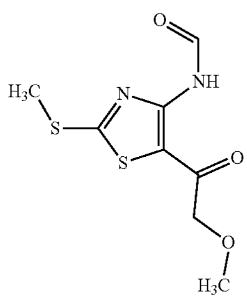 | Reference Example 29 (500 mg) | 488 mg | 247 |
| 44 | 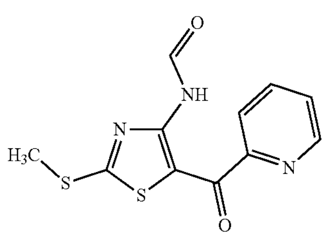 [SMILES: CSc1nc(NC=O)c(C(=O)c2ccccn2)s1] | Reference Example 30 (1.29 g) | 1.22 g | 280 |
| 45 | 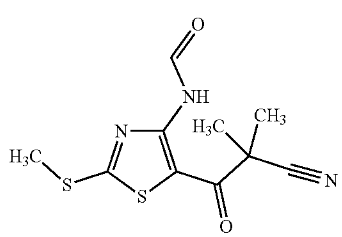 [SMILES: CSc1nc(NC=O)c(C(=O)C(C)(C)C#N)s1] | Reference Example 31 (920 mg) | 700 mg | 270 |
| 46 | 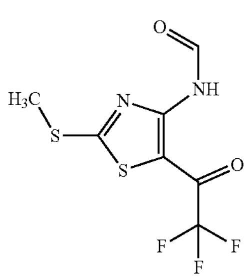 | Reference Example 32 (500 mg) | 152 mg | 271 |

Reference Example 47

N-[5-acetyl-2-(methylsulfanyl)-1,3-thiazol-4-yl]-2-methoxyacetamide

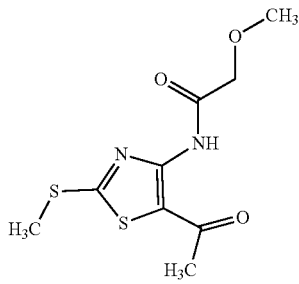

To a 1,4-dioxane solution (3.00 mL) of the compound (150 mg) obtained in Reference Example 33 were added, under ice-cooling, pyridine (3.00 mL) and methoxyacetyl chloride (0.0870 mL), and the reaction mixture was stirred at room temperature for 1 hr. After confirmation of the completion of the reaction, water was added to the mixture and the mixture was extracted twice with chloroform. The organic layer was dried over anhydrous magnesium sulfate, filtered and concentrated. The obtained residue was purified by silica gel column chromatography (solvent; hexane/ethyl acetate=70/30-40/60) to give the title compound (119 mg).
MS(ESI)m/z; 261[M+H]$^+$ The following Tables show the compounds obtained by treating the corresponding compounds by a method similar to that in Reference Example 47.

TABLE 18

| Reference Example | structure | starting material | yield | MS (ESI) m/z [M + H]$^+$ |
|---|---|---|---|---|
| 48 | 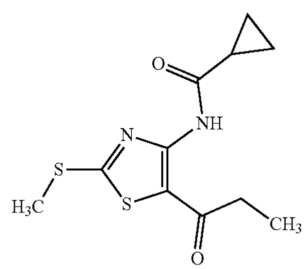 [SMILES: CCC(=O)c1sc(SC)nc1NC(=O)C1CC1] | Reference Example 22 (500 mg) | 592 mg | 271 |
| 49 | 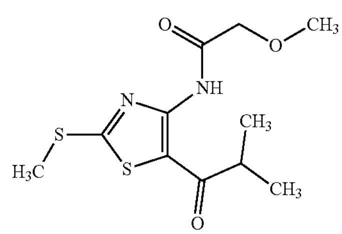 | Reference Example 24 (343 mg) | 300 mg | 289 |
| 50 | 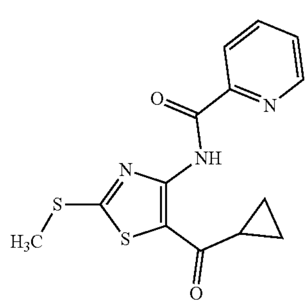 [SMILES: CSc1nc(NC(=O)c2ccccn2)c(C(=O)C2CC2)s1] | Reference Example 21 (1.80 g) | 1.60 g | 320 |

TABLE 18-continued

| Reference Example | structure | starting material | yield | MS (ESI) m/z [M + H]+ |
|---|---|---|---|---|
| 51 | 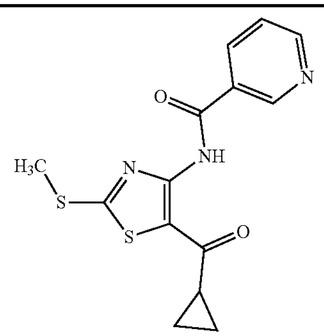 | Reference Example 21 (107 mg) | 152 mg | 320 |
| 52 | 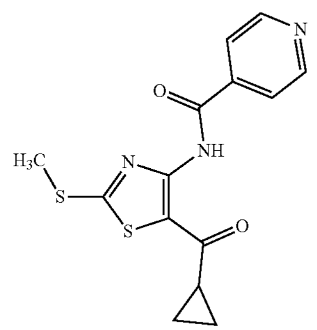 [SMILES: CSc1nc(NC(=O)c2ccncc2)c(C(=O)C2CC2)s1] | Reference Example 21 (500 mg) | 377 mg | 320 |
| 53 | 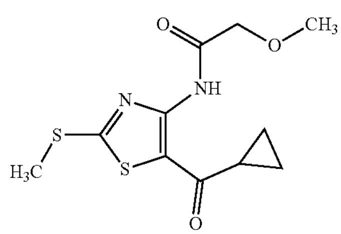 | Reference Example 21 (600 mg) | 593 mg | 287 |
| 54 | 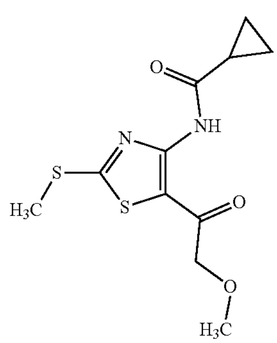 [SMILES: COCC(=O)c1sc(SC)nc1NC(=O)C1CC1] | Reference Example 29 (505 mg) | 258 mg | 287 |
| 55 | 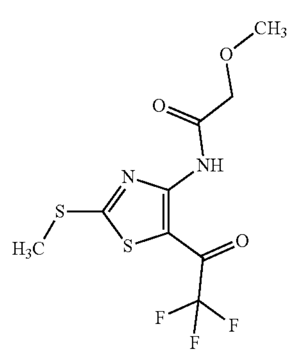 | Reference Example 32 (300 mg) | 192 mg | 315 |

TABLE 18-continued

| Reference Example | structure | starting material | yield | MS (ESI) m/z [M + H]+ |
|---|---|---|---|---|
| 56 | 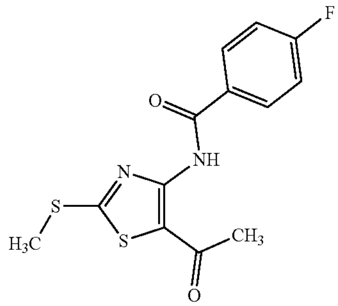 [SMILES: CSc1nc(NC(=O)c2ccc(F)cc2)c(C(C)=O)s1] | Reference Example 33 (414 mg) | 241 mg | 311 |
| 57 | 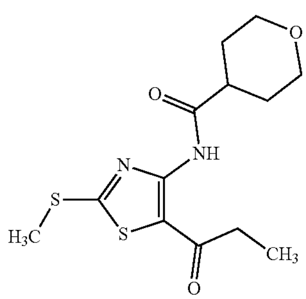 [SMILES: CCC(=O)c1sc(SC)nc1NC(=O)C1CCOCC1] | Reference Example 22 (405 mg) | 590 mg | 315 |
| 58 | 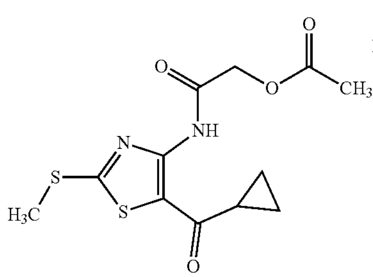 [SMILES: CSc1nc(NC(=O)COC(C)=O)c(C(=O)C2CC2)s1] | Reference Example 21 (3.00 g) | 3.02 g | 315 |

Reference Example 59

N-[5-acetyl-2-(methylsulfanyl)-1,3-thiazol-4-yl]-2,2,2-trifluoroacetamide

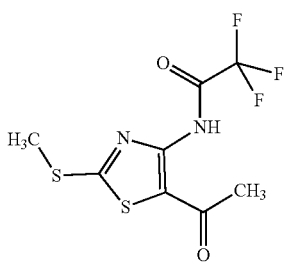 [SMILES: CSc1nc(NC(=O)C(F)(F)F)c(C(C)=O)s1]

To a dichloromethane solution (30.0 mL) of the compound (1.67 g) obtained in Reference Example 33 were added, under ice-cooling, pyridine (780 mg) and trifluoroacetic anhydride (2.05 g), and the reaction mixture was stirred at the same temperature for 1 hr. After confirmation of the completion of the reaction, aqueous citric acid solution was added, and the mixture was extracted twice with chloroform. The organic layer was dried over anhydrous magnesium sulfate, filtered and concentrated to give the title compound (2.48 g).

MS(ESI)m/z; 285[M+H]+

The following Table shows the compounds obtained by treating the corresponding compounds by a method similar to that in Reference Example 59.

TABLE 19

| Reference Example | structure | starting material | yield | MS (ESI) m/z [M + H]+ |
|---|---|---|---|---|
| 60 | ![structure 60] | Reference Example 22 (3.65 g) | 5.00 g | 299 |
| 61 | ![structure 61] | Reference Example 29 (500 mg) | 587 mg | 315 |
| 62 | ![structure 62] | Reference Example 34 (400 mg) | 300 mg | 337 |

Reference Example 63

3-methoxy-N-[2-(methylsulfanyl)-5-propanoyl-1,3-thiazol-4-yl]propanamide

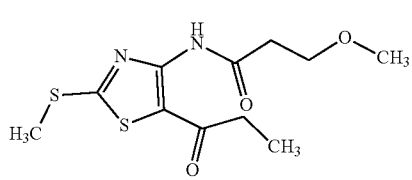

To a dichloroethane solution (30.0 mL) of 3-methoxypropionic acid (4.60 g) were added, under ice-cooling, oxalyl chloride (4.90 mL) and DMF (2 drops), and the reaction mixture was stirred at room temperature for 2 hr. The reaction mixture was added under ice-cooling to a pyridine solution (50.0 mL) of the compound (4.50 g) obtained in Reference Example 22, and the mixture was stirred at room temperature for 2 hr. After confirmation of the completion of the reaction, 1.0 mol/L hydrochloric acid was added, and the mixture was extracted twice with chloroform. The organic layer was dried over anhydrous magnesium sulfate, filtered and concentrated. The obtained residue was purified by silica gel column chromatography (solvent; hexane/ethyl acetate=70/30-0/100) to give the title compound (1.85 g).

MS(ESI)m/z; 289[M+H]+

The following Tables show the compounds obtained by treating the corresponding compounds by a method similar to that in Reference Example 63.

TABLE 20

| Reference Example | structure | starting material | yield | MS (ESI) m/z [M + H]+ |
|---|---|---|---|---|
| 64 | (structure) | Reference Example 21 (600 mg) | 934 mg | 327 |
| 65 | (structure) | Reference Example 21 (4.80 g) | 437 mg | 341 |
| 66 | (structure) | Reference Example 21 (322 mg) | 280 mg | 315 |
| 67 | (structure) | Reference Example 22 (284 mg) | 347 mg | 303 |

TABLE 20-continued

| Reference Example | structure | starting material | yield | MS (ESI) m/z [M + H]+ |
|---|---|---|---|---|
| 68 | 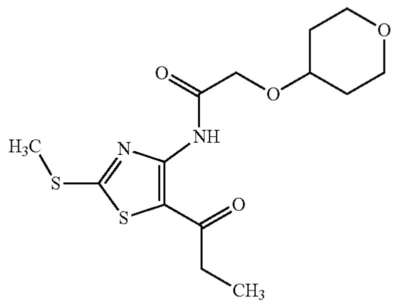 [SMILES: CCC(=O)c1sc(SC)nc1NC(=O)COC1CCOCC1] | Reference Example 22 (370 mg) | 181 mg | 345 |
| 69 | 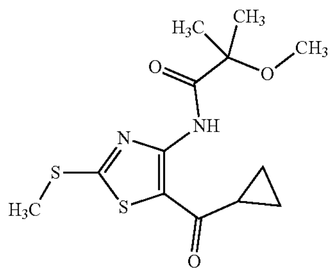 | Reference Example 21 (387 mg) | 468 mg | 315 |
| 70 | 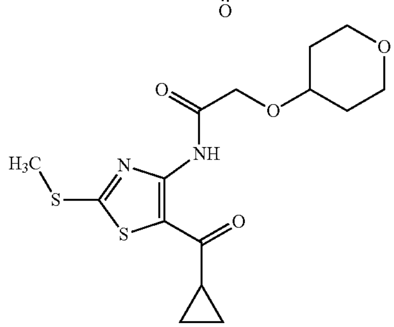 | Reference Example 21 (370 mg) | 162 mg | 357 |

Reference Example 71

N-{[5-acetyl-2-(methylsulfanyl)-1,3-thiazol-4-yl]carbamoyl}-2,2,2-trichloroacetamide

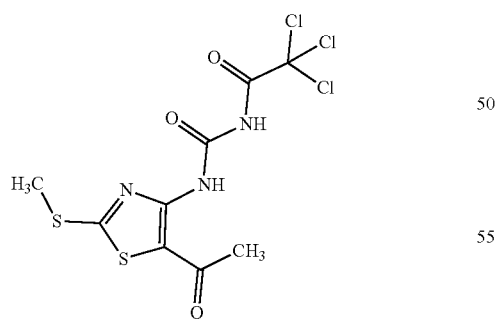

To a THF solution (200 mL) of the compound (5.00 g) obtained in Reference Example 33 was added, under ice-cooling, trichloroacetyl isocyanate (4.22 mL), and the reaction mixture was stirred at room temperature for 4 hr. After confirmation of the completion of the reaction, the solid was collected by filtration and dried to give the title compound (9.51 g).

MS(ESI)m/z; 376, 378[M+H]+

Reference Example 72

2,2,2-trichloro-N-{[2-(methylsulfanyl)-5-propanoyl-1,3-thiazol-4-yl]carbamoyl}acetamide

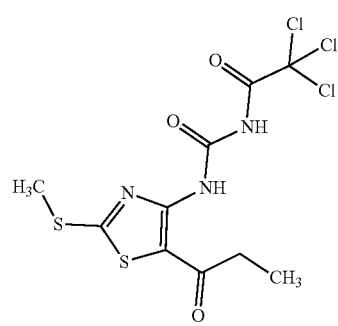 [SMILES: CCC(=O)c1sc(SC)nc1NC(=O)NC(=O)C(Cl)(Cl)Cl]

The compound (5.00 g) obtained in Reference Example 22 was treated by a method similar to that in Reference Example 71 to give the title compound (9.47 g).

MS(ESI)m/z; 390, 392[M+H]+

Reference Example 73

7-methyl-2-(methylsulfanyl)[1,3]thiazolo[4,5-d]pyrimidin-5(4H)-one

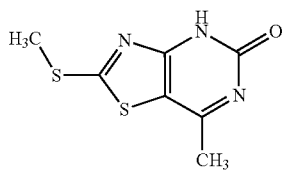

To a methanol solution (200 mL) of the compound (9.50 g) obtained in Reference Example 71 was added at room temperature 2.0 mol/L aqueous sodium carbonate solution (100 mL), and the reaction mixture was stirred at the same temperature for 3 hr. After confirmation of the completion of the reaction, at room temperature, acetic acid (24.0 mL) was added and the solid was collected by filtration. The filtrate was concentrated under reduced pressure, and the residue was extracted twice with chloroform. The organic layer was dried over anhydrous sodium sulfate, filtered and concentrated. The obtained residue was combined with the solid obtained earlier, 50% ethanol-water was added, and the solid was collected by filtration and dried to give the title compound (5.33 g).
MS(ESI)m/z; 214[M+H]$^+$

Reference Example 74

7-ethyl-2-(methylsulfanyl)[1,3]thiazolo[4,5-d]pyrimidin-5(4H)-one

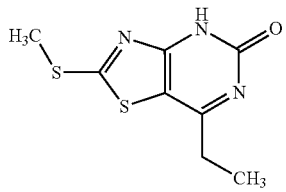

The compound (9.47 g) obtained in Reference Example 72 was treated by a method similar to that in Reference Example 73 to give the title compound (5.30 g).
MS(ESI)m/z; 228[M+H]$^+$

Reference Example 75

7-cyclopropyl-2-(methylsulfanyl)[1,3]thiazolo[4,5-d]pyrimidin-5(4H)-one

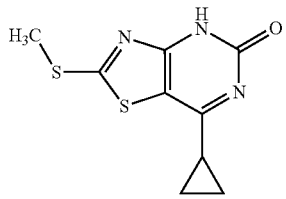

To a THF solution (30 mL) of the compound (1.00 g) obtained in Reference Example 21 was added, under ice-cooling, trichloroacetyl isocyanate (0.720 mL), and the reaction mixture was stirred at room temperature for 40 min. After confirmation of the completion of the reaction, at room temperature, 2.0 mol/L aqueous sodium carbonate solution (15.0 mL) was added, and the reaction mixture was stirred at the same temperature for 3 hr. After confirmation of the completion of the reaction, the reaction mixture was concentrated under reduced pressure, and neutralized with 1.0 mol/L hydrochloric acid at room temperature. The resultant product was collected by filtration and dried to give the title compound (926 mg).
MS(ESI)m/z; 240[M+H]$^+$

Reference Example 76

5,7-dimethyl[1,3]thiazolo[4,5-d]pyrimidine-2(3H)-thione

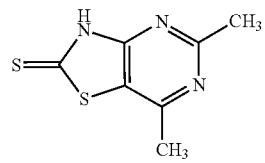

An N-methylpyrrolidone solution (10.0 mL) of 4-amino-5-chloro-2,6-dimethylpyrimidine (2.00 g) and potassium ethyl xanthogenate (5.09 g) was stirred with heating at 120° C. for 5.5 hr. The reaction mixture was cooled to room temperature, and acetic acid and water were added. The precipitated solid was collected by filtration, washed with water and dried under reduced pressure to give the title compound (883 mg).
MS(ESI)m/z; 198[M+H]$^+$

Reference Example 77

2-chloro-4-(2,4-dimethoxybenzylamino)-6-methylpyrimidine

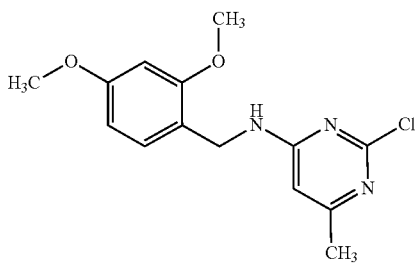 [SMILES: COc1ccc(CNc2cc(C)nc(Cl)n2)c(OC)c1]

To an acetonitrile solution (100 mL) of 2,4-dichloro-6-methylpyrimidine (3.26 g) were added at room temperature, triethylamine (5.58 mL) and 2,4-dimethoxybenzylamine (3.37 mL), and the reaction mixture was stirred at room temperature for 6 hr. To the reaction mixture was added saturated aqueous sodium hydrogen carbonate solution, and the mixture was extracted twice with ethyl acetate. The organic layer was dried over anhydrous sodium sulfate, filtered and concentrated. The obtained residue was purified by silica gel column chromatography (solvent; hexane/ethyl acetate=95/5-40/60). To the obtained resultant product was added diisopropy ether, and the solid was collected by filtration to give the title compound (3.35 g).

MS(ESI)m/z; 294, 296[M+H]$^+$

Reference Example 78

4-(2,4-dimethoxybenzylamino)-2-ethoxy-6-methyl-pyrimidine

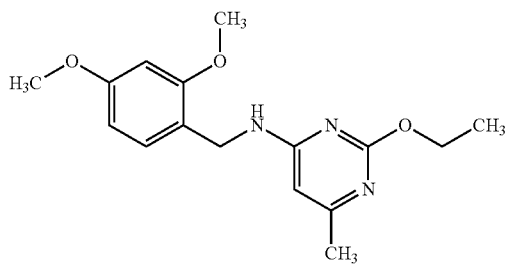 [SMILES: CCOc1nc(C)cc(NCc2ccc(OC)cc2OC)n1]

An ethanol solution (50.0 mL) of the compound (1.50 g) obtained in Reference Example 77 and sodium ethoxide (21 w/w % ethanol solution, 3.80 mL) was stirred under microwave irradiation at 150° C. for 10 min. The reaction mixture was concentrated, and the obtained residue was purified by silica gel column chromatography (solvent; hexane/ethyl acetate=70/30-20/80). To the obtained resultant product was added diisopropy ether, and the solid was collected by filtration to give the title compound (991 mg).

MS(ESI)m/z; 304[M+H]$^+$

Reference Example 79

5-bromo-4-(2,4-dimethoxybenzylamino)-2-ethoxy-6-methylpyrimidine

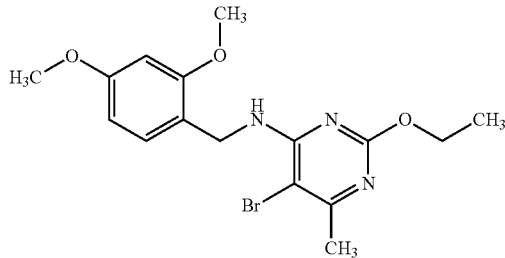 [SMILES: CCOc1nc(C)c(Br)c(NCc2ccc(OC)cc2OC)n1]

To a chloroform solution (20.0 mL) of the compound (672 mg) obtained in Reference Example 78 was added at room temperature, N-bromosuccinimide (394 mg), and the reaction mixture was stirred at room temperature for 1 hr. The reaction mixture was concentrated and the obtained residue was purified by silica gel column chromatography (solvent; hexane/ethyl acetate=95/5-80/20) to give the title compound (839 mg).

MS(ESI)m/z; 382, 384[M+H]$^+$

Reference Example 80

4-amino-5-bromo-2-ethoxy-6-methylpyrimidine

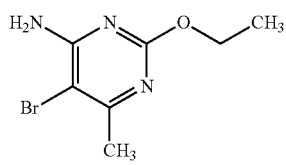

A trifluoroacetic acid solution (15.0 mL) of the compound (1.14 g) obtained in Reference Example 79 was heated under reflux for 2 hr. After cooling to room temperature, the reaction mixture was concentrated. To the obtained residue was added diisopropy ether, and the solid was collected by filtration to give the title compound (633 mg).

MS(ESI)m/z; 232, 234[M+H]$^+$

Reference Example 81

5-ethoxy-7-methyl[1,3]thiazolo[4,5-d]pyrimidine-2(3H)-thione

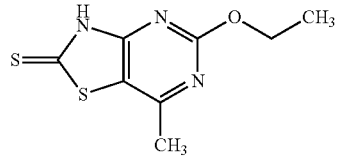

The compound (629 mg) obtained in Reference Example 80 was treated by a method similar to that in Reference Example 76 to give the title compound (347 mg).

MS(ESI)m/z; 228[M+H]$^+$

Reference Example 82

2-(methylsulfanyl)-7-(pyrrolidin-1-yl)[1,3]thiazolo[4,5-d]pyrimidine

To a THF solution (20 mL) of the compound (500 mg) obtained in Reference Example 13 were added at room temperature triethylamine (470 mg) and pyrrolidine (180 mg), and the reaction mixture was stirred at the same temperature for 1 hr. After confirmation of the completion of the reaction, water was added, and the mixture was extracted twice with methylene chloride. The combined organic layer was washed with saturated brine, dried over anhydrous sodium sulfate, filtered and concentrated. The obtained residue was purified by silica gel column chromatography (solvent; hexane/ethyl acetate=50/50-0/100) to give the title compound (420 mg).

MS(ESI)m/z; 396[M+H]$^+$

The following Tables show the compounds obtained by treating the corresponding compounds by a method similar to that in Reference Example 82.

TABLE 21

| Reference Example | structure | starting material | yield | MS (ESI) m/z [M + H]+ |
|---|---|---|---|---|
| 83 | 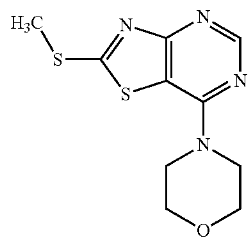 [SMILES: CSc1nc2ncnc(N3CCOCC3)c2s1] | Reference Example 13 (500 mg) | 309 mg | 269 |
| 84 | 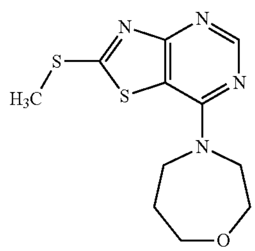 [SMILES: CSc1nc2ncnc(N3CCCOCC3)c2s1] | Reference Example 13 (400 mg) | 310 mg | 283 |
| 85 | 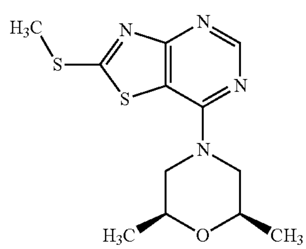 | Reference Example 13 (300 mg) | 281 mg | 297 |
| 86 | 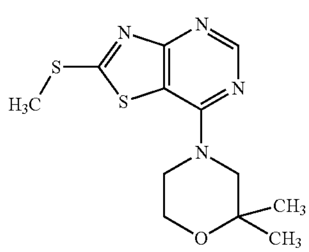 | Reference Example 13 (400 mg) | 370 mg | 297 |
| 87 | 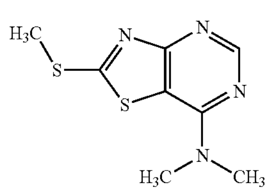 | Reference Example 13 (620 mg) | 472 mg | 227 |
| 88 | 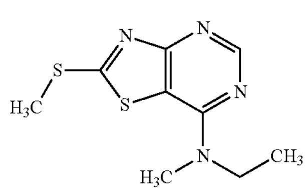 | Reference Example 13 (350 mg) | 174 mg | 241 |

TABLE 21-continued

| Reference Example | structure | starting material | yield | MS (ESI) m/z [M + H]+ |
|---|---|---|---|---|
| 89 | 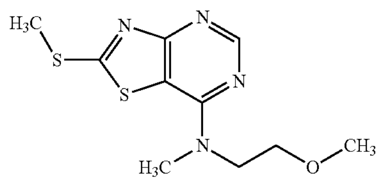 | Reference Example 13 (400 mg) | 273 mg | 271 |
| 90 | 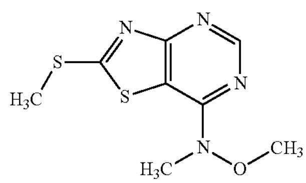 | Reference Example 13 (700 mg) | 410 mg | 243 |
| 91 | 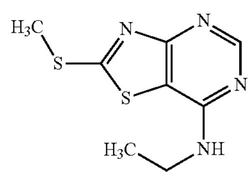 | Reference Example 13 (400 mg) | 95.2 mg | 227 |
| 92 | 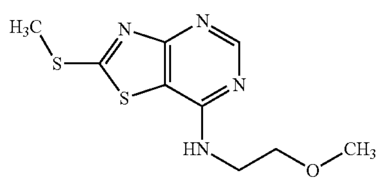 | Reference Example 13 (400 mg) | 114 mg | 257 |
| 93 | 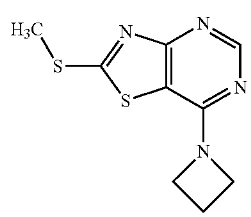 | Reference Example 13 (500 mg) | 57.0 mg | 239 |
| 94 | 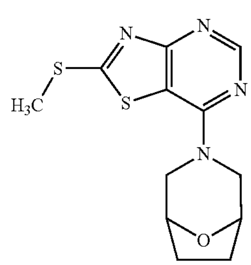 [SMILES: CSc1nc2ncnc(N3CC4CCC(C3)O4)c2s1] | Reference Example 13 (239 mg) | 224 mg | 295 |
| 95 | 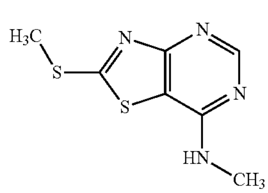 | Reference Example 13 (265 mg) | 188 mg | 213 |

TABLE 21-continued

| Reference Example | structure | starting material | yield | MS (ESI) m/z [M + H]+ |
|---|---|---|---|---|
| 96 | 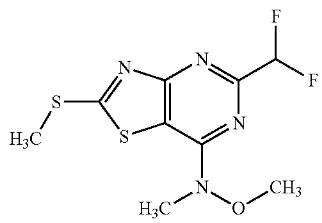 [SMILES: CON(C)c1nc(C(F)F)nc2nc(SC)sc12] | Reference Example 14 (600 mg) | 550 mg | 293 |
| 97 | 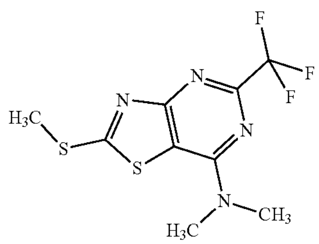 [SMILES: CSc1nc2nc(C(F)(F)F)nc(N(C)C)c2s1] | Reference Example 15 (440 mg) | 420 mg | 295 |
| 98 | 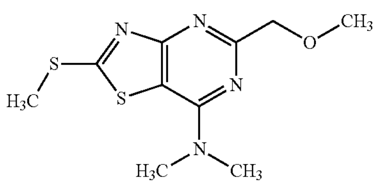 | Reference Example 16 (450 mg) | 460 mg | 271 |
| 99 | 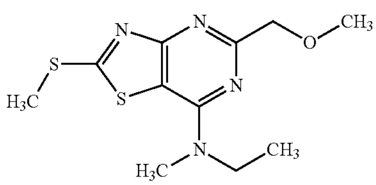 | Reference Example 16 (410 mg) | 350 mg | 285 |
| 100 | 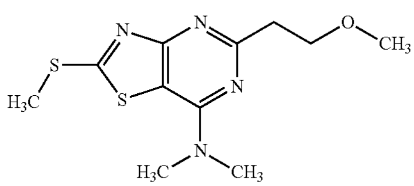 | Reference Example 17 (450 mg) | 350 mg | 285 |
| 101 | 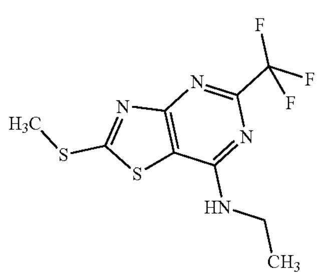 [SMILES: CCNc1nc(C(F)(F)F)nc2nc(SC)sc12] | Reference Example 15 (450 mg) | 220 mg | 295 |
| 102 | 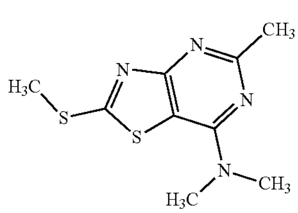 | Reference Example 18 (450 mg) | 200 mg | 241 |

Reference Example 103

2-(methylsulfanyl)-7-phenoxy[1,3]thiazolo[4,5-d]pyrimidine

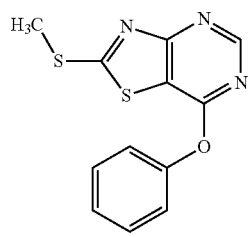 [SMILES: CSc1nc2ncnc(Oc3ccccc3)c2s1]

To a DMF solution (5.00 mL) of the compound (200 mg) obtained in Reference Example 13 were added, under ice-cooling, sodium hydride (60% w/w, 41.0 mg) and phenol (96.0 mg), and the reaction mixture was stirred at the same temperature for 1 hr. After confirmation of the completion of the reaction, water and 1.0 mol/L hydrochloric acid were added, and the mixture was extracted twice with methylene chloride. The combined organic layer was washed with saturated brine, dried over anhydrous sodium sulfate, filtered and concentrated. The obtained residue was purified by silica gel column chromatography (solvent; hexane/ethyl acetate=80/20-50/50) to give the title compound (210 mg).

MS(ESI)m/z; 276[M+H]$^+$

Reference Example 104

7-ethoxy-2-(methylsulfanyl)[1,3]thiazolo[4,5-d]pyrimidine

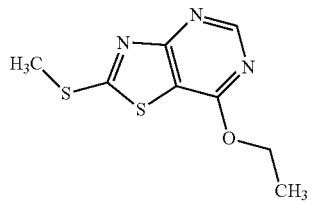

To a THF solution (70.0 mL) of the compound (3.30 g) obtained in Reference Example 2 were added at room temperature triphenylphosphine (5.70 g), ethanol (1.15 g) and diisopropyl azodicarboxylate (1.9 mol/L toluene solution, 13.5 mL), and the reaction mixture was stirred at the same temperature for 2 hr. After confirmation of the completion of the reaction, water was added, and the mixture was extracted twice with methylene chloride. The combined organic layer was washed with saturated brine, dried over anhydrous sodium sulfate, filtered and concentrated. The obtained residue was purified by silica gel column chromatography (solvent; hexane/ethyl acetate=95/5-80/20) to give the title compound (940 mg).

MS(ESI)m/z; 228[M+H]$^+$

The following Table shows the compounds obtained by treating the corresponding compounds by a method similar to that in Reference Example 104.

TABLE 22

| Reference Example | structure | starting material | yield | MS (ESI) m/z [M + H]$^+$ |
|---|---|---|---|---|
| 105 | 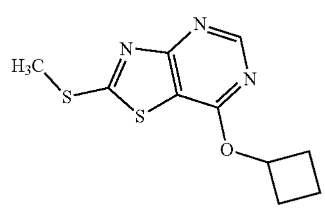 [SMILES: CSc1nc2ncnc(OC3CCC3)c2s1] | Reference Example 2 (1.50 g) | 750 mg | 254 |
| 106 | 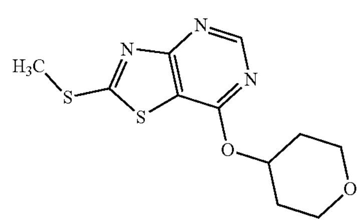 [SMILES: CSc1nc2ncnc(OC3CCOCC3)c2s1] | Reference Example 2 (1.50 g) | 800 mg | 284 |
| 107 | 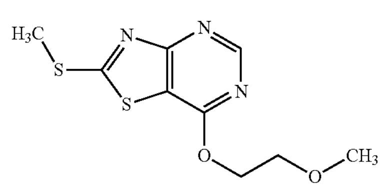 | Reference Example 2 (500 mg) | 178 mg | 258 |

TABLE 22-continued

| Reference Example | structure | starting material | yield | MS (ESI) m/z [M + H]+ |
|---|---|---|---|---|
| 108 | 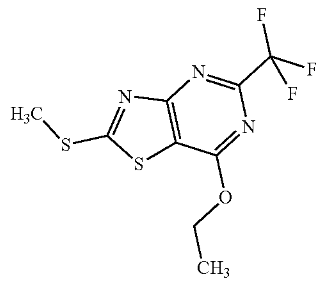 [SMILES: CCOc1nc(C(F)(F)F)nc2nc(SC)sc12] | Reference Example 9 (1.50 g) | 1.00 g | 296 |
| 109 | 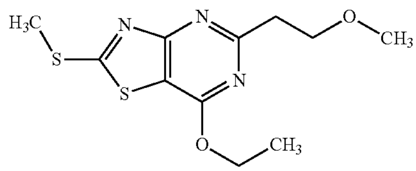 | Reference Example 11 (500 mg) | 310 mg | 286 |
| 110 | 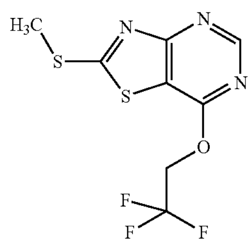 [SMILES: CSc1nc2ncnc(OCC(F)(F)F)c2s1] | Reference Example 2 (500 mg) | 160 mg | 282 |
| 111 | 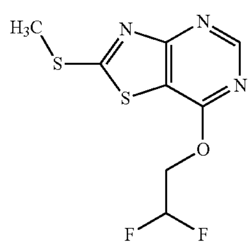 [SMILES: CSc1nc2ncnc(OCC(F)F)c2s1] | Reference Example 2 (600 mg) | 500 mg | 264 |
| 112 | 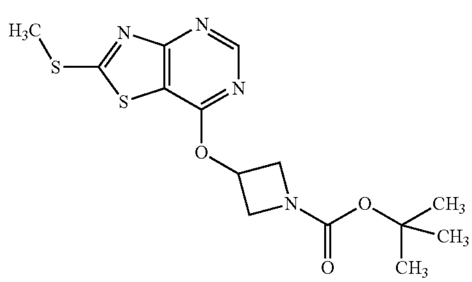 [SMILES: CSc1nc2ncnc(OC3CN(C(=O)OC(C)(C)C)C3)c2s1] | Reference Example 2 (1.00 g) | 594 mg | 355 |

Reference Example 113

2-(methylsulfanyl)-7-(propan-2-yloxy)[1,3]thiazolo[4,5-d]pyrimidine

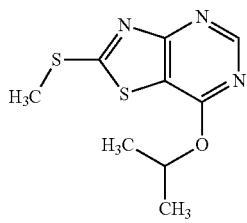

To a mixed solution of the compound (398.5 mg) obtained in Reference Example 2 in THF (5.00 mL) and N-methylmorpholine (1.00 mL) were added at room temperature tributylphosphine (4.44 mL), 2-propanol (1.39 mL) and N,N,N',N'-tetramethylazodicarboxamide (3.09 g), and the reaction mixture was stirred with heating at 80° C. for 20 hr. After confirmation of the completion of the reaction, the mixture was cooled to room temperature, water was added, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=95/5-50/50) to give the title compound (96.5 mg).

MS(ESI)m/z; 242[M+H]$^+$

The following Table shows the compounds obtained by treating the corresponding compounds by a method similar to that in Reference Example 113.

TABLE 23

| Reference Example | structure | starting material | yield | MS (ESI) m/z [M + H]$^+$ |
|---|---|---|---|---|
| 114 | 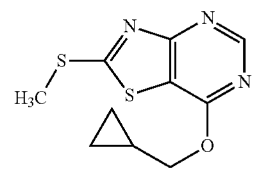 [SMILES: CSc1nc2ncnc(OCC3CC3)c2s1] | Reference Example 2 (399 mg) | 89.9 mg | 254 |
| 115 | 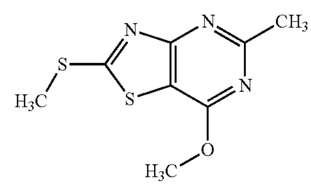 | Reference Example 20 (320 mg) | 54.1 mg | 228 |
| 116 | 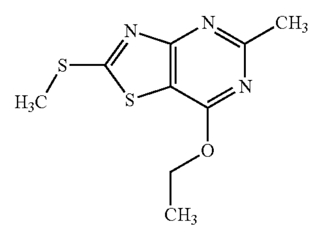 | Reference Example 20 (320 mg) | 164 mg | 242 |
| 117 | 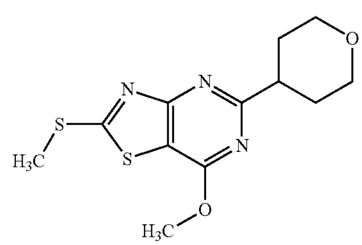 [SMILES: COc1nc(C2CCOCC2)nc2nc(SC)sc12] | Reference Example 12 (200 mg) | 115 mg | 298 |
| 118 | 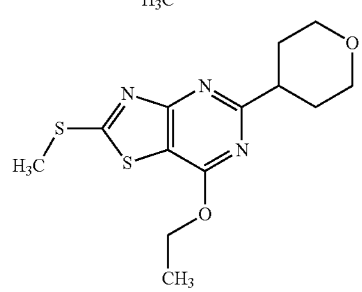 | Reference Example 12 (200 mg) | 157 mg | 312 |

Reference Example 119

7-cyclopropyl-2-(methylsulfanyl)[1,3]thiazolo[4,5-d]pyrimidine

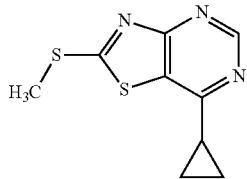

A mixed solution of the compound (538 mg) obtained in Reference Example 35, acetic acid (1.00 mL) and ammonium formate (1.40 g) was stirred with heating at 120° C. for 1.5 hr. After confirmation of the completion of the reaction, the mixture was cooled to room temperature, water was added, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=90/10-60/40) to give the title compound (318 mg).

MS(ESI)m/z; 224[M+H]$^+$

The following Tables show the compounds obtained by treating the corresponding compounds by a method similar to that in Reference Example 119.

TABLE 24

| Reference Example | structure | starting material | yield | MS (ESI) m/z [M + H]$^+$ |
|---|---|---|---|---|
| 120 | 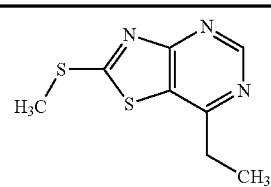 | Reference Example 36 (433 mg) | 277 mg | 212 |
| 121 | 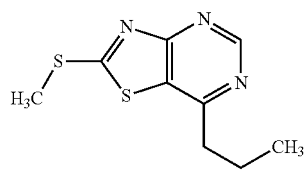 | Reference Example 37 (523 mg) | 324 mg | 226 |
| 122 | 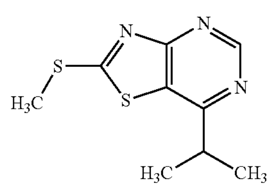 | Reference Example 38 (537 mg) | 308 mg | 226 |
| 123 | 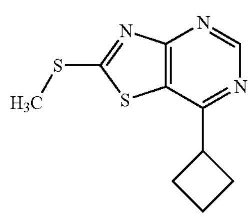 | Reference Example 39 (526 mg) | 313 mg | 238 |
| 124 | 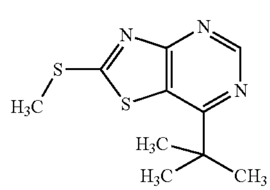 | Reference Example 40 (1.16 g) | 620 mg | 240 |
| 125 | 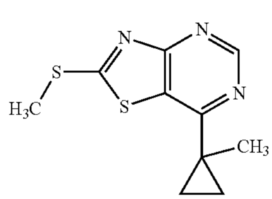 | Reference Example 41 (1.15 g) | 630 mg | 238 |

TABLE 24-continued

| Reference Example | structure | starting material | yield | MS (ESI) m/z [M + H]+ |
|---|---|---|---|---|
| 126 | 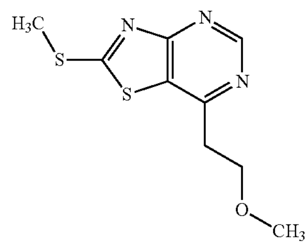 | Reference Example 42 (850 mg) | 180 mg | 242 |
| 127 | 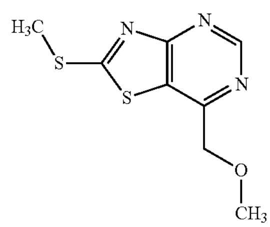 | Reference Example 43 (487 mg) | 310 mg | 228 |
| 128 | 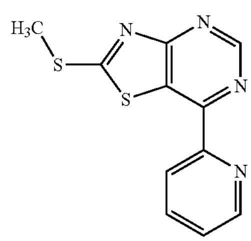 [SMILES: CSc1nc2ncnc(-c3ccccn3)c2s1] | Reference Example 44 (1.22 g) | 700 mg | 261 |
| 129 | 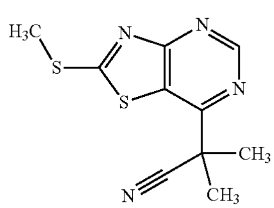 [SMILES: CSc1nc2ncnc(C(C)(C)C#N)c2s1] | Reference Example 45 (700 mg) | 53.0 mg | 251 |
| 130 | 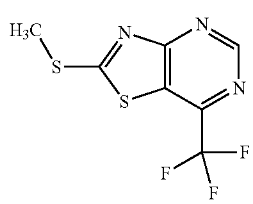 | Reference Example 46 (147 mg) | 116 mg | 252 |
| 131 | 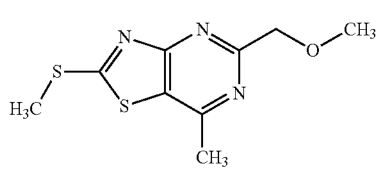 | Reference Example 47 (98.0 mg) | 63.0 mg | 242 |
| 132 | 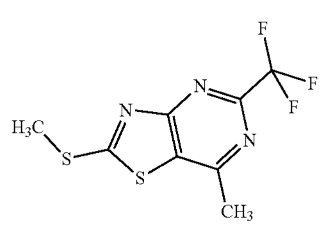 [SMILES: CSc1nc2nc(C(F)(F)F)nc(C)c2s1] | Reference Example 59 (2.48 g) | 1.05 g | 266 |

TABLE 24-continued

| Reference Example | structure | starting material | yield | MS (ESI) m/z [M + H]+ |
|---|---|---|---|---|
| 133 | 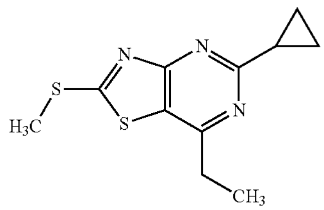 [SMILES: CCc1nc(C2CC2)nc2nc(SC)sc12] | Reference Example 48 (582 mg) | 461 mg | 252 |
| 134 | 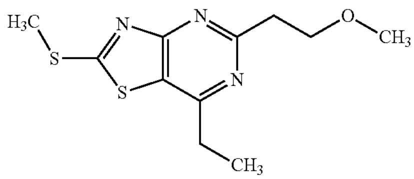 | Reference Example 63 (1.85 g) | 540 mg | 270 |
| 135 | 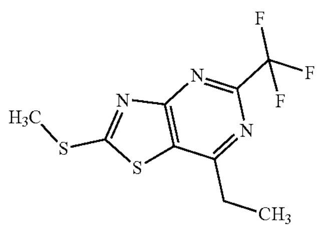 [SMILES: CCc1nc(C(F)(F)F)nc2nc(SC)sc12] | Reference Example 60 (5.00 g) | 580 mg | 280 |
| 136 | 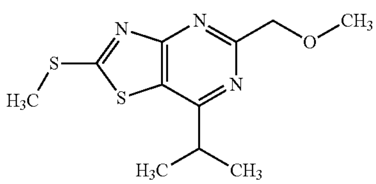 | Reference Example 49 (300 mg) | 142 mg | 270 |
| 137 | 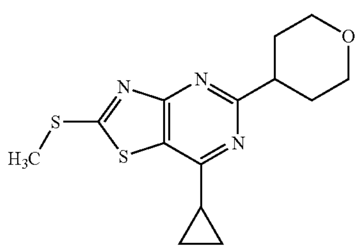 [SMILES: CSc1nc2nc(C3CCOCC3)nc(C3CC3)c2s1] | Reference Example 64 (930 mg) | 502 mg | 308 |
| 138 | 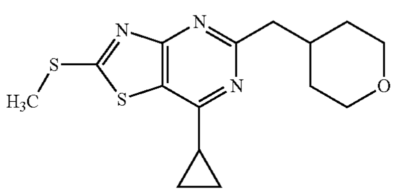 | Reference Example 65 (437 mg) | 177 mg | 322 |
| 139 | 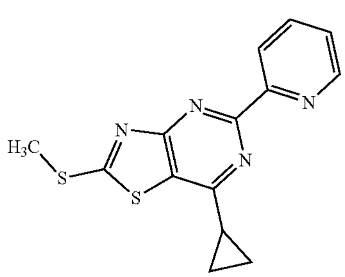 [SMILES: CSc1nc2nc(-c3ccccn3)nc(C3CC3)c2s1] | Reference Example 50 (800 mg) | 210 mg | 301 |

TABLE 24-continued

| Reference Example | structure | starting material | yield | MS (ESI) m/z [M + H]+ |
|---|---|---|---|---|
| 140 | 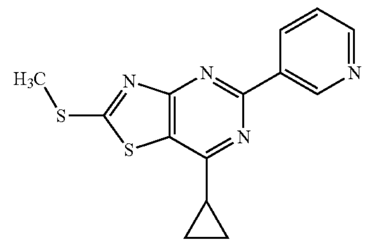 [SMILES: CSc1nc2nc(-c3cccnc3)nc(C3CC3)c2s1] | Reference Example 51 (501 mg) | 215 mg | 301 |
| 141 | 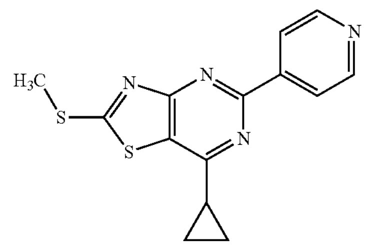 [SMILES: CSc1nc2nc(-c3ccncc3)nc(C3CC3)c2s1] | Reference Example 52 (377 mg) | 84.0 mg | 301 |
| 142 | 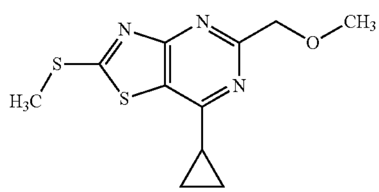 | Reference Example 53 (593 mg) | 260 mg | 268 |
| 143 | 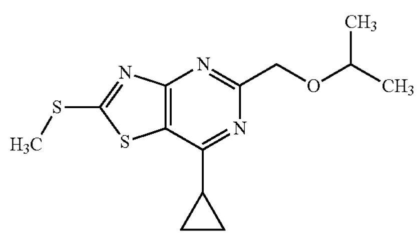 [SMILES: CSc1nc2nc(COC(C)C)nc(C3CC3)c2s1] | Reference Example 66 (280 mg) | 121 mg | 296 |
| 144 | 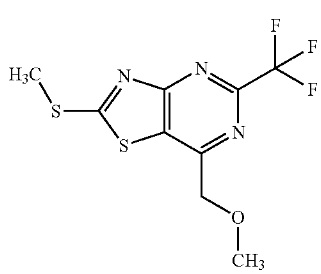 [SMILES: COCc1nc(C(F)(F)F)nc2nc(SC)sc12] | Reference Example 61 (580 mg) | 132 mg | 296 |
| 145 | 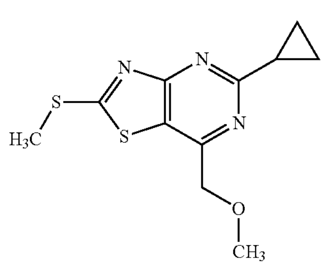 [SMILES: COCc1nc(C2CC2)nc2nc(SC)sc12] | Reference Example 54 (258 mg) | 182 mg | 268 |

TABLE 24-continued

| Reference Example | structure | starting material | yield | MS (ESI) m/z [M + H]+ |
|---|---|---|---|---|
| 146 | 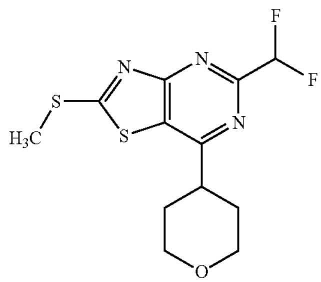 [SMILES: CSc1nc2nc(C(F)F)nc(C3CCOCC3)c2s1] | Reference Example 62 (3.80 g) | 130 mg | 318 |
| 147 | 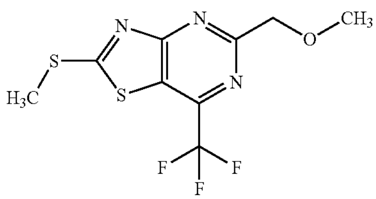 | Reference Example 55 (250 mg) | 98.0 mg | 296 |
| 148 | 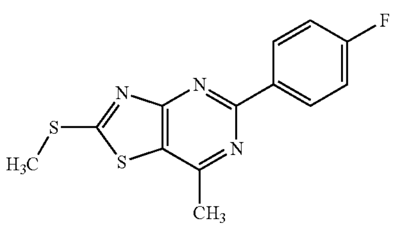 [SMILES: CSc1nc2nc(-c3ccc(F)cc3)nc(C)c2s1] | Reference Example 56 (240 mg) | 130 mg | 292 |
| 149 | 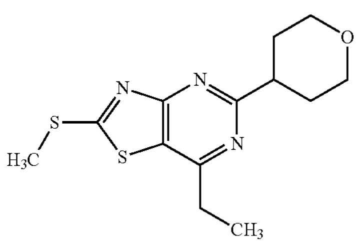 [SMILES: CCc1nc(C2CCOCC2)nc2nc(SC)sc12] | Reference Example 57 (590 mg) | 416 mg | 296 |
| 150 | 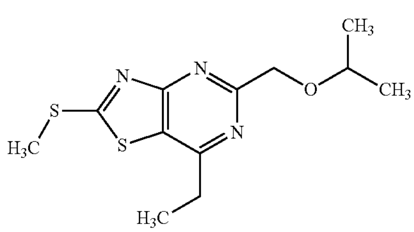 [SMILES: CCc1nc(COC(C)C)nc2nc(SC)sc12] | Reference Example 67 (336 mg) | 230 mg | 284 |
| 151 | 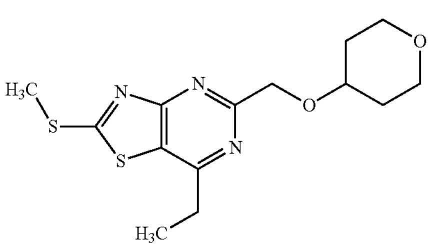 [SMILES: CCc1nc(COC2CCOCC2)nc2nc(SC)sc12] | Reference Example 68 (180 mg) | 131 mg | 326 |

TABLE 24-continued

| Reference Example | structure | starting material | yield | MS (ESI) m/z [M + H]+ |
|---|---|---|---|---|
| 152 | ![structure] | Reference Example 69 (448 mg) | 142 mg | 296 |
| 153 | ![structure] | Reference Example 70 (161 mg) | 52.0 mg | 338 |
| 154 | ![structure] | Reference Example 58 (3.02 g) | 670 mg | 254 |

Reference Example 155

7-cyclopropyl-5-[(N,N-dimethylamino)methyl]-2-(methylsulfanyl)[1,3]thiazolo[4,5-d]pyrimidine

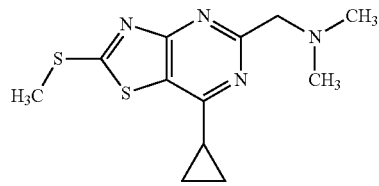

To a dichloromethane solution (1.70 mL) of the compound (103 mg) obtained in Reference Example 154 were added, under ice-cooling, triethylamine (0.0690 mL) and methanesulfonyl chloride (0.0350 mL), and the reaction mixture was stirred at the same temperature for 1 hr. The reaction mixture was diluted with DMF (1.00 mL), and added to a DMF solution (1.00 mL) of dimethylamine (2.0 mol/L THF solution, 0.610 mL) at 0° C., and the mixture was stirred at room temperature for 2 hr. After confirmation of the completion of the reaction, saturated aqueous sodium hydrogen carbonate solution was added, and the mixture was extracted twice with chloroform. The combined organic layer was washed with saturated brine, dried over anhydrous sodium sulfate, filtered and concentrated. The obtained residue was purified by NH silica gel column chromatography (solvent; hexane/ethyl acetate=80/20-0/100) to give the title compound (72.0 mg).

MS(ESI)m/z; 281[M+H]+

Reference Example 156

7-methyl-2-(methylsulfanyl)-5-[(tetrahydro-2H-pyran-4-yl)oxy][1,3]thiazolo[4,5-d]pyrimidine

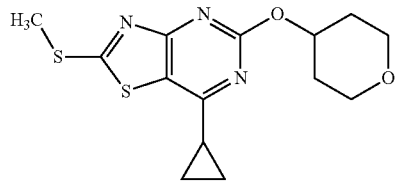 [SMILES: CSc1nc2nc(OC3CCOCC3)nc(C3CC3)c2s1]

To a mixed solution of the compound (213 mg) obtained in Reference Example 73 in THF (15.0 mL) and N-methylmorpholine (3.00 mL) were added at room temperature tributylphosphine (0.370 mL), tetrahydro-2H-pyran-4-ol (0.146 mL) and N,N,N',N'-tetramethylazodicarboxamide (258 mg), and the reaction mixture was stirred with heating at 80° C. for 3 hr. After confirmation of the completion of the reaction, the mixture was cooled to room temperature, water was added, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=60/40-40/60) to give the title compound (166 mg).

MS(ESI)m/z; 298[M+H]+

Reference Example 157

7-ethyl-2-(methylsulfanyl)-5-[(tetrahydro-2H-pyran-4-yl)oxy][1,3]thiazolo[4,5-d]pyrimidine

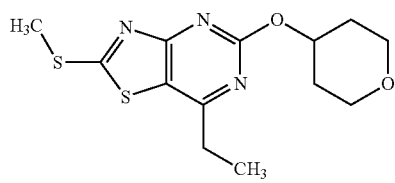 [SMILES: CCc1nc(OC2CCOCC2)nc2nc(SC)sc12]

The compound (455 mg) obtained in Reference Example 74 was treated by a method similar to that in Reference Example 156 to give the title compound (124 mg).
MS(ESI)m/z; 312[M+H]$^+$

Reference Example 158

7-cyclopropyl-2-(methylsulfanyl)-5-[(tetrahydro-2H-pyran-4-yl)oxy][1,3]thiazolo[4,5-d]pyrimidine

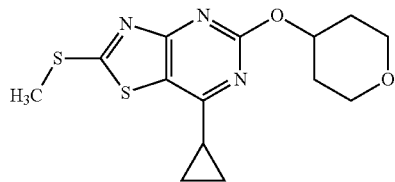

The compound (300 mg) obtained in Reference Example 75 was treated by a method similar to that in Reference Example 156 to give the title compound (130 mg).
MS(ESI)m/z; 324[M+H]$^+$

Reference Example 159

5-ethoxy-7-ethyl-2-(methylsulfanyl)[1,3]thiazolo[4,5-d]pyrimidine

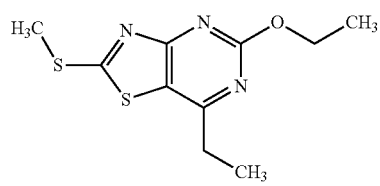

To a DMF solution (5.00 mL) of the compound (227 mg) obtained in Reference Example 74 were added at room temperature potassium carbonate (415 mg) and ethyl iodide (0.241 mL), and the reaction mixture was stirred at the same temperature for 2 hr. After confirmation of the completion of the reaction, water was added, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=70/30-0/100) to give the title compound (78.9 mg).
MS(ESI)m/z; 256[M+H]$^+$

Reference Example 160

5-chloro-7-methyl-2-(methylsulfanyl)[1,3]thiazolo[4,5-d]pyrimidine

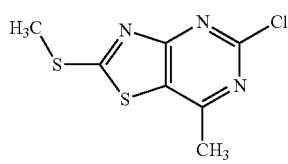

To the compound (2.00 g) obtained in Reference Example 73 were added at room temperature N,N-diethylaniline (3.00 mL) and phosphorus oxychloride (13.7 mL), and the reaction mixture was stirred at 110° C. for 14 hr. After ice-cooling, the reaction mixture was poured into ice water by small portions, and the precipitated resultant product was dissolved in chloroform. The mixture was neutralized with saturated aqueous sodium hydrogen carbonate solution and extracted twice with chloroform. The combined organic layer was washed with saturated brine, dried over anhydrous sodium sulfate, filtered and concentrated. The obtained residue was purified by silica gel column chromatography (solvent; hexane/ethyl acetate=95/5-70/30) to give the title compound (1.85 g).
MS(ESI)m/z; 232, 234[M+H]$^+$

Reference Example 161

5-chloro-7-ethyl-2-(methylsulfanyl)[1,3]thiazolo[4,5-d]pyrimidine

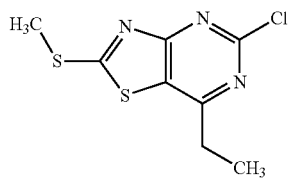

The compound (961 mg) obtained in Reference Example 74 was treated by a method similar to that in Reference Example 160 to give the title compound (944 mg).
MS(ESI)m/z; 246, 248[M+H]$^+$ Reference Example 162

5-chloro-7-cyclopropyl-2-(methylsulfanyl)[1,3]thiazolo[4,5-d]pyrimidine

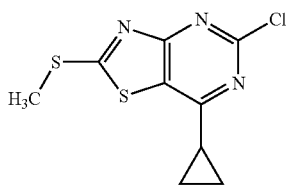

The compound (900 mg) obtained in Reference Example 75 was treated by a method similar to that in Reference Example 160 to give the title compound (255 mg).

MS(ESI)m/z; 258, 260[M+H]$^+$

Reference Example 163

5,7-dimethyl-2-(methylsulfanyl)[1,3]thiazolo[4,5-d]pyrimidine

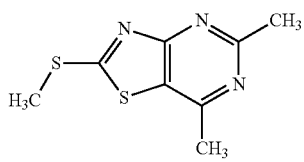

To a 1.0 mol/L aqueous sodium hydroxide solution (8.00 mL) of the compound (630 mg) obtained in Reference Example 76 was added at room temperature dimethyl sulfate (0.360 mL), and the reaction mixture was stirred at the same temperature for 1 hr. After confirmation of the completion of the reaction, the reaction mixture was extracted twice with chloroform. The combined organic layer was washed with saturated brine, dried over anhydrous sodium sulfate, filtered and concentrated. The obtained residue was purified by silica gel column chromatography (solvent; hexane/ethyl acetate=30/70-0/100) to give the title compound (440 mg).

MS(ESI)m/z; 212[M+H]$^+$

Reference Example 164

5-ethoxy-7-methyl-2-(methylsulfanyl)[1,3]thiazolo[4,5-d]pyrimidine

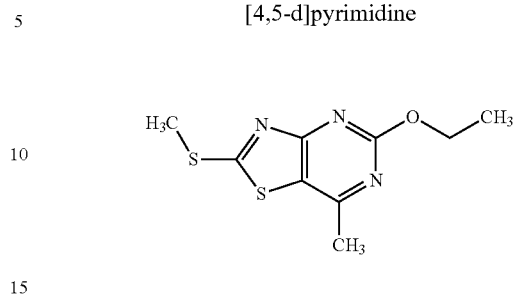

To a DMF solution (5.00 mL) of the compound (347 mg) obtained in Reference Example 81 were added at room temperature potassium carbonate (253 mg) and methyl iodide (0.120 mL), and the reaction mixture was stirred at the same temperature for 3 hr. After confirmation of the completion of the reaction, water was added, and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=95/5-60/40) to give the title compound (349 mg).

MS(ESI)m/z; 242[M+H]$^+$

Reference Example 165

7-ethoxy-2-(methylsulfinyl)[1,3]thiazolo[4,5-d]pyrimidine

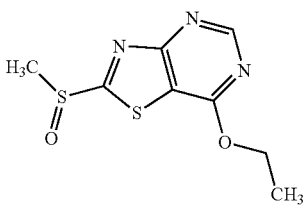

To a methylene chloride solution (35.0 mL) of the compound (930 mg) obtained in Reference Example 104 was added, under ice-cooling, mCPBA (69-75% w/w, 1.10 g), and the reaction mixture was stirred at room temperature for 2 hr. To the reaction mixture were added aqueous sodium thiosulfate solution, and saturated aqueous sodium hydrogen carbonate solution, and the mixture was extracted twice with chloroform. The organic layer was dried over anhydrous sodium sulfate, filtered and concentrated to give the title compound (900 mg).

MS(ESI)m/z; 244[M+H]$^+$

The following Tables show the compounds obtained by treating the corresponding compounds by a method similar to that in Reference Example 165.

TABLE 25

| Reference Example | structure | starting material | yield | MS (ESI) m/z [M + H]+ |
|---|---|---|---|---|
| 166 | 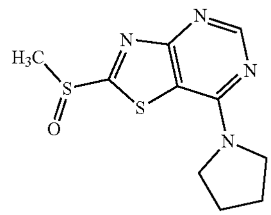 [SMILES: CS(=O)c1nc2ncnc(N3CCCC3)c2s1] | Reference Example 82 (210 mg) | 200 mg | 269 |
| 167 | 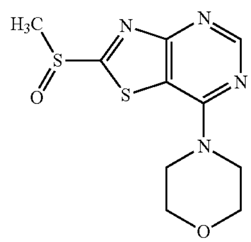 [SMILES: CS(=O)c1nc2ncnc(N3CCOCC3)c2s1] | Reference Example 83 (300 mg) | 278 mg | 285 |
| 168 | 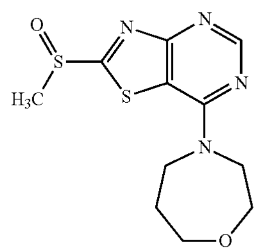 [SMILES: CS(=O)c1nc2ncnc(N3CCCOCC3)c2s1] | Reference Example 84 (290 mg) | 290 mg | 299 |
| 169 | 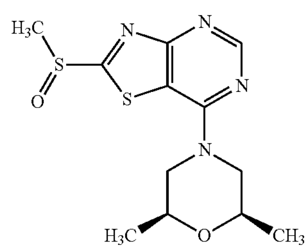 | Reference Example 85 (255 mg) | 305 mg | 313 |
| 170 | 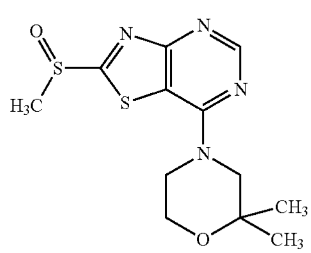 | Reference Example 86 (370 mg) | 290 mg | 313 |
| 171 | 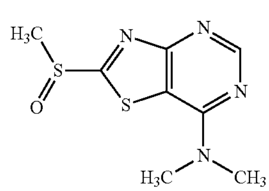 | Reference Example 87 (421 mg) | 421 mg | 243 |

TABLE 25-continued

| Reference Example | structure | starting material | yield | MS (ESI) m/z [M + H]+ |
|---|---|---|---|---|
| 172 | 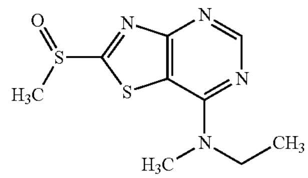 [SMILES: CCN(C)c1ncnc2nc(S(C)=O)sc12] | Reference Example 88 (174 mg) | 189 mg | 257 |
| 173 | 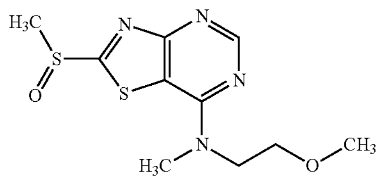 | Reference Example 89 (270 mg) | 222 mg | 287 |
| 174 | 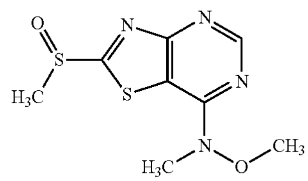 | Reference Example 90 (400 mg) | 260 mg | 259 |
| 175 | 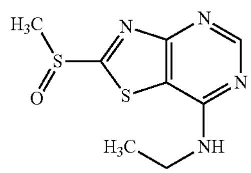 | Reference Example 91 (93.0 mg) | 134 mg | 243 |
| 176 | 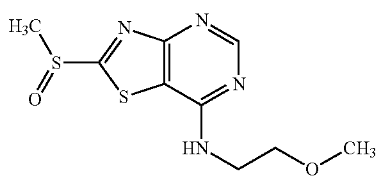 | Reference Example 92 (111 mg) | 119 mg | 273 |
| 177 | 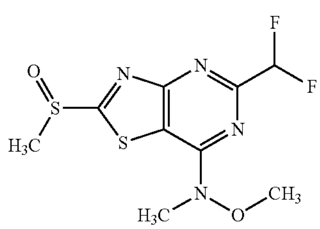 [SMILES: CON(C)c1nc(C(F)F)nc2nc(S(C)=O)sc12] | Reference Example 96 (540 mg) | 480 mg | 309 |
| 178 | 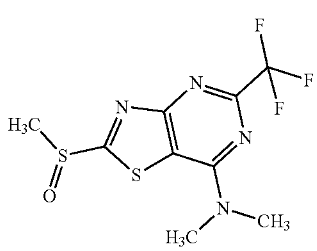 [SMILES: CN(C)c1nc(C(F)(F)F)nc2nc(S(C)=O)sc12] | Reference Example 97 (240 mg) | 170 mg | 311 |
| 179 | 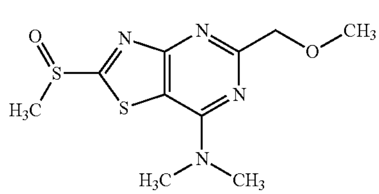 | Reference Example 98 (450 mg) | 300 mg | 287 |

TABLE 25-continued

| Reference Example | structure | starting material | yield | MS (ESI) m/z [M + H]+ |
|---|---|---|---|---|
| 180 | 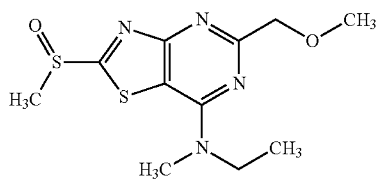 | Reference Example 99 (340 mg) | 300 mg | 301 |
| 181 | 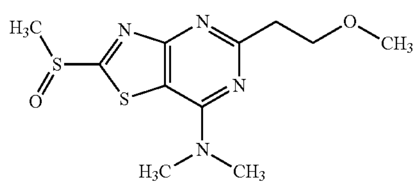 [SMILES: COCCc1nc(N(C)C)c2sc(S(C)=O)nc2n1] | Reference Example 100 (340 mg) | 260 mg | 301 |
| 182 | 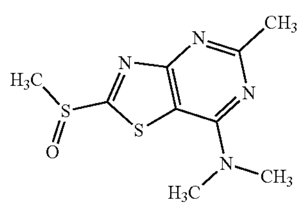 | Reference Example 102 (200 mg) | 200 mg | 257 |
| 183 | 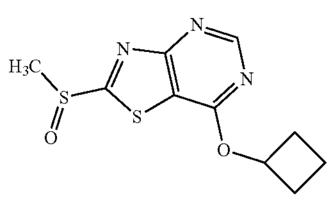 [SMILES: CS(=O)c1nc2ncnc(OC3CCC3)c2s1] | Reference Example 105 (680 mg) | 530 mg | 270 |
| 184 | 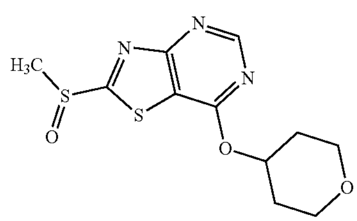 [SMILES: CS(=O)c1nc2ncnc(OC3CCOCC3)c2s1] | Reference Example 106 (800 mg) | 620 mg | 300 |
| 185 | 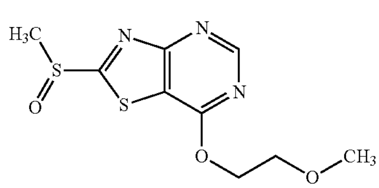 | Reference Example 107 (170 mg) | 190 mg | 274 |
| 186 | 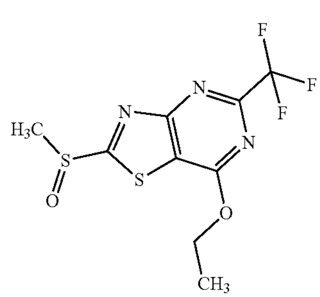 [SMILES: CCOc1nc(C(F)(F)F)nc2nc(S(C)=O)sc12] | Reference Example 108 (400 mg) | 300 mg | 312 |

TABLE 25-continued

| Reference Example | structure | starting material | yield | MS (ESI) m/z [M + H]+ |
|---|---|---|---|---|
| 187 | 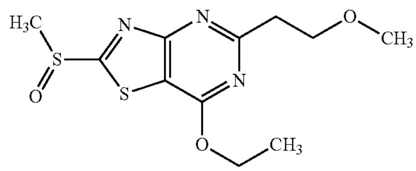 | Reference Example 109 (300 mg) | 260 mg | 302 |
| 188 | 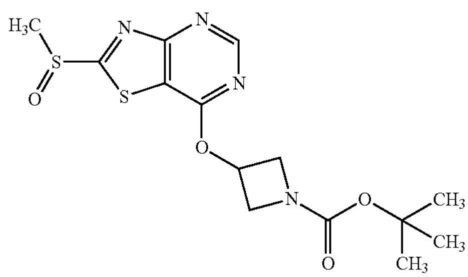 [SMILES: CS(=O)c1nc2ncnc(OC3CN(C(=O)OC(C)(C)C)C3)c2s1] | Reference Example 112 (341 mg) | 358 mg | 371 |
| 189 | 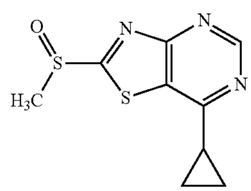 | Reference Example 119 (318 mg) | 335 mg | 240 |
| 190 | 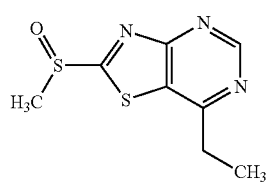 | Reference Example 120 (277 mg) | 273 mg | 228 |
| 191 | 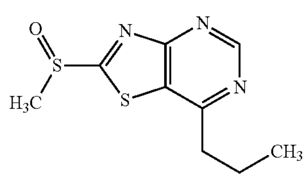 | Reference Example 121 (324 mg) | 336 mg | 242 |
| 192 | 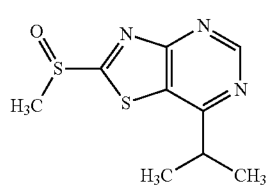 | Reference Example 122 (308 mg) | 319 mg | 242 |
| 193 | 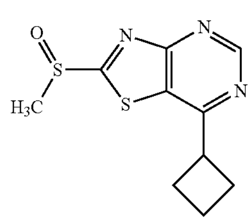 [SMILES: CS(=O)c1nc2ncnc(C3CCC3)c2s1] | Reference Example 123 (313 mg) | 323 mg | 254 |

TABLE 25-continued

| Reference Example | structure | starting material | yield | MS (ESI) m/z [M + H]+ |
|---|---|---|---|---|
| 194 | 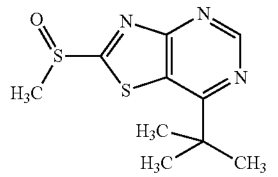 [SMILES: CS(=O)c1nc2ncnc(C(C)(C)C)c2s1] | Reference Example 124 (300 mg) | 300 mg | 256 |
| 195 | 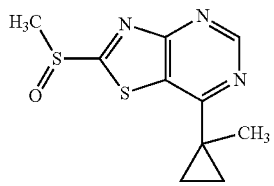 | Reference Example 125 (300 mg) | 300 mg | 254 |
| 196 | 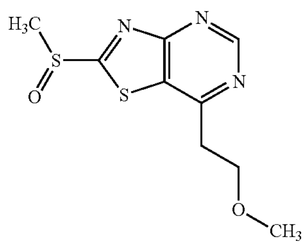 | Reference Example 126 (180 mg) | 100 mg | 258 |
| 197 | 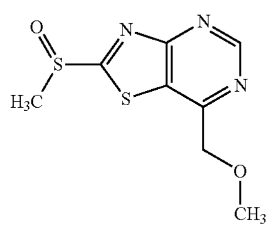 | Reference Example 127 (290 mg) | 287 mg | 244 |
| 198 | 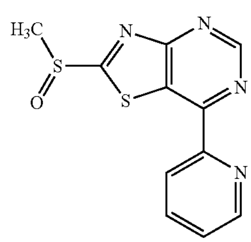 [SMILES: CS(=O)c1nc2ncnc(-c3ccccn3)c2s1] | Reference Example 120 (700 mg) | 540 mg | 277 |
| 199 | 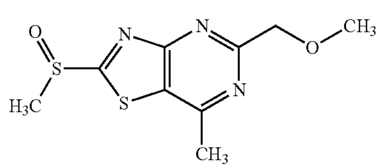 | Reference Example 131 (59.0 mg) | 56.0 mg | 258 |
| 200 | 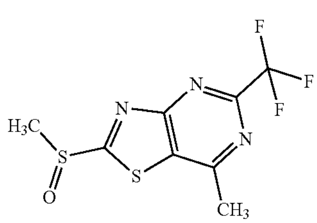 [SMILES: Cc1nc(C(F)(F)F)nc2nc(S(C)=O)sc12] | Reference Example 132 (350 mg) | 290 mg | 282 |

TABLE 25-continued

| Reference Example | structure | starting material | yield | MS (ESI) m/z [M + H]+ |
|---|---|---|---|---|
| 201 | 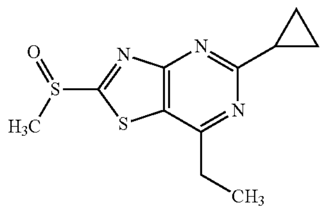 [SMILES: CCc1nc(C2CC2)nc2nc(S(C)=O)sc12] | Reference Example 131 (200 mg) | 202 mg | 268 |
| 202 | 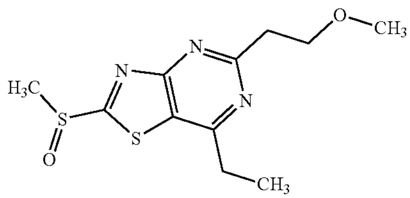 | Reference Example 134 (540 mg) | 470 mg | 286 |
| 203 | 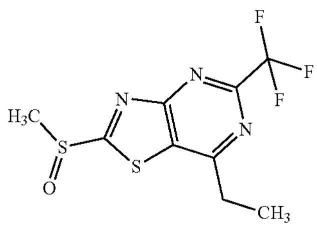 [SMILES: CCc1nc(C(F)(F)F)nc2nc(S(C)=O)sc12] | Reference Example 135 (290 mg) | 230 mg | 296 |
| 204 | 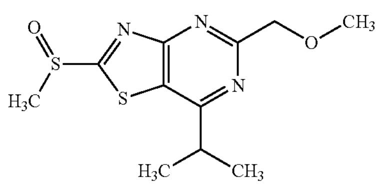 | Reference Example 136 (142 mg) | 153 mg | 286 |
| 205 | 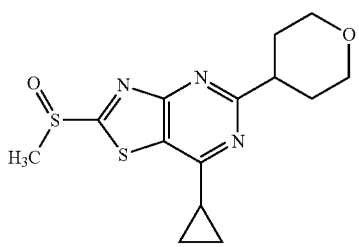 [SMILES: CS(=O)c1nc2nc(C3CCOCC3)nc(C3CC3)c2s1] | Reference Example 137 (500 mg) | 522 mg | 324 |
| 206 | 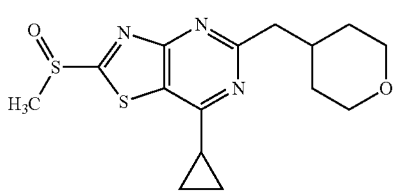 [SMILES: CS(=O)c1nc2nc(CC3CCOCC3)nc(C3CC3)c2s1] | Reference Example 131 (197 mg) | 56.0 mg | 338 |
| 207 | 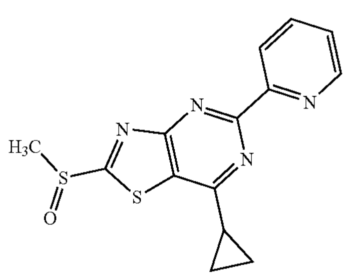 [SMILES: CS(=O)c1nc2nc(-c3ccccn3)nc(C3CC3)c2s1] | Reference Example 139 (380 mg) | 260 mg | 317 |

TABLE 25-continued

| Reference Example | structure | starting material | yield | MS (ESI) m/z [M + H]+ |
|---|---|---|---|---|
| 208 | 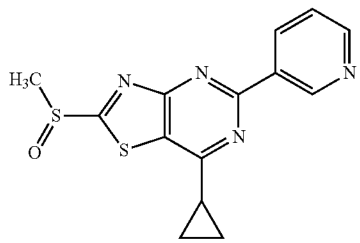 [SMILES: CS(=O)c1nc2nc(-c3cccnc3)nc(C3CC3)c2s1] | Reference Example 140 (215 mg) | 199 mg | 317 |
| 209 | 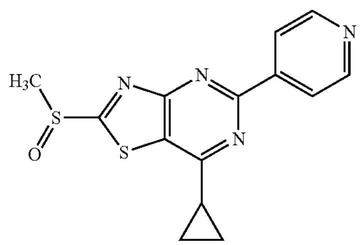 [SMILES: CS(=O)c1nc2nc(-c3ccncc3)nc(C3CC3)c2s1] | Reference Example 141 (84.0 mg) | 86.5 mg | 317 |
| 210 | 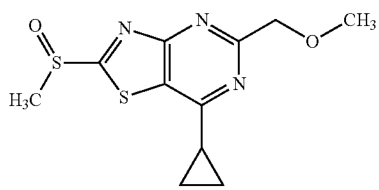 | Reference Example 142 (260 mg) | 270 mg | 284 |
| 211 | 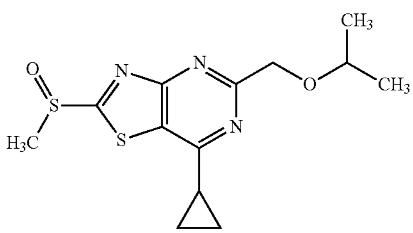 [SMILES: CC(C)OCc1nc(C2CC2)c2sc(S(C)=O)nc2n1] | Reference Example 143 (121 mg) | 126 mg | 312 |
| 212 | 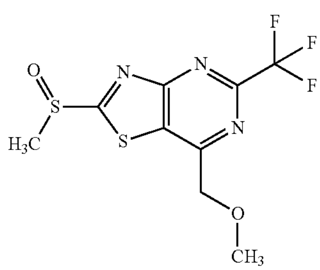 [SMILES: COCc1nc(C(F)(F)F)nc2nc(S(C)=O)sc12] | Reference Example 144 (155 mg) | 150 mg | 312 |
| 213 | 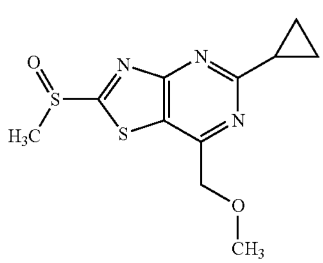 [SMILES: COCc1nc(C2CC2)nc2nc(S(C)=O)sc12] | Reference Example 145 (182 mg) | 180 mg | 284 |

TABLE 25-continued

| Reference Example | structure | starting material | yield | MS (ESI) m/z [M + H]+ |
|---|---|---|---|---|
| 214 | 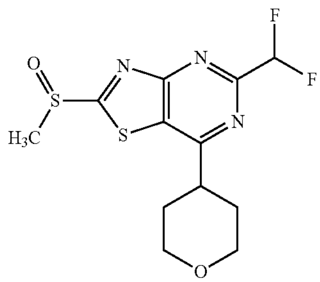 [SMILES: CS(=O)c1nc2nc(C(F)F)nc(C3CCOCC3)c2s1] | Reference Example 146 (200 mg) | 170 mg | 334 |
| 215 | 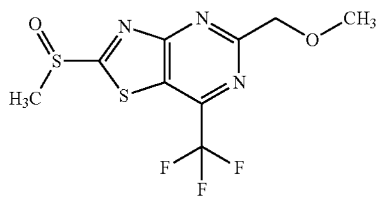 | Reference Example 147 (97.0 mg) | 95.0 mg | 312 |
| 216 | 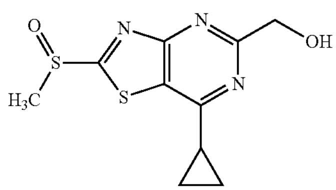 [SMILES: CS(=O)c1nc2nc(CO)nc(C3CC3)c2s1] | Reference Example 154 (275 mg) | 283 mg | 270 |
| 217 | 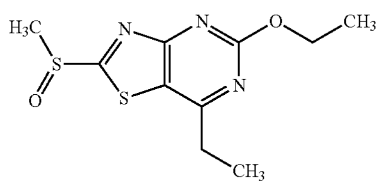 [SMILES: CCOc1nc(CC)c2sc(S(C)=O)nc2n1] | Reference Example 159 (191 mg) | 198 mg | 272 |
| 218 | 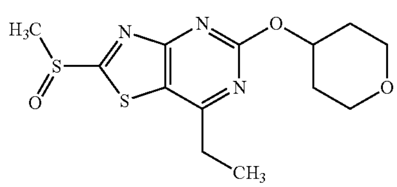 [SMILES: CCc1nc(OC2CCOCC2)nc2nc(S(C)=O)sc12] | Reference Example 157 (124 mg) | 140 mg | 328 |
| 219 | 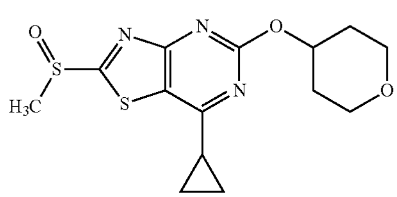 [SMILES: CS(=O)c1nc2nc(OC3CCOCC3)nc(C3CC3)c2s1] | Reference Example 158 (120 mg) | 130 mg | 340 |
| 220 | 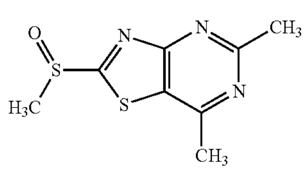 | Reference Example 163 (416 mg) | 327 mg | 228 |

Reference Example 221

7-cyclopropyl-5-[(N,N-dimethylamino)methyl]-2-(methylsulfinyl)[1,3]thiazolo[4,5-d]pyrimidine

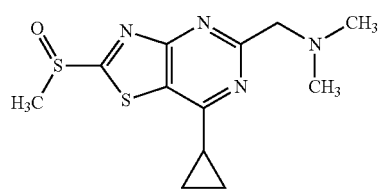

To a methylene chloride solution (6.00 mL) of the compound (132 mg) obtained in Reference Example 155 and trifluoroacetic acid (0.0700 mL) was added, under ice-cooling, mCPBA (69-75% w/w, 119 mg), and the reaction mixture was stirred at room temperature for 2 hr. To the reaction mixture were added aqueous sodium thiosulfate solution and saturated aqueous sodium hydrogen carbonate solution, and the mixture was extracted twice with chloroform. The organic layer was dried over anhydrous sodium sulfate, filtered and concentrated to give the title compound (95.0 mg).

MS(ESI)m/z; 297[M+H]$^+$

Reference Example 222

2-(4-methoxybenzylamino)-4,5-dimethylpyridine

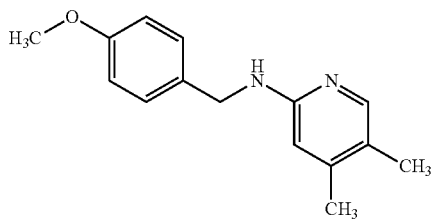

A mixture of 4,5-dimethyl-2-fluoropyridine (708 mg) synthesized by the method described in WO 2005/028444 in and 4-methoxybenzylamine (2.39 mL) was stirred at 150° C. for 15 hr. After cooling to room temperature, to the reaction mixture was added ethyl acetate, and the mixture was washed once with water. The organic layer was dried over anhydrous sodium sulfate, filtered and concentrated. The obtained residue was purified by silica gel column chromatography (solvent; hexane/ethyl acetate=90/10-50/50) to give the title compound (421 mg).

MS(ESI)m/z; 243[M+H]$^+$

Reference Example 223

5-bromo-2-(4-methoxybenzylamino)-4-methylpyridine

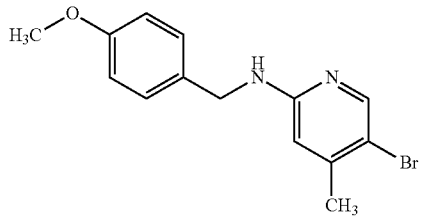

5-Bromo-2-fluoro-4-methylpyridine (2.70 g) was treated by a method similar to that in Reference Example 222 to give the title compound (4.13 g).

MS(ESI)m/z; 307, 309[M+H]$^+$

Reference Example 224

2-amino-5-cyclopropylpyridine

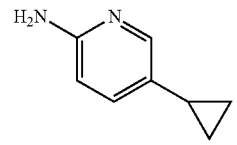

A mixture of 2-amino-5-bromopyridine (3.00 g), cyclopropylboronic acid (2.23 g), cesium carbonate (16.9 g) and dichlorobis(tricyclohexylphosphine)palladium (1.28 g) in 1,4-dioxane (11.5 mL) was heated under reflux under a nitrogen atmosphere for 10 hr. After cooling to room temperature, water was added, and the mixture was extracted twice with ethyl acetate. The organic layer was dried over anhydrous sodium sulfate, filtered and concentrated, and the obtained residue was purified by silica gel column chromatography (solvent; hexane/ethyl acetate=70/30-0/100) to give the title compound (1.28 g).

MS(ESI)m/z; 135[M+H]$^+$

Reference Example 225

2-amino-5-(prop-1-en-2-yl)pyridine

A mixture of 2-amino-5-bromopyridine (1.00 g), 2-(propan-2-yl)-4,4,5,5-tetramethyl-1,3,2-dioxaborolane (1.46 g), tripotassium phosphate (5.52 g) and dichlorobis(tricyclohexylphosphine)palladium (427 mg) in toluene (116 mL) was heated under reflux under a nitrogen atmosphere for 11 hr. After cooling to room temperature, water was added, and the mixture was extracted twice with ethyl acetate. The organic layer was dried over anhydrous sodium sulfate, filtered and concentrated, and the obtained residue was purified by silica gel column chromatography (solvent; hexane/ethyl acetate=70/30-0/100) to give the title compound (880 mg).

MS(ESI)m/z; 135[M+H]$^+$

Reference Example 226

2-amino-5-ethenylpyridine

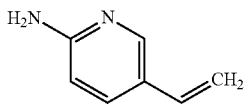

2-Amino-5-bromopyridine (5.00 g) was treated by a method similar to that in Reference Example 225 to give the title compound (2.40 g).

MS(ESI)m/z; 121[M+H]$^+$

Reference Example 227

5-ethenyl-2-(4-methoxybenzylamino)-4-methylpyridine

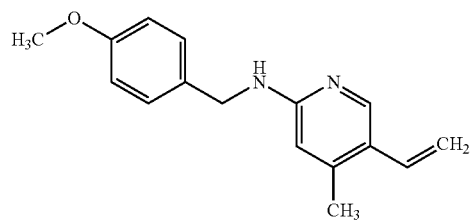 [SMILES: C=Cc1cnc(NCc2ccc(OC)cc2)cc1C]

The compound (2.50 g) obtained in Reference Example 223 was treated by a method similar to that in Reference Example 225 to give the title compound (1.59 g).

MS(ESI)m/z; 255[M+H]$^+$

Reference Example 228

2-amino-5-(propan-2-yl)pyridine

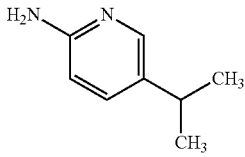

To an ethanol solution (20.0 mL) of the compound (880 mg) obtained in Reference Example 225 was added 10% palladium carbon (400 mg), and the reaction mixture was stirred under a hydrogen atmosphere at room temperature for 6 hr. The reaction mixture was filtered through diatomaceous earth and concentrated under reduced pressure, and the obtained residue was purified by NH silica gel column chromatography (solvent; hexane/ethyl acetate=90/10-40/60) to give the title compound (585 mg).

MS (ESI)m/z; 137[M+H]$^+$

Reference Example 229

2-amino-5-ethylpyridine

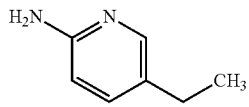

The compound (2.40 g) obtained in Reference Example 226 was treated by a method similar to that in Reference Example 228 to give the title compound (2.35 g).

MS(ESI)m/z; 123[M+H]$^+$

Reference Example 230

5-ethyl-2-(4-methoxybenzylamino)-4-methylpyridine

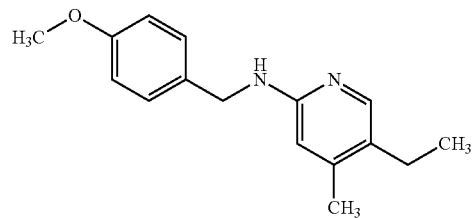 [SMILES: CCc1cnc(NCc2ccc(OC)cc2)cc1C]

The compound (1.60 g) obtained in Reference Example 227 was treated by a method similar to that in Reference Example 228 to give the title compound (1.62 g).

MS(ESI)m/z; 257[M+H]$^+$

Reference Example 231

2-amino-4,5-dimethylpyridine

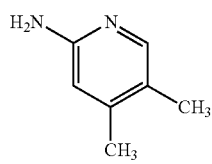

A trifluoroacetic acid solution (4.00 mL) of the compound (421 mg) obtained in Reference Example 222 was stirred at room temperature for 2 hr. After confirmation of the completion of the reaction, the reaction mixture was concentrated and the obtained residue was dissolved in chloroform and washed once with water. The organic layer was dried over anhydrous sodium sulfate, filtered and concentrated to give the title compound (242 mg).

MS(ESI)m/z; 123[M+H]$^+$

Reference Example 232

2-amino-5-ethyl-4-methylpyridine

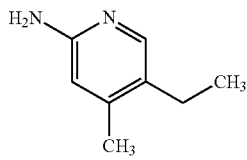

The compound (1.59 g) obtained in Reference Example 230 was treated by a method similar to that in Reference Example 231 to give the title compound (1.29 g).

MS(ESI)m/z; 137[M+H]$^+$

Reference Example 233

2-chloro-5-(2-cyanopropan-2-yl)pyridine

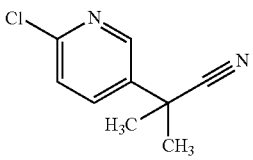

To a DMF solution (250 mL) of (6-chloropyridin-3-yl)acetonitrile (15.0 g) were added, at 0° C., methyl iodide (33.5 g) and sodium hydride (60% w/w, 8.65 g), and the reaction mixture was stirred at the same temperature for 1.5 hr. Under ice-cooling, water was added and the mixture was extracted twice with ethyl acetate. The organic layer was dried over anhydrous sodium sulfate, filtered and concentrated, and the obtained residue was purified by silica gel column chromatography (solvent; hexane/ethyl acetate=100/0-60/40) to give the title compound (15.3 g).

MS(ESI)m/z; 181[M+H]$^+$

Reference Example 234

2-chloro-5-(1-cyanocyclobutyl)pyridine

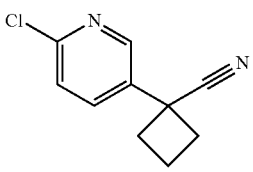 [SMILES: N#CC1(c2ccc(Cl)nc2)CCC1]

(6-Chloropyridin-3-yl)acetonitrile (1.50 g) was treated by a method similar to that in Reference Example 233 to give the title compound (1.00 g).

MS(ESI)m/z; 193[M+H]$^+$

Reference Example 235

2-chloro-5-(4-cyanotetrahydro-2H-pyran-4-yl)pyridine

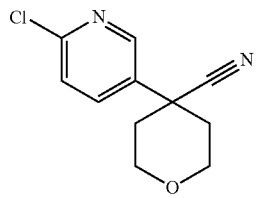 [SMILES: N#CC1(c2ccc(Cl)nc2)CCOCC1]

(6-Chloropyridin-3-yl)acetonitrile (2.00 g) was treated by a method similar to that in Reference Example 233 to give the title compound (1.25 g).

MS(ESI)m/z; 223[M+H]$^+$

Reference Example 236 methyl 1-(6-chloropyridin-3-yl)cyclopropanecarboxylate

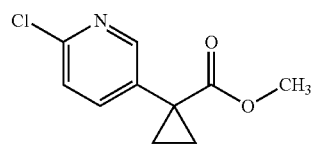

Methyl (6-chloropyridin-3-yl)acetate (2.55 g) synthesized by the method described in WO 2003/99793 was treated by a method similar to that in Reference Example 233 to give the title compound (1.57 g).

MS(ESI)m/z; 223[M+H]$^+$

Reference Example 237

2-chloro-5-(1-hydroxymethylcyclopropyl)pyridine

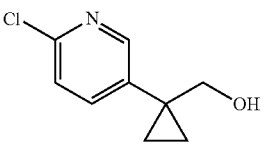 [SMILES: OCC1(c2ccc(Cl)nc2)CC1]

To a diethyl ether solution (30.0 mL) of the compound (1.47 g) obtained in Reference Example 236 was added, at 0° C., lithium aluminum hydride (264 mg), and the reaction mixture was stirred at the same temperature for 1 hr. Under ice-cooling, water (264 μL) and 15% aqueous sodium hydroxide solution (264 μL) were added, and the mixture was filtered through diatomaceous earth. The solvent was evaporated under reduced pressure, and the obtained residue was purified by silica gel column chromatography (solvent; hexane/ethyl acetate=70/30-20/80) to give the title compound (963 mg).

MS(ESI)m/z; 184[M+H]$^+$

Reference Example 238

2-chloro-5-(1-methoxymethylcyclopropyl)pyridine

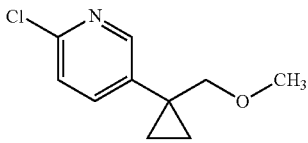

To a DMF solution (40.0 mL) of the compound (1.03 g) obtained in Reference Example 237 were added, at 0° C., methyl iodide (952 mg) and sodium hydride (60% w/w, 246 mg), and the reaction mixture was stirred at the same temperature for 1 hr. Under ice-cooling, saturated aqueous ammonium chloride solution was added, and the mixture was extracted twice with ethyl acetate. The organic layer was dried over anhydrous sodium sulfate, filtered and concentrated, and the obtained residue was purified by silica gel column chromatography (solvent; hexane/ethyl acetate=95/5-60/40) to give the title compound (974 mg).

MS(ESI)m/z; 198[M+H]$^+$

Reference Example 239

2-amino-5-(2-cyanopropan-2-yl)pyridine

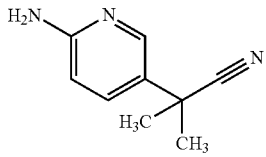

A mixture of the compound (15.3 g) obtained in Reference Example 233, benzophenone imine (18.4 g), palladium acetate (949 mg), (±)—2,2'-bis(diphenylphosphino)-1,1'-binaphthyl (5.26 g) and cesium carbonate (41.3 g) in 1,4-dioxane (330 mL) was heated under reflux at 80° C. for 2 hr. After cooling to room temperature, benzophenone imine (4.59 g), palladium acetate (474 mg) and (±)—2,2'-bis(diphenylphosphino)-1,1'-binaphthyl (2.63 g) were added, and the reaction mixture was heated under reflux at 80° C. for 3 hr. Under ice-cooling, ethyl acetate was added and the mixture was filtered through diatomaceous earth. The solvent was evaporated under reduced pressure and, under ice-cooling, methanol (200 mL), water (14.0 mL) and concentrated hydrochloric acid (28.0 mL) were added, and the reaction mixture was stirred at room temperature overnight. The solvent was evaporated under reduced pressure, 1.0 mol/L hydrochloric acid (270 mL) was added, and the mixture was washed once with chloroform. The aqueous layer was neutralized with 20% aqueous sodium hydroxide solution and extracted 3 times with chloroform. The organic layer was dried over anhydrous sodium sulfate, filtered and concentrated, and the obtained residue was purified by NH silica gel column chromatography (solvent; hexane/ethyl acetate=70/30-0/100) to give the title compound (9.07 g).

MS(ESI)m/z; 162[M+H]$^+$

Reference Example 240

2-amino-5-(1-cyanocyclobutyl)pyridine

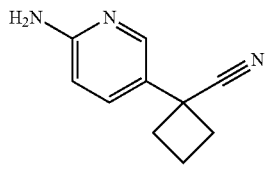 [SMILES: N#CC1(c2ccc(N)nc2)CCC1]

The compound (1.00 g) obtained in Reference Example 234 was treated by a method similar to that in Reference Example 239 to give the title compound (591 mg).

MS(ESI)m/z; 174[M+H]$^+$

Reference Example 241

2-amino-5-(4-cyanotetrahydro-2H-pyran-4-yl)pyridine

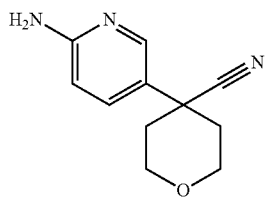 [SMILES: N#CC1(c2ccc(N)nc2)CCOCC1]

The compound (1.25 g) obtained in Reference Example 235 was treated by a method similar to that in Reference Example 239 to give the title compound (851 mg).

MS(ESI)m/z; 204[M+H]$^+$

Reference Example 242

2-amino-5-(1-methoxymethylcyclopropyl)pyridine

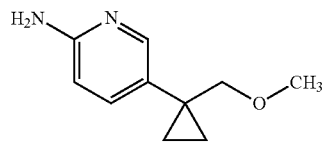

The compound (974 mg) obtained in Reference Example 238 was treated by a method similar to that in Reference Example 239 to give the title compound (509 mg).

MS(ESI)m/z; 179[M+H]$^+$

Reference Example 243

N-[(3-bromo-5-methylpyridin-2-yl)carbamothioyl]benzamide

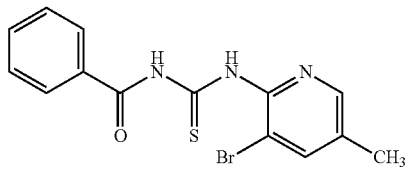 [SMILES: Cc1cnc(NC(=S)NC(=O)c2ccccc2)c(Br)c1]

An acetone solution (22.0 mL) of ammonium thiocyanate (5.96 g) and benzoyl chloride (11.0 g) was heated under reflux for 5 min. After cooling to room temperature, an acetone solution (22.0 mL) of 2-amino-3-bromo-5-methylpyridine (14.1 g) was added, and the reaction mixture was heated under reflux for 3.5 hr. After cooling to room temperature, water was added, and the resulting solid was collected by filtration and dried to give the title compound (22.6 g).

MS(ESI)m/z; 350, 352[M+H]$^+$

Reference Example 244

N-[(3,5-dibromopyridin-2-yl)carbamothioyl]benzamide

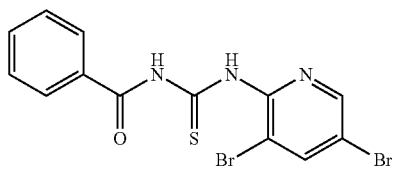 [SMILES: O=C(NC(=S)Nc1ncc(Br)cc1Br)c1ccccc1]

2-Amino-3,5-dibromopyridine (25.0 g) was treated by a method similar to that in Reference Example 243 to give the title compound (39.4 g).

MS(ESI)m/z; 416[M+H]$^+$

Reference Example 245

N-[(3,5-dibromo-6-methylpyridin-2-yl)carbamothioyl]benzamide

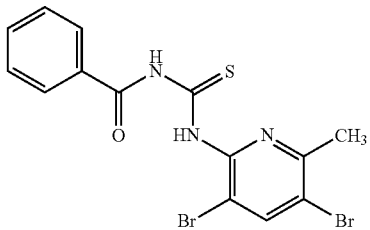 [SMILES: Cc1nc(NC(=S)NC(=O)c2ccccc2)c(Br)cc1Br]

An acetone solution (14.0 mL) of 2-amino-3,5-dibromo-6-methylpyridine (5.05 g) and benzoyl isothiocyanate (3.25 g) was heated under reflux for 8 hr. After cooling to room temperature, diisopropy ether was added, and the resulting solid was collected by filtration and dried to give the title compound (6.67 g).

MS(ESI)m/z; 428, 430, 432[M+H]$^+$

Reference Example 246

N-(6-methyl[1,3]thiazolo[4,5-b]pyridin-2-yl)benzamide

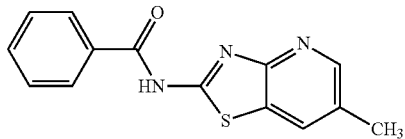 [SMILES: Cc1cnc2nc(NC(=O)c3ccccc3)sc2c1]

An N-methylpyrrolidone solution (160 mL) of the compound (22.6 g) obtained in Reference Example 243 and sodium methoxide (6.96 g) was stirred with heating at 120° C. for 3 hr. After cooling to 0° C., the reaction mixture was neutralized with 1.0 mol/L hydrochloric acid and water was further added. The resulting solid was collected by filtration, washed with water and dried to give the title compound (11.1 g).

MS(ESI)m/z; 270[M+H]$^+$

Reference Example 247

N-(6-bromo[1,3]thiazolo[4,5-b]pyridin-2-yl)benzamide

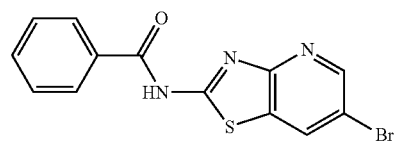 [SMILES: O=C(Nc1nc2ncc(Br)cc2s1)c1ccccc1]

The compound (15.0 g) obtained in Reference Example 244 was treated by a method similar to that in Reference Example 246 to give the title compound (7.46 g).

MS(ESI)m/z; 334, 336[M+H]$^+$

Reference Example 248

N-(6-bromo-5-methyl[1,3]thiazolo[4,5-b]pyridin-2-yl)benzamide

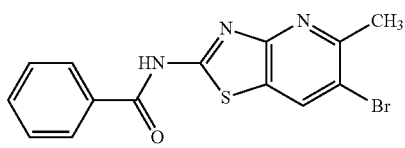 [SMILES: Cc1nc2nc(NC(=O)c3ccccc3)sc2cc1Br]

The compound (6.67 g) obtained in Reference Example 245 was treated by a method similar to that in Reference Example 246 to give the title compound (1.79 g).

MS(ESI)m/z; 348, 350[M+H]$^+$

Reference Example 249

2-amino-6-methyl[1,3]thiazolo[4,5-b]pyridine

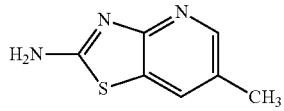

To a mixed solution of concentrated sulfuric acid (144 mL)-water (61.8 mL) was added the compound (11.1 g) obtained in Reference Example 246 at 0° C., and the reaction mixture was stirred with heating at 120° C. for 1.5 hr. After cooling to 0° C., sodium hydroxide (280 g) was added. The resulting solid was collected by filtration, washed with water and dried to give the title compound (5.58 g).
MS(ESI)m/z; 166[M+H]$^+$

Reference Example 250

2-amino-6-bromo[1,3]thiazolo[4,5-b]pyridine

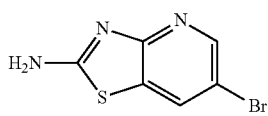 [SMILES: Nc1nc2ncc(Br)cc2s1]

The compound (4.46 g) obtained in Reference Example 247 was treated by a method similar to that in Reference Example 249 to give the title compound (2.42 g).
MS(ESI)m/z; 230, 232[M+H]$^+$

Reference Example 251

2-amino-6-bromo-5-methyl[1,3]thiazolo[4,5-b]pyridine

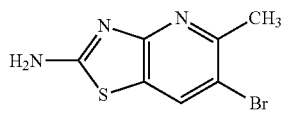

The compound (1.79 g) obtained in Reference Example 248 was treated by a method similar to that in Reference Example 249 to give the title compound (1.11 g).
MS(ESI)m/z; 244, 246[M+H]$^+$

Reference Example 252

6-bromo-2-(2,5-dimethyl-1H-pyrrol-1-yl)[1,3]thiazolo[4,5-b]pyridine

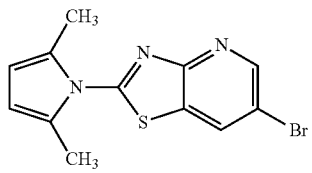 [SMILES: Cc1ccc(C)n1-c1nc2ncc(Br)cc2s1]

A toluene solution (16.0 mL) of the compound (2.00 g) obtained in Reference Example 250, n-hexane-2,5-dione (2.04 mL) and p-toluenesulfonic acid monohydrate (165 mg) was heated under reflux overnight. Under ice-cooling, saturated aqueous sodium hydrogen carbonate solution was added, and the mixture was extracted twice with chloroform. The organic layer was dried over anhydrous sodium sulfate, filtered and concentrated, and the obtained residue was purified by silica gel column chromatography (solvent; hexane/ethyl acetate=100/0-80/20) to give the title compound (1.50 g).
MS(ESI)m/z; 308, 310[M+H]$^+$

Reference Example 253

6-bromo-2-(2,5-dimethyl-1H-pyrrol-1-yl)-5-methyl[1,3]thiazolo[4,5-b]pyridine

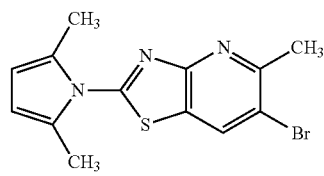

The compound (1.11 g) obtained in Reference Example 251 was treated by a method similar to that in Reference Example 252 to give the title compound (977 mg).
MS(ESI)m/z; 322, 324[M+H]$^+$

Reference Example 254

2-(2,5-dimethyl-1H-pyrrol-1-yl)-6-(1-hydroxycyclobutyl)[1,3]thiazolo[4,5-b]pyridine

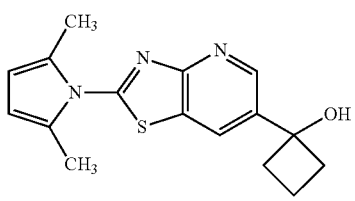 [SMILES: Cc1ccc(C)n1-c1nc2ncc(C3(O)CCC3)cc2s1]

To a THF solution (20.0 mL) of the compound (500 mg) obtained in Reference Example 252 were added at -78° C. n-butyllithium (1.67 mol/L hexane solution, 1.16 mL) and cyclobutanone (148 mg), and the reaction mixture was stirred at the same temperature for 1 hr. After heating to room temperature, saturated aqueous ammonium chloride solution was added, and the mixture was extracted twice with ethyl acetate. The organic layer was dried over anhydrous sodium sulfate, filtered and concentrated, and the obtained residue was purified by silica gel column chromatography (solvent; hexane/ethyl acetate=80/20-20/80) to give the title compound (344 mg).
MS(ESI)m/z; 300[M+H]$^+$

Reference Example 255

2-(2,5-dimethyl-1H-pyrrol-1-yl)-6-(3-hydroxyoxetan-3-yl)[1,3]thiazolo[4,5-b]pyridine

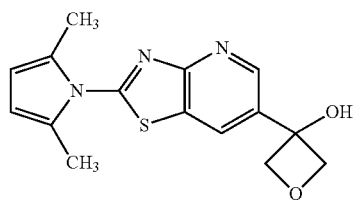 [SMILES: Cc1ccc(C)n1-c1nc2ncc(C3(O)COC3)cc2s1]

The compound (400 mg) obtained in Reference Example 252 was treated by a method similar to that in Reference Example 254 to give the title compound (134 mg).
MS(ESI)m/z; 302[M+H]$^+$

Reference Example 256

2-(2,5-dimethyl-1H-pyrrol-1-yl)-6-(1-methoxycyclobutyl)[1,3]thiazolo[4,5-b]pyridine

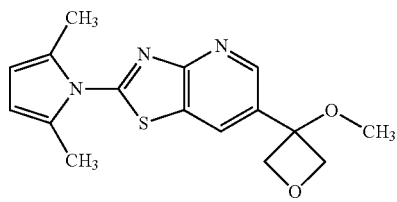 [SMILES: COC1(c2cnc3nc(-n4c(C)ccc4C)sc3c2)COC1]

To a DMF solution (6.00 mL) of the compound (244 mg) obtained in Reference Example 254 were added at 0° C. methyl iodide (139 mg) and sodium hydride (60% w/w, 36.0 mg), and the reaction mixture was stirred at the same temperature for 1 hr. Under ice-cooling, saturated aqueous ammonium chloride solution was added, and the mixture was extracted twice with ethyl acetate. The organic layer was dried over anhydrous sodium sulfate, filtered and concentrated, and the obtained residue was purified by silica gel column chromatography (solvent; hexane/ethyl acetate=90/10-50/50) to give the title compound (187 mg).
MS(ESI)m/z; 314[M+H]$^+$

Reference Example 257

2-(2,5-dimethyl-1H-pyrrol-1-yl)-6-(3-methoxyoxetan-3-yl)[1,3]thiazolo[4,5-b]pyridine

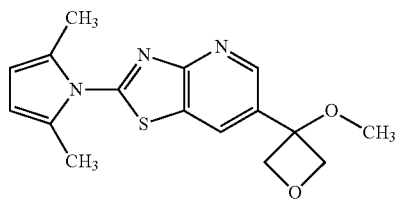 [SMILES: COC1(c2cnc3nc(-n4c(C)ccc4C)sc3c2)COC1]

The compound (134 mg) obtained in Reference Example 255 was treated by a method similar to that in Reference Example 256 to give the title compound (139 mg).
MS(ESI)m/z; 316[M+H]$^+$

Reference Example 258

6-(3,6-dihydro-2H-pyran-4-yl)-2-(2,5-dimethyl-1H-pyrrol-1-yl)[1,3]thiazolo[4,5-b]pyridine

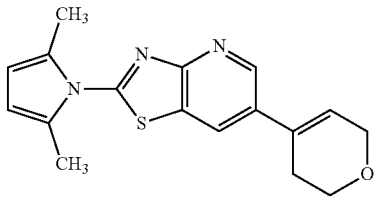 [SMILES: Cc1ccc(C)n1-c1nc2ncc(C3=CCOCC3)cc2s1]

A mixed solution of the compound (500 mg) obtained in Reference Example 252, 2-(3,6-dihydro-2H-pyran-4-yl)-4,4,5,5-tetramethyl-1,3,2-dioxaborolane (533 mg), tetrakis(triphenylphosphine)palladium (93.7 mg) and sodium carbonate (516 mg) in DMF (5.00 mL)-water (0.500 mL) was stirred with heating under a nitrogen atmosphere at 80° C. for 8 hr. After cooling to room temperature, water was added, and the mixture was extracted twice with ethyl acetate. The organic layer was dried over anhydrous sodium sulfate, filtered and concentrated, and the obtained residue was purified by silica gel column chromatography (solvent; hexane/ethyl acetate=80/20-50/50) to give the title compound (390 mg).
MS(ESI)m/z; 312[M+H]$^+$

Reference Example 259

2-(2,5-dimethyl-1H-pyrrol-1-yl)-6-(tetrahydro-2H-pyran-4-yl)[1,3]thiazolo[4,5-b]pyridine

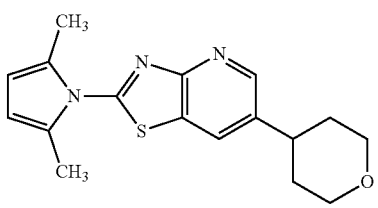 [SMILES: Cc1ccc(C)n1-c1nc2ncc(C3CCOCC3)cc2s1]

To a methanol solution (4.00 mL) of the compound (341 mg) obtained in Reference Example 258 was added 10% palladium carbon (680 mg), and the mixture was stirred under a hydrogen atmosphere at room temperature for 14 hr. The reaction mixture was filtered through diatomaceous earth and concentrated under reduced pressure. The obtained residue was purified by silica gel column chromatography (solvent; hexane/ethyl acetate=80/20-50/50) to give the title compound (70.0 mg).
MS(ESI)m/z; 314[M+H]$^+$

Reference Example 260

6-cyanomethyl-2-(2,5-dimethyl-1H-pyrrol-1-yl)-5-methyl[1,3]thiazolo[4,5-b]pyridine

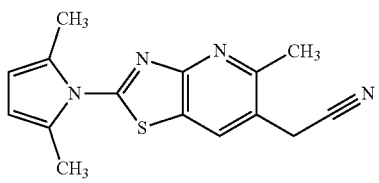 [SMILES: Cc1nc2nc(-n3c(C)ccc3C)sc2cc1CC#N]

A solution of the compound (885 mg) obtained in Reference Example 253, (trimethylsilyl)acetonitrile (1.13 mL), zinc fluoride (426 mg), tris(dibenzylideneacetone)(chloroform)dipalladium(0) (228 mg) and 4,5-bis(diphenylphosphino)-9,9-dimethylxanthene (255 mg) in DMF (6.60 mL) was stirred with heating under a nitrogen atmosphere at 90° C. for 7 hr. After cooling to room temperature, water was added, and the mixture was extracted twice with ethyl acetate. The organic layer was dried over anhydrous sodium sulfate, filtered and concentrated, and the obtained residue was purified by silica gel column chromatography (solvent; hexane/ethyl acetate=85/15-40/60) to give the title compound (622 mg).
MS(ESI)m/z; 283[M+H]$^+$

Reference Example 261

6-(2-cyanopropan-2-yl)-2-(2,5-dimethyl-1H-pyrrol-1-yl)-5-methyl[1,3]thiazolo[4,5-b]pyridine

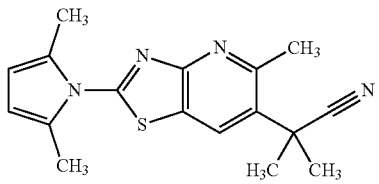 [SMILES: Cc1nc2nc(-n3c(C)ccc3C)sc2cc1C(C)(C)C#N]

To a DMF solution (3.00 mL) of the compound (335 mg) obtained in Reference Example 260 were added at 0° C. methyl iodide (338 mg) and sodium hydride (60% w/w, 105 mg), and the reaction mixture was stirred at the same temperature for 1 hr. Under ice-cooling, water was added, and the mixture was extracted twice with ethyl acetate. The organic layer was dried over anhydrous sodium sulfate, filtered and concentrated, and the obtained residue was purified by silica gel column chromatography (solvent; hexane/ethyl acetate=90/10-50/50) to give the title compound (256 mg).
MS(ESI)m/z; 311[M+H]$^+$

Reference Example 262

2-amino-6-(1-hydroxycyclobutyl)[1,3]thiazolo[4,5-b]pyridine

A mixed solution of the compound (204 mg) obtained in Reference Example 254 in trifluoroacetic acid (5.00 mL)-water (5.00 mL) was stirred with heating at 50° C. for 2 hr. After cooling to room temperature, the solvent was evaporated under reduced pressure, chloroform was added, and the mixture was washed twice with saturated aqueous sodium hydrogen carbonate solution. The organic layer was dried over anhydrous sodium sulfate, filtered and concentrated. To the obtained residue was added diisopropy ether, and the solid was collected by filtration and dried to give the title compound (85.0 mg).
MS(ESI)m/z; 222[M+H]$^+$ The following Table shows the compounds obtained by treating the corresponding compounds by a method similar to that in Reference Example 262.

TABLE 26

| Reference Example | structure | starting material | yield | MS(ESI) m/z [M + H]$^+$ |
|---|---|---|---|---|
| 263 | ![structure] | Reference Example 256 (187 mg) | 94.0 mg | 236 |
| 264 | ![structure] | Reference Example 257 (139 mg) | 48.0 mg | 238 |
| 265 | ![structure] | Reference Example 259 (86.1 mg) | 40.0 mg | 236 |

TABLE 26-continued

| Reference Example | structure | starting material | yield | MS(ESI) m/z [M + H]+ |
|---|---|---|---|---|
| 266 | ![structure with H2N-thiazolo[5,4-b]pyridine-CH3 and C(CH3)2CN] | Reference Example 261 (256 mg) | 179 mg | 233 |

Reference Example 267

2-amino-3-bromo-5-cyclopropylpyridine

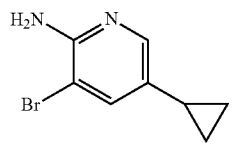

To an acetonitrile solution (40.0 mL) of the compound (1.28 g) obtained in Reference Example 224 was added N-bromosuccinimide (1.70 g) at 0° C., and the reaction mixture was stirred at the same temperature for 2 hr. The reaction mixture was concentrated under reduced pressure, and the residue was purified by silica gel column chromatography (solvent; hexane/ethyl acetate=95/5-50/50) to give the title compound (1.29 g).

MS(ESI)m/z; 213, 215[M+H]+

The following Table shows the compounds obtained by treating the corresponding compounds by a method similar to that in Reference Example 267.

TABLE 27

| Reference Example | structure | starting material | yield | MS(ESI) m/z [M + H]+ |
|---|---|---|---|---|
| 268 | H2N-pyridine with Br and CH(CH3)2 | Reference Example 228 (414 mg) | 404 mg | 215, 217 |
| 269 | H2N-pyridine with Br and CH3 | Reference Example 229 (2.35 g) | 3.01 g | 201, 203 |
| 270 | H2N-pyridine with Br, CH3, CH3 | Reference Example 231 (212 mg) | 182 mg | 201, 203 |
| 271 | H2N-pyridine with Br, CH3, CH3 | Reference Example 232 (1.29 g) | 888 mg | 215, 217 |
| 272 | H2N-pyridine with Br and C(CH3)2CN | Reference Example 239 (9.07 g) | 12.8 g | 240, 242 |

TABLE 27-continued

| Reference Example | structure | starting material | yield | MS(ESI) m/z [M + H]+ |
|---|---|---|---|---|
| 273 | H2N-pyridine(Br)-cyclobutane-CN | Reference Example 240 (591 mg) | 798 mg | 252, 254 |
| 274 | H2N-pyridine(Br)-tetrahydropyran-CN | Reference Example 241 (851 mg) | 1.22 g | 282, 284 |
| 275 | H2N-pyridine(Br)-cyclopropyl-CH2-O-CH3 | Reference Example 242 (509 mg) | 592 mg | 257, 259 |
| 276 | H2N-pyridine(Br)(CH3)(F) | 2-amino-5-fluoro-4-methyl-pyridine (2.00 g) | 1.44 g | 205, 207 |

Reference Example 277

6-cyclopropyl[1,3]thiazolo[4,5-b]pyridine-2(3H)-thione

An N-methylpyrrolidone solution (5.50 mL) of the compound (1.09 g) obtained in Reference Example 267 and potassium ethyl xanthogenate (2.05 g) was stirred with heating at 150° C. for 4 hr. The reaction mixture was cooled to room temperature, and acetic acid and water were added. The precipitated solid was collected by filtration, washed with water and dried under reduced pressure to give the title compound (996 mg).

MS(ESI)m/z; 209[M+H]+

The following Tables show the compounds obtained by treating the corresponding compounds by a method similar to that in Reference Example 277.

TABLE 28

| Reference Example | structure | starting material | yield | MS(ESI) m/z [M + H]+ |
|---|---|---|---|---|
| 278 | thiazolo[4,5-b]pyridine-2-thione with CH(CH3)2 | Reference Example 268 (404 mg) | 361 mg | 211 |
| 279 | thiazolo[4,5-b]pyridine-2-thione with CH2CH3 | Reference Example 269 (3.01 g) | 2.80 g | 197 |

TABLE 28-continued

| Reference Example | structure | starting material | yield | MS(ESI) m/z [M + H]+ |
|---|---|---|---|---|
| 280 | 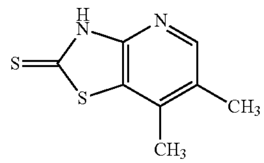 | Reference Example 270 (288 mg) | 267 mg | 197 |
| 281 | 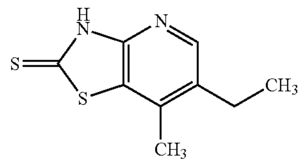 | Reference Example 271 (888 mg) | 832 mg | 211 |
| 282 | 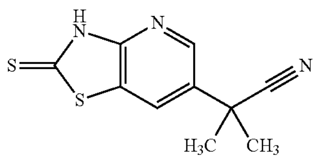 | Reference Example 272 (12.8 g) | 12.4 g | 236 |
| 283 | 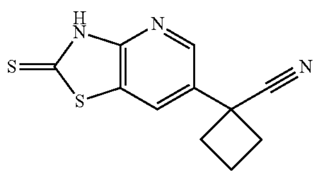 [SMILES: N#CC1(c2cnc3[nH]c(=S)sc3c2)CCC1] | Reference Example 273 (798 mg) | 748 mg | 248 |
| 284 | 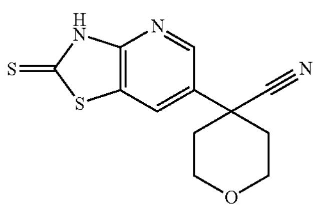 [SMILES: N#CC1(c2cnc3[nH]c(=S)sc3c2)CCOCC1] | Reference Example 274 (1.18 g) | 1.00 g | 278 |
| 285 | 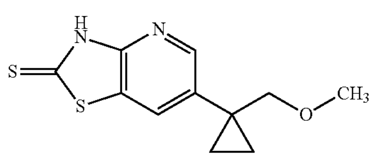 [SMILES: COCC1(c2cnc3[nH]c(=S)sc3c2)CC1] | Reference Example 275 (296 mg) | 250 mg | 253 |
| 286 | 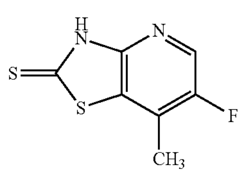 | Reference Example 276 (1.44 g) | 973 mg | 201 |
| 287 | 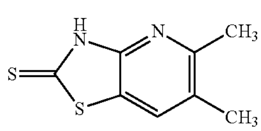 | 2-amino-3-bromo-5,6-dimethyl-pyridine (18.8 g) | 17.8 g | 197 |
| 288 | 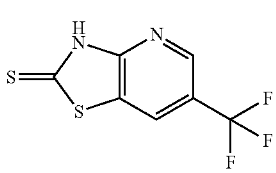 [SMILES: FC(F)(F)c1cnc2[nH]c(=S)sc2c1] | 2-amino-3-chloro-5-trifluoro-methylpyridine (2.00 g) | 2.06 g | 237 |

Reference Example 289

2-chloro-6-cyclopropyl[1,3]thiazolo[4,5-b]pyridine

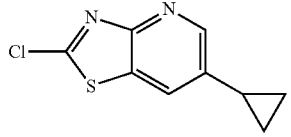 [SMILES: Clc1nc2ncc(C3CC3)cc2s1]

To a dichloromethane solution (1.30 mL) of the compound (200 mg) obtained in Reference Example 277 was added at room temperature sulfuryl chloride (0.600 mL), and the reaction mixture was stirred at the same temperature for 3 hr and further stirred with heating at 60° C. for 1 hr. After cooling to room temperature, ethyl acetate was added, and the mixture was washed with saturated aqueous sodium hydrogen carbonate solution. The organic layer was dried over anhydrous magnesium sulfate, filtered and concentrated. The obtained residue was purified by silica gel column chromatography (solvent; hexane/ethyl acetate=90/10-50/50) to give the title compound (22.0 mg).

MS(ESI)m/z; 211, 213[M+H]$^+$

The following Table shows the compounds obtained by treating the corresponding compounds by a method similar to that in Reference Example 289.

TABLE 29

| Reference Example | structure | starting material | yield | MS(ESI) m/z [M + H]$^+$ |
|---|---|---|---|---|
| 290 | 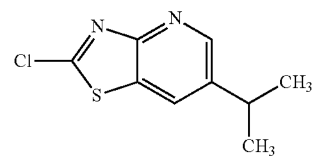 | Reference Example 278 (361 mg) | 152 mg | 213, 215 |
| 291 | 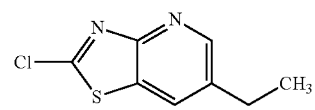 | Reference Example 279 (2.80 g) | 316 mg | 199, 201 |
| 292 | 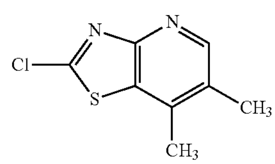 | Reference Example 280 (100 mg) | 81.0 mg | 199, 201 |
| 293 | 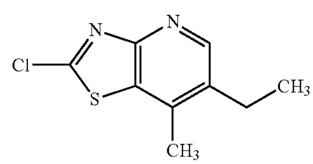 | Reference Example 281 (200 mg) | 114 mg | 213, 215 |
| 294 | 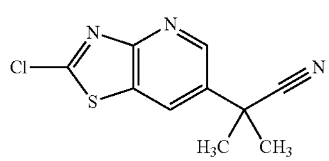 | Reference Example 282 (1.60 g) | 1.52 g | 238, 240 |
| 295 | 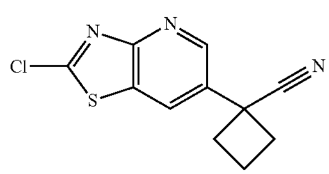 [SMILES: N#CC1(c2cnc3nc(Cl)sc3c2)CCC1] | Reference Example 283 (348 mg) | 294 mg | 250, 252 |
| 296 | 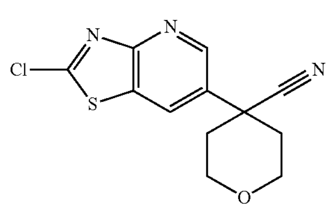 [SMILES: N#CC1(c2cnc3nc(Cl)sc3c2)CCOCC1] | Reference Example 284 (1.00 g) | 858 mg | 280, 282 |

TABLE 29-continued

| Reference Example | structure | starting material | yield | MS(ESI) m/z [M + H]+ |
|---|---|---|---|---|
| 297 | ![structure] | Reference Example 285 (250 mg) | 244 mg | 255, 257 |
| 298 | ![structure] | Reference Example 286 (450 mg) | 292 mg | 203, 205 |
| 299 | ![structure] | Reference Example 287 (17.8 g) | 12.3 g | 199, 201 |
| 300 | ![structure] | Reference Example 288 (500 mg) | 247 mg | 239, 241 |

Reference Example 301

2-chloro-6-methyl[1,3]thiazolo[4,5-b]pyridine

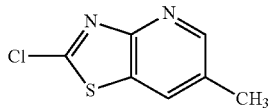

To acetonitrile (28.0 mL) were added t-butyl nitrite (1.08 mL) and cupric chloride (976 mg) at room temperature, and the reaction mixture was stirred with heating at 60° C. for 30 min. The compound (1.00 g) obtained in Reference Example 249 was added, and the reaction mixture was stirred with heating at 60° C. for 2 hr. After cooling to 0° C., 28% aqueous ammonia (38.6 mL) was added, and the mixture was extracted twice with chloroform, dried over anhydrous magnesium sulfate, filtered and concentrated, and the obtained residue was purified by silica gel column chromatography (solvent; hexane/ethyl acetate=90/10-50/50) to give the title compound (416 mg).

MS(ESI)m/z; 185, 187[M+H]+

The following Table shows the compounds obtained by treating the corresponding compounds by a method similar to that in Reference Example 301.

TABLE 30

| Reference Example | structure | starting material | yield | MS(ESI) m/z [M + H]+ |
|---|---|---|---|---|
| 302 | ![structure] | Reference Example 250 (930 mg) | 661 mg | 249, 251 |
| 303 | ![structure] | Reference Example 262 (85.0 mg) | 48.0 mg | 241, 243 |

TABLE 30-continued

| Reference Example | structure | starting material | yield | MS(ESI) m/z [M + H]⁺ |
|---|---|---|---|---|
| 304 | ![structure](chloro-thiazolo-pyridine with cyclobutyl-OMe) | Reference Example 263 (94.0 mg) | 55.0 mg | 255, 257 |
| 305 | ![structure](chloro-thiazolo-pyridine with oxetanyl-OMe) | Reference Example 264 (48.0 mg) | 18.0 mg | 257, 259 |
| 306 | ![structure](chloro-thiazolo-pyridine with tetrahydropyranyl) | Reference Example 265 (40.0 mg) | 10.2 mg | 255, 257 |
| 307 | ![structure](chloro-thiazolo-pyridine with CH₃ and C(CH₃)₂CN) | Reference Example 266 (179 mg) | 109 mg | 252, 254 |

Reference Example 308

5-cyano-2-(4-methoxybenzylamino)-4-methylpyridine

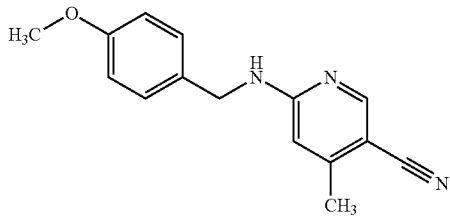 [SMILES: COc1ccc(CNc2cc(C)c(C#N)cn2)cc1]

A DMF solution (6.60 mL) of the compound (500 mg) obtained in Reference Example 223, zinc cyanide (383 mg), tris(dibenzylideneacetone)dipalladium(0) (149 mg), 1,1'-bis(diphenylphosphino)ferrocene (181 mg) and water (66.0 µL) was stirred with heating under a nitrogen atmosphere at 120° C. for 19 hr. After cooling to room temperature, water was added, and the mixture was extracted twice with ethyl acetate. The organic layer was dried over anhydrous magnesium sulfate, filtered and concentrated, and the obtained residue was purified by silica gel column chromatography (solvent; chloroform) to give the title compound (353 mg).

MS(ESI)m/z; 254[M+H]⁺

Reference Example 309

3-bromo-5-cyano-2-(4-methoxybenzylamino)-4-methylpyridine

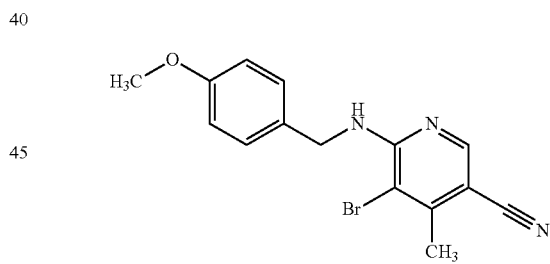

To an acetonitrile solution (8.00 mL) of the compound (353 mg) obtained in Reference Example 308 was added N-bromosuccinimide (248 mg) at 0° C., and the reaction mixture was stirred at room temperature for 30 min. A 0.1 mol/L aqueous sodium thiosulfate solution was added, and the mixture was extracted twice with ethyl acetate. The organic layer was dried over anhydrous magnesium sulfate, filtered and concentrated, and the obtained residue was purified by silica gel column chromatography (solvent; hexane/ethyl acetate=100/0-60/40) to give the title compound (413 mg).

MS(ESI)m/z; 332, 334[M+H]⁺

Reference Example 310

2-amino-3-bromo-5-cyano-4-methylpyridine

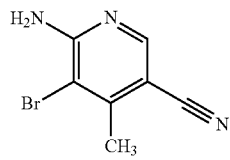

A trifluoroacetic acid solution (3.00 mL) of the compound (413 mg) obtained in Reference Example 309 was stirred at room temperature for 1.5 hr. After confirmation of the completion of the reaction, the reaction mixture was concentrated, and the obtained residue was dissolved in chloroform and washed once with water. The organic layer was dried over anhydrous sodium sulfate, filtered and concentrated, and the obtained residue was purified by silica gel column chromatography (solvent; chloroform) to give the title compound (258 mg).
MS(ESI)m/z; 212, 214[M+H]$^+$

Reference Example 311

4-cyano-2-(4-methoxybenzylamino)pyridine

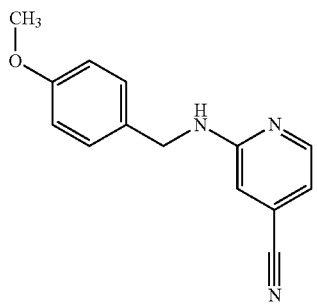 [SMILES: COc1ccc(CNc2cc(C#N)ccn2)cc1]

A mixture of 2-chloro-4-cyanopyridine (20.0 g) and 4-methoxybenzylamine (41.0 mL) was stirred with heating at 150° C. for 2 hr. After cooling to room temperature, to the reaction mixture was added ethyl acetate, and the mixture was washed once with water. The organic layer was dried over anhydrous sodium sulfate, filtered and concentrated. The obtained residue was purified by silica gel column chromatography (solvent; hexane/ethyl acetate=90/10-60/40) to give the title compound (6.29 g).

Reference Example 312

5-bromo-4-cyano-2-(4-methoxybenzylamino)pyridine

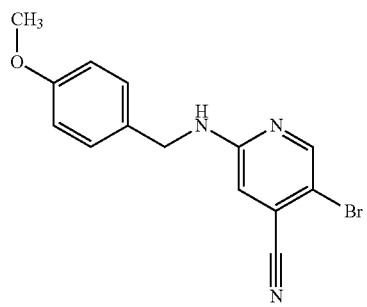 [SMILES: COc1ccc(CNc2cc(C#N)c(Br)cn2)cc1]

The compound (4.12 g) obtained in Reference Example 311 was treated by a method similar to that in Reference Example 309 to give the title compound (4.69 g).
MS(ESI)m/z; 318, 320[M+H]$^+$

Reference Example 313

4-cyano-2-(4-methoxybenzylamino)-5-methylpyridine

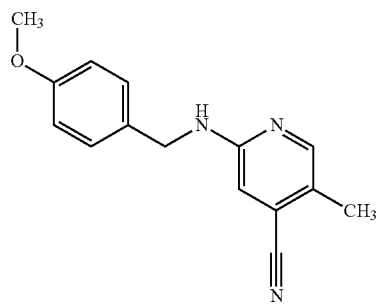 [SMILES: COc1ccc(CNc2cc(C#N)c(C)cn2)cc1]

A mixture of the compound (300 mg) obtained in Reference Example 312, potassium methyltrifluoroborate (253 mg), tetrakis(triphenylphosphine)palladium (54.0 mg) and potassium carbonate (287 mg) in DMF (3.00 mL)-water (1.50 mL) was stirred with heating under a nitrogen atmosphere at 120° C. for 9 hr. After cooling to room temperature, water was added, and the mixture was extracted twice with ethyl acetate. The organic layer was dried over anhydrous sodium sulfate, filtered and concentrated, and the obtained residue was purified by silica gel column chromatography (solvent; hexane/ethyl acetate=90/10-60/40) to give the title compound (150 mg).
MS(ESI)m/z; 254[M+H]$^+$

Reference Example 314

3-bromo-4-cyano-2-(4-methoxybenzylamino)-5-methylpyridine

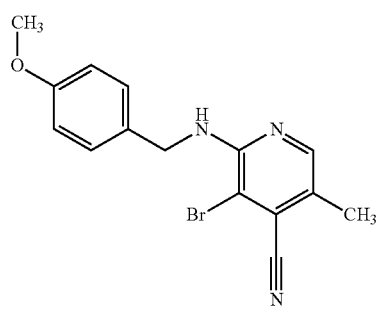 [SMILES: COc1ccc(CNc2ncc(C)c(C#N)c2Br)cc1]

The compound (145 mg) obtained in Reference Example 313 was treated by a method similar to that in Reference Example 309 to give the title compound (133 mg).
MS(ESI)m/z; 332, 334[M+H]$^+$

Reference Example 315

2-amino-3-bromo-4-cyano-5-methylpyridine

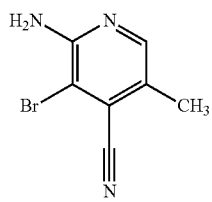

The compound (587 mg) obtained in Reference Example 314 was treated by a method similar to that in Reference Example 310 to give the title compound (339 mg).
MS(ESI)m/z; 212, 214 [M+H]$^+$

Reference Example 316

2-amino-3-bromo-4-methylpyridine

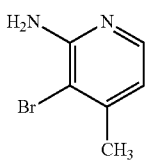

To a THF solution (40.0 mL) of 2-amino-3,5-dibromo-4-methylpyridine (2.00 g) was added n-butyllithium (1.67 mol/L hexane solution, 9.0 mL) at −78° C., and the reaction mixture was stirred at the same temperature for 1 hr. Water was added, and the mixture was extracted twice with chloroform. The organic layer was dried over anhydrous sodium sulfate, filtered and concentrated, and the obtained residue was purified by silica gel column chromatography (solvent; hexane/ethyl acetate=85/15-60/40) to give the title compound (1.00 g).
MS(ESI)m/z; 187, 189[M+H]$^+$

Reference Example 317

2-chloro-5-fluoro-4-(hydroxymethyl)pyridine

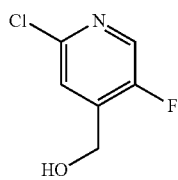

To a THF solution (50.0 mL) of 2-chloro-5-fluoropyridine-4-carboxylic acid (5.00 g) was added carbonyldiimidazole (7.00 g) at room temperature, and the reaction mixture was stirred with heating at 70° C. for 1 hr. After cooling to room temperature, the reaction mixture was added to an aqueous solution (150 mL) of sodium borohydride (5.40 g) at 0° C., and the reaction mixture was stirred at the same temperature for 1 hr. The reaction mixture was neutralized with 1.0 mol/L hydrochloric acid and extracted twice with ethyl acetate. The organic layer was dried over anhydrous sodium sulfate, filtered and concentrated, and the obtained residue was purified by silica gel column chromatography (solvent; chloroform/methanol=100/0-95/5) to give the title compound (3.90 g).
MS(ESI)m/z; 162[M+H]$^+$

Reference Example 318

2-chloro-4-(hydroxymethyl)pyridine

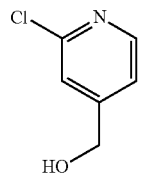

2-Chloropyridine-4-carboxylic acid (5.00 g) was treated by a method similar to that in Reference Example 317 to give the title compound (4.00 g).
MS(ESI)m/z; 144, 146[M+H]$^+$

Reference Example 319

2-chloro-5-fluoro-4-(methoxymethyl)pyridine

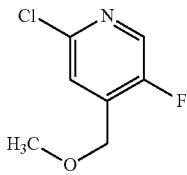

To a DMF solution (80.0 mL) of the compound (3.90 g) obtained in Reference Example 317 were added methyl iodide (5.20 g) and sodium hydride (60% w/w, 1.00 g) at 0° C., and the reaction mixture was stirred at the same temperature for 1 hr. Under ice-cooling, saturated aqueous ammonium chloride solution was added, and the mixture was extracted twice with ethyl acetate. The organic layer was dried over anhydrous sodium sulfate, filtered and concentrated, and the obtained residue was purified by silica gel column chromatography (solvent; hexane/ethyl acetate=90/10-80/20) to give the title compound (3.57 g).
MS(ESI)m/z; 176[M+H]$^+$

Reference Example 320

2-chloro-4-(methoxymethyl)pyridine

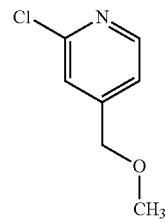

The compound (4.00 g) obtained in Reference Example 318 was treated by a method similar to that in Reference Example 319 to give the title compound (4.00 g).

MS(ESI)m/z; 158, 160[M+H]$^+$

Reference Example 321

2-amino-5-fluoro-4-(methoxymethyl)pyridine

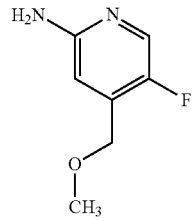

A 1,4-dioxane solution (70.0 mL) of the compound (3.57 g) obtained in Reference Example 319, benzophenone imine (4.10 g), palladium acetate (230 mg), (±)-2,2'-bis(diphenylphosphino)-1,1'-binaphthyl (1.30 g) and cesium carbonate (10.0 g) was heated under reflux at 80° C. for 6 hr. Under ice-cooling, water was added and the mixture was extracted twice with ethyl acetate. The organic layer was dried over anhydrous sodium sulfate, filtered and concentrated. To the obtained residue was added THF (50.0 mL), 6.0 mol/L hydrochloric acid (50.0 mL) at room temperature, and the reaction mixture was stirred at the same temperature for 2 hr. Water was added, and the mixture was washed with ethyl acetate. The aqueous layer was neutralized with 6.0 mol/L aqueous sodium hydroxide solution and extracted 3 times with ethyl acetate. The organic layer was dried over anhydrous sodium sulfate, filtered and concentrated, and the obtained residue was purified by silica gel column chromatography (solvent; chloroform/methanol=100/0-95/5) to give the title compound (1.76 g).

MS(ESI)m/z; 157[M+H]$^+$

Reference Example 322

2-amino-4-(methoxymethyl)pyridine

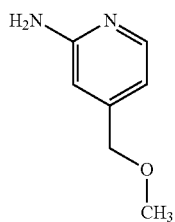

The compound (3.50 g) obtained in Reference Example 320 was treated by a method similar to that in Reference Example 321 to give the title compound (1.50 g).

MS(ESI)m/z; 139[M+H]$^+$

Reference Example 323

2-amino-3-bromo-5-fluoro-4-(methoxymethyl)pyridine

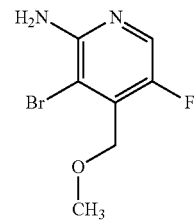

The compound (1.76 g) obtained in Reference Example 321 was treated by a method similar to that in Reference Example 309 to give the title compound (730 mg).

MS(ESI)m/z; 235, 237[M+H]$^+$

Reference Example 324

2-amino-3,5-dibromo-4-(methoxymethyl)pyridine

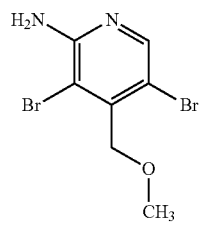

To an acetonitrile solution (100 mL) of the compound (1.50 g) obtained in Reference Example 322 was added N-bromosuccinimide (3.90 g) at 0° C., and the reaction mixture was stirred at room temperature for 1 hr. A 0.1 mol/L aqueous sodium thiosulfate solution was added, and the mixture was extracted twice with ethyl acetate. The organic layer was dried over anhydrous magnesium sulfate, filtered and concentrated, and the obtained residue was purified by silica gel column chromatography (solvent; hexane/ethyl acetate=100/0-75/25) to give the title compound (2.90 g).

MS(ESI)m/z; 295, 297, 299[M+H]$^+$

Reference Example 325

2-amino-3-bromo-4-(methoxymethyl)pyridine

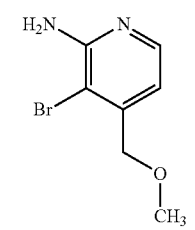

The compound (2.00 g) obtained in Reference Example 324 was treated by a method similar to that in Reference Example 316 to give the title compound (520 mg).

MS(ESI)m/z; 217, 219[M+H]$^+$

Reference Example 326

2-amino-3,5-dibromo-4-ethylpyridine

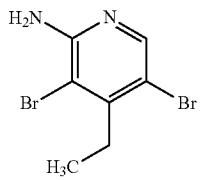

2-Amino-4-ethylpyridine (5.00 g) was treated by a method similar to that in Reference Example 324 to give the title compound (6.90 g).
MS(ESI)m/z; 279, 281, 283 [M+H]$^+$

Reference Example 327 ethyl 2-chloro-4-ethoxypyridine-5-carboxylate

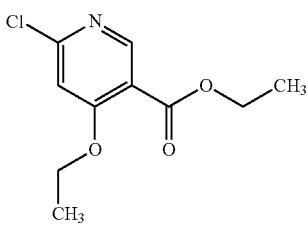

To an ethanol solution (200 mL) of 2,4-dichloropyridine-4-carboxylic acid methyl ester (5.00 g) was added sodium ethoxide (20% ethanol solution, 8.3 g) at 0° C., and the reaction mixture was stirred at the same temperature for 6 hr and at room temperature overnight. The solvent was evaporated under reduced pressure, water was added, and the mixture was extracted twice with ethyl acetate. The organic layer was dried over anhydrous magnesium sulfate, filtered and concentrated, and the obtained residue was purified by silica gel column chromatography (solvent; hexane/ethyl acetate=100/0-80/20) to give the title compound (3.30 g).
MS(ESI)m/z; 230, 232[M+H]$^+$

Reference Example 328

2-chloro-4-ethoxypyridine-5-carboxylic acid

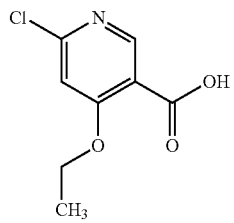

To an ethanol solution (33.0 mL) of the compound (3.30 g) obtained in Reference Example 327 was added 1.0 mol/L aqueous sodium hydroxide solution (16.0 mL) at 0° C. and the reaction m mixture was stirred at room temperature for 1 hr. 1.0 mol/L hydrochloric acid (16.0 mL) was added at 0° C., and the mixture was extracted twice with ethyl acetate. The organic layer was dried over anhydrous magnesium sulfate, filtered and concentrated to give the title compound (2.74 g).
MS(ESI)m/z; 202, 204[M+H]$^+$

Reference Example 329

2-chloro-4-ethoxy-5-(hydroxymethyl)pyridine

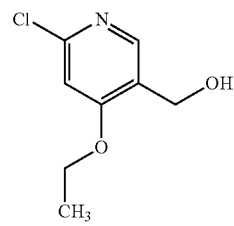

The compound (2.74 g) obtained in Reference Example 328 was treated by a method similar to that in Reference Example 317 to give the title compound (2.35 g).
MS(ESI)m/z; 188, 190[M+H]$^+$

Reference Example 330

2-chloro-4-ethoxy-5-(methoxymethyl)pyridine

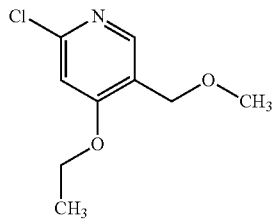

The compound (2.35 g) obtained in Reference Example 329 was treated by a method similar to that in Reference Example 319 to give the title compound (2.10 g).
MS(ESI)m/z; 202, 204[M+H]$^+$

Reference Example 331

2-amino-4-ethoxy-5-(methoxymethyl)pyridine

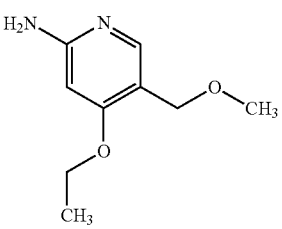

The compound (2.10 g) obtained in Reference Example 330 was treated by a method similar to that in Reference Example 321 to give the title compound (1.00 g).
MS(ESI)m/z; 183[M+H]$^+$

Reference Example 332

2-amino-3-bromo-4-ethoxy-5-(methoxymethyl)pyridine

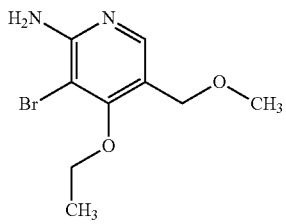

The compound (1.00 g) obtained in Reference Example 331 was treated by a method similar to that in Reference Example 309 to give the title compound (1.34 g).
MS(ESI)m/z; 261, 263[M+H]$^+$

Reference Example 333

2-chloro-5-(3-methyl-1,2,4-oxadiazol-5-yl)pyridine

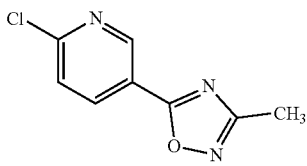

A mixture of 2-chloropyridine-5-carboxamide (4.20 g) and dimethylacetamide dimethyl acetal (10.0 g) was stirred with heating at 120° C. for 3 hr. The reaction mixture was concentrated under reduced pressure and a mixed solution of hydroxylamine hydrochloride (2.24 g), 1.0 mol/L aqueous sodium hydroxide solution (33.0 mL) and acetic acid (30.0 mL) was added. 1,4-Dioxane (30.0 mL) was further added, and the reaction mixture was stirred with heating at 80° C. for 3 hr. After cooling to room temperature, water was added, and the mixture was extracted twice with chloroform. The organic layer was dried over anhydrous magnesium sulfate, filtered and concentrated, and the obtained residue was purified by silica gel column chromatography (solvent; chloroform/methanol=100/0-95/5) to give the title compound (3.66 g).
MS(ESI)m/z; 196, 198[M+H]$^+$

Reference Example 334

2-(4-methoxybenzylamino)-5-(3-methyl-1,2,4-oxadiazol-5-yl)pyridine

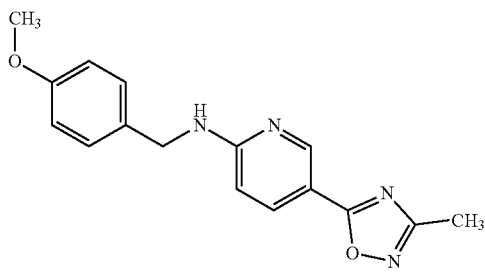 [SMILES: COc1ccc(CNc2ccc(-c3nc(C)no3)cn2)cc1]

The compound (1.50 g) obtained in Reference Example 333 was treated by a method similar to that in Reference Example 311 to give the title compound (2.10 g).
MS(ESI)m/z; 297[M+H]$^+$

Reference Example 335

2-amino-5-(3-methyl-1,2,4-oxadiazol-5-yl)pyridine

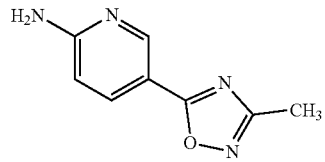

The compound (2.10 g) obtained in Reference Example 334 was treated by a method similar to that in Reference Example 310 to give the title compound (1.18 g).
MS (ESI)m/z; 177[M+H]$^+$

Reference Example 336

2-amino-3-bromo-5-(3-methyl-1,2,4-oxadiazol-5-yl)pyridine

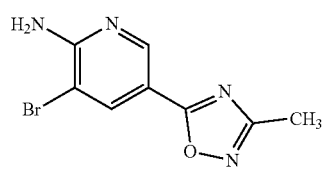

The compound (1.18 g) obtained in Reference Example 335 was treated by a method similar to that in Reference Example 309 to give the title compound (1.22 g).
MS(ESI)m/z; 255, 257[M+H]$^+$

Reference Example 337

2-chloro-4-(5-methyl-1,2,4-oxadiazol-3-yl)pyridine

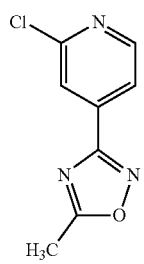

To an ethanol solution (160 mL) of 2-chloro-4-cyanopyridine (8.00 g) were added hydroxylamine hydrochloride (9.60 g) and triethylamine (14.6 g) at room temperature, and the reaction mixture was stirred with heating at 100° C. for 2 hr. After cooling to room temperature, the solvent was evaporated under reduced pressure, water was added, and the mixture was extracted twice with chloroform. The organic layer was dried over anhydrous magnesium sulfate, filtered and concentrated. To the obtained residue were added acetic acid (100 mL), acetic anhydride (11.8 g) and paratoluenesulfonic acid monohydrate (1.10 g), and the reaction mixture was stirred with heating at 100° C. for 2 hr. After cooling to room temperature, the solvent was evaporated under reduced pressure, water was added, and the mixture was extracted twice with chloroform. The organic layer was washed with saturated aqueous sodium hydrogen carbonate solution, dried over anhydrous magnesium sulfate, filtered and concentrated. The obtained residue was purified by silica gel column chromatography (solvent; hexane/ethyl acetate=80/20-50/50) to give the title compound (7.29 g).

MS(ESI)m/z; 196, 198[M+H]$^+$

Reference Example 338

2-(4-methoxybenzylamino)-4-(5-methyl-1,2,4-oxadiazol-3-yl)pyridine

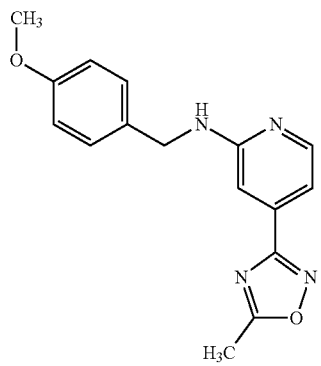 [SMILES: COc1ccc(CNc2cc(-c3noc(C)n3)ccn2)cc1]

The compound (7.29 g) obtained in Reference Example 337 was treated by a method similar to that in Reference Example 311 to give the title compound (2.64 g).

MS(ESI)m/z; 297[M+H]$^+$

Reference Example 339

3,5-dibromo-2-(4-methoxybenzylamino)-4-(5-methyl-1,2,4-oxadiazol-3-yl)pyridine

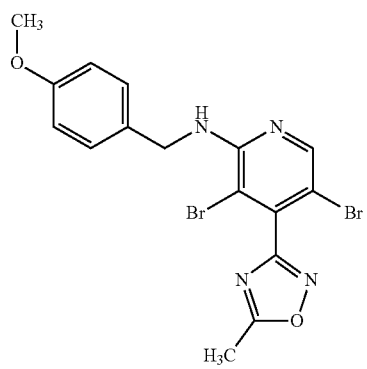 [SMILES: COc1ccc(CNc2ncc(Br)c(-c3noc(C)n3)c2Br)cc1]

The compound (2.64 g) obtained in Reference Example 338 was treated by a method similar to that in Reference Example 324 to give the title compound (2.30 g).

MS(ESI)m/z; 453, 455, 457[M+H]$^+$

Reference Example 340

2-amino-3,5-dibromo-4-(5-methyl-1,2,4-oxadiazol-3-yl)pyridine

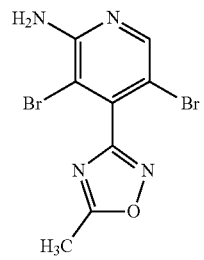

The compound (2.30 g) obtained in Reference Example 339 was treated by a method similar to that in Reference Example 310 to give the title compound (1.45 g).

MS(ESI)m/z; 333, 335, 337[M+H]$^+$

Reference Example 341

2-amino-3-bromo-5-cyanopyridine

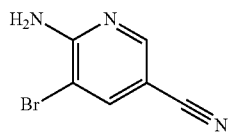

To a chloroform solution (160 mL) of 2-amino-5-cyanopyridine (10.0 g) were added bromine (4.50 mL) and water (40.0 mL) at 0° C., and the reaction mixture was stirred at room temperature for 2.5 hr. Aqueous sodium thiosulfate solution and aqueous sodium hydrogen carbonate solution were added and the mixture was extracted twice with chloroform. The organic layer was dried over anhydrous magnesium sulfate, filtered and concentrated to give the title compound (15.8 g).

MS(ESI)m/z; 198, 200[M+H]$^+$

Reference Example 342

2-amino-5-bromo-4-ethylpyridine

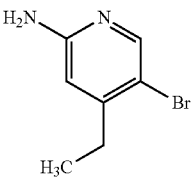

2-Amino-4-ethylpyridine (5.00 g) was treated by a method similar to that in Reference Example 309 to give the title compound (8.33 g).

MS(ESI)m/z; 201, 203[M+H]$^+$

Reference Example 343

2-amino-5-cyano-4-ethylpyridine

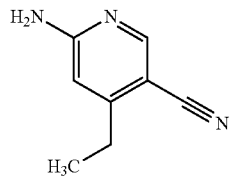

To an N-methylpyrrolidone solution (30.0 mL) of the compound (7.30 g) obtained in Reference Example 342 was added cuprous cyanide (6.50 g) at room temperature, and the reaction mixture was stirred with heating at 180° C. for 8 hr. After cooling to room temperature, a small amount of aqueous ammonia was added and the mixture was extracted 4 times with ethyl acetate. The organic layer was dried over anhydrous magnesium sulfate, filtered and concentrated. To the obtained residue was added diethyl ether, and the solid was collected by filtration and dried to give the title compound (3.80 g).

MS(ESI)m/z; 148[M+H]$^+$

Reference Example 344

2-amino-3-bromo-5-cyano-4-ethylpyridine

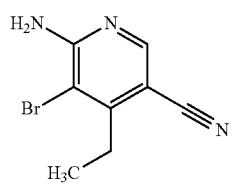

The compound (4.28 g) obtained in Reference Example 343 was treated by a method similar to that in Reference Example 309 to give the title compound (6.51 g).

MS(ESI)m/z; 226, 228[M+H]$^+$

Reference Example 345

6-cyano-7-methyl[1,3]thiazolo[4,5-b]pyridine-2(3H)-thione

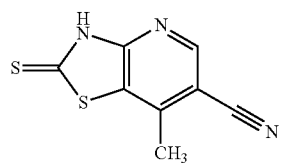

An N-methylpyrrolidone solution (3.00 mL) of the compound (258 mg) obtained in Reference Example 310 and potassium ethyl xanthogenate (489 mg) was stirred with heating at 150° C. for 3 hr. The reaction mixture was cooled to room temperature, and acetic acid and water were added. The precipitated solid was collected by filtration, washed with water and dried under reduced pressure to give the title compound (213 mg).

MS(ESI)m/z; 208[M+H]$^+$

The following Table shows the compounds obtained by treating the corresponding compounds by a method similar to that in Reference Example 345.

TABLE 31

| Reference Example | structure | starting material | yield | MS(ESI) m/z [M + H]$^+$ |
|---|---|---|---|---|
| 346 | ![structure] | Reference Example 326 (6.90 g) | 6.83 g | 275, 277 |
| 347 | ![structure] | Reference Example 332 (1.34 g) | 810 mg | 257 |

TABLE 31-continued

| Reference Example | structure | starting material | yield | MS(ESI) m/z [M + H]+ |
|---|---|---|---|---|
| 348 | 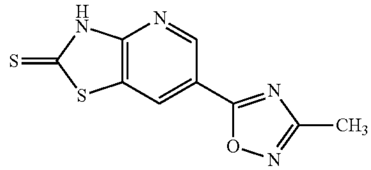 [SMILES: Cc1noc(-c2cnc3[nH]c(=S)sc3c2)n1] | Reference Example 336 (1.12 g) | 1.09 g | 251 |
| 349 | 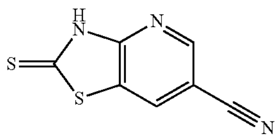 [SMILES: N#Cc1cnc2[nH]c(=S)sc2c1] | Reference Example 341 (7.50 g) | 6.64 g | 194 |
| 350 | 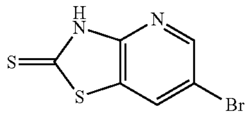 [SMILES: S=c1[nH]c2ncc(Br)cc2s1] | 2-amino-3,5-dibromo-pyridine (24.0 g) | 23.8 g | 247, 249 |
| 351 | 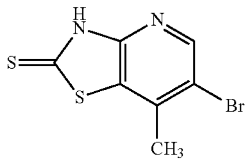 | 2-amino-3,5-dibromo-4-methyl-pyridine (3.00 g) | 2.90 g | 261, 263 |

Reference Example 352

6-cyano-7-methyl-2-(methylsulfanyl)[1,3]thiazolo[4,5-b]pyridine

To a 1.0 mol/L aqueous sodium hydroxide solution (4.60 mL) of the compound (860 mg) obtained in Reference Example 345 was added dimethyl sulfate (471 μL) at room temperature, and the reaction mixture was stirred at the same temperature for 30 min. After confirmation of the completion of the reaction, water was added. The resulting solid was collected by filtration and purified by silica gel column chromatography (solvent; hexane/ethyl acetate=95/5-50/50) to give the title compound (576 mg).

MS(ESI)m/z; 222[M+H]+

The following Table shows the compounds obtained by treating the corresponding compounds by a method similar to that in Reference Example 352.

TABLE 32

| Reference Example | structure | starting material | yield | MS(ESI) m/z [M + H]+ |
|---|---|---|---|---|
| 353 | 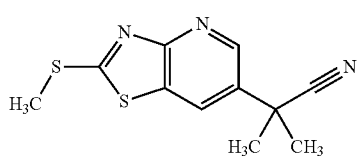 | Reference Example 282 (5.00 g) | 4.81 g | 250 |
| 354 | 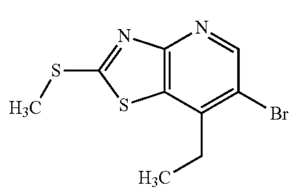 | Reference Example 346 (6.83 g) | 4.02 g | 289, 291 |

TABLE 32-continued

| Reference Example | structure | starting material | yield | MS(ESI) m/z [M + H]+ |
|---|---|---|---|---|
| 355 | H3C-S-[thiazolo[4,5-b]pyridine with OCH3 and OCH2CH3 substituents] | Reference Example 347 (750 mg) | 650 mg | 271 |
| 356 | H3C-S-[thiazolo[4,5-b]pyridine with oxadiazole-CH3 substituent] | Reference Example 348 (1.09 g) | 880 mg | 265 |
| 357 | H3C-S-[thiazolo[4,5-b]pyridine with CN substituent] | Reference Example 349 (6.64 g) | 5.35 g | 208 |
| 358 | H3C-S-[thiazolo[4,5-b]pyridine with Br substituent] | Reference Example 350 (24.1 g) | 15.9 g | 261, 263 |
| 359 | H3C-S-[thiazolo[4,5-b]pyridine with Br and CH3 substituents] | Reference Example 351 (24.1 g) | 15.9 g | 261, 263 |

Reference Example 360

7-cyano-6-methyl-2-(methylsulfanyl)[1,3]thiazolo[4,5-b]pyridine

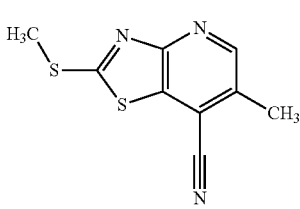

An N-methylpyrrolidone solution (3.00 mL) of the compound (328 mg) obtained in Reference Example 315 and potassium ethyl xanthogenate (621 mg) was stirred with heating at 120° C. for 4 hr. The reaction mixture was cooled to room temperature, and acetic acid and water were added. The precipitated solid was collected by filtration, washed with water and dried under reduced pressure. To a 1.0 mol/L aqueous sodium hydroxide solution (1.50 mL) of the obtained solid was added dimethyl sulfate (135 μL) at room temperature, and the reaction mixture was stirred at the same temperature for 30 min. After confirmation of the completion of the reaction, water was added. The resulting solid was collected by filtration and purified by silica gel column chromatography (solvent; hexane/ethyl acetate=80/20-60/40) to give the title compound (576 mg).

MS(ESI)m/z; 222[M+H]+

The following Table shows the compounds obtained by treating the corresponding compounds by a method similar to that in Reference Example 360.

TABLE 33

| Reference Example | structure | starting material | yield | MS(ESI) m/z [M + H]+ |
|---|---|---|---|---|
| 361 | (structure) | Reference Example 316 (1.00 g) | 300 mg | 197 |
| 362 | (structure) | Reference Example 323 (730 mg) | 170 mg | 197 |
| 363 | (structure) | Reference Example 324 (900 mg) | 230 mg | 305, 307 |
| 364 | (structure) | Reference Example 325 (520 mg) | 170 mg | 227 |
| 365 | (structure) | Reference Example 340 (1.45 g) | 410 mg | 343, 345 |
| 366 | (structure) | Reference Example 344 (6.50 g) | 2.08 g | 236 |

Reference Example 367

6-(5-methyl-1,2,4-oxadiazol-3-yl)-2-(methylsulfanyl)[1,3]thiazolo[4,5-b]pyridine

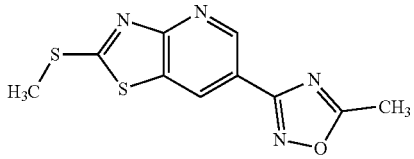

To an ethanol solution (50.0 mL) of the compound (2.07 g) obtained in Reference Example 357 were added hydroxylamine hydrochloride (1.75 g) and triethylamine (4.00 mL) at room temperature, and the reaction mixture was stirred with heating at 50° C. for 12 hr. After cooling to room temperature, the solvent was evaporated under reduced pressure, water was added, and the mixture was extracted twice with chloroform. The organic layer was dried over anhydrous magnesium sulfate, filtered and concentrated. To the obtained residue were added acetic acid (10.0 mL), acetic anhydride (1.60 mL) and paratoluenesulfonic acid monohydrate (73.0 mg), and the reaction mixture was stirred with heating at 90° C. for 2 hr. After cooling to room temperature, the solvent was evaporated under reduced pressure, ethyl acetate was added to the obtained residue and the solid was collected by filtration and dried to give the title compound (1.15 g).
MS(ESI)m/z; 265[M+H]$^+$

Reference Example 368

6-[2-(5-methyl-1,2,4-oxadiazol-3-yl)propan-2-yl]-2-(methylsulfanyl)[1,3]thiazolo[4,5-b]pyridine

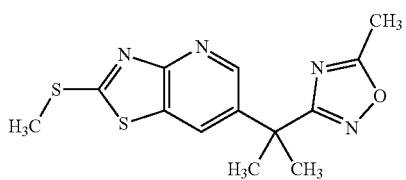 [SMILES: CSc1nc2ncc(C(C)(C)c3noc(C)n3)cc2s1]

The compound (800 mg) obtained in Reference Example 353 was treated by a method similar to that in Reference Example 367 to give the title compound (440 mg).
MS(ESI)m/z; 307[M+H]$^+$

Reference Example 369

6-methyl-7-(5-methyl-1,2,4-oxadiazol-3-yl)-2-(methylsulfanyl)[1,3]thiazolo[4,5-b]pyridine

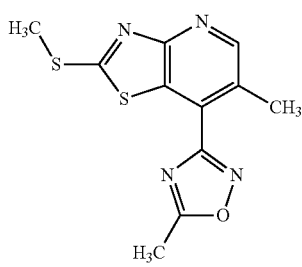

The compound (1.05 g) obtained in Reference Example 360 was treated by a method similar to that in Reference Example 367 to give the title compound (235 mg).
MS(ESI)m/z; 279[M+H]$^+$

Reference Example 370

7-ethyl-6-(5-methyl-1,2,4-oxadiazol-3-yl)-2-(methylsulfanyl)[1,3]thiazolo[4,5-b]pyridine

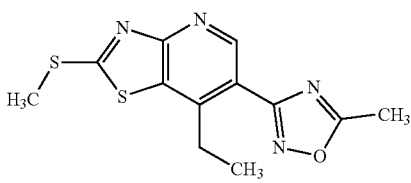

The compound (500 mg) obtained in Reference Example 366 was treated by a method similar to that in Reference Example 367 to give the title compound (106 mg).
MS(ESI)m/z; 293[M+H]$^+$

Reference Example 371

6-hydroxy-2-(methylsulfanyl)[1,3]thiazolo[4,5-b]pyridine

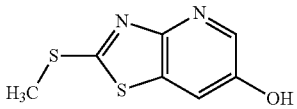

A 1,4-dioxane solution (30.0 mL) of the compound (2.00 g) obtained in Reference Example 358, 4,4,5,5-tetramethyl-2-(4,4,5,5-tetramethyl-1,3,2-dioxaborolan-2-yl)-1,3,2-dioxaborolane (2.92 g), palladium acetate (138 mg), 2-(dicyclohexylphosphino)-2',4',6'-triisopropylbiphenyl (584 mg) and potassium acetate (3.01 g) was heated under reflux for 3 hr. After cooling to room temperature, the solvent was evaporated under reduced pressure. Dichloromethane (20.0 mL) was added, 30% hydrogen peroxide water (4.00 mL) was added at 0° C., and the reaction mixture was stirred at room temperature for 1 hr. A 30% hydrogen peroxide water (4.00 mL) was added, and the reaction mixture was further stirred for 1.5 hr. An aqueous sodium thiosulfate solution was added at 0° C., and the mixture was stirred for 30 min and extracted twice with chloroform. The organic layer was dried over anhydrous magnesium sulfate, filtered and concentrated. The obtained residue was purified by silica gel column chromatography (solvent; chloroform/methanol=100/0-90/10) to give the title compound (811 mg).
MS(ESI)m/z; 199[M+H]$^+$

Reference Example 372

2-(methylsulfanyl)-6-[(oxetan-3-yl)oxy][1,3]thiazolo[4,5-b]pyridine

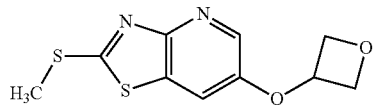 [SMILES: CSc1nc2ncc(OC3COC3)cc2s1]

To a THF solution (4.00 mL) of the compound (150 mg) obtained in Reference Example 371 were added triphenylphosphine (299 mg), 3-hydroxyoxetane (84.0 mg) and diisopropyl azodicarboxylate (1.9 mmol/L toluene solution, 600 µL) at room temperature, and the reaction mixture was stirred with heating at 70° C. for 12 hr. After cooling to room temperature, the solvent was evaporated under reduced pressure. The obtained residue was purified by NH silica gel column chromatography (solvent; hexane/ethyl acetate=50/50-0/100) to give the title compound (201 mg).

MS(ESI)m/z; 255[M+H]$^+$

Reference Example 373

2-(methylsulfanyl) [1,3]thiazolo[4,5-b]pyridine-6-carboxylic acid

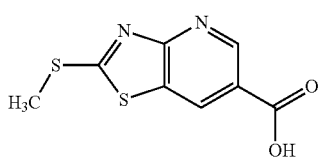

To the compound (2.07 g) obtained in Reference Example 357 were added acetic acid (5.00 mL), sulfuric acid (5.0 mL) and water (5.00 mL), and the reaction mixture was stirred with heating at 100° C. for 28 hr. After cooling to room temperature, water (100 mL) was added and the resulting solid was collected by filtration and dried to give the title compound (108 mg).

MS(ESI)m/z; 227[M+H]$^+$

Reference Example 374

N'-acetyl-2-(methylsulfanyl)[1,3]thiazolo[4,5-b]pyridine-6-carbohydrazide

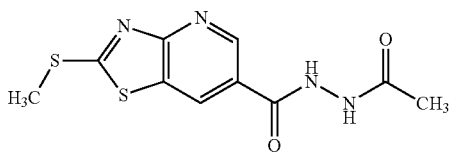 [SMILES: CSc1nc2ncc(C(=O)NNC(C)=O)cc2s1]

To a THF solution (20.0 mL) of Reference Example 373 (730 mg) were added acetylhydrazide (250 mg), EDC hydrochloride (680 mg), HOBt monohydrate (520 mg) and triethylamine (1.00 mL) at room temperature, and the reaction mixture was stirred at the same temperature overnight. Water was added, the mixture was extracted with ethyl acetate, and the organic layer was dried over anhydrous sodium sulfate, filtered and concentrated to give the title compound (640 mg).

MS(ESI)m/z; 283[M+H]$^+$

Reference Example 375

6-(5-methyl-1,3,4-oxadiazol-2-yl)-2-(methylsulfanyl)[1,3]thiazolo[4,5-b]pyridine

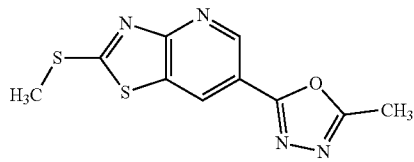

To a 1,2-dichloroethane solution (12.0 mL) of the compound (210 mg) obtained in Reference Example 374 was added phosphorus oxychloride (170 mg) at room temperature, and the reaction mixture was stirred with heating at 80° C. for 6 hr. After cooling to room temperature, the solvent was evaporated under reduced pressure. To the obtained residue was added diethyl acetate and the solid was collected by filtration and dried to give the title compound (190 mg).

MS(ESI)m/z; 265[M+H]$^+$

Reference Example 376 methyl 2-methyl-2-[2-(methylsulfanyl)[1,3]thiazolo[4,5-b]pyridin-6-yl]propanoate

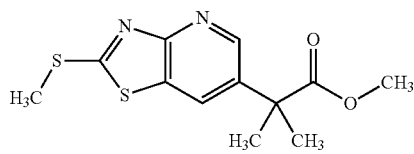

To the compound (2.30 g) obtained in Reference Example 353 were added acetic acid (8.00 mL), sulfuric acid (12.0 mL) and water (8.00 mL), and the reaction mixture was stirred with heating at 100° C. for 5 hr. After cooling to 0° C., the reaction mixture was neutralized with 20% aqueous sodium hydroxide solution and extracted 3 times with chloroform. The organic layer was dried over anhydrous sodium sulfate, filtered and concentrated. To a methanol solution (30.0 mL) of the obtained residue was added sulfuric acid (492 µL) at 0° C., and the reaction mixture was heated under reflux for 15 hr. The reaction mixture was cooled to room temperature and extracted 3 times with chloroform. The organic layer was washed with saturated aqueous sodium hydrogen carbonate solution, dried over anhydrous sodium sulfate, filtered and concentrated, and the obtained residue was purified by silica gel column chromatography (solvent; hexane/ethyl acetate=90/10-50/50) to give the title compound (2.18 g).

MS(ESI)m/z; 283[M+H]$^+$

Reference Example 377

2-methyl-2-[2-(methylsulfanyl)[1,3]thiazolo[4,5-b]pyridin-6-yl]propanoic acid

To a THF solution (10.0 mL) of the compound (500 mg) obtained in Reference Example 376 was added 1.0 mol/L aqueous sodium hydroxide solution (3.60 mL) at room temperature, and the reaction mixture was stirred with heating at 70° C. for 2 hr. After cooling to 0° C., the reaction mixture was neutralized with 1.0 mol/L hydrochloric acid (3.60 mL) and extracted twice with chloroform. The organic layer was dried over anhydrous sodium sulfate, filtered and concentrated to give the title compound (360 mg).

MS(ESI)m/z; 269[M+H]$^+$

Reference Example 378

2-methyl-2-[2-(methylsulfanyl)[1,3]thiazolo[4,5-b]pyridin-6-yl]propanamide

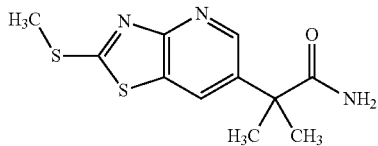 [SMILES: CSc1nc2ncc(C(C)(C)C(N)=O)cc2s1]

To a dichloromethane suspension (30.0 mL) of the compound (360 mg) obtained in Reference Example 377 were added oxalyl chloride (340 mg) and DMF (2 drops) at 0° C., and the reaction mixture was stirred at room temperature for 2 hr. The reaction mixture was added to a mixed solution of 28% aqueous ammonia solution (5.00 mL) and water (10.0 mL) at 0° C., and the mixture was stirred at room temperature for 30 min. The resulting solid was collected by filtration and dried to give the title compound (120 mg).

MS(ESI)m/z; 268[M+H]$^+$

Reference Example 379

6-[2-(3-methyl-1,2,4-oxadiazol-5-yl)propan-2-yl]-2-(methylsulfanyl)[1,3]thiazolo[4,5-b]pyridine

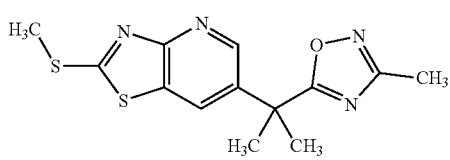

A mixture of the compound (120 mg) obtained in Reference Example 378 and dimethylacetamide dimethyl acetal (1.70 g) was stirred with heating at 120° C. for 3 hr. The reaction mixture was concentrated under reduced pressure, and a mixed solution of hydroxylamine hydrochloride (38.0 mg), 1.0 mol/L aqueous sodium hydroxide solution (550 μL) and acetic acid (1.00 mL) was added. Furthermore, 1,4-dioxane (1.00 mL) was added and the reaction mixture was stirred with heating at 80° C. for 2 hr. After cooling to room temperature, water was added, and the mixture was extracted twice with chloroform. The organic layer was dried over anhydrous magnesium sulfate, filtered and concentrated, and the obtained residue was purified by silica gel column chromatography (solvent; hexane/ethyl acetate=70/30-30/70) to give the title compound (80.0 mg).

MS(ESI)m/z; 307[M+H]$^+$

Reference Example 380 ethyl 7-ethyl-5-hydroxy-2-(methylsulfanyl)[1,3]thiazolo[4,5-b]pyridine-6-carboxylate

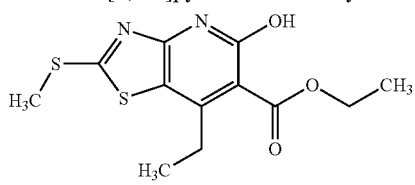

To the compound (5.00 g) obtained in Reference Example 22 was added N,N-diisopropylethylamine (8.60 mL) at room temperature, ethylmalonyl chloride (6.30 mL) was further added, and the reaction mixture was stirred at the same temperature for 1 hr. Water was added, and the mixture was neutralized with 1.0 mol/L hydrochloric acid and extracted twice with ethyl acetate. The organic layer was dried over anhydrous magnesium sulfate, filtered and concentrated. To a THF solution (150 mL) of the obtained residue was added potassium t-butoxide (5.54 g) at room temperature, and the reaction mixture was heated under reflux for 1 hr. The reaction mixture was cooled to room temperature, neutralized with 1.0 mol/L hydrochloric acid and extracted twice with ethyl acetate. The organic layer was dried over anhydrous magnesium sulfate, filtered and concentrated. To the resulting solid was added ethyl acetate and the mixture was stirred. The solid was collected by filtration and dried to give the title compound (5.60 g).

MS(ESI)m/z; 299[M+H]$^+$

Reference Example 381 ethyl 7-ethyl-2-(methylsulfanyl)-5-{[(trifluoromethyl)sulfonyl]oxy}[1,3]thiazolo[4,5-b]pyridine-6-carboxylate

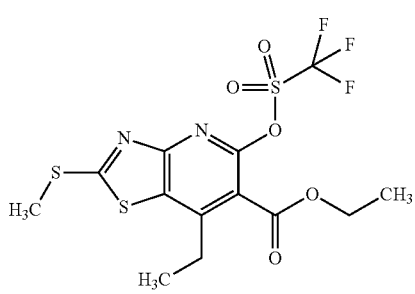 [SMILES: CCOC(=O)c1c(OS(=O)(=O)C(F)(F)F)nc2nc(SC)sc2c1CC]

To a dichloromethane solution (40.0 mL) of the compound (2.00 g) obtained in Reference Example 380 were added triethylamine (1.10 mL), N,N-dimethylaminopyridine (10.0 mg) and trifluoromethanesulfonic anhydride (1.30 mL) at 0° C., and the reaction mixture was stirred at the same temperature for 1 hr. Water was added and the mixture was extracted twice with chloroform. The organic layer was dried over anhydrous magnesium sulfate, filtered and concentrated, and the obtained residue was purified by silica gel column chromatography (solvent; hexane/ethyl acetate=95/5-80/20) to give the title compound (2.06 g).

MS(ESI)m/z; 431[M+H]$^+$

Reference Example 382 ethyl 7-ethyl-2-(methylsulfanyl)[1,3]thiazolo[4,5-b]pyridine-6-carboxylate

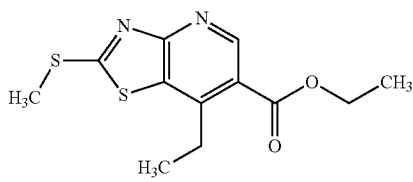

An N-methylpyrrolidone solution (40.0 mL) of the compound (2.06 g) obtained in Reference Example 381, N,N-diisopropylethylamine (2.50 mL), formic acid (270 μL) and tetrakis(triphenylphosphine)palladium (550 mg) was stirred with heating at 100° C. for 2 hr. After cooling to room temperature, water was added and the mixture was extracted twice with ethyl acetate. The organic layer was dried over anhydrous magnesium sulfate, filtered and concentrated, and the obtained residue was purified by silica gel column chromatography (solvent; hexane/ethyl acetate=95/5-70/30) to give the title compound (974 mg).

MS(ESI)m/z; 283[M+H]$^+$

Reference Example 383

7-ethyl-2-(methylsulfanyl)[1,3]thiazolo[4,5-b]pyridine-6-carboxylic acid

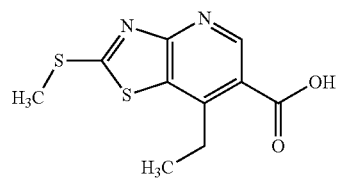 [SMILES: CCc1c(C(=O)O)cnc2nc(SC)sc12]

The compound (1.02 g) obtained in Reference Example 382 was treated by a method similar to that in Reference Example 377 to give the title compound (809 mg).

MS(ESI)m/z; 255[M+H]$^+$

Reference Example 384

7-ethyl-6-(3-methyl-1,2,4-oxadiazol-5-yl)-2-(methylsulfanyl)[1,3]thiazolo[4,5-b]pyridine

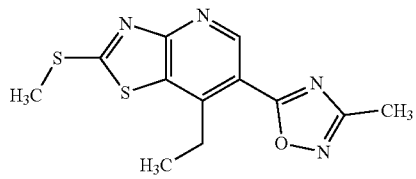

To a DMF solution (2.00 mL) of the compound (200 mg) obtained in Reference Example 383 were added EDC hydrochloride (301 mg), HOBt monohydrate (240 mg) and acetamide oxime (116 mg) at room temperature, and the reaction mixture was stirred at 80° C. for 2.5 hr. After confirmation of the completion of the reaction, water was added to the reaction mixture, and the mixture was extracted twice with ethyl acetate. The organic layer was washed once with water, dried over anhydrous magnesium sulfate, filtered and concentrated. The residue was purified by silica gel column chromatography (solvent; hexane/ethyl acetate=80/20-50/50) to give the title compound (51.0 mg).

MS(ESI)m/z; 293[M+H]$^+$

Reference Example 385

7-ethyl-N-methoxy-N-methyl-2-(methylsulfanyl)[1,3]thiazolo[4,5-b]pyridine-6-carboxamide

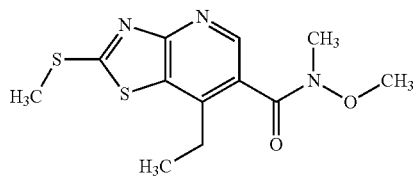

To a DMF solution (5.00 mL) of the compound (300 mg) obtained in Reference Example 383 were added EDC hydrochloride (340 mg), HOBt monohydrate (270 mg), N,O-dimethylhydroxylamine hydrochloride (172 mg) and N,N-diisopropylethylamine (310 μL) at room temperature, and the reaction mixture was stirred at the same temperature overnight. After confirmation of the completion of the reaction, water was added to the reaction mixture, and the mixture was extracted twice with ethyl acetate. The organic layer was washed once with water, dried over anhydrous magnesium sulfate, filtered and concentrated. The residue was purified by silica gel column chromatography (solvent; hexane/ethyl acetate=80/20-50/50) to give the title compound (306 mg).

MS(ESI)m/z; 298[M+H]$^+$

Reference Example 386

7-ethyl-2-(methylsulfanyl)[1,3]thiazolo[4,5-b]pyridine-6-carbaldehyde

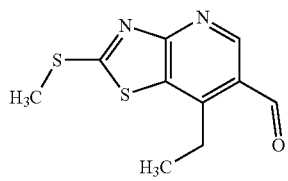

To a THF solution (5.00 mL) of the compound (150 mg) obtained in Reference Example 385 was added diisobutylaluminum hydride (1.0 mol/L toluene solution, 600 μL) at 0° C., and the reaction mixture was stirred at the same temperature for 40 min. After confirmation of the completion of the reaction, the reaction mixture was neutralized with 1.0 mol/L hydrochloric acid and extracted twice with ethyl acetate. The organic layer was washed once with water, dried over anhydrous magnesium sulfate, filtered and concentrated. The residue was purified by silica gel column chromatography (solvent; hexane/ethyl acetate=50/50-0/100) to give the title compound (105 mg).

MS(ESI)m/z; 239[M+H]$^+$

Reference Example 387

7-ethyl-6-(1-methyl-4,5-dihydro-1H-imidazol-2-yl)-2-(methylsulfanyl)[1,3]thiazolo[4,5-b]pyridine

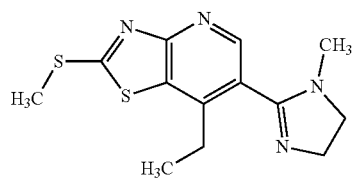 [SMILES: CCc1c(C2=NCCN2C)cnc2nc(SC)sc12]

To a t-butanol solution (7.00 mL) of the compound (170 mg) obtained in Reference Example 386 was added N-methylethylenediamine (68.0 μL) at room temperature, and the reaction mixture was stirred at the same temperature for 30 min. Potassium carbonate (236 mg) and iodine (217 mg) were added and the reaction mixture was stirred with heating at 70° C. for 2 hr. After cooling to room temperature, aqueous sodium thiosulfate solution was added and the mixture was extracted twice with ethyl acetate. The organic layer was washed once with water, dried over anhydrous magnesium sulfate, filtered and concentrated. The residue was purified by silica gel column chromatography (solvent; chloroform/methanol=100/0-95/5) to give the title compound (163 mg).

MS(ESI)m/z; 293[M+H]$^+$

Reference Example 388

7-ethyl-6-(1-methyl-1H-imidazol-2-yl)-2-(methylsulfanyl)[1,3]thiazolo[4,5-b]pyridine

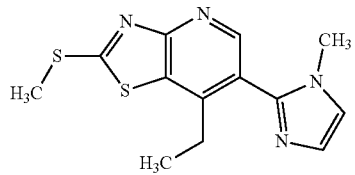 [SMILES: CCc1c(-c2nccn2C)cnc2nc(SC)sc12]

To a chloroform solution (3.00 mL) of the compound (82.0 mg) obtained in Reference Example 387 was added manganese dioxide (286 mg) at room temperature, and the reaction mixture was stirred with heating at 50° C. for 5.5 hr. The reaction mixture was cooled to room temperature, filtered through diatomaceous earth and the filtrate was concentrated under reduced pressure. The residue was purified by NH silica gel column chromatography (solvent; hexane/ethyl acetate=50/50-0/100) to give the title compound (37.0 mg).

MS(ESI)m/z; 291[M+H]$^+$

Reference Example 389

6-amino-7-ethyl-2-(methylsulfanyl)[1,3]thiazolo[4,5-b]pyridine

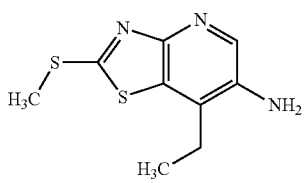

To a t-butanol solution (60.0 mL) of the compound (1.00 g) obtained in Reference Example 383 were added diphenylphosphoryl azide (1.30 mL) and triethylamine (820 μL) at room temperature, and the reaction mixture was stirred with heating at 90° C. for 3 hr. After cooling to room temperature, water was added and the mixture was extracted twice with chloroform. The organic layer was dried over anhydrous sodium sulfate, filtered and concentrated. To the obtained residue were added dichloromethane (30.0 mL), trifluoroacetic acid (15.0 mL) at room temperature, and the reaction mixture was stirred at the same temperature overnight. The solvent was evaporated under reduced pressure, saturated aqueous sodium hydrogen carbonate solution was added and the mixture was extracted twice with ethyl acetate. The combined organic layer was washed with saturated brine, dried over anhydrous sodium sulfate, filtered and concentrated. The obtained residue was purified by silica gel column chromatography (solvent; hexane/ethyl acetate=50/50-0/100) to give the title compound (339 mg).

MS(ESI)m/z; 226[M+H]$^+$

Reference Example 390

N-[7-ethyl-2-(methylsulfanyl)[1,3]thiazolo[4,5-b]pyridin-6-yl]formamide

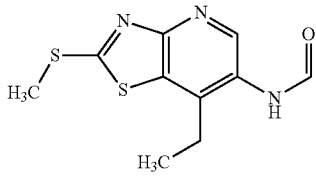 [SMILES: CCc1c(NC=O)cnc2nc(SC)sc12]

A mixed solution of acetic anhydride (340 μL) and formic acid (540 μL) was stirred at room temperature for 3 hr. A THF solution (2.00 mL) of the compound (324 mg) obtained in Reference Example 389 was added at room temperature, and the reaction mixture was stirred at the same temperature for 1 hr. Saturated aqueous sodium hydrogen carbonate solution was added and the mixture was extracted twice with chloroform. The combined organic layer was washed with saturated brine, dried over anhydrous sodium sulfate, filtered and concentrated to give the title compound (47.0 mg).
MS(ESI)m/z; 254[M+H]$^+$

Reference Example 391

N-[7-ethyl-2-(methylsulfanyl)[1,3]thiazolo[4,5-b]pyridin-6-yl]-N-(2-oxopropyl)formamide

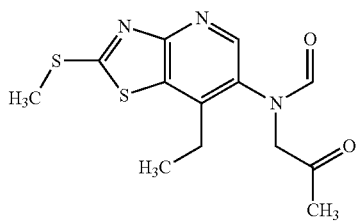 [SMILES: CCc1c(N(C=O)CC(C)=O)cnc2nc(SC)sc12]

To a DMF solution (3.00 mL) of the compound (340 mg) obtained in Reference Example 390 were added chloroacetone (320 μL) and potassium iodide (22.0 mg) at room temperature, and the reaction mixture was stirred at the same temperature for 3 days. Water was added and the mixture was extracted twice with ethyl acetate. The organic layer was dried over anhydrous sodium sulfate, filtered and concentrated. The obtained residue was purified by silica gel column chromatography (solvent; hexane/ethyl acetate=50/50-0/100) to give the title compound (352 mg).
MS(ESI)m/z; 310[M+H]$^+$

Reference Example 392

7-ethyl-6-(4-methyl-1H-imidazol-1-yl)-2-(methylsulfanyl)[1,3]thiazolo[4,5-b]pyridine

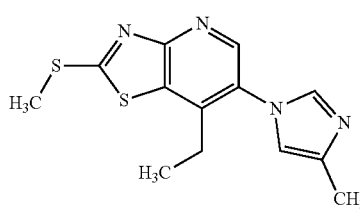

To an acetic acid solution (3.00 mL) of the compound (347 mg) obtained in Reference Example 391 was added ammonium acetate (432 mg) at room temperature, and the reaction mixture was stirred with heating at 120° C. for 2.5 hr. After cooling to room temperature, aqueous potassium carbonate solution was added and the mixture was extracted twice with ethyl acetate. The organic layer was dried over anhydrous sodium sulfate, filtered and concentrated. The obtained residue was purified by NH silica gel column chromatography (solvent; hexane/ethyl acetate=50/50-0/100) to give the title compound (230 mg).
MS(ESI)m/z; 291[M+H]$^+$

Reference Example 393 methyl 2-(methylsulfanyl)[1,3]thiazolo[4,5-b]pyridine-6-carboxylate

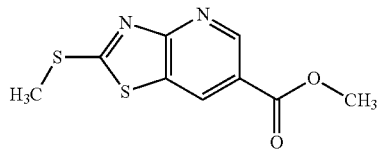

The compound (5.00 g) obtained in Reference Example 357 was treated by a method similar to that in Reference Example 376 to give the title compound (754 mg).
MS(ESI)m/z; 241[M+H]$^+$

Reference Example 394

6-(hydroxymethyl)-2-(methylsulfanyl) [1,3]thiazolo[4,5-b]pyridine

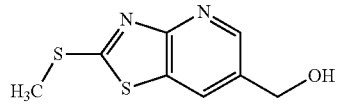

To a THF solution (5.00 mL) of the compound (250 mg) obtained in Reference Example 393 was added lithium aluminum hydride (40.0 mg) at 0° C., and the reaction mixture was stirred at the same temperature for 30 min. The reaction mixture was neutralized with aqueous sodium hydroxide solution at 0° C. and extracted twice with ethyl acetate. The organic layer was dried over anhydrous sodium sulfate, filtered and concentrated. The obtained residue was purified by silica gel column chromatography (solvent; hexane/ethyl acetate=50/50-0/100) to give the title compound (75.0 mg).
MS(ESI)m/z; 213[M+H]$^+$

Reference Example 395

6-(methoxymethyl)-2-(methylsulfanyl)[1,3]thiazolo[4,5-b]pyridine

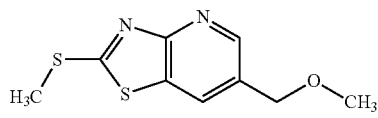

To a DMF solution (3.00 mL) of the compound (71.0 mg) obtained in Reference Example 394 were added methyl iodide (37.0 μL) and sodium hydride (60% w/w, 16 mg) at 0° C., and the reaction mixture was stirred at the same temperature for 2.5 hr. Under ice-cooling, water was added, and the mixture was extracted twice with ethyl acetate. The organic layer was dried over anhydrous sodium sulfate, filtered and concentrated, and the obtained residue was purified by silica gel column chromatography (solvent; hexane/ethyl acetate=80/20-50/50) to give the title compound (45.0 mg).

MS(ESI)m/z; 227[M+H]$^+$

Reference Example 396

6-(cyanomethyl)-7-methyl-2-(methylsulfanyl)[1,3]thiazolo[4,5-b]pyridine

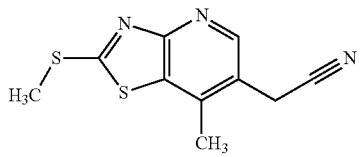

A solution of the compound (1.24 g) obtained in Reference Example 359, (trimethylsilyl)acetonitrile (1.85 mL), zinc fluoride (699 mg), tris(dibenzylideneacetone)(chloroform)dipalladium(0) (467 mg) and 4,5-bis(diphenylphosphino)-9,9-dimethylxanthene (50.0 mg) in DMF (8.00 mL) was stirred with heating under a nitrogen atmosphere at 90° C. for 5 hr. After cooling to room temperature, water was added and the mixture was extracted twice with ethyl acetate. The organic layer was dried over anhydrous sodium sulfate, filtered and concentrated, and the obtained residue was purified by silica gel column chromatography (solvent; chloroform/methanol=100/0-95/5) to give the title compound (199 mg).

MS(ESI)m/z; 236[M+H]$^+$

Reference Example 397

6-(2-cyanopropan-2-yl)-7-methyl-2-(methylsulfanyl)[1,3]thiazolo[4,5-b]pyridine

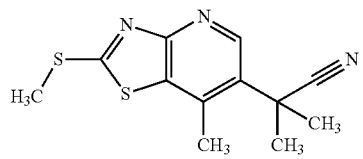 [SMILES: CSc1nc2ncc(C(C)(C)C#N)c(C)c2s1]

To a DMF solution (2.50 mL) of the compound (227 mg) obtained in Reference Example 396 were added methyl iodide (144 μL) and sodium hydride (60% w/w, 85.0 mg) at 0° C., and the reaction mixture was stirred at the same temperature for 1 hr. Under ice-cooling, water was added and the mixture was extracted twice with ethyl acetate. The organic layer was dried over anhydrous sodium sulfate, filtered and concentrated, and the obtained residue was purified by silica gel column chromatography (solvent; hexane/ethyl acetate=85/15-35/65) to give the title compound (65.0 mg).

MS(ESI)m/z; 264[M+H]$^+$

Reference Example 398 ethyl 7-bromo-2-(methylsulfanyl)[1,3]thiazolo[4,5-b]pyridine-6-carboxylate

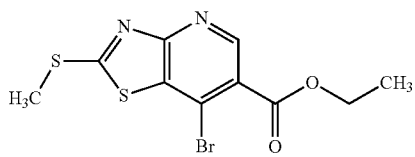 [SMILES: CCOC(=O)c1cnc2nc(SC)sc2c1Br]

To a DMF solution (22.0 mL) of ethyl 7-hydroxy-2-(methylsulfanyl)[1,3]thiazole[4,5-b]pyridine-6-carboxylate (3.00 g) synthesized by the method described in J. Heterocyclic Chem. 401-406 (1984) was added phosphorus tribromide (3.30 g) at 0° C., and the reaction mixture was stirred at room temperature for 1 hr. Under ice-cooling, water was added, and a precipitated solid was collected by filtration. The obtained solid was dissolved in chloroform, dried over sodium sulfate, filtered and concentrated. The obtained residue was purified by silica gel column chromatography (solvent; chloroform/methanol=100/0-95/5) to give the title compound (3.30 g).

MS(ESI)m/z; 333, 335[M+H]$^+$

Reference Example 399 ethyl 7-cyclopropyl-2-(methylsulfanyl)[1,3]thiazolo[4,5-b]pyridine-6-carboxylate

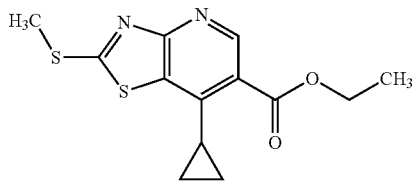 [SMILES: CCOC(=O)c1cnc2nc(SC)sc2c1C1CC1]

A 1,4-dioxane solution (6.00 mL) of the compound (200 mg) obtained in Reference Example 398, cyclopropylboronic acid (78.0 mg), cesium carbonate (590 mg) and dichlorobis(tricyclohexylphosphine)palladium (45.0 mg) was heated under reflux under a nitrogen atmosphere for 5 hr. After cooling to room temperature, water was added and the mixture was extracted twice with ethyl acetate. The organic layer was dried over anhydrous sodium sulfate, filtered and concentrated, and the obtained residue was purified by silica gel column chromatography (solvent; hexane/ethyl acetate=70/30-0/100) to give the title compound (65.0 mg).

MS(ESI)m/z; 295[M+H]$^+$

Reference Example 400

7-cyclopropyl-2-(methylsulfanyl)[1,3]thiazolo[4,5-b]pyridine-6-carboxylic acid

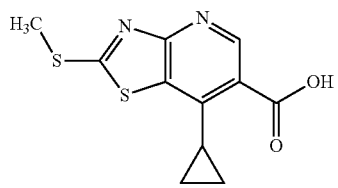 [SMILES: CSc1nc2ncc(C(=O)O)c(C3CC3)c2s1]

The compound (1.78 g) obtained in Reference Example 399 was treated by a method similar to that in Reference Example 377 to give the title compound (600 mg).
MS(ESI)m/z; 267[M+H]$^+$

Reference Example 401

7-cyclopropyl-6-(hydroxymethyl)-2-(methylsulfanyl)[1,3]thiazolo[4,5-b]pyridine

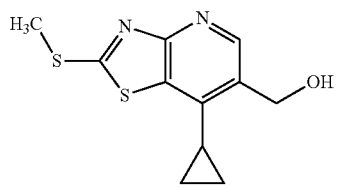 [SMILES: CSc1nc2ncc(CO)c(C3CC3)c2s1]

To a THF solution (10.0 mL) of the compound (600 mg) obtained in Reference Example 400 was added carbonyldiimidazole (550 mg) at room temperature, and the reaction mixture was stirred with heating at 80° C. for 2 hr. After cooling to room temperature, the reaction mixture was added to an aqueous solution (20.0 mL) of sodium borohydride (260 mg) at 0° C., and the reaction mixture was stirred at the same temperature for 1 hr. The reaction mixture was neutralized with 1.0 mol/L hydrochloric acid and extracted twice with ethyl acetate. The organic layer was dried over anhydrous sodium sulfate, filtered and concentrated, and the obtained residue was purified by silica gel column chromatography (solvent; chloroform/methanol-100/0-95/5) to give the title compound (460 mg).
MS(ESI)m/z; 253[M+H]$^+$

Reference Example 402

7-cyclopropyl-6-(methoxymethyl)-2-(methylsulfanyl)[1,3]thiazolo[4,5-b]pyridine

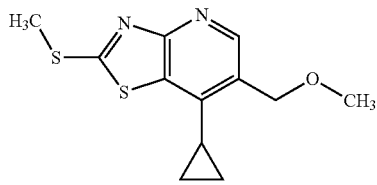

The compound (460 mg) obtained in Reference Example 401 was treated by a method similar to that in Reference Example 395 to give the title compound (110 mg).
MS(ESI)m/z; 267[M+H]$^+$

Reference Example 403

7-cyclopropyl-2-(methylsulfanyl)[1,3]thiazolo[4,5-b]pyridine-6-carboxamide

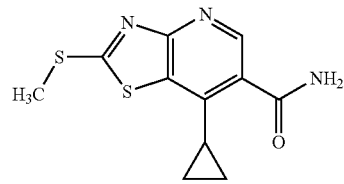 [SMILES: CSc1nc2ncc(C(N)=O)c(C3CC3)c2s1]

The compound (320 mg) obtained in Reference Example 400 was treated by a method similar to that in Reference Example 378 to give the title compound (146 mg).
MS(ESI)m/z; 266[M+H]$^+$

Reference Example 404

6-cyano-7-cyclopropyl-2-(methylsulfanyl)[1,3]thiazolo[4,5-b]pyridine

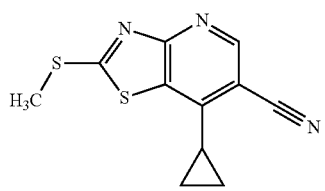 [SMILES: CSc1nc2ncc(C#N)c(C3CC3)c2s1]

To a dichloromethane solution (4.00 mL) of the compound (140 mg) obtained in Reference Example 403 were added triethylamine (146 μL) and trifluoromethanesulfonic anhydride (170 μL) at 0° C., and the reaction mixture was stirred at 0° C. for 3 hr. Water was added and the mixture was extracted twice with ethyl acetate. The organic layer was dried over anhydrous sodium sulfate, filtered and concentrated, and the obtained residue was purified by silica gel column chromatography (solvent; hexane/ethyl acetate=80/20-60/40) to give the title compound (89.0 mg).
MS(ESI)m/z; 248[M+H]$^+$

Reference Example 405

7-cyclopropyl-6-(5-methyl-1,2,4-oxadiazol-3-yl)-2-(methylsulfanyl)[1,3]thiazolo[4,5-b]pyridine

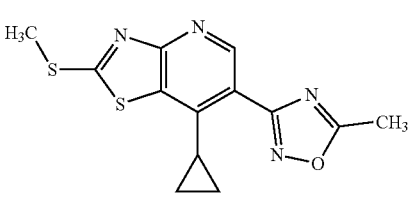

The compound (400 mg) obtained in Reference Example 404 was treated by a method similar to that in Reference Example 367 to give the title compound (51.0 mg).

MS(ESI)m/z; 305[M+H]$^+$

Reference Example 406

7-cyclopropyl-6-(3-methyl-1,2,4-oxadiazol-5-yl)-2-(methylsulfanyl)[1,3]thiazolo[4,5-b]pyridine

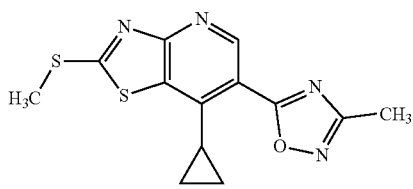

The compound (100 mg) obtained in Reference Example 400 was treated by a method similar to that in Reference Example 384 to give the title compound (63.0 mg).

MS(ESI)m/z; 305[M+H]$^+$

Reference Example 407

N'-acetyl-7-cyclopropyl-2-(methylsulfanyl)[1,3]thiazolo[4,5-b]pyridine-6-carbohydrazide

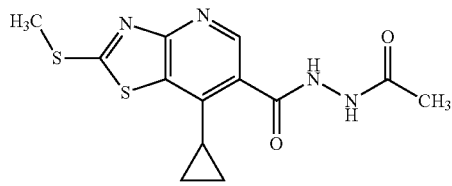 [SMILES: CSc1nc2ncc(C(=O)NNC(C)=O)c(C3CC3)c2s1]

The compound (500 mg) obtained in Reference Example 400 was treated by a method similar to that in Reference Example 374 to give the title compound (521 mg).

MS(ESI)m/z; 323[M+H]$^+$

Reference Example 408

7-cyclopropyl-6-(5-methyl-1,3,4-oxadiazol-2-yl)-2-(methylsulfanyl)[1,3]thiazolo[4,5-b]pyridine

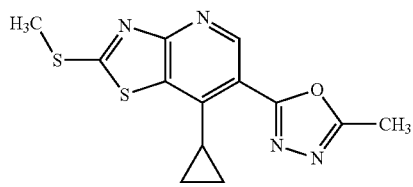

The compound (250 mg) obtained in Reference Example 407 was treated by a method similar to that in Reference Example 375 to give the title compound (156 mg).

MS(ESI)m/z; 305[M+H]$^+$

Reference Example 409

6-cyano-7-methyl-2-(methylsulfonyl)[1,3]thiazolo[4,5-b]pyridine

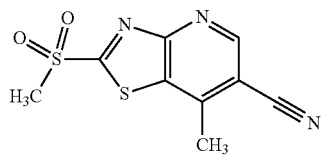 [SMILES: Cc1c(C#N)cnc2nc(S(C)(=O)=O)sc12]

To a methylene chloride solution (12.0 mL) of the compound (576 mg) obtained in Reference Example 352 was added, under ice-cooling, mCPBA (69-75% w/w, 1.43 g), and the reaction mixture was stirred at room temperature for 3 hr. To the reaction mixture were added 0.1 mol/L aqueous sodium thiosulfate solution and saturated aqueous sodium hydrogen carbonate solution, and the mixture was extracted twice with chloroform. The organic layer was dried over anhydrous sodium sulfate, filtered and concentrated, and the residue was purified by silica gel column chromatography (solvent; chloroform/methanol=100/0-90/10) to give the title compound (422 mg).

MS(ESI)m/z; 254[M+H]$^+$

Reference Example 410

7-cyano-6-methyl-2-(methylsulfinyl) [1,3]thiazolo[4,5-b]pyridine

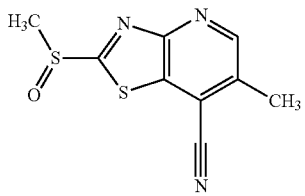

To a methylene chloride solution (4.00 mL) of the compound (143 mg) obtained in Reference Example 360 was added, under ice-cooling, mCPBA (69-75% w/w, 178 mg), and the reaction mixture was stirred at room temperature for 1.5 hr. To the reaction mixture were added 0.1 mol/L aqueous sodium thiosulfate solution and saturated aqueous sodium hydrogen carbonate solution, and the mixture was extracted twice with chloroform. The organic layer was dried over anhydrous sodium sulfate, filtered and concentrated, and the residue was purified by silica gel column chromatography (solvent; hexane/ethyl acetate=50/50-0/100) to give the title compound (125 mg).

MS(ESI)m/z; 238[M+H]$^+$

The following Tables show the compounds obtained by treating the corresponding compounds by a method similar to that in Reference Example 410.

TABLE 34

| Reference Example | structure | starting material | yield | MS(ESI) m/z [M + H]+ |
|---|---|---|---|---|
| 411 | (methylsulfinyl-thiazolo[5,4-b]pyridinyl with C(CH3)2CN) | Reference Example 353 (300 mg) | 158 mg | 266 |
| 412 | (methylsulfinyl-thiazolo[5,4-b]pyridine with CH3) | Reference Example 361 (300 mg) | 270 mg | 213 |
| 413 | (methylsulfinyl-thiazolo[5,4-b]pyridine with Br and CH2OCH3) | Reference Example 363 (300 mg) | 158 mg | 321, 323 |
| 414 | (methylsulfinyl-thiazolo[5,4-b]pyridine with CH2OCH3) | Reference Example 364 (170 mg) | 180 mg | 243 |
| 415 | (methylsulfinyl-thiazolo[5,4-b]pyridine with Br and CH2CH3) | Reference Example 354 (1.42 g) | 1.72 g | 305, 307 |
| 416 | (methylsulfinyl-thiazolo[5,4-b]pyridine with methyl-oxadiazolyl) | Reference Example 356 (880 mg) | 710 mg | 281 |
| 417 | (methylsulfinyl-thiazolo[5,4-b]pyridine with Br and methyl-oxadiazolyl) | Reference Example 365 (410 mg) | 410 mg | 359, 361 |

TABLE 34-continued

| Reference Example | structure | starting material | yield | MS(ESI) m/z [M + H]+ |
|---|---|---|---|---|
| 418 | 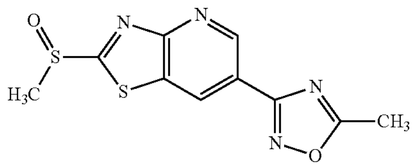 [SMILES: Cc1nc(-c2cnc3nc(S(C)=O)sc3c2)no1] | Reference Example 367 (1.41 g) | 1.42 g | 281 |
| 419 | 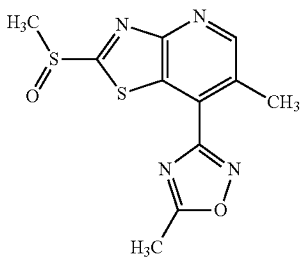 [SMILES: Cc1nc(-c2c(C)cnc3nc(S(C)=O)sc23)no1] | Reference Example 369 (235 mg) | 230 mg | 295 |
| 420 | 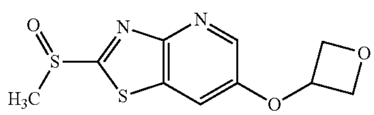 [SMILES: CS(=O)c1nc2ncc(OC3COC3)cc2s1] | Reference Example 372 (201 mg) | 83.0 mg | 271 |
| 421 | 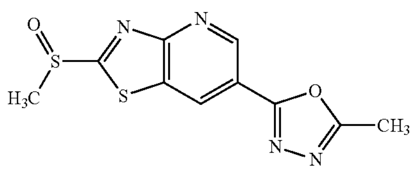 | Reference Example 375 (530 mg) | 520 mg | 281 |
| 422 | 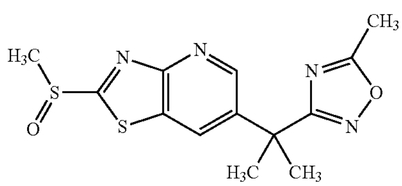 [SMILES: Cc1nc(C(C)(C)c2cnc3nc(S(C)=O)sc3c2)no1] | Reference Example 368 (430 mg) | 350 mg | 323 |
| 423 | 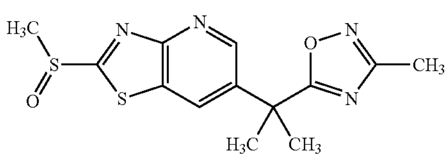 | Reference Example 379 (80.0 mg) | 82.0 mg | 323 |
| 424 | 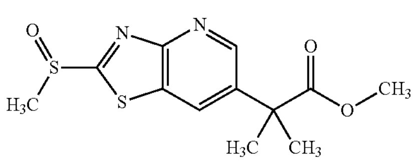 | Reference Example 376 (529 mg) | 486 mg | 299 |
| 425 | 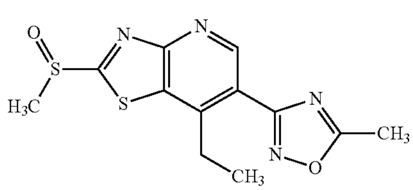 | Reference Example 370 (104 mg) | 120 mg | 309 |

TABLE 34-continued

| Reference Example | structure | starting material | yield | MS(ESI) m/z [M + H]+ |
|---|---|---|---|---|
| 426 | ![structure] | Reference Example 384 (49.0 mg) | 63.0 mg | 309 |
| 427 | ![structure] | Reference Example 395 (44.0 mg) | 51.0 mg | 243 |
| 428 | ![structure] | Reference Example 397 (65.0 mg) | 45.0 mg | 280 |
| 429 | ![structure] | Reference Example 404 (87.0 mg) | 54.0 mg | 264 |
| 430 | ![structure] | Reference Example 357 (5.35 g) | 3.84 g | 224 |

Reference Example 431 tert-butyl (R)-1-(6-cyano[1,3]thiazolo[4,5-b]pyridin-2-yl)pyrrolidine-2-carboxylate

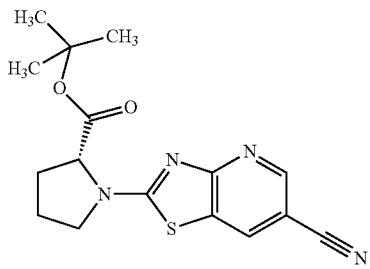 [SMILES: CC(C)(C)OC(=O)[C@H]1CCCN1c1nc2ncc(C#N)cc2s1]

A mixture of the compound (2.80 g) obtained in Reference Example 430, D-proline t-butyl ester (2.14 g), N,N-diisopropylethylamine (6.60 mL) and THF (15.0 mL) was stirred with heating at 120° C. for 3 hr. After standing overnight, water was added. The resulting solid was collected by filtration, dried and purified by silica gel column chromatography (solvent; chloroform/methanol=100/0-95/5) to give the title compound (2.77 g).

MS(ESI)m/z; 331[M+H]+

Reference Example 432

(R)-1-(6-cyano[1,3]thiazolo[4,5-b]pyridin-2-yl)pyrrolidine-2-carboxylic acid

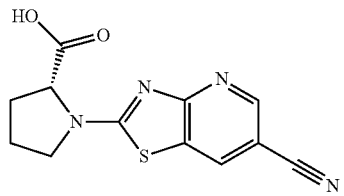 [SMILES: N#Cc1cnc2nc(N3CCC[C@@H]3C(=O)O)sc2c1]

To a dichloromethane solution (15.0 mL) of the compound (2.45 g) obtained in Reference Example 431 was added trifluoroacetic acid (15.0 mL) at 0° C., and the reaction mixture was stirred at room temperature for 3.5 hr. The solvent was evaporated under reduced pressure, to the resulting solid was added diethyl ether, the mixture was stirred, and the solid was collected by filtration and dried to give the title compound (2.26 g).

MS(ESI)m/z; 275[M+H]+

Reference Example 433

2-amino-5,6-dimethylpyrazine

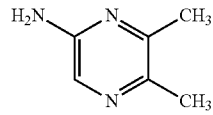

An aqueous solution (40.0 mL) of 2,3-butanedione (1.55 g) and sodium acetate (4.72 g) was added to a methanol solution (40.0 mL) of 2-aminoacetamidine dihydrobromide (4.24 g) at −30° C. over 10 min. Furthermore, 3.6 mol/L aqueous sodium hydroxide solution (17.0 mL) was added, and the reaction mixture was stirred at 0° C. for 30 min and at room temperature overnight. Methanol was evaporated under reduced pressure, water was added, and the mixture was extracted 3 times with ethyl acetate. The organic layer was dried over anhydrous sodium sulfate, filtered and concentrated, and the obtained residue was purified by silica gel column chromatography (solvent; hexane/ethyl acetate=50/50-0/100) to give the title compound (410 mg).

MS(ESI)m/z; 124[M+H]$^+$

Reference Example 434

2-amino-5-ethenylpyrazine

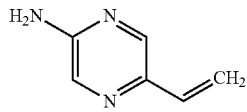

A 1,4-dioxane solution (33.0 mL) of 2-amino-5-bromopyrazine (2.99 g) synthesized by the method described in Heterocycles 2012, 1323-1339 (2012), 4,4,5,5-tetramethyl-2-vinyl-1,3,2-dioxaborolane (1.00 g), cesium carbonate (4.37 g) and dichlorobis(tricyclohexylphosphine)palladium (395 mg) was heated under reflux under a nitrogen atmosphere for 14 hr. After cooling to room temperature, water was added and the mixture was extracted twice with ethyl acetate. The organic layer was dried over anhydrous sodium sulfate, filtered and concentrated, and the obtained residue was purified by silica gel column chromatography (solvent; hexane/ethyl acetate=70/30-0/100) to give the title compound (1.40 g).

MS(ESI)m/z; 122[M+H]$^+$

Reference Example 435

2-amino-5-cyclopropylpyrazine

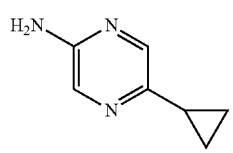

2-Amino-5-bromopyrazine (2.99 g) was treated by a method similar to that in Reference Example 434 to give the title compound (1.07 g).

MS(ESI)m/z; 136[M+H]$^+$

Reference Example 436

2-amino-5-ethylpyrazine

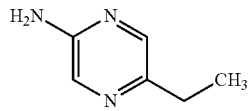

A mixture of the compound (1.40 g) obtained in Reference Example 434 and 10% palladium carbon (1.40 g) in methanol (45.0 mL) was stirred under a hydrogen atmosphere at room temperature for 3 hr. The reaction mixture was filtered through diatomaceous earth and concentrated to give the title compound (1.40 g).

MS(ESI)m/z; 124[M+H]$^+$

Reference Example 437

2-amino-3-bromo-5,6-dimethylpyrazine

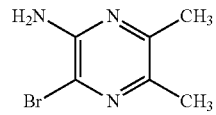

To an acetonitrile solution (8.00 mL) of the compound (519 mg) obtained in Reference Example 433 was added N-bromosuccinimide (749 mg) at 0° C., and the reaction mixture was stirred at room temperature for 30 min. Aqueous sodium thiosulfate solution was added and the mixture was extracted twice with ethyl acetate. The organic layer was dried over anhydrous magnesium sulfate, filtered and concentrated, and the obtained residue was purified by silica gel column chromatography (solvent; hexane/ethyl acetate=100/0-60/40) to give the title compound (619 mg).

MS(ESI)m/z; 202, 204[M+1-1]$^+$

Reference Example 438

2-amino-3-bromo-5-ethylpyrazine

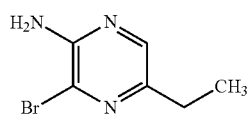

The compound (110 mg) obtained in Reference Example 436 was treated by a method similar to that in Reference Example 437 to give the title compound (70.0 mg).

MS(ESI)m/z; 202, 204[M+H]+

Reference Example 439

2-amino-3-bromo-5-cyclopropylpyrazine

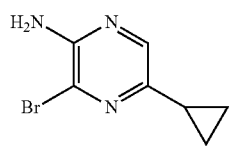

The compound (570 mg) obtained in Reference Example 435 was treated by a method similar to that in Reference Example 437 to give the title compound (312 mg).
MS(ESI)m/z; 214, 216[M+H]+

Reference Example 440

6-methyl[1,3]thiazolo[4,5-b]pyrazine-2(3H)-thione

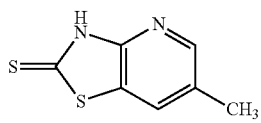

An N-methylpyrrolidone solution (10.0 mL) of 2-amino-3-bromo-5-methylpyrazine (2.00 g) synthesized by the method described in U.S. Pat. No. 5,866,568A1 and potassium ethyl xanthogenate (3.41 g) was stirred with heating at 150° C. for 4 hr. The reaction mixture was cooled to room temperature and 0.5 mol/L hydrochloric acid (20 mL) was added. The precipitated solid was collected by filtration, washed with water and dried under reduced pressure to give the title compound (1.75 g).
MS(ESI)m/z; 184[M+H]+

The following Table shows the compounds obtained by treating the corresponding compounds by a method similar to that in Reference Example 440.

Reference Example 444

6-bromo-2-(2,5-dimethyl-1H-pyrrol-1-yl)[1,3]thiazolo[4,5-b]pyrazine

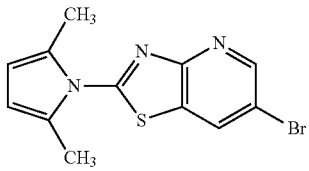

A mixture of 2-amino-6-bromo[1,3]thiazolo[4,5-b]pyrazine (8.00 g) synthesized by the method described in EP2351744A1, n-hexane-2,5-dione (8.10 mL) and p-toluenesulfonic acid monohydrate (658 mg) in toluene (86.0 mL) was heated under reflux overnight. Under ice-cooling, saturated aqueous sodium hydrogen carbonate solution was added and the mixture was extracted twice with chloroform. The organic layer was dried over anhydrous sodium sulfate, filtered and concentrated, and the obtained residue was purified by silica gel column chromatography (solvent; hexane/ethyl acetate=100/0-80/20) to give the title compound (8.33 g).
MS(ESI)m/z; 309, 311[M+H]+

Reference Example 445

2-(2,5-dimethyl-1H-pyrrol-1-yl)-6-phenyl[1,3]thiazolo[4,5-b]pyrazine

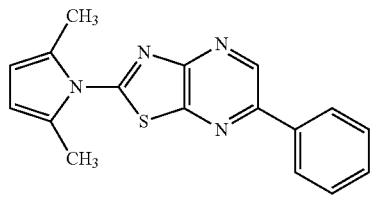 [SMILES: Cc1ccc(C)n1-c1nc2ncc(-c3ccccc3)nc2s1]

TABLE 35

| Reference Example | structure | starting material | yield | MS(ESI) m/z [M + H]+ |
|---|---|---|---|---|
| 441 | ![structure] | Reference Example 437 (619 mg) | 539 mg | 198 |
| 442 | ![structure] | Reference Example 438 (600 mg) | 395 mg | 198 |
| 443 | ![structure] | Reference Example 439 (312 mg) | 209 mg | 210 |

A mixture of the compound (800 mg) obtained in Reference Example 444, phenylboronic acid (379 mg), tetrakis(triphenylphosphine)palladium (180 mg) and 2.0 mol/L aqueous sodium carbonate solution (7.50 mL) in 1,4-dioxane (20.0 mL) was stirred with heating under a nitrogen atmosphere at 100° C. for 3 hr. After cooling to room temperature, water was added and the mixture was extracted twice with ethyl acetate. The organic layer was dried over anhydrous sodium sulfate, filtered and concentrated, and the obtained residue was purified by silica gel column chromatography (solvent; hexane/ethyl acetate=100/0-80/20) to give the title compound (630 mg).

MS(ESI)m/z; 307[M+H]$^+$

Reference Example 446

2-(2,5-dimethyl-1H-pyrrol-1-yl)-6-ethoxy[1,3]thiazolo[4,5-b]pyrazine

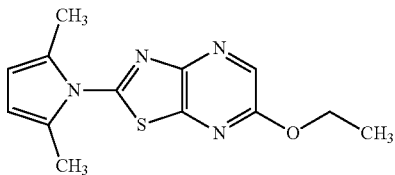 [SMILES: CCOc1cnc2nc(-n3c(C)ccc3C)sc2n1]

An ethanol solution (20.0 mL) of the compound (800 mg) obtained in Reference Example 444 and sodium ethoxide (20% ethanol solution, 1.68 g) was stirred with heating at 80° C. for 2.5 hr. After cooling to room temperature, ethanol was evaporated under reduced pressure, water was added, and the mixture was extracted twice with chloroform. The organic layer was dried over anhydrous sodium sulfate, filtered and concentrated, and the obtained residue was purified by silica gel column chromatography (solvent; hexane/ethyl acetate=100/0-80/20) to give the title compound (623 mg).

MS(ESI)m/z; 275[M+H]$^+$

Reference Example 447

2-(2,5-dimethyl-1H-pyrrol-1-yl)-6-(N,N-dimethylamino) [1,3]thiazolo[4,5-b]pyrazine

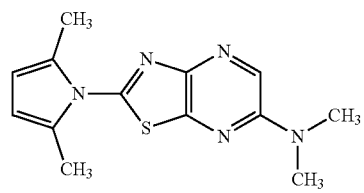 [SMILES: Cc1ccc(C)n1-c1nc2ncc(N(C)C)nc2s1]

A mixture of the compound (500 mg) obtained in Reference Example 444, dimethylamine hydrochloride (264 mg), palladium acetate (36.0 mg), (±)-2,2'-bis(diphenylphosphino)-1,1'-binaphthyl (201 mg) and cesium carbonate (2.11 g) in 1,4-dioxane (6.00 mL) was heated under reflux at 80° C. for 3 hr. Under ice-cooling, water was added and the mixture was extracted twice with ethyl acetate. The organic layer was dried over anhydrous sodium sulfate, filtered and concentrated. The obtained residue was purified by silica gel column chromatography (solvent; hexane/ethyl acetate=100/0-60/40) to give the title compound (1.76 g).

MS(ESI)m/z; 274[M+H]$^+$

Reference Example 448

2-amino-6-phenyl[1,3]thiazolo[4,5-b]pyrazine

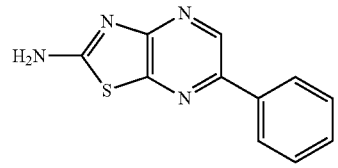 [SMILES: Nc1nc2ncc(-c3ccccc3)nc2s1]

A mixed solution of the compound (630 mg) obtained in Reference Example 445 in trifluoroacetic acid (14.0 mL)-water (14.0 mL) was stirred with heating at 60° C. for 8 hr. After cooling to room temperature, the solvent was evaporated under reduced pressure, chloroform was added and the mixture was washed twice with saturated aqueous sodium hydrogen carbonate solution. The organic layer was dried over anhydrous sodium sulfate, filtered and concentrated. To the obtained residue was added diisopropy ether, and the solid was collected by filtration and dried to give the title compound (456 mg).

MS(ESI)m/z; 229[M+H]$^+$

Reference Example 449

2-amino-6-ethoxy[1,3]thiazolo[4,5-b]pyrazine

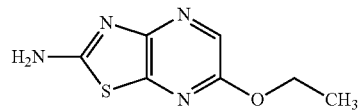

The compound (623 mg) obtained in Reference Example 446 was treated by a method similar to that in Reference Example 448 to give the title compound (350 mg).

MS(ESI)m/z; 197[M+H]$^+$

Reference Example 450

2-amino-6-(N,N-dimethylamino)-[1,3]thiazolo[4,5-b]pyrazine

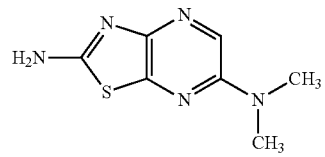

The compound (295 mg) obtained in Reference Example 447 was treated by a method similar to that in Reference Example 448 to give the title compound (209 mg).

MS(ESI)m/z; 196[M+H]$^+$

Reference Example 451

2-chloro-6-methyl[1,3]thiazolo[4,5-b]pyrazine

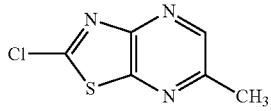

To a dichloromethane solution (40.0 mL) of the compound (1.75 g) obtained in Reference Example 440 was added sulfuryl chloride (6.00 mL) at room temperature, and the reaction mixture was stirred at the same temperature for 3 hr. The reaction mixture was neutralized with 5.0 mol/L aqueous sodium hydroxide solution and extracted twice with chloroform. The organic layer was dried over anhydrous magnesium sulfate, filtered and concentrated to give the title compound (1.57 g).
MS(ESI)m/z; 186, 188[M+H]$^+$

Reference Example 452

2-chloro-5,6-dimethyl[1,3]thiazolo[4,5-b]pyrazine

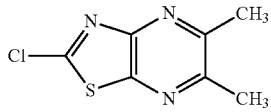

The compound (270 mg) obtained in Reference Example 441 was treated by a method similar to that in Reference Example 451 to give the title compound (238 mg).
MS(ESI)m/z; 200, 202[M+H]$^+$

Reference Example 453

2-chloro-6-ethyl[1,3]thiazolo[4,5-b]pyrazine

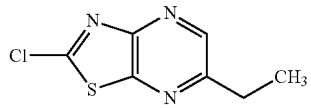

The compound (395 mg) obtained in Reference Example 442 was treated by a method similar to that in Reference Example 451 to give the title compound (195 mg).
MS(ESI)m/z; 200, 202[M+H]$^+$

Reference Example 454

2-chloro-6-phenyl[1,3]thiazolo[4,5-b]pyrazine

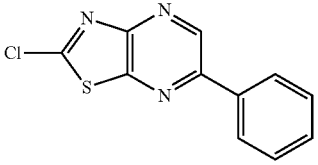 [SMILES: Clc1nc2ncc(-c3ccccc3)nc2s1]

To acetonitrile (10.0 mL) were added tert-butyl nitrite (357 μL) and cupric chloride (323 mg) at room temperature, and the reaction mixture was stirred with heating at 60° C. for 2 hr. The compound (456 mg) obtained in Reference Example 448 was added, and the reaction mixture was stirred with heating at 60° C. for 4 hr. After cooling to 0° C., 28% aqueous ammonia was added and the mixture was extracted 4 times with dichloromethane. The organic layer was dried over anhydrous magnesium sulfate, filtered and concentrated, and the obtained residue was purified by silica gel column chromatography (solvent; hexane/ethyl acetate=90/10-75/25) to give the title compound (48.0 mg).
MS(ESI)m/z; 248, 250[M+H]$^+$

Reference Example 455

2-chloro-6-ethoxy[1,3]thiazolo[4,5-b]pyrazine

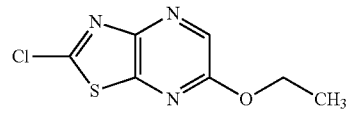

The compound (350 mg) obtained in Reference Example 449 was treated by a method similar to that in Reference Example 454 to give the title compound (209 mg).
MS(ESI)m/z; 216, 218[M+H]$^+$

Reference Example 456

2-chloro-6-(N,N-dimethylamino)[1,3]thiazolo[4,5-b]pyrazine

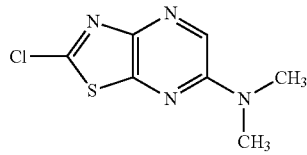

The compound (209 mg) obtained in Reference Example 450 was treated by a method similar to that in Reference Example 454 to give the title compound (48.0 mg).
MS(ESI)m/z; 215, 217[M+H]$^+$

Reference Example 457

6-cyclopropyl-2-methylsulfanyl[1,3]thiazolo[4,5-b]pyrazine

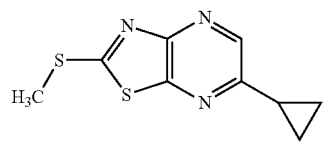

To a 1.0 mol/L aqueous sodium hydroxide solution (1.20 mL) of the compound (209 mg) obtained in Reference Example 443 was added dimethyl sulfate (114 μL) at room temperature, and the reaction mixture was stirred at the same temperature for 30 min. After confirmation of the completion of the reaction, water was added and the resulting solid was collected by filtration and dried to give the title compound (203 mg).

MS(ESI)m/z; 224[M+H]$^+$

Reference Example 458

6-cyclopropyl-2-methylsulfinyl[1,3]thiazolo[4,5-b]pyrazine

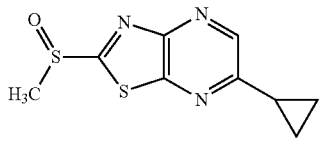

To a methylene chloride solution (8.00 mL) of the compound (203 mg) obtained in Reference Example 457 was added, under ice-cooling, mCPBA (69-75% w/w) (156 mg), and the reaction mixture was stirred at room temperature for 1.5 hr. To the reaction mixture were added aqueous sodium thiosulfate solution and saturated aqueous sodium hydrogen carbonate solution, and the mixture was extracted twice with chloroform. The organic layer was dried over anhydrous sodium sulfate, filtered and concentrated, and the residue was purified by silica gel column chromatography (solvent; hexane/ethyl acetate=90/10-50/50) to give the title compound (149 mg).

MS(ESI)m/z; 240[M+H]$^+$

Reference Example 459 benzyl (R)-2-[(3-bromo-5-methylpyridin-2-yl)carbamoyl]pyrrolidine-1-carboxylate

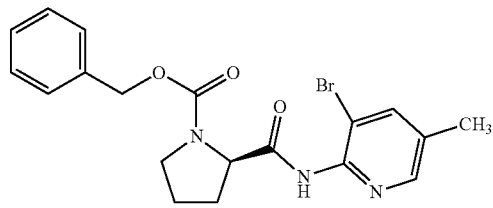 [SMILES: Cc1cnc(NC(=O)[C@H]2CCCN2C(=O)OCc2ccccc2)c(Br)c1]

To a THF solution (20.0 mL) of N-carbobenzoxy-D-proline (1.34 g) were added triethylamine (820 mg) and isobutyl chloroformate (810 mg) at 0° C., and the reaction mixture was stirred at room temperature for 30 min. Triethylamine (820 mg) and 2-amino-3-bromo-5-methylpyridine (1.00 g) were added at room temperature, and the reaction mixture was stirred with heating at 80° C. for 12 hr. After cooling to room temperature, water was added to the reaction mixture, and the mixture was extracted 3 times with ethyl acetate. The organic layer was dried over anhydrous magnesium sulfate, filtered and concentrated. The residue was purified by silica gel column chromatography (solvent; ethyl acetate/methanol=100/0-95/5) to give the title compound (1.05 g).

MS(ESI)m/z; 418, 420[M+H]$^+$

Reference Example 460 benzyl (R)-2-[(3-bromo-5-ethylpyridin-2-yl)carbamoyl]pyrrolidine-1-carboxylate

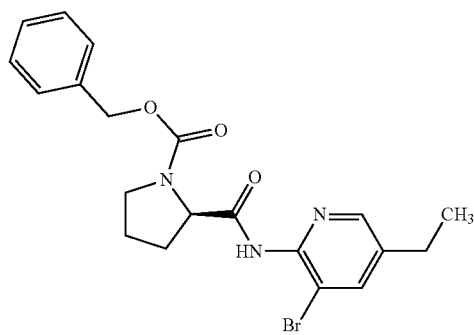 [SMILES: CCc1cnc(NC(=O)[C@H]2CCCN2C(=O)OCc2ccccc2)c(Br)c1]

The compound (1.80 g) obtained in Reference Example 269 was treated by a method similar to that in Reference Example 459 to give the title compound (2.79 g).

MS(ESI)m/z; 432, 434[M+H]$^+$

Reference Example 461 benzyl (R)-2-[(3-bromo-5,6-dimethylpyridin-2-yl)carbamoyl]pyrrolidine-1-carboxylate

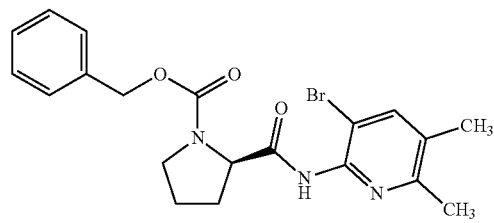 [SMILES: Cc1cc(Br)c(NC(=O)[C@H]2CCCN2C(=O)OCc2ccccc2)nc1C]

2-Amino-3-bromo-5,6-dimethylpyridine (5.00 g) was treated by a method similar to that in Reference Example 459 to give the title compound (10.7 g).

MS(ESI)m/z; 432, 434[M+H]$^+$

Reference Example 462

6-methyl-2-[(R)-pyrrolidin-2-yl][1,3]thiazolo[4,5-b]pyridine

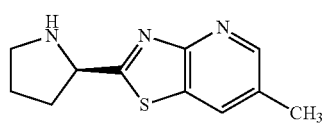

To the compound (586 mg) obtained in Example 193 was added 30% hydrobromic acid-acetic acid solution (3.30 mL) at room temperature, and the reaction mixture was stirred at the same temperature for 1 hr. To the reaction mixture was added chloroform (200 mL) and, under ice-cooling, the mixture was neutralized with 1.0 mol/L aqueous sodium hydroxide solution. The aqueous layer was extracted once with chloroform, and the combined organic layer was washed with saturated brine, dried over anhydrous sodium sulfate, filtered and concentrated. The residue was purified by NH silica gel column chromatography (solvent; ethyl acetate/methanol=100/0-95/5) to give the title compound (72.0 mg).
MS(ESI)m/z; 220[M+H]⁺

Reference Example 463

6-ethyl-2-[(R)-pyrrolidin-2-yl][1,3]thiazolo[4,5-b]pyridine

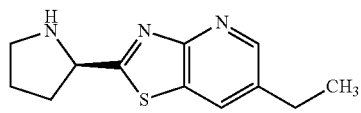 [SMILES: CCc1cnc2nc([C@H]3CCCN3)sc2c1]

The compound (2.30 g) obtained in Example 194 was treated by a method similar to that in Reference Example 462 to give the title compound (850 mg).
MS(ESI)m/z; 234[M+H]⁺

Reference Example 464

5,6-dimethyl-2-[(R)-pyrrolidin-2-yl][1,3]thiazolo[4,5-b]pyridine

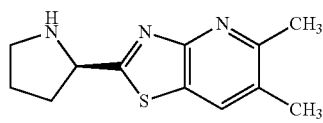 [SMILES: Cc1cc2sc([C@H]3CCCN3)nc2nc1C]

The compound (6.00 g) obtained in Example 195 was treated by a method similar to that in Reference Example 462 to give the title compound (650 mg).
MS(ESI)m/z; 234[M+H]⁺

Reference Example 465

2,6-difluoropyridine-3-carboxamide

To a dichloroethane solution (28.0 mL) of 2,6-difluoropyridine-3-carboxylic acid (3.41 g) was added thionyl chloride (9.16 mL) at room temperature, and the reaction mixture was stirred at 70° C. for 3 hr. After cooling to room temperature, the solvent was evaporated under reduced pressure. To a diethyl ether solution (46.0 mL) of the residue was added 28% aqueous ammonia (4.60 mL) at 0° C. and the mixture was stirred for 10 min. Saturated aqueous sodium hydrogen carbonate solution was added and the mixture was extracted with ethyl acetate. The organic layer was dried over anhydrous magnesium sulfate, filtered and concentrated to give the title compound (3.05 g).
MS(ESI)m/z; 159[M+H]⁺

Reference Example 466

2-amino-6-fluoropyridine-3-carboxamide

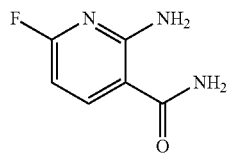 [SMILES: NC(=O)c1ccc(F)nc1N]

Ammonia gas was blown into a formamide solution (20.0 mL) of the compound (3.04 g) obtained in Reference Example 465 at 0° C., and the reaction mixture was stood at room temperature for 17 hr. Water (about 30 mL) was added and the resultant solid was filtered off and the filtrate was extracted with ethyl acetate. The organic layer was dried over anhydrous magnesium sulfate, filtered and concentrated. To the residue was added ethyl acetate and the solid was filtered off. The filtrate was purified by silica gel column chromatography (solvent; hexane/ethyl acetate=50/50-25/75) to give the title compound (930 mg).
MS(ESI)m/z; 156[M+H]⁺

Reference Example 467

7-fluoropyrido[2,3-d]pyrimidin-4(3H)-one

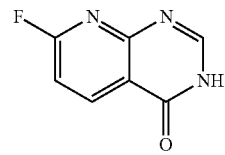

A mixture of the compound (928 mg) obtained in Reference Example 466 and triethyl orthoformate (30.0 ml) was stirred at 150° C. for 8 hr. Paratoluenesulfonic acid (52.0 mg) was added and the reaction mixture was further stirred at 150° C. for 7 hr. After cooling to room temperature, hexane was added and the resulting solid was collected by filtration and dried to give the title compound (880 mg).
MS(ESI)m/z; 166[M+H]⁺

Reference Example 468

4-chloro-7-fluoropyrido[2,3-d]pyrimidine

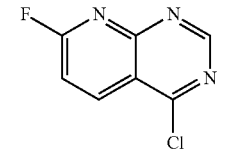 [SMILES: Fc1ccc2c(Cl)ncnc2n1]

To the compound (270 mg) obtained in Reference Example 467 were added phosphorus oxychloride (3.05 mL)

and N,N-diisopropylethylamine (0.513 mL), and the reaction mixture was stirred at 70° C. for 1 hr. After cooling to room temperature, diethyl ether was added, ice water was further added, and the mixture was extracted with ethyl acetate. The organic layer was washed with saturated brine, dried over anhydrous magnesium sulfate, filtered and concentrated. To the obtained residue was added ethyl acetate, and the solid was collected by filtration to give the title compound (250 mg).

MS(ESI)m/z; 184, 186[M+H]$^+$

Reference Example 469

4-amino-N-methyl-2-(methylsulfanyl)-1,3-thiazole-5-carboxamide

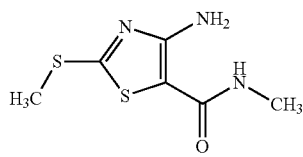

To a DMF solution (10.0 mL) of 4-amino-2-(methylsulfanyl)-1,3-thiazole-5-carboxylic acid (400 mg) synthesized by the method described in J. Heterocyclic Chem. 1361-1366 (1984) were added EDC hydrochloride (604 mg), HOBt monohydrate (482 g), N,N-diisopropylethylamine (0.550 mL) and methylamine (12 mol/L aqueous solution, 0.350 mL), and the reaction mixture was stirred at room temperature overnight. To the reaction mixture was added water and the mixture was extracted 3 times with ethyl acetate. The organic layer was dried over anhydrous magnesium sulfate, filtered and concentrated under reduced pressure, and the obtained residue was purified by silica gel column chromatography (solvent; hexane/ethyl acetate=80/20-50/50) to give the title compound (260 mg).

MS(ESI)m/z; 204[M+H]$^+$

Reference Example 470

5,6-dimethyl-2-(methylsulfanyl)[1,3]thiazolo[4,5-d]pyrimidin-7(6H)-one

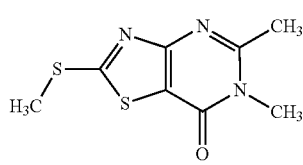

The compound (260 mg) obtained in Reference Example 469 was added to triethyl orthoacetate (1.40 mL), and the reaction mixture was heated at 120° C. for 1 hr. Acetic anhydride (1.40 mL) was added and the reaction mixture was further heated at 120° C. for 3 hr. After cooling to room temperature, the solvent was evaporated under reduced pressure. To the residue were added xylene (4.00 mL) and paratoluenesulfonic acid (small amount), and the reaction mixture was heated under reflux for 1 hr. After cooling to room temperature, water was added and the mixture was extracted 3 times with ethyl acetate. The organic layer was dried over anhydrous magnesium sulfate, filtered and concentrated under reduced pressure, and the obtained residue was purified by silica gel column chromatography (solvent; hexane/ethyl acetate=60/40-0/100) to give the title compound (63.0 mg).

MS(ESI)m/z; 228[M+H]$^+$

Reference Example 471

(R)—N-benzylpyrrolidine-2-carboxamide hydrochloride

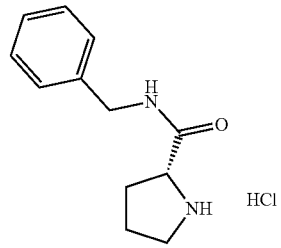 [SMILES: O=C(NCc1ccccc1)[C@H]1CCCN1 ; Cl]

To a DMF solution (40.0 mL) of N-(tert-butoxycarbonyl)-D-proline (4.00 g) were added benzylamine (2.00 g), EDC hydrochloride (5.40 g), HOBt monohydrate (4.30 g) and N,N-diisopropylethylamine (3.60 g), and the reaction mixture was stirred at room temperature for 1 hr. After confirmation of the completion of the reaction, water (200 mL) was added to the reaction mixture, and the mixture was extracted twice with ethyl acetate. The organic layer was washed once with water, dried over anhydrous magnesium sulfate, filtered and concentrated. The residue was purified by silica gel column chromatography (solvent; hexane/ethyl acetate=80/20-50/50) and concentrated. The obtained resultant product was dissolved in methanol (100 mL), hydrogen chloride (4.0 mol/L 1,4-dioxane solution, 50 mL) was added, and the mixture was stirred at room temperature for 2 hr. After confirmation of the completion of the reaction, the solvent was evaporated, and ethyl acetate was added to the residue. The solid was collected by filtration to give the title compound (3.80 g).

MS(ESI)m/z; 205[M+H]$^+$

Reference Example 472

(R)—N-(4-fluorobenzyl)-pyrrolidine-2-carboxamide hydrochloride

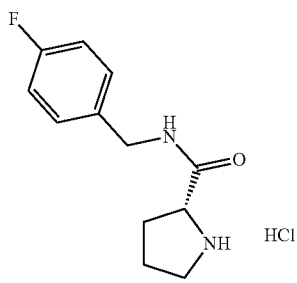 [SMILES: O=C(NCc1ccc(F)cc1)[C@H]1CCCN1 ; Cl]

4-Fluorobenzylamine (3.19 mL) was treated by a method similar to that in Reference Example 471 to give the title compound (5.31 g).

MS(ESI)m/z; 223[M+H]$^+$

Reference Example 473

(R)—N-[(1R)-1-phenylethyl]pyrrolidine-2-carboxamide hydrochloride

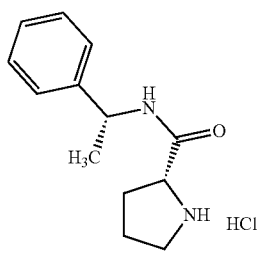 [SMILES: C[C@@H](NC(=O)[C@H]1CCCN1)c1ccccc1 ; Cl]

(R)-1-phenylethylamine (43.2 g) was treated by a method similar to that in Reference Example 471 to give the title compound (83.0 g).

MS(ESI)m/z; 219[M+H]$^+$

Reference Example 474

(R)—N-benzyl-2-(W-methylamino)propionamide hydrochloride

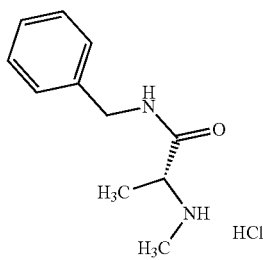

N-(tert-butoxycarbonyl)-N-methyl-D-alanine (2.00 g) and benzylamine (1.27 g) were treated by a method similar to that in Reference Example 471 to give the title compound (2.15 g).

MS(ESI)m/z; 193[M+H]$^+$

Pharmacological Experiment

KAT-II inhibitory test

Test Compound

The compounds described in the above-mentioned Examples were used for the KAT-II inhibitory test.

Preparation of Human Recombinant KAT-II

Human recombinant KAT-II was prepared as follows.

His tag and maltose binding protein tag were added to the N-terminal of a gene encoding human KAT-II (Genbank accession number: AF481738.1), and the obtained gene was incorporated into pET32 (Merck Nihon Millipore), which is an *Escherichia coli* expression vector. Human recombinant KAT-II produced by BL21(DE3) *Escherichia coli* (Merck Nihon Millipore, 69450) transformed using the plasmid was purified using an amylose resin column (New England Biolabs, #800-21 L).

Test Method

The inhibitory action of the test compound on human recombinant KAT-II was determined by the following method.

To a reaction mixture (45 µL) containing 3.0 µmol/L kynurenine, 10 µmol/L pyridoxal phosphate, 2.0 ng/µL human recombinant KAT-II, and 150 mmol/L tris(hydroxymethyl)aminomethane-acetate buffer (pH 8.0) was added a 10% dimethyl sulfoxide solution (5 µL) of each test compound prepared, and the mixture was reacted at 37° C. for 1 hr. After the reaction, 50% trichloroacetic acid (5 µL) was added to terminate the reaction.

The resultant kynurenic acid was quantified as follows by high performance liquid chromatography. An enzyme reaction mixture was separated by an octadecylsilane reversed-phase column (SC-50DS, Eicom Corporation; mobile phase: 250 mmol/L zinc acetate, 50 mmol/L sodium acetate, and 5.0% acetonitrile (pH 6.2)) incubated at 30° C., and kynurenic acid was quantified using a fluorescence detector (RF-20Axs, Shimadzu Corporation) at excitation wavelength 354 nm, detection wavelength 460 nm. The analytical curve was drawn every time by an external standard method. Each test compound was tested by dual measurement at each concentration. The kynurenic acid level in the presence of a test compound at each concentration was converted into % relative to kynurenic acid resulting from a reaction with an enzyme alone as 100%, and the obtained values were fitted to S-curve to determine IC$_{50}$.

Results

The IC$_H$ values of respective test compounds are shown in the following Tables.

TABLE 36

| Example | KAT-II inhibitory test IC$_{50}$ (µmol/L) |
|---|---|
| 2 | 0.047 |
| 6 | 0.071 |
| 10 | 0.035 |
| 14 | 0.027 |
| 15 | 0.082 |
| 17 | 0.064 |
| 18 | 0.050 |
| 19 | 0.037 |
| 20 | 0.14 |
| 23 | 0.026 |
| 24 | 0.20 |
| 26 | 0.12 |
| 28 | 0.19 |
| 30 | 0.27 |
| 31 | 0.065 |
| 32 | 0.39 |
| 33 | 0.60 |
| 34 | 0.64 |
| 35 | 0.29 |
| 36 | 0.064 |
| 38 | 0.41 |
| 39 | 0.35 |
| 41 | 0.17 |
| 46 | 0.035 |
| 49 | 0.076 |
| 55 | 0.41 |
| 56 | 0.23 |
| 58 | 0.64 |
| 66 | 0.012 |
| 67 | 0.012 |
| 70 | 0.16 |
| 75 | 0.095 |
| 76 | 1.5 |
| 78 | 0.55 |
| 83 | 0.013 |
| 84 | 0.39 |
| 88 | 0.42 |
| 89 | 0.046 |
| 90 | 0.13 |
| 92 | 2.1 |
| 93 | 0.14 |
| 98 | 0.075 |

TABLE 36-continued

| Example | KAT-II inhibitory test IC$_{50}$ (μmol/L) |
|---|---|
| 100 | 0.24 |
| 101 | 0.15 |
| 103 | 0.20 |
| 106 | 0.92 |
| 109 | 0.84 |
| 111 | 0.21 |
| 113 | 0.085 |
| 115 | 0.070 |
| 116 | 0.090 |
| 117 | 0.17 |
| 119 | 0.90 |
| 120 | 0.53 |
| 124 | 0.71 |
| 126 | 0.19 |
| 127 | 0.28 |
| 128 | 0.77 |
| 129 | 0.072 |
| 134 | 0.20 |
| 136 | 0.49 |
| 141 | 0.32 |
| 148 | 0.093 |
| 149 | 0.11 |
| 151 | 0.27 |
| 159 | 0.64 |
| 161 | 0.081 |
| 162 | 0.30 |
| 163 | 0.91 |
| 164 | 0.15 |
| 170 | 0.034 |
| 171 | 0.39 |
| 175 | 0.36 |
| 176 | 0.19 |
| 178 | 0.90 |
| 183 | 0.64 |
| 187 | 0.14 |
| 188 | 0.30 |
| 189 | 0.21 |
| 190 | 0.49 |
| 191 | 0.21 |
| 192 | 0.033 |
| 196 | 2.9 |
| 197 | 3.0 |
| 203 | 7.4 |

INDUSTRIAL APPLICABILITY

Compound (I) or a pharmacologically acceptable salt thereof of the present invention shows a KAT-II inhibitory action. Therefore, compound (I) or a pharmacologically acceptable salt thereof of the present invention is useful for the prophylaxis or treatment of various diseases (e.g., schizophrenia) involving KAT-II.

This application is based on a patent application No. 2015-208176 filed in Japan (filing date: Oct. 22, 2015), the is contents of which are incorporated in full herein.

The invention claimed is:
1. A compound represented by the formula (I):

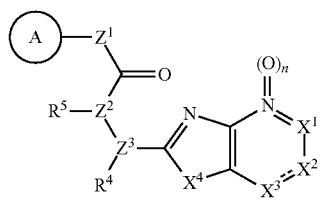

(I)

wherein
ring A is an optionally substituted aromatic group,
$X^1$ is $CR^1$ or a nitrogen atom,
a part represented by the following formula in the formula (I):

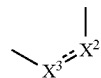

is the following A) or B),
A) ====
is a double bond,
$X^2$ is a nitrogen atom or $CR^2$, and
$X^3$ is a nitrogen atom or $CR^3$;
B) ====
is a single bond,
$X^2$ is $NR^2$, and
$X^3$ is carbonyl;
$X^4$ is sulfur atom, an oxygen atom or —CH=CH—,
$Z^1$ is an oxygen atom, —C($R^6$)($R^7$)—, —NH—, —C($R^6$)($R^7$)—NH—, —NH—C($R^6$)($R^7$)—, —C($R^6$)($R_7$)—O—, —O—C($R^6$)($R^7$)— or a single bond (where the left end shows a bond to ring A, and the right end shows a bond to the adjacent carbonyl),
one of $Z^2$ and $Z^3$ is CH and the other is a nitrogen atom, or both are nitrogen atoms,
$R^1$ is a group represented by the following formula (i-a), (i-b) or (i-c):

(i-a)

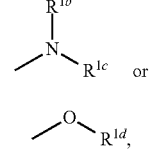
(i-b)

or

(i-c)

$R^2$ is a group represented by the following formula (ii-a), (ii-b) or (ii-c):

(ii-a)

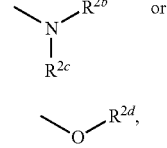
(ii-b)

or (ii-c)

$R^3$ is a group represented by the following formula (iii-a), (iii-b) or (iii-c):

(iii-a)

-continued

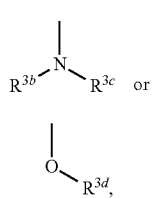 (iii-b)

or

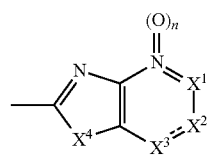 (iii-c)

$R^4$ and $R^5$ are each independently optionally substituted alkyl or optionally substituted cycloalkyl, or $R^4$ and $R^5$ are bonded to each other to form, together with the adjacent $Z^2$ and $Z^3$, an optionally substituted nitrogen-containing non-aromatic heterocycle, $R^6$ and $R^7$ are each independently a hydrogen atom, optionally substituted alkyl, or optionally substituted cycloalkyl, or $R^6$ and $R^7$ are bonded to each other to form, together with the adjacent carbon atom, an optionally substituted cycloalkane, $R^{1a}$, $R^{1b}$, $R^{1c}$, $R^{1d}$, $R^{2a}$, $R^{2b}$, $R^{2c}$, $R^{2d}$ $R^{3a}$, $R^{3b}$ and $R^{3d}$ are each independently a hydrogen atom, optionally substituted alkyl, cyano, a halogen atom, optionally substituted cycloalkyl, optionally substituted aryl, optionally substituted non-aromatic heterocyclic group or optionally substituted heteroaryl, $R^{3c}$ is optionally substituted alkyl, cyano, optionally substituted alkoxy, a halogen atom, optionally substituted cycloalkyl, optionally substituted aryl, optionally substituted non-aromatic heterocyclic group or optionally substituted heteroaryl, and n is 0 or 1, or a pharmacologically acceptable salt thereof, excluding 2-oxazolo[4,5-b]pyridin-2-yl-pyrrolidine-1-carboxylic acid benzyl ester or a pharmacologically acceptable salt thereof.

2. The compound according to claim 1, wherein $X^4$ is a sulfur atom, or a pharmacologically acceptable salt thereof.

3. The compound according to claim 1, wherein $X^4$ is —CH=CH—, or a pharmacologically acceptable salt thereof.

4. The compound according to claim 1, wherein, in the formula (I), a part represented by the following formula:

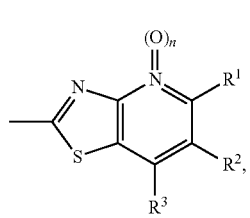

is a group represented by the formula (iv-a), (iv-b), (iv-c), (iv-d) or (iv-e):

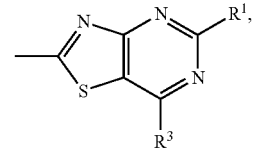 (iv-a)

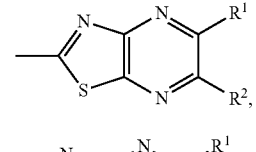 (iv-b)

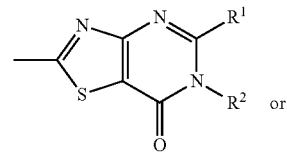 (iv-c)

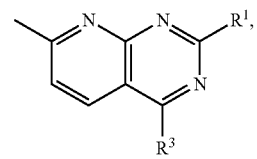 (iv-d)

or

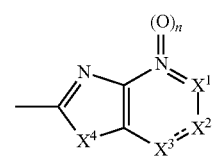 (iv-e)

or a pharmacologically acceptable salt thereof.

5. The compound according to claim 4, wherein, in the formula (I), a part represented by the following formula:

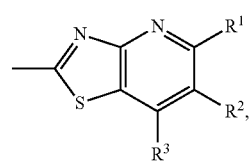

is a group represented by the formula (iv-a1), (iv-b) or (iv-c):

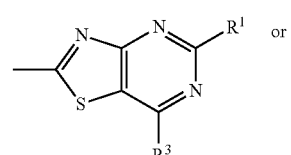 (iv-a1)

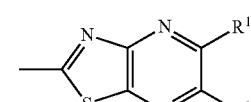 (iv-b)

or

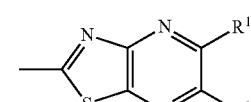 (iv-c)

or a pharmacologically acceptable salt thereof.

6. The compound according to claim 1, wherein, in the formula (I), a part represented by the following formula:

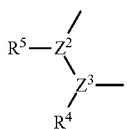

is a group represented by the formula (v-a):

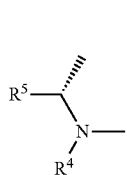

or a pharmacologically acceptable salt thereof.

7. The compound according to claim 6, wherein $R^4$ and $R^5$ are each independently (a) alkyl optionally substituted by 1, 2 or 3 groups selected from the group consisting of $C_1$-$C_6$ alkoxy and monocyclic heteroaryl; or (b) $C_3$-$C_8$ cycloalkyl, or a pharmacologically acceptable salt thereof.

8. The compound according to claim 4, wherein, in the formula (I), a part represented by the following formula:

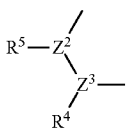

is a group represented by the formula (v-a1):

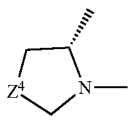

wherein $Z^4$ is $CH_2$, $CF_2$ or a sulfur atom, or a pharmacologically acceptable salt thereof.

9. The compound according to claim 8, wherein $Z^1$ is —C($R^6$)($R^7$)—NH—, or a pharmacologically acceptable salt thereof.

10. The compound according to claim 1, wherein, in the formula (I), a part represented by the following formula:

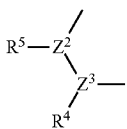

is a part represented by the formula (v-b):

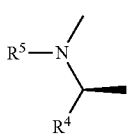

or a pharmacologically acceptable salt thereof.

11. The compound according to claim 10, wherein $R^4$ and $R^5$ are bonded to each other to form, together with the adjacent nitrogen atom and carbon atom, optionally substituted pyrrolidine, or a pharmacologically acceptable salt thereof.

12. The compound according to claim 1, 4 or 8, wherein ring A is a group represented by the formula (vi):

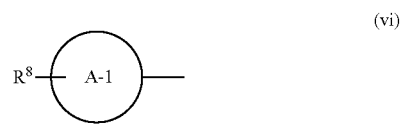

wherein ring A-1 is $C_6$-$C_{11}$ monocyclic or bicyclic aryl, $R^8$ is a hydrogen atom, $C_1$-$C_6$ alkyl, $C_1$-$C_6$ halogenoalkyl, cyano or a halogen atom, $R^1$ is a group represented by the following formula (i-a), (i-b) or (i-c):

$R^{1a}$ is (a) a hydrogen atom; (b) $C_1$-$C_6$ alkyl optionally substituted by 1, 2 or 3 groups selected from the group consisting of amino (optionally substituted by 1 or 2 $C_1$-$C_6$ alkyls), hydroxy, $C_1$-$C_6$ alkoxy, monocyclic nonaromatic heterocyclyloxy, a halogen atom, and a monocyclic nonaromatic heterocyclic group; (c) a halogen atom; (d) $C_3$-$C_5$ cycloalkyl; (e) phenyl optionally substituted by 1, 2 or 3 halogen atoms; (f) a monocyclic nonaromatic heterocyclic group; or (g) monocyclic heteroaryl optionally substituted by 1, 2 or 3 $C_1$-$C_6$ alkyls, $R^{1b}$ is $C_1$-$C_6$ alkyl,
$R^{1c}$ is $C_1$-$C_6$ alkyl,
$R^{1d}$ is (a) $C_1$-$C_6$ alkyl or (b) a monocyclic nonaromatic heterocyclic group, $R^2$ is a group represented by the following formula (ii-a), (ii-b) or (ii-c):

$R^{2a}$ is (a) a hydrogen atom; (b) $C_1$-$C_6$ alkyl optionally substituted by 1, 2 or 3 groups selected from the group consisting of cyano, $C_1$-$C_6$ alkoxycarbonyl, amino (optionally substituted by 1 or 2 $C_1$-$C_6$ alkyls), hydroxy, $C_1$-$C_6$ alkoxy, a halogen atom, a monocyclic nonaromatic heterocyclic group and monocyclic heteroaryl (optionally substituted by one C1-C6 alkyl); (c) cyano; (d) a halogen atom; (e) C3-C8 cycloalkyl optionally substituted by 1, 2 or 3 groups selected from the group consisting of $C_1$-$C_6$ alkyl (optionally substituted by 1, 2 or 3 $C_1$-$C_6$ alkoxys), cyano, hydroxy and $C_1$-$C_6$ alkoxy; (f) phenyl; (g) a monocyclic nonaromatic heterocyclic group optionally substituted by 1, 2 or 3 groups selected from the group consisting of cyano and $C_1$-$C_6$ alkoxy; or (h) monocyclic heteroaryl optionally substituted by 1, 2 or 3 C1-$C_6$ alkyls, $R^{2b}$ is $C_1$-$C_6$ alkyl,
$R^{2c}$ is $C_1$-$C_6$ alkyl,
$R^{2d}$ is (a) $C_1$-$C_6$ alkyl or (b) a monocyclic nonaromatic heterocyclic group,
$R^3$ is a group represented by the following formula (iii-a), (iii-b) or (iii-c):

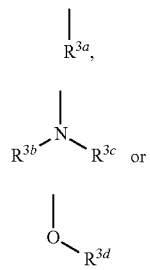

$R^{3a}$a is (a) a hydrogen atom; (b) $C_1$-$C_6$ alkyl optionally substituted by 1, 2 or 3 groups selected from the group consisting of cyano, $C_1$-$C_6$ alkoxy and a halogen atom; (c) cyano; (d) a halogen atom; (e) $C_3$-$C_8$ cycloalkyl optionally substituted by 1, 2 or 3 $C_1$-$C_6$ alkyls; (f) a monocyclic or bicyclic nonaromatic heterocyclic group optionally substituted by 1, 2 or 3 $C_1$-$C_6$ alkyls; or (g) monocyclic heteroaryl optionally substituted by 1, 2 or 3 $C_1$-$C_6$ alkyls, $R^{3b}$ is (a) a hydrogen atom; or (b) $C_1$-$C_6$ alkyl optionally substituted by 1, 2 or 3 $C_1$-$C_6$ alkoxys, $R^{3c}$ is (a) $C_1$-$C_6$ alkyl optionally substituted by 1, 2 or 3 $C_1$-$C_6$ alkoxys; or (b) $C_1$-$C_6$ alkoxy, $R^{3d}$ is (a) $C_1$-C6 alkyl optionally substituted by 1, 2 or 3 groups selected from the group consisting of $C_1$-$C_6$ alkoxy, a halogen atom and $C_3$-$C_8$ cycloalkyl; (b) $C_3$-$C_a$ cycloalkyl; (c) phenyl; or (d) a monocyclic nonaromatic heterocyclic group optionally substituted by 1, 2 or 3 groups selected from the group consisting of $C_1$-$C_6$ alkyl and $C_1$-$C_6$ alkoxycarbonyl, or a pharmacologically acceptable salt thereof.

13. A compound selected from the group consisting of
(R)—N-benzyl-147-(N-methoxy-N-methylamino)[1,3]thiazolo [4,5-d]pyrimidin-2-yl]pyrrolidine-2-carboxamide;
   (R)—N-benzyl-1-[7-(N,N-dimethylamino)-5-methyl[1,3]thiazolo[4,5-d]pyrimidin-2-yl]pyrrolidine-2-carboxamide;
   (R)—N-benzyl-1-(7-ethoxy[1,3]thiazolo[4,5-d]pyrimidin-2-yppyrrolidine-2-carboxamide;
   (R)—N-benzyl-1-(7-cyclopropyl[1,3]thiazolo[4,5-d]pyrimidin-2-yl)pyrrolidine-2-carboxamide;
   (R)—N-benzyl-1-[7-(1-methylcyclopropyl)[1,3]thiazolo [4,5-d]pyrimidin-2-ylipyrrolidine-2-carboxamide;
   (R)—N-benzyl-24N'-(7-cyclopropyl[1,3]thiazolo[4,5-d]pyrimidin-2-yl)-N'-methylamino]propionamide;
   (R)—N-benzyl-146-(2-cyanopropan-2-yl)[1,3]thiazolo [4,5-b]pyridin-2-yl]pyrrolidine-2-carboxamide;
   (R)-146-(5-methyl-1,2,4-oxadiazol-3-yl)[1,3]thiazolo[4, 5-b]pyridin-2-yl]-N-[(1R)-1-phenylethyl]pyrrolidine-2-carboxamide; and
   (R)—N-benzyl-1-(6-cyclopropyl[1,3]thiazolo[4,5-b] pyrazin-2-yl)pyrrolidine-2-carboxamide, or a pharmacologically acceptable salt thereof.

14. A pharmaceutical composition, comprising:
a compound represented by the formula (I):

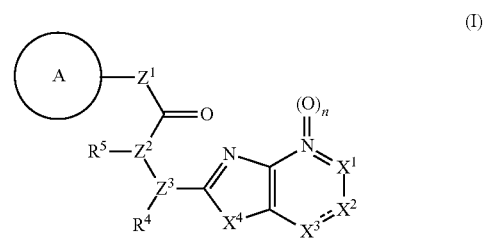

wherein
ring A is an optionally substituted aromatic group,
$X^1$ is $CR^1$ or a nitrogen atom,
a part represented by the following formula in the formula (I):

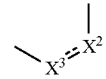

is the following A) or B),
A) ---- is a double bond,
   $X^2$ is a nitrogen atom or $CR^2$, and
   $X^3$ is a nitrogen atom or $CR^3$;
B) ---- is a single bond,
   $X^2$ is $NR^2$, and
   $X^3$ is carbonyl;
$X^4$ is sulfur atom, an oxygen atom or —CHCH—,
$Z^1$ is an oxygen atom, —C(R$^6$)(R$^7$)—, —NH—, —C(R$^6$)(R$^7$)—NH—, —NH—C(R$^6$)(R$^7$)—, —C(R$^6$)(R$^7$)—O—, —O—C(R$^6$)(R$^7$)— or a single bond (where the left end shows a bond to ring A, and the right end shows a bond to the adjacent carbonyl),
one of $Z^2$ and $Z^3$ is CH and the other is a nitrogen atom, or both are nitrogen atoms,
$R^1$ is a group represented by the following formula (i-a), (i-b) or (i-c):

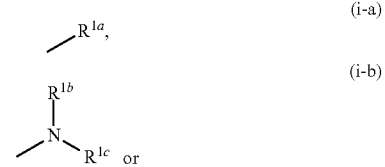

-continued

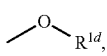
(i-c)

$R^2$ is a group represented by the following formula (ii-a), (ii-b) or (ii-c):

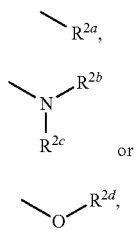
(ii-a)
(ii-b)
or
(ii-c)

$R^3$ is a group represented by the following formula (iii-a), (iii-b) or (iii-c):

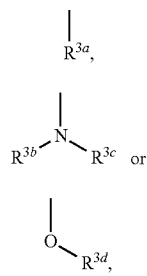
(iii-a)
(iii-b)
or
(iii-c)

$R^4$ and $R^5$ are each independently optionally substituted alkyl or optionally substituted cycloalkyl, or $R^4$ and $R^5$ are bonded to each other to form, together with the adjacent $Z^2$ and $Z^3$, an optionally substituted nitrogen-containing non-aromatic heterocycle, $R^6$ and $R^7$ are each independently a hydrogen atom, optionally substituted alkyl, or optionally substituted cycloalkyl, or $R^6$ and $R^7$ are bonded to each other to form, together with the adjacent carbon atom, an optionally substituted cycloalkane, $R^{1a}$, $R^{1b}$, $R^{1c}$, $R^{1d}$, $R^{2a}$, $R^{2b}$, $R^{2c}$, $R^{2d}$ $R^{3a}$, $R^{3b}$ and $R^{3d}$ are each independently a hydrogen atom, optionally substituted alkyl, cyano, a halogen atom, optionally substituted cycloalkyl, optionally substituted aryl, optionally substituted non-aromatic heterocyclic group or optionally substituted heteroaryl, $R^{3c}$ is optionally substituted alkyl, cyano, optionally substituted alkoxy, a halogen atom, optionally substituted cycloalkyl, optionally substituted aryl, optionally substituted non-aromatic heterocyclic group or optionally substituted heteroaryl, and n is 0 or 1, or a pharmacologically acceptable salt thereof; and a pharmaceutically acceptable carrier.

15. A method for the treatment of a disease selected from the group consisting of schizophrenia, bipolar disorder, attention deficit/hyperactivity disorder, Alzheimer's disease, major depression, autism, cerebrovascular dementia, HIV encephalopathy, and age-related cognitive dysfunction, which comprises administering, to the patient, an effective amount of a compound represented by the formula (I):

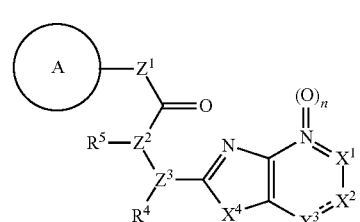
(I)

wherein
ring A is an optionally substituted aromatic group,
$X^1$ is $CR^1$ or a nitrogen atom,
a part represented by the following formula in the formula (I):

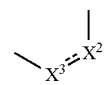

is the following A) or B), A)

---- is a double bond,
$X^2$ is a nitrogen atom or $CR^2$, and
$X^3$ is a nitrogen atom or $CR_3$;

B)

---- is a single bond,
$X^2$ is $NR^2$, and
$X^3$ is carbonyl;
$X^4$ is sulfur atom, an oxygen atom or —CHCH—,
$Z^1$ is an oxygen atom, —C($R^6$)($R^7$)—, —NH—, —C($R^6$)($R^7$)—NH—, —NH—C($R^6$)($R^7$)—, —C($R^6$)($R^7$)—O—, —O—C($R^6$)($R^7$)— or a single bond (where the left end shows a bond to ring A, and the right end shows a bond to the adjacent carbonyl),
one of $Z^2$ and $Z^3$ is CH and the other is a nitrogen atom, or both are nitrogen atoms,
$R^1$ is a group represented by the following formula (i-a), (i-b) or (i-c):

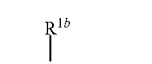
(i-a)

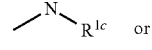
(i-b)
or

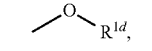
(i-c)

$R^2$ is a group represented by the following formula (ii-a), (ii-b) or (ii-c):

(ii-a)

-continued

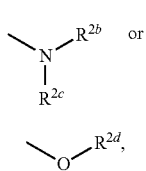
(ii-b)

(ii-c)

$R^3$ is a group represented by the following formula (iii-a), (iii-b) or (iii-c):

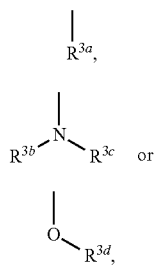
(iii-a)

(iii-b)

(iii-c)

$R^4$ and $R^5$ are each independently optionally substituted alkyl or optionally substituted cycloalkyl, or $R^4$ and $R^5$ are bonded to each other to form, together with the adjacent $Z^2$ and $Z^3$, an optionally substituted nitrogen-containing non-aromatic heterocycle, $R^6$ and $R^7$ are each independently a hydrogen atom, optionally substituted alkyl, or optionally substituted cycloalkyl, or $R^6$ and $R^7$ are bonded to each other to form, together with the adjacent carbon atom, an optionally substituted cycloalkane, $R^{1a}$, $R^{1b}$, $R^{1c}$, $R^{1d}$, $R^{2a}$, $R^{2b}$, $R^{2c}$, $R^{2d}$ $R^{3a}$, $R^{3b}$ and $R^{3d}$ are each independently a hydrogen atom, optionally substituted alkyl, cyano, a halogen atom, optionally substituted cycloalkyl, optionally substituted aryl, optionally substituted non-aromatic heterocyclic group or optionally substituted heteroaryl, $R^{3c}$ is optionally substituted alkyl, cyano, optionally substituted alkoxy, a halogen atom, optionally substituted cycloalkyl, optionally substituted aryl, optionally substituted non-aromatic heterocyclic group or optionally substituted heteroaryl, and n is 0 or 1, or a pharmacologically acceptable salt thereof.

* * * * *

UNITED STATES PATENT AND TRADEMARK OFFICE
CERTIFICATE OF CORRECTION

PATENT NO. : 10,793,582 B2
APPLICATION NO. : 15/769835
DATED : October 6, 2020
INVENTOR(S) : Masahiro Okuyama et al.

Page 1 of 2

It is certified that error appears in the above-identified patent and that said Letters Patent is hereby corrected as shown below:

In the Claims

In Claim 1, at Column 329, Line 22:
Replace "$R^{2d}d$" with -- $R^{2d}$, --

In Claim 12, at Column 332, Line 16:
Replace "C6-C$_{11}$" with -- $C_6$-$C_{11}$ --

In Claim 12, at Column 333, Line 3:
Replace "C1-C6 alkyl)" with -- $C_1$-$C_6$ alkyl) --

In Claim 12, at Column 333, Line 4:
Replace "C3-C8 cycloalkyl" with -- $C_3$-$C_8$ cycloalkyl --

In Claim 12, at Column 333, Line 12:
Replace "C1-C$_6$ alkyls" with -- $C_1$-$C_6$ alkyls --

In Claim 12, at Column 333, Line 47:
Replace "$C_1$-C6 alkyl" with -- $C_1$-$C_6$ alkyl --

In Claim 13, at Column 333, Line 57:
Replace "(R)-N-benzyl-147-(N-methoxy-N-methylamino)" with -- (R)-N-benzyl-1-[7-(N-methoxy-N-methylamino) --

In Claim 13, at Column 333, Line 63:
Replace "2-yppyrrolidine-2-carboxamide" with -- 2-yl)pyrrolidine-2-carboxamide --

In Claim 13, at Column 333, Line 67:
Replace "ylipyrrolidine-2-carboxamide" with -- yl]pyrrolidine-2-carboxamide --

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,793,582 B2

In Claim 13, at Column 334, Line 1:
Replace "N-benzyl-24N'" with -- N-benzyl-2-[N' --

In Claim 13, at Column 334, Line 3:
Replace "N-benzyl-146" with -- N-benzyl-1-1[6 --

In Claim 13, at Column 334, Line 5:
Replace "(R)-146-" with -- (R)-1-[6- --

In Claim 14, at Column 334, Line 48:
Replace "-CHCH-," with -- -CH=CH-, --

In Claim 14, at Column 335, Line 49:
Replace "$R^{2d}d$" with -- $R^{2d}$, --

In Claim 15, at Column 336, Line 27:
Replace "is the following A) or B), A)" with
-- is the following A) or B),
     A) --

In Claim 15, at Column 336, Line 38:
Replace "-CHCH-," with -- -CH=CH-, --

In Claim 15, at Column 338, Line 13:
Replace "$R^{2d}d$" with -- $R^{2d}$, --